US009688699B2

(12) United States Patent
Vakalopoulos et al.

(10) Patent No.: US 9,688,699 B2
(45) Date of Patent: Jun. 27, 2017

(54) 3-(PYRIMIDINE-2-YL)IMIDAZO[1,2-A]PYRIDINES

(71) Applicant: Bayer Pharma Aktiengesellschaft, Berlin (DE)

(72) Inventors: Alexandros Vakalopoulos, Hilden (DE); Alexey Gromov, Erkrath (DE); Markus Follmann, Köln (DE); Damian Brockschnieder, Haan (DE); Johannes-Peter Stasch, Grottaferrata (IT); Tobias Marquardt, Wuppertal (DE); Adrian Tersteegen, Wuppertal (DE); Frank Wunder, Wuppertal (DE); Gorden Redlich, Bochum (DE); Dieter Lang, Velbert (DE); Volkhart Min-Jian Li, Velbert (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/116,366

(22) PCT Filed: Feb. 17, 2015

(86) PCT No.: PCT/EP2015/053252
§ 371 (c)(1),
(2) Date: Aug. 3, 2016

(87) PCT Pub. No.: WO2015/124544
PCT Pub. Date: Aug. 27, 2015

(65) Prior Publication Data
US 2016/0347770 A1    Dec. 1, 2016

(30) Foreign Application Priority Data

Feb. 19, 2014  (EP) .................................... 14155731

(51) Int. Cl.
| C07D 519/00 | (2006.01) |
| A61K 45/06 | (2006.01) |
| A61K 31/53 | (2006.01) |
| A61K 31/519 | (2006.01) |

(52) U.S. Cl.
CPC .......... *C07D 519/00* (2013.01); *A61K 31/519* (2013.01); *A61K 31/53* (2013.01); *A61K 45/06* (2013.01)

(58) Field of Classification Search
CPC .... C07D 519/00; A61K 31/519; A61K 31/53; A61K 45/06
See application file for complete search history.

(56) References Cited

U.S. PATENT DOCUMENTS

| 5,593,993 A | 1/1997 | Morin, Jr. et al. |
| 5,691,336 A | 11/1997 | Dorn et al. |
| 5,698,704 A | 12/1997 | Jackson |
| 6,180,656 B1 | 1/2001 | Fürstner et al. |
| 6,403,588 B1 | 6/2002 | Hayakawa et al. |
| 7,173,037 B2 | 2/2007 | Alonso-Alija et al. |
| 8,129,423 B2 | 3/2012 | Ackermann et al. |
| 8,198,449 B2 | 6/2012 | Pracitto et al. |
| 8,212,041 B2 | 7/2012 | Albrecht et al. |
| 8,536,338 B2 | 9/2013 | Pracitto et al. |
| 8,673,903 B2 | 3/2014 | Hübsch et al. |
| 8,765,769 B2 | 7/2014 | Follmann et al. |
| 8,778,964 B2 | 7/2014 | Vakalopoulos et al. |
| 8,796,305 B2 | 8/2014 | Vakalopoulos et al. |
| 8,859,569 B2 | 10/2014 | Follmann et al. |
| 8,865,734 B2 | 10/2014 | No et al. |
| 8,946,215 B2 | 2/2015 | Vakalopoulos et al. |
| 8,969,045 B2 | 3/2015 | Burkhardt et al. |
| 9,029,389 B2 | 5/2015 | No et al. |
| 9,126,998 B2 | 9/2015 | Vakalopoulos et al. |
| 2004/0176396 A1 | 9/2004 | Biftu et al. |
| 2005/0228004 A1 | 10/2005 | Gudmundsson et al. |
| 2006/0135517 A1 | 6/2006 | Lee et al. |
| 2008/0051409 A1 | 2/2008 | Gmeiner et al. |
| 2009/0181941 A1 | 7/2009 | Leblanc et al. |
| 2010/0298314 A1 | 11/2010 | Reddy et al. |
| 2011/0306618 A1 | 12/2011 | Buettelmann et al. |
| 2012/0029002 A1 | 2/2012 | Straub et al. |
| 2014/0088080 A1 | 3/2014 | Koga et al. |
| 2014/0100229 A1 | 4/2014 | Follmann et al. |

(Continued)

FOREIGN PATENT DOCUMENTS

| DE | 196 42 255 A1 | 4/1998 |
| EP | 0 266 890 A1 | 5/1988 |

(Continued)

OTHER PUBLICATIONS

Bitler et al., "The Preparation and Properties of Crystalline Firefly Luciferin," Archives of Biochemistry and Biophysics, (1957), vol. 72, No. 2, pp. 358-368.
Bodanszky et al., "The Practice of Peptide Synthesis," Second, Revised Edition, Springer-Verlag Berlin Heidelberg 1994, pp. 1-24.
Chen et al., "Cyclic Guanosine Monophosphate Signalling Pathway in Pulmonary Arterial Hypertension," Vascular Pharmacology, (Mar. 2013), vol. 58, Issue 3, pp. 211-218.
Dembinski, "Recent Advances in the Mitsunobu Reaction: Modified Reagents and the Quest for Chromatography-Free Separation," European Journal of Organic Chemistry, (Jul. 2004), vol. 2004, Issue 13, pp. 2763-2772.
Deng et al., "Studies on Phosphoroheterocycle Chemistry II: A Simple and New Route to 1,3,2-Diazaphospholidine-4-thione 2-sulfide Derivatives," Synthesis, (2001), No. 16, pp. 2445-2449.
Florentin et al., "Etude des pKa et de la Protodéboronation des Acides Furanneboroniques," Journal of Heterocyclic Chemistry, (Dec. 1976), vol. 13, Issue 6, pp. 1265-1272.
Glass et al., "Stimulation of Human Platelet Guanylate Cyclase by Fatty Acids," The Journal of Biological Chemistry, (Feb. 25, 1977), vol. 252, No. 4, pp. 1279-1285.

(Continued)

*Primary Examiner* — Yong Chu
(74) *Attorney, Agent, or Firm* — Buchanan Ingersoll & Rooney PC

(57) ABSTRACT

The present application relates to novel 3-(pyrimidin-2-yl)imidazo[1,2-a]pyridines, to processes for preparation thereof, to the use thereof, alone or in combinations, for the treatment and/or prophylaxis of diseases, and to the use thereof for production of medicaments for the treatment and/or prophylaxis of diseases, especially for the treatment and/or prophylaxis of cardiovascular disorders.

11 Claims, No Drawings

(56) References Cited

U.S. PATENT DOCUMENTS

| | | | |
|---|---|---|---|
| 2014/0171434 A1* | 6/2014 | Follmann | C07D 487/04 514/243 |
| 2014/0179672 A1 | 6/2014 | Vakalopoulos et al. | |
| 2014/0350020 A1 | 11/2014 | Follmann et al. | |
| 2014/0357637 A1 | 12/2014 | Follmann et al. | |
| 2015/0274719 A1 | 10/2015 | Vakalopoulos et al. | |
| 2016/0347770 A1 | 12/2016 | Vakalopoulos et al. | |

FOREIGN PATENT DOCUMENTS

| | | |
|---|---|---|
| EP | 1 277 754 A1 | 1/2003 |
| EP | 2 716 642 A1 | 4/2014 |
| JP | H01-258674 A | 10/1989 |
| JP | 2003-313126 A | 11/2003 |
| WO | 89/03833 A1 | 5/1989 |
| WO | 96/34866 A1 | 11/1996 |
| WO | 98/16223 A1 | 4/1998 |
| WO | 01/96335 A1 | 12/2001 |
| WO | 03/095451 A1 | 11/2003 |
| WO | 2005/058325 A1 | 6/2005 |
| WO | 2005/073205 A1 | 8/2005 |
| WO | 2005/090358 A2 | 9/2005 |
| WO | 2006/015737 A1 | 2/2006 |
| WO | 2006/135667 A1 | 12/2006 |
| WO | 2007/002181 A2 | 1/2007 |
| WO | 2008/008539 A2 | 1/2008 |
| WO | 2008/032191 A2 | 3/2008 |
| WO | 2008/082490 A2 | 7/2008 |
| WO | 2008/134553 A1 | 11/2008 |
| WO | 2008/148867 A2 | 12/2008 |
| WO | 2009/155527 A2 | 12/2009 |
| WO | 2010/030538 A2 | 3/2010 |
| WO | 2010/065275 A1 | 6/2010 |
| WO | 2010/079120 A1 | 7/2010 |
| WO | 2010/101949 A1 | 9/2010 |
| WO | 2010/125102 A1 | 11/2010 |
| WO | 2010/136971 A1 | 12/2010 |
| WO | 2011/088045 A1 | 7/2011 |
| WO | 2011/113606 A1 | 9/2011 |
| WO | 2011/141409 A1 | 11/2011 |
| WO | 2011/149921 A1 | 12/2011 |
| WO | 2012/004258 A1 | 1/2012 |
| WO | 2012/004259 A1 | 1/2012 |
| WO | 2012/006760 A1 | 1/2012 |
| WO | 2012/143510 A1 | 10/2012 |
| WO | 2012/143796 A2 | 10/2012 |
| WO | 2012/152629 A1 | 11/2012 |
| WO | 2012/165399 A1 | 12/2012 |
| WO | 2013/030288 A1 | 3/2013 |
| WO | 2013/104703 A1 | 7/2013 |
| WO | 2014/068099 A1 | 5/2014 |
| WO | 2015/124544 A1 | 8/2015 |

OTHER PUBLICATIONS

Greene et al., "The Role of Protective Groups in Organic Synthesis," Greene's Protective Groups in Organic Synthesis, Fourth Edition, (2007), pp. 1-15.

Hassan et al., "Aryl-Aryl Bond Formation One Century after the Discovery of the Ullmann Reaction," Chemical Reviews, (Mar. 8, 2002), vol. 102, No. 5, pp. 1359-1469.

Hjørringgaard et al., "An Automatic Solid-Phase Synthesis of Peptaibols," The Journal of Organic Chemistry, (2009), vol. 74, No. 3, pp. 1329-1332.

Hoenicka et al., "Purified Soluble Guanylyl Cyclase Expressed in a Baculovirus/Sf9 System: Stimulation by YC-1, . Nitric Oxide, and Carbon Monoxide," Journal of Molecular Medicine, (Jan. 1999), vol. 77, No. 1, pp. 14-23.

Hughes, "The Mitsunobu Reaction," Organic Reactions, (1992), vol. 42, Chapter 2, Published by John Wiley & Sons, Inc., pp. 335-395 and 636-656.

Kozo et al., "Spontaneous Hypertension in Rats," Int Rev. Exp. Pathol, (1969), vol. 7, pp. 227-270.

Lasker et al., "Targeting Soluble Guanylate Cyclase for the Treatment of Pulmonary Hypertension," Expert Review of Respiratory Medicine, (Apr. 2011), vol. 5, Issue 2, pp. 153-161.

Ogrel et al., "Synthesis of 15N-Labelled D-Isovaline and α-Aminoisobutyric Acid," European Journal of Organic Chemistry, (Mar. 2000), vol. 2000, Issue 5, pp. 857-859.

Pettibone et al., "A Structurally Novel Stimulator of Guanylate Cyclase with Long-Lasting Hypotensive Activity in the Dog," European Journal of Pharmacology, (Oct. 22, 1985), vol. 116, No. 3, pp. 307-312.

Soler et al., "Betulinic Acid Derivatives: A New Class of Specific Inhibitors of Human Immunodeficiency Virus Type 1 Entry," Journal of Medicinal Chemistry, (1996), vol. 39, Issue 5, pp. 1069-1083.

Van Den Buuse, "Circadian Rhythms of Blood Pressure, Heart Rate, and Locomotor Activity in Spontaneously Hypertensive Rats as Measured with Radio-Telemetry," Physiology & Behavior, (Apr. 1994), vol. 55, Issue 4, pp. 783-787.

Witte et al., "Experimental heart failure in rats: effects on cardiovascular circadian rhythms and on myocardial β-adrenergic signaling," Cardiovascular Research, (Aug. 2000), vol. 47, No. 2, pp. 350-358.

Yu et al., "Vasorelaxant Effect of Isoliquiritigenin, a Novel Soluble Guanylate Cyclase Activator, in Rat Aorta," British Journal of Pharmacology, (Apr. 1995), vol. 114, No. 38, pp. 1587-1594.

Albersen et al., "Synergistic Effects of BAY 60/4552 and Vardenafil on Relaxation of Corpus Cavernosum Tissue of Patients with Erectile Dysfunction and Clinical Phosphodiesterase Type 5 Inhibitor Failure," Journal of Sexual Medicine, (2013), vol. 10, No. 5, pp. 1268-1277.

Cui et al., "Structure Based Drug Design of Crizotinib (PF-02341066), a Potent and Selective Dual Inhibitor of Mesenchymal—Epithelial Transition Factor (c-MET) Kinase and Anaplastic Lymphoma Kinase (ALK)," Journal of Medicinal Chemistry, (2011), vol. 54, No. 18, pp. 6342-6363.

Daley et al., "The First Complete Identification of a Diastereomeric Catalyst-Substrate (Alkoxide) Species in an Enantioselective Ketone Hydrogenation. Mechanistic Investigations," Journal of the American Chemical Society, (2002), vol. 124, No. 14, pp. 3680-3691.

Evgenov et al., "NO-Independent Stimulators and Activators of Soluble Guanylate Cyclase: Discovery and Therapeutic Potential," Nature Reviews Drug Discovery, (2006), vol. 5, No. 9, pp. 755-768.

Gensini et al., "3-Azabicyclo[3.1.0]hex-1-ylamines by Ti-Mediated Intramolecular Reductive Cyclopropanation of α-(N-Allylamino)-Substituted N,N-Dialkylcarboxamides and Carbonitriles," European Journal of Organic Chemistry, (2002), vol. 2002, No. 15, pp. 2499-2507.

Hamill et al., "Improved Patch-Clamp Techniques for High-Resolution Current Recording from Cells and Cell-Free Membrane Patches," Pflügers Archiv, (1981), vol. 391, No. 2, pp. 85-100.

Himmel et al., "Suitability of Commonly Used Excipients for Electrophysiological In-Vitro Safety Pharmacology Assessment of Effects on hERG Potassium Current and on Rabbit Purkinje Fiber Action Potential," Journal of Pharmacological and Toxicological Methods, (2007), vol. 56, No. 2, pp. 145-158.

Ko et al., "YC-1, a Novel Activator of Platelet Guanylate Cyclase," Blood, (1994), vol. 84, No. 12, pp. 4226-4233.

Mittendorf et al., "Discovery of Riociguat (BAY 63-2521): A Potent, Oral Stimulator of Soluble Guanylate Cyclase for the Treatment of Pulmonary Hypertension," ChemMedChem, (2009), vol. 4, No. 5, pp. 853-865.

Mülsch et al., "Effect of YC-1, an NO-independent, superoxide-sensitive stimulator of soluble guanylyl cyclase, on smooth muscle responsiveness to nitrovasodilators," British Journal of Pharmacology, (1997), vol. 120, No. 4, pp. 681-689.

Oudot et al., "Combination of BAY 60/4552 and Vardenafil Exerts Proerectile Facilitator Effects in Rats With Cavemous Nerve Injury: A Proof of Concept Study for the Treatment of Phosphodiesterase Type 5 Inhibitor Failure," European Urology, (2011), vol. 60, No. 5, pp. 1020-1026.

(56) References Cited

OTHER PUBLICATIONS

Palmer et al., "Synthesis and Evaluation of 7H-8,9-Dihydropyrano[2,3-c]imidazo[1,2-a]pyridines as Potassium-Competitive Acid Blockers," Journal of Medicinal Chemistry, (2007), vol. 50, No. 24, pp. 6240-6264.

Scheel et al., "Introduction of a Modular Automated Voltage-Clamp Platform and Its Correlation with Manual Human Ether-Ä-go-goRelated Gene Voltage-Clamp Data," ASSAY and Drug Development Technologies, (2011), vol. 9, No. 6, pp. 600-607.

Sharkovska et al., "Nitric Oxide-Independent Stimulation of Soluble Guanylate Cyclase Reduces Organ Damage in Experimental Low-Renin and High-Renin Models," Journal of Hypertension, (2010), vol. 28, No. 8, pp. 1666-1675.

Stasch et al., "Pharmacological Actions of a Novel NO-Independent Guanylyl Cyclase Stimulator, BAY 41-8543: in vitro Studies," British Journal of Pharmacology, (2002), vol. 135, No. 2, pp. 333-343.

Stasch et al., "Soluble Guanylate Cyclase as an Emerging Therapeutic Target in Cardiopulmonary Disease," Circulation, (2011), vol. 123, No. 20, pp. 2263-2273.

Stasch et al., "Cardiovascular Actions of a Novel No-Independent Guanylyl Cyclase Stimulator, BAY 41/8543: in vivo Studies," British Journal of Pharmacology, (2002), vol. 135, No. 2, pp. 344-355.

Wunder et al., "A Cell-Based cGMP Assay Useful for Ultra-High-Throughput Screening and Identification of Modulators of the Nitric Oxide/cGMP Pathway," Analytical Biochemistry, (2005), vol. 339, No. 1, pp. 104-112.

Zhou et al., "Properties of HERG Channels Stably Expressed in HEK 293 Cells Studied at Physiological Temperature," Biophysical Journal, (1998), vol. 74, No. 1, pp. 230-241.

International Search Report (Form PCT/ISA/220 and PCT/ISA/210) and the Written Opinion of the International Searching Authority (Form PCT/ISA/237) issued on May 18, 2015, by European Patent Office in corresponding International Application No. PCT/EP2015/053252 and an English Translation thereof. (21 pages).

\* cited by examiner

3-(PYRIMIDINE-2-YL)IMIDAZO[1,2-A]PYRIDINES

The present application relates to novel 3-(pyrimidin-2-yl)imidazo[1,2-a]pyridines, to processes for preparation thereof, to the use thereof, alone or in combinations, for the treatment and/or prophylaxis of diseases, and to the use thereof for production of medicaments for the treatment and/or prophylaxis of diseases, especially for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be classified into two groups either by structural features or by the type of ligands: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory centre. This is of central importance for the activation mechanism. NO is able to bind to the iron atom of haem and thus markedly increase the activity of the enzyme. Haem-free preparations cannot, by contrast, be stimulated by NO. Carbon monoxide (CO) is also able to bind to the central iron atom of haem, but the stimulation by CO is much less than that by NO.

By forming cGMP, and owing to the resulting regulation of phosphodiesterases (PDE), ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attack at the central iron atom of haem. In addition to the side effects, the development of tolerance is one of the crucial disadvantages of this mode of treatment.

A few years ago, some substances which stimulate soluble guanylate cyclase directly, i.e. without prior release of NO, were described, for example 3-(5'-hydroxymethyl-2'-furyl)-1-benzylindazole 5 [YC-1; Wu et al., Blood 84 (1994), 4226; Mülsch et al., Brit. J. Pharmacol. 120 (1997), 681]. The more recent stimulators of soluble guanylate cyclase include among others BAY 41-2272, BAY 41-8543 and riociguat (BAY 63-2521) (see, for example, Stasch J.-P. et al., Nat. Rev. Drug Disc. 2006; 5: 755-768; Stasch J.-P. et al., Chem Med Chem 2009; 4: 853-865. Stasch J.-P. et al., Circulation 2011; 123: 2263-2273). Interestingly, some of these sGC stimulators, for example YC-1 or BAY 41-2272, also exhibit PDE 5-inhibitory action in addition to direct guanylate cyclase stimulation. In order to maximize the cGMP pathway, it is pharmacologically desirable to stimulate the synthesis of cGMP and simultaneously to inhibit degradation via PDE 5. This dual principle is particularly advantageous in pharmacological terms (see, for example, Oudout et al., Eur. Urol. 2011, 60, 1020-1026; Albersen et al., J Sex Med. 2013; 10, 1268-1277).

The dual principle is fulfilled in the context of the present invention when the inventive compounds exhibit an effect on recombinant guanylate cyclase reporter cell lines according to the study in B-2 as the minimal effective concentration (MEC) of ≤3 µM and exhibit inhibition of human phosphodiesterase 5 (PDE 5) according to the study in B-3 as $IC_{50}$<100 nM.

Phosphodiesterase 5 (PDE 5) is the name of one of the enzymes which cleave the phosphoric ester bond in cGMP, forming 5'-guanosine monophosphate (5'-GMP). In humans, phosphodiesterase 5 occurs, for example, in the smooth musculature of the corpus cavernosum penis and the pulmonary arteries. Blockage of cGMP degradation by inhibition of PDE 5 (with, for example, sildenafil, vardenafil or tadalafil) leads to increased signals of the relaxation signal pathways and specifically to increased blood supply in the corpus cavernosum penis and lower pressure in the pulmonary blood vessels. They are used for treatment of erectile dysfunction and of pulmonary arterial hypertension. As well as PDE 5, there are further exclusively cGMP-cleaving phosphodiesterases (Stasch J.-P. et al. Circulation 2011; 123, 2263-2273).

WO 03/095451 discloses carbamate-substituted 3-pyrimidinylpyrazolopyridines as stimulators of soluble guanylate cyclase. WO 2010/065275 and WO 2011/149921 disclose substituted pyrrolo- and dihydropyridopyrimidines as sGC activators. As sGC stimulators, WO 2012/004259 describes fused aminopyrimidines, and WO 2012/004258, WO 2012/143510, WO 2012/152629 and WO 2013/030288 fused pyrimidines and triazines. Various imidazo[1,2-a]pyridine derivatives which can be used for treating disorders are described, inter alia, in EP 0 266 890-A1, WO 89/03833-A1, JP 01258674-A [cf. Chem. Abstr. 112:178986], WO 96/34866-A1, EP 1 277 754-A1, WO 2006/015737-A1, WO 2008/008539-A2, WO 2008/082490-A2, WO 2008/134553-A1, WO 2010/030538-A2, WO 2011/113606-A1 and WO 2012/165399-A1.

It was an object of the present invention to provide novel substances which act as stimulators of soluble guanylate cyclase and also as stimulators of soluble guanylate cyclase and phosphodiesterase-5 inhibitors (dual principle) and have an identical or improved therapeutic profile compared to the compounds known from the prior art, for example with respect to their in vivo properties, for example their pharmacokinetic and pharmacodynamic characteristics and/or their metabolic profile and/or their dose-activity relationship.

The present invention provides compounds of the general formula (I)

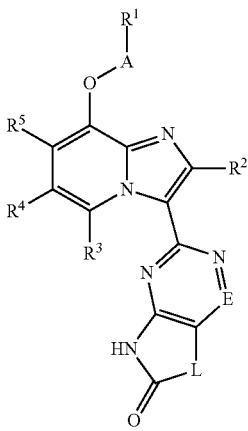
(I)

in which
A represents CH$_2$, CD$_2$ or CH(CH$_3$),
R$^1$ represents (C$_4$-C$_6$)-alkyl, (C$_3$-C$_7$)-cycloalkyl or phenyl,
 where (C$_4$-C$_6$)-alkyl may be substituted by 1 or 2 substituents independently of one another selected from the group consisting of fluorine and trifluoromethyl,
 where (C$_3$-C$_7$)-cycloalkyl may be substituted by 1 to 4 substituents independently of one another selected from the group consisting of fluorine, trifluoromethyl and (C$_1$-C$_4$)-alkyl,
 and
 where phenyl may be substituted by 1 to 4 substituents independently of one another selected from the group consisting of halogen, cyano, monofluoromethyl, difluoromethyl, trifluoromethyl, (C$_1$-C$_4$)-alkyl, (C$_3$-C$_6$)-cycloalkyl, (C$_1$-C$_4$)-alkoxy, difluoromethoxy and trifluoromethoxy,
R$^2$ represents hydrogen, (C$_1$-C$_4$)-alkyl, (C$_1$-C$_4$)-alkoxy-(C$_1$-C$_4$)-alkyl, cyclopropyl, monofluoromethyl, difluoromethyl or trifluoromethyl,
R$^3$ represents hydrogen,
R$^4$ represents hydrogen, halogen, cyano, monofluoromethyl, difluoromethyl, trifluoromethyl, (C$_1$-C$_4$)-alkyl, ethynyl, (C$_3$-C$_7$)-cycloalkyl or (C$_1$-C$_4$)-alkoxy,
R$^5$ represents hydrogen,
E represents nitrogen or CR$^6$,
 where
 R$^6$ represents hydrogen, deuterium, halogen, cyano, difluoromethyl, trifluoromethyl, (C$_1$-C$_6$)-alkyl, (C$_2$-C$_6$)-alkynyl, cyclopropyl, cyclobutyl, hydroxy, —OR$^7$, —NR$^8$R$^9$, hydroxycarbonyl, (C$_1$-C$_4$)-alkoxycarbonyl, —C(=O)—NR$^{10}$R$^{11}$, 5- or 6-membered heteroaryl,
  in which (C$_1$-C$_6$)-alkyl may be substituted by 1 to 3 substituents independently of one another selected from the group consisting of fluorine, difluoromethyl, trifluoromethyl, (C$_1$-C$_4$)-alkoxy, hydroxy, amino, —N(C=O)R$^{12}$, (C$_1$-C$_4$)-alkylsulphonylamino, (C$_3$-C$_6$)-cycloalkylsulphonylamino, cyclopropyl and cyclobutyl,
   in which R$^{12}$ represents (C$_3$-C$_7$)-cycloalkyl or (C$_1$-C$_4$)-alkyl,
    in which (C$_1$-C$_4$)-alkyl may be substituted by trifluoromethyl or difluoromethyl,
  in which (C$_2$-C$_6$)-alkynyl may be substituted by 1 or 2 substituents independently of one another selected from the group consisting of difluoromethyl, trifluoromethyl, hydroxy, amino, cyclopropyl and cyclobutyl,
  in which 5- or 6-membered heteroaryl may be substituted by 1 to 3 substituents independently of one another selected from the group consisting of fluorine, chlorine, (C$_1$-C$_4$)-alkyl, hydroxy, amino and cyclopropyl,
  in which R$^7$ represents (C$_1$-C$_6$)-alkyl or 5-membered heteroaryl,
   in which (C$_1$-C$_6$)-alkyl may be substituted by trifluoromethyl, (C$_1$-C$_4$)-alkoxy, hydroxy, cyclopropyl or cyclobutyl,
  in which R$^8$ represents hydrogen, (C$_1$-C$_6$)-alkyl or (C$_3$-C$_7$)-cycloalkyl,
   in which (C$_3$-C$_7$)-cycloalkyl may be substituted by 1 to 3 substituents independently of one another selected from the group consisting of (C$_1$-C$_4$)-alkyl, hydroxy, amino, fluorine, trifluoromethyl and difluoromethyl,
   and
   in which (C$_1$-C$_6$)-alkyl may be substituted by 1 to 4 substituents independently of one another selected from the group consisting of fluorine, (C$_1$-C$_4$)-alkyl, (C$_3$-C$_7$)-cycloalkyl, (C$_1$-C$_4$)-alkoxy, hydroxy, amino, trifluoromethyl, difluoromethyl, monofluoromethyl, 5- to 7-membered azaheterocyclyl and phenyl,
    in which phenyl may be substituted by 1 to 3 substituents independently of one another selected from the group consisting of halogen, cyano, (C$_1$-C$_4$)-alkyl and (C$_1$-C$_4$)-alkoxy,
    in which 5- to 7-membered azaheterocyclyl may be substituted by 1 to 4 fluorine substituents,
    and
    in which (C$_3$-C$_7$)-cycloalkyl may be substituted by 1 to 3 substituents independently of one another selected from the group consisting of halogen, (C$_1$-C$_4$)-alkyl and hydroxy,
  in which R$^9$ represents hydrogen or (C$_1$-C$_6$)-alkyl,
  or
  R$^8$ and R$^9$ together with the nitrogen atom to which they are attached form a 3- to 8-membered heterocycle,
   in which the 3- to 8-membered heterocycle may be substituted by 1 or 2 substituents independently of one another selected from the group consisting of fluorine, (C$_1$-C$_4$)-alkyl, hydroxycarbonyl, (C$_1$-C$_4$)-alkoxycarbonyl, hydroxy and amino,
    in which (C$_1$-C$_4$)-alkyl may be substituted by hydroxycarbonyl, (C$_1$-C$_4$)-alkoxycarbonyl, hydroxy or amino,
  in which R$^{10}$ represents hydrogen, (C$_1$-C$_6$)-alkyl or (C$_3$-C$_7$)-cycloalkyl,
   in which (C$_3$-C$_7$)-cycloalkyl may be substituted by 1 to 3 substituents independently of one another selected from the group consisting of (C$_1$-C$_6$)-alkyl, hydroxy, trifluoromethyl and difluoromethyl,
   and
   in which (C$_1$-C$_6$)-alkyl may be substituted by 1 to 4 substituents independently of one another selected from the group consisting of fluorine, (C$_3$-C$_7$)-cycloalkyl, (C$_1$-C$_4$)-alkoxy, hydroxy, amino, trifluoromethyl and difluoromethyl,
  in which R$^{11}$ represents hydrogen or (C$_1$-C$_4$)-alkyl,
  or
  R$^{10}$ and R$^{11}$ together with the nitrogen atom to which they are attached form a 3- to 7-membered heterocycle, in which the 3- to 7-membered heterocycle may be substituted by 1 to 3 substituents independently of one another selected from the group consisting of fluorine, $(C_1-C_4)$-alkyl, hydroxy and amino,
in which $(C_1-C_4)$-alkyl may be substituted by hydroxy, L represents a $\#^1$-$CR^{13A}R^{13B}$—$(CR^{14A}R^{14B})_m$-$\#^2$ group,
where
$\#^1$ represents the point of attachment to the carbonyl group,
$\#^2$ represents the point of attachment to the pyrimidine or triazine ring,
m represents a number 0, 1 or 2,
$R^{13A}$ represents hydrogen, trifluoromethyl or $(C_1-C_4)$-alkyl,
$R^{13B}$ represents hydrogen, difluoromethyl, trifluoromethyl, $(C_1-C_4)$-alkyl or $(C_3-C_7)$-cycloalkyl,
in which $(C_1-C_6)$-alkyl may be substituted by 1 to 3 substituents independently of one another selected from the group consisting of fluorine, cyano, trifluoromethyl, $(C_3-C_7)$-cycloalkyl, difluoromethoxy and trifluoromethoxy,
or
$R^{13A}$ and $R^{13B}$ together with the carbon atom to which they are attached form a 3- to 6-membered carbocycle,
$R^{14A}$ represents hydrogen, fluorine, $(C_1-C_4)$-alkyl or hydroxy,
$R^{14B}$ represents hydrogen, fluorine, $(C_1-C_4)$-alkyl or trifluoromethyl,
and the N-oxides, salts, solvates, salts of the N-oxides and solvates of the N-oxides and salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are mentioned below as working examples and the salts, solvates and solvates of the salts thereof if the compounds that are encompassed by formula (I) and are mentioned below are not already salts, solvates and solvates of the salts.

Preferred salts in the context of the present invention are physiologically acceptable salts of the compounds of the invention. Also encompassed are salts which are not themselves suitable for pharmaceutical applications but can be used, for example, for isolation or purification of the compounds according to the invention.

Physiologically acceptable salts of the compounds of the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatographic processes are preferably used for this purpose, especially HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass from the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3H$ or $^{14}C$ isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting materials.

The present invention additionally also encompasses prodrugs of the compounds according to the invention. The term "prodrugs" in this context refers to compounds which may themselves be biologically active or inactive but are reacted (for example metabolically or hydrolytically) to give compounds according to the invention during their residence time in the body.

In the context of the present invention, unless specified otherwise, the substituents are defined as follows:

Alkyl in the context of the invention is a straight-chain or branched alkyl radical having 1 to 6 carbon atoms. Preferred examples include: methyl, ethyl, n-propyl, isopropyl, n-butyl, isobutyl, 1-methylpropyl, tert-butyl, n-pentyl, 1-methylbutyl, 2-methylbutyl, 3-methylbutyl, isopentyl, n-hexyl, 1-methylpentyl, 1-ethylbutyl, 2-methylpentyl, 2-ethylbutyl, 3-methylpentyl, 4-methylpentyl.

Cycloalkyl in the context of the invention is a monocyclic saturated alkyl radical having 3 to 7 carbon atoms. Preferred examples include: cyclopropyl, cyclobutyl, cyclopentyl, cyclohexyl and cycloheptyl.

5- to 7-membered azaheterocyclyl in the context of the invention is a monocyclic saturated heterocycle which has a total of 5 to 7 ring atoms, contains a nitrogen atom and may additionally contain a further ring heteroatom from the group of N, O, S, SO and $SO_2$, and is attached via a ring nitrogen atom. Examples include: pyrrolidinyl, pyrazolidinyl, piperidinyl, piperazinyl, morpholinyl, thiomorpholinyl, 1,1-dioxothiomorpholinyl, hexahydroazepinyl and hexahydro-1,4-diazepinyl.

Alkoxy in the context of the invention is a straight-chain or branched alkoxy radical having 1 to 4 carbon atoms. Preferred examples include: methoxy, ethoxy, n-propoxy, isopropoxy, 1-methylpropoxy, n-butoxy, isobutoxy and tert-butoxy.

$(C_1-C_4)$-Alkylsulphonylamino in the context of the invention is an amino group having a straight-chain or branched alkylsulphonyl substituent which has 1 to 4 carbon atoms in the alkyl radical and is attached to the nitrogen atom via the sulphonyl group. Preferred examples include: methylsulphonylamino, ethylsulphonylamino, propylsulphonylamino, n-butylsulphonylamino, isobutylsulphonylamino and tert-butylsulphonylamino.

$(C_3-C_6)$-Cycloalkylsulphonylamino in the context of the invention is an amino group having a cycloalkylsulphonyl substituent which has 3 to 6 carbon atoms in the cycloalkyl ring and is attached to the nitrogen atom via the sulphonyl group. Preferred examples include: cyclopropylsulphonylamino, cyclobutylsulphonylamino, cyclopentylsulphonylamino, cyclohexylsulphonylamino.

Heterocyclyl or heterocycle in the context of the invention is a monocyclic or bicyclic saturated or partially unsaturated heterocycle which has a total of 3 to 7 ring atoms, contains one to three ring heteroatoms from the group consisting of N, O and S and is attached via a ring nitrogen atom. Examples include: azetidinyl, oxetanyl, pyrrolidinyl, pyrazolidinyl, tetrahydrofuranyl, thiolanyl, piperidinyl, piperazinyl, tetrahydropyranyl, morpholinyl, thiomorpholinyl, azepanyl, diazepanyl, dihydropyrrolyl, tetrahydropyridinyl, dihydrooxazinyl, dihydropyrazinyl or 3-azabicyclo[3.1.0]hex-3-yl. Preference is given to a saturated 5- or 6-membered heterocycle having one or two ring heteroatoms from the group consisting of N, O and S. Examples include: azetidinyl, oxetanyl, pyrrolidinyl, pyrazolidinyl, tetrahydrofuranyl, piperidinyl, piperazinyl, tetrahydropyranyl, morpholinyl and thiomorpholinyl. Preference is given to a saturated bicycle having one or two ring heteroatoms from the group consisting of N, O and S. Examples include: 3-azabicyclo[3.1.0]hex-3-yl.

Heteroaryl in the context of the invention is a monocyclic or optionally bicyclic aromatic heterocycle (heteroaromatic) which has a total of 5 to 10 ring atoms, contains up to three identical or different ring heteroatoms from the group consisting of N, O and S and is attached via a ring carbon atom or optionally via a ring nitrogen atom. Examples include: furyl, pyrrolyl, thienyl, pyrazolyl, imidazolyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrrolo[2,3-b]pyridine, pyrazolo[1,5-a]pyridine, pyrazolo[3,4-b]pyridinyl. Preferred examples include: pyrazolyl, imidazolyl, isoxazolyl, pyridyl, indolyl, indazolyl, quinolinyl, isoquinolinyl, naphthyridinyl, quinazolinyl, quinoxalinyl, phthalazinyl, pyrrolo[2,3-b]pyridine, pyrazolo[1,5-a]pyridine, pyrazolo[3,4-b]pyridinyl.

Halogen in the context of the invention includes fluorine, chlorine, bromine and iodine. Preference is given to chlorine or fluorine.

An oxo group in the context of the invention is an oxygen atom bonded via a double bond to a carbon or sulphur atom.

When radicals in the compounds of the invention are substituted, the radicals may be mono- or polysubstituted, unless specified otherwise. In the context of the present invention, all radicals which occur more than once are defined independently of one another. Substitution by one, two or three identical or different substituents is preferred.

Preference is given in the context of the present invention to compounds of the formula (I) in which A represents $CH_2$, $R^1$ represents phenyl,
  where phenyl may be substituted by 1 to 4 substituents independently of one another selected from the group consisting of fluorine, chlorine, cyano and methyl, $R^2$ represents hydrogen, methyl, ethyl or cyclopropyl, $R^3$ represents hydrogen, $R^4$ represents hydrogen, fluorine, chlorine, methyl or ethyl, $R^5$ represents hydrogen, E represents nitrogen or $CR^6$,
  where
    $R^6$ represents hydrogen, chlorine, iodine, cyano, $(C_1-C_6)$-alkyl, $(C_2-C_6)$-alkynyl, cyclopropyl, hydroxy, —$OR^7$, —$NR^8R^9$, hydroxycarbonyl, $(C_1-C_4)$-alkoxycarbonyl, —C(=O)—$NR^{10}R^{11}$ or 5-membered heteroaryl,
      in which $(C_1-C_6)$-alkyl may be substituted by 1 to 3 substituents independently of one another selected from the group consisting of fluorine, difluoromethyl, trifluoromethyl, methoxy, ethoxy, hydroxy, amino, —N(C=O)$R^{12}$, methylsulphonylamino, cyclopropyl and cyclobutyl,
        in which $R^{12}$ represents cyclopropyl, cyclobutyl, methyl or ethyl,
      in which $(C_2-C_6)$-alkynyl may be substituted by cyclopropyl or cyclobutyl,
      in which 5-membered heteroaryl may be substituted by chlorine, methyl, ethyl or hydroxy,
      in which $R^7$ represents $(C_1-C_4)$-alkyl or pyrazolyl,
        in which $(C_1-C_4)$-alkyl may be substituted by trifluoromethyl, methoxy, hydroxy or cyclopropyl,
      in which $R^8$ represents hydrogen, $(C_1-C_4)$-alkyl or $(C_3-C_6)$-cycloalkyl,
        in which $(C_3-C_6)$-cycloalkyl may be substituted by 1 to 4 substituents independently of one another selected from the group consisting of methyl, ethyl and hydroxy,
        and
        in which $(C_1-C_4)$-alkyl may be substituted by 1 to 4 substituents independently of one another selected from the group consisting of fluorine, $(C_1-C_4)$-alkyl, $(C_3-C_5)$-cycloalkyl, pyrrolidinyl, piperidinyl, methoxy, ethoxy, hydroxy, amino, trifluoromethyl, difluoromethyl, monofluoromethyl and phenyl,
in which phenyl may be substituted by 1 to 3 substituents independently of one another selected from the group consisting of fluorine, chlorine, cyano and methoxy,
in which pyrrolidinyl and piperidinyl may be disubstituted by fluorine,
and
in which $(C_3-C_7)$-cycloalkyl may be substituted by hydroxy,
in which $R^9$ represents hydrogen or methyl,
or
$R^8$ and $R^9$ together with the nitrogen atom to which they are attached form a 4- to 7-membered heterocycle,
in which the 4- to 7-membered heterocycle may be substituted by 1 or 2 substituents independently of one another selected from the group consisting of $(C_1-C_4)$-alkyl, hydroxycarbonyl, hydroxy and amino,
in which $(C_1-C_4)$-alkyl may be substituted by hydroxycarbonyl, hydroxy or amino,
in which $R^{10}$ represents hydrogen, $(C_1-C_4)$-alkyl or $(C_3-C_6)$-cycloalkyl,
in which $(C_3-C_6)$-cycloalkyl may be substituted by 1 to 3 substituents independently of one another selected from the group consisting of methyl, ethyl and hydroxy,
and
in which $(C_1-C_4)$-alkyl may be substituted by 1 or 2 substituents independently of one another selected from the group consisting of fluorine, hydroxy, amino, trifluoromethyl and difluoromethyl,
in which $R^1$ represents hydrogen or methyl,
or
$R^{10}$ and $R^{11}$ together with the nitrogen atom to which they are attached form a 4- to 6-membered heterocycle,
in which the 4- to 6-membered heterocycle may be substituted by 1 to 3 substituents independently of one another selected from the group consisting of fluorine, methyl, ethyl, hydroxy and amino,
in which methyl and ethyl may be substituted by hydroxy,
L represents a $\#^1$-$CR^{13A}R^{13B}$—$(CR^{14A}R^{14B})_m$-$\#^2$ group,
where
$\#^1$ represents the point of attachment to the carbonyl group,
$\#^2$ represents the point of attachment to the pyrimidine or triazine ring,
m represents a number 0,
$R^{13A}$ represents hydrogen or methyl,
$R^{13B}$ represents hydrogen, difluoromethyl, trifluoromethyl or methyl,
or
$R^{13A}$ and $R^{13B}$ together with the carbon atom to which they are attached form a cyclopropyl ring,
and the N-oxides, salts, solvates, salts of the N-oxides and solvates of the N-oxides and salts thereof.

In the context of the present invention, particular preference is given to compounds of the formula (I) in which
A represents $CH_2$,
$R^1$ represents a phenyl group of the formula

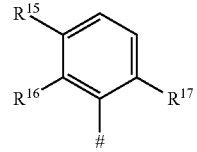

where
\# represents the point of attachment to A,
and
$R^{15}$ represents hydrogen or fluorine,
$R^{16}$ and $R^{17}$ represent fluorine,
$R^2$ represents methyl,
$R^3$ represents hydrogen,
$R^4$ represents hydrogen, chlorine or methyl,
$R^5$ represents hydrogen,
E represents nitrogen or $CR^6$,
where
$R^6$ represents hydrogen, chlorine, ethynyl, —$OR^7$, —$NR^8R^9$, —C(=O)—$NR^{10}R^{11}$, 1H-pyrazol-1-yl or 1,3-thiazol-5-yl,
in which ethynyl is substituted by cyclopropyl,
in which 1H-pyrazol-1-yl and 1,3-thiazol-5-yl may be substituted by methyl, ethyl or hydroxy,
in which $R^7$ represents methyl, ethyl or 1H-pyrazol-4-yl,
in which methyl may be substituted by cyclopropyl,
in which ethyl may be substituted by trifluoromethyl, methoxy or hydroxy,
in which $R^8$ represents hydrogen, ethyl, propyl or $(C_4-C_6)$-cycloalkyl,
in which $(C_4-C_6)$-cycloalkyl may be substituted by 1 or 2 methyl or hydroxy substituents,
and
in which ethyl and propyl may be substituted by 1 to 3 substituents independently of one another selected from the group consisting of fluorine, methyl, ethyl, propyl, cyclopropyl, methoxy, hydroxy, amino, trifluoromethyl, difluoromethyl, monofluoromethyl and phenyl,
in which phenyl may be substituted by 1 or 2 substituents independently of one another selected from the group consisting of fluorine, chlorine and methoxy,
and
in which $(C_4-C_7)$-cycloalkyl may be substituted by hydroxy,
in which $R^9$ represents hydrogen,
or
$R^8$ and $R^9$ together with the nitrogen atom to which they are attached form a piperidinyl, pyrrolidinyl or 3-azabicyclo[3.1.0]hex-3-yl ring,
in which the piperidinyl and pyrrolidinyl ring may be substituted by methyl,
in which methyl may be substituted by hydroxycarbonyl or hydroxy,
and
in which the 3-azabicyclo[3.1.0]hex-3-yl ring may be substituted by amino, in which $R^{10}$ represents hydrogen, methyl, ethyl, n-propyl or cyclopropyl,
in which methyl, ethyl and n-propyl may be substituted by 1 or 2 substituents independently of one another selected from the group consisting of fluorine, amino and trifluoromethyl,
in which $R^{11}$ represents hydrogen,
or
$R^{10}$ and $R^{11}$ together with the nitrogen atom to which they are attached form a pyrrolidinyl, piperidinyl or piperazinyl ring,
in which the pyrrolidinyl ring may be substituted by 1 to 3 substituents independently of one another selected from the group consisting of fluorine, methyl, hydroxy and amino,
in which methyl may be substituted by hydroxy,
in which the piperazinyl ring may be substituted at the nitrogen atom by methyl,
L represents a $\#^1$-$CR^{13A}R^{13B}$-$\#^2$ group,
where
$\#^1$ represents the point of attachment to the carbonyl group,
$\#^2$ represents the point of attachment to the pyrimidine or triazine ring,
$R^{13A}$ represents methyl,
$R^{13B}$ represents trifluoromethyl or methyl,
and the N-oxides, salts, solvates, salts of the N-oxides and solvates of the N-oxides and salts thereof.

In the context of the present invention, preference is also given to compounds of the formula (I) in which
$R^1$ represents a phenyl group of the formula

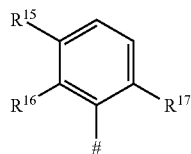

where
# represents the point of attachment to A,
and
$R^{15}$ represents hydrogen or fluorine,
$R^{16}$ and $R^{17}$ represent fluorine,
and the N-oxides, salts, solvates, salts of the N-oxides and solvates of the N-oxides and salts thereof.

In the context of the present invention, preference is also given to compounds of the formula (I) in which
$R^1$ represents a phenyl group of the formula

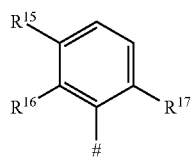

where
# represents the point of attachment to A,
and
$R^{15}$ represents hydrogen,
$R^{16}$ and $R^{17}$ represent fluorine,
and the N-oxides, salts, solvates, salts of the N-oxides and solvates of the N-oxides and salts thereof.

In the context of the present invention, preference is also given to compounds of the formula (I) in which
$R^1$ represents a phenyl group of the formula

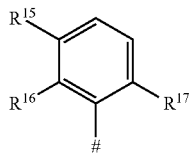

where
# represents the point of attachment to A,
and
$R^{15}$ represents fluorine,
$R^{16}$ and $R^{17}$ represent fluorine,
and the N-oxides, salts, solvates, salts of the N-oxides and solvates of the N-oxides and salts thereof.

In the context of the present invention, preference is also given to compounds of the formula (I) in which
$R^2$ represents methyl,
and the N-oxides, salts, solvates, salts of the N-oxides and solvates of the N-oxides and salts thereof.

In the context of the present invention, preference is also given to compounds of the formula (I) in which
E represents nitrogen,
and the N-oxides, salts, solvates, salts of the N-oxides and solvates of the N-oxides and salts thereof.

In the context of the present invention, preference is also given to compounds of the formula (I) in which
E represents $CR^6$,
where
$R^6$ represents hydrogen, chlorine, ethynyl, —$OR^7$, —$NR^8R^9$, —C(=O)—$NR^{10}R^{11}$, 1H-pyrazol-1-yl or 1,3-thiazol-5-yl,
in which ethynyl is substituted by cyclopropyl,
in which 1H-pyrazol-1-yl and 1,3-thiazol-5-yl may be substituted by methyl, ethyl or hydroxy,
in which $R^7$ represents methyl, ethyl or 1H-pyrazol-4-yl,
in which methyl may be substituted by cyclopropyl,
in which ethyl may be substituted by trifluoromethyl, methoxy or hydroxy,
in which $R^8$ represents hydrogen, ethyl, propyl or ($C_4$-$C_6$)-cycloalkyl,
in which ($C_4$-$C_6$)-cycloalkyl may be substituted by 1 or 2 methyl or hydroxy substituents,
and
in which ethyl and propyl may be substituted by 1 to 3 substituents independently of one another selected from the group consisting of fluorine, methyl, ethyl, cyclopropyl, propyl, methoxy, hydroxy, amino, trifluoromethyl, difluoromethyl, monofluoromethyl and phenyl,
in which phenyl may be substituted by 1 or 2 substituents independently of one another selected from the group consisting of fluorine, chlorine and methoxy,
and
in which ($C_4$-$C_7$)-cycloalkyl may be substituted by hydroxy,
in which $R^9$ represents hydrogen,
or
$R^8$ and $R^9$ together with the nitrogen atom to which they are attached form a piperidinyl, pyrrolidinyl or 3-azabicyclo[3.1.0]hex-3-yl ring, in which the piperidinyl and pyrrolidinyl ring may be substituted by methyl,
in which methyl may be substituted by hydroxycarbonyl or hydroxy,
and
in which the 3-azabicyclo[3.1.0]hex-3-yl ring may be substituted by amino,
in which $R^{10}$ represents hydrogen, methyl, ethyl, n-propyl or cyclopropyl,
in which methyl, ethyl and n-propyl may be substituted by 1 or 2 substituents independently of one another selected from the group consisting of fluorine, amino and trifluoromethyl,
in which $R^{11}$ represents hydrogen,
or
$R^{10}$ and $R^{11}$ together with the nitrogen atom to which they are attached form a pyrrolidinyl, piperidinyl or piperazinyl ring,
in which the pyrrolidinyl ring may be substituted by 1 to 3 substituents independently of one another selected from the group consisting of fluorine, methyl, hydroxy and amino,
in which methyl may be substituted by hydroxy,
in which the piperazinyl ring may be substituted at the nitrogen atom by methyl,
and the N-oxides, salts, solvates, salts of the N-oxides and solvates of the N-oxides and salts thereof.

In the context of the present invention, particular preference is also given to compounds of the formula (I) in which
E represents $CR^6$,
where
$R^6$ represents —$NR^8R^9$ or —C(=O)—$NR^{10}R^{11}$,
in which $R^8$ represents hydrogen, ethyl, propyl or ($C_4$-$C_6$)-cycloalkyl,
in which ($C_4$-$C_6$)-cycloalkyl may be substituted by 1 or 2 methyl or hydroxy substituents,
and
in which ethyl and propyl may be substituted by 1 to 3 substituents independently of one another selected from the group consisting of fluorine, methyl, ethyl, cyclopropyl, propyl, methoxy, hydroxy, amino, trifluoromethyl, difluoromethyl, monofluoromethyl and phenyl,
in which phenyl may be substituted by 1 or 2 substituents independently of one another selected from the group consisting of fluorine, chlorine and methoxy,
and
in which ($C_4$-$C_7$)-cycloalkyl may be substituted by hydroxy,
in which $R^9$ represents hydrogen,
or
$R^8$ and $R^9$ together with the nitrogen atom to which they are attached form a piperidinyl, pyrrolidinyl or 3-azabicyclo[3.1.0]hex-3-yl ring,
in which the piperidinyl and pyrrolidinyl ring may be substituted by methyl,
in which methyl may be substituted by hydroxycarbonyl or hydroxy,
and
in which the 3-azabicyclo[3.1.0]hex-3-yl ring may be substituted by amino,
in which $R^{10}$ represents hydrogen, methyl, ethyl, n-propyl or cyclopropyl,
in which methyl, ethyl and n-propyl may be substituted by 1 or 2 substituents independently of one another selected from the group consisting of fluorine, amino and trifluoromethyl,
in which $R^{11}$ represents hydrogen,
or
$R^{10}$ and $R^{11}$ together with the nitrogen atom to which they are attached form a pyrrolidinyl, piperidinyl or piperazinyl ring,
in which the pyrrolidinyl ring may be substituted by 1 to 3 substituents independently of one another selected from the group consisting of fluorine, methyl, hydroxy and amino,
in which methyl may be substituted by hydroxy,
in which the piperazinyl ring may be substituted at the nitrogen atom by methyl,
and the N-oxides, salts, solvates, salts of the N-oxides and solvates of the N-oxides and salts thereof.

In the context of the present invention, preference is also given to compounds of the formula (I) in which
L represents a $\#^1$-$CR^{13A}R^{13B}$-$\#^2$ group,
where
$\#^1$ represents the point of attachment to the carbonyl group,
$\#^2$ represents the point of attachment to the pyrimidine or triazine ring,
$R^{13A}$ represents methyl,
$R^{13B}$ represents trifluoromethyl or methyl,
and the N-oxides, salts, solvates, salts of the N-oxides and solvates of the N-oxides and salts thereof.

In the context of the present invention, preference is also given to compounds of the formula (I) in which
$R^4$ represents hydrogen, chlorine or methyl,
and the N-oxides, salts, solvates, salts of the N-oxides and solvates of the N-oxides and salts thereof.

In the context of the present invention, particular preference is also given to compounds of the formula (I) in which
$R^4$ represents chlorine,
and the N-oxides, salts, solvates, salts of the N-oxides and solvates of the N-oxides and salts thereof.

Irrespective of the particular combinations of the radicals specified, the individual radical definitions specified in the particular combinations or preferred combinations of radicals are also replaced as desired by radical definitions of other combinations.

Particular preference is given to combinations of two or more of the preferred ranges mentioned above.

The invention further provides a process for preparing the compounds of the formula (I) according to the invention, characterized in that
a compound of the formula (II)

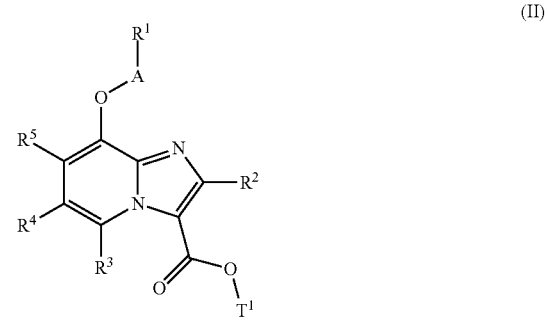

in which A, $R^1$, $R^2$, $R^3$, $R^4$ and $R^5$ each have the meanings given above and $T^1$ represents $(C_1-C_4)$-alkyl or benzyl,
is reacted in an inert solvent in the presence of a suitable base or acid to give a carboxylic acid of the formula (III)

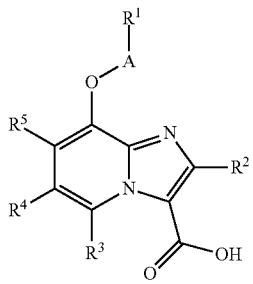
(III)

in which A, $R^1$, $R^2$, $R^3$, $R^4$ and $R^5$ each have the meanings given above,
and this is subsequently converted in an inert solvent under amide coupling conditions with an ammonium salt into a compound of the formula (IV)

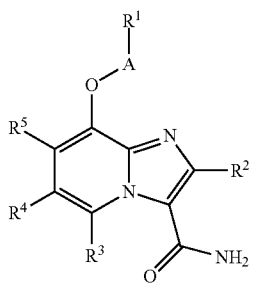
(IV)

in which A, $R^1$, $R^2$, $R^3$, $R^4$ and $R^5$ each have the meanings given above, and this is then reacted in an inert solvent with trifluoroacetic anhydride to give a compound of the formula (V)

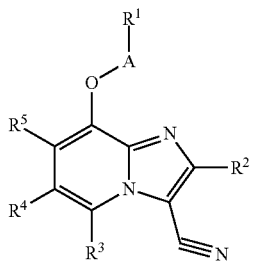
(V)

in which A, $R^1$, $R^2$, $R^3$, $R^4$ and $R^5$ each have the meanings given above, this is converted in the presence of an alkyl-aluminum reagent in an inert solvent into an amidine of the formula (VI)

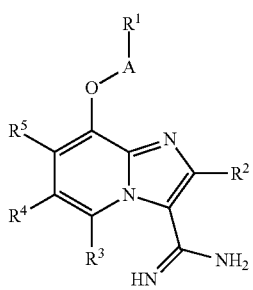
(VI)

in which A, $R^1$, $R^2$, $R^3$, $R^4$ and $R^5$ each have the meanings given above,
or
a compound of the formula (V) is converted in a suitable solvent in the presence of a suitable base with hydroxylamine initially into a compound of the formula (VIa)

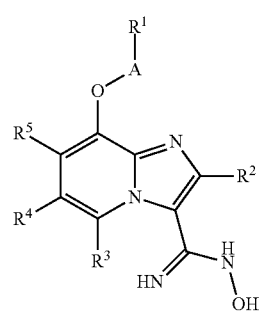
(VIa)

in which A, $R^1$, $R^2$, $R^3$, $R^4$ and $R^5$ each have the meanings given above, this is then converted by hydrogenolysis in the presence of a palladium catalyst, for example palladium on activated carbon, in an inert solvent, for example ethanol or ethyl acetate, into an amidine of the formula (VI), this is reacted in an inert solvent in the presence of a suitable base with a compound of the formula (VII)

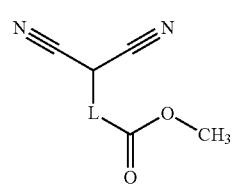
(VII)

to give a compound of the formula (VIII)

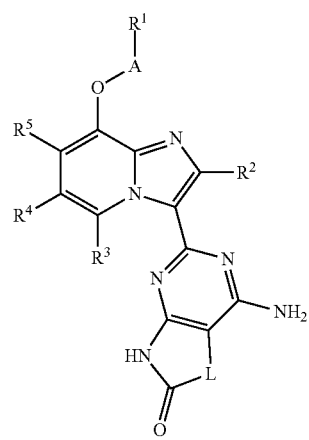
(VIII)

in which A, $R^1$, $R^2$, $R^3$, $R^4$, $R^5$ and L each have the meanings given above,
the amino group is converted in an inert solvent with isopentyl nitrite and a halogen equivalent into a compound of the formula (IX)

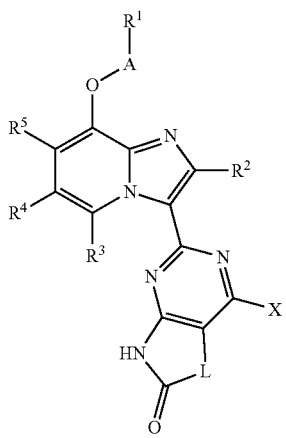

(IX)

in which A, $R^1$, $R^2$, $R^3$, $R^4$, $R^5$ and L each have the meanings given above and
X represents chlorine, bromine or iodine,
and this

[A] is subsequently reacted in an inert solvent, optionally in the presence of a suitable base, with a compound of the formula (X)

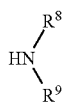

(X)

in which $R^8$ and $R^9$ have the meanings given above, to give a compound of the formula (I-A)

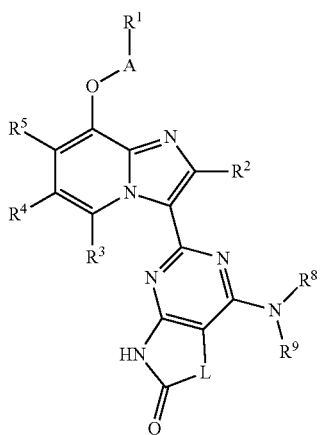

(I-A)

in which A, $R^1$, $R^2$, $R^3$, $R^4$, $R^5$, $R^8$, $R^9$ and L each have the meanings given above
or

[B] the iodide of the formula (IX) is reacted in an inert solvent, optionally in the presence of a suitable base and copper(I) iodide, with a compound of the formula (XI)

 (XI)

in which $R^7$ has the meaning given above to give a compound of the formula (I-B)

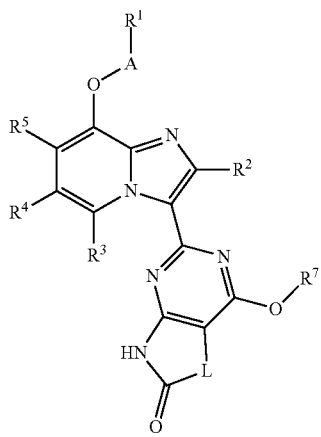

(I-B)

in which A, $R^1$, $R^2$, $R^3$, $R^4$, $R^5$, $R^7$ and L each have the meanings given above
or

[C] the iodide of the formula (IX) is reacted in an inert solvent, optionally in the presence of a suitable base, with copper(I) cyanide to give a compound of the formula (I-C)

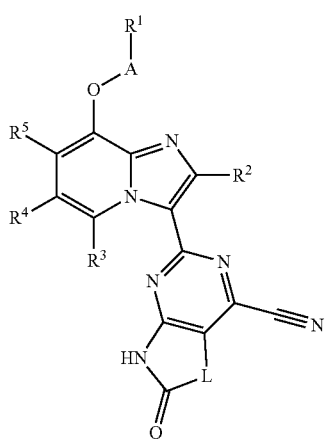

(I-C)

in which A, $R^1$, $R^2$, $R^3$, $R^4$, $R^5$ and L each have the meanings given above, and this is converted in an inert solvent with a suitable aqueous base into a compound of the formula (I-D)

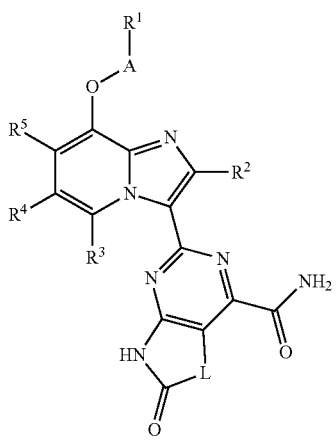

(I-D)

in which A, R¹, R², R³, R⁴, R⁵ and L each have the meanings given above, and this is subsequently converted in an inert solvent with a suitable aqueous acid into an acid of the formula (I-E)

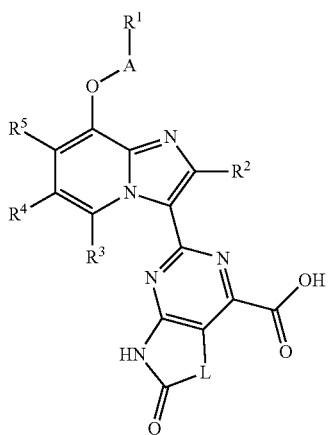

(I-E)

in which A, R¹, R², R³, R⁴, R⁵ and L each have the meanings given above, and this is subsequently converted in an inert solvent under amide coupling conditions with an amine of the formula (XII)

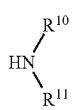

(XII)

in which $R^{10}$ and $R^{11}$ each have the meanings given above, into a compound of the formula (I-F)

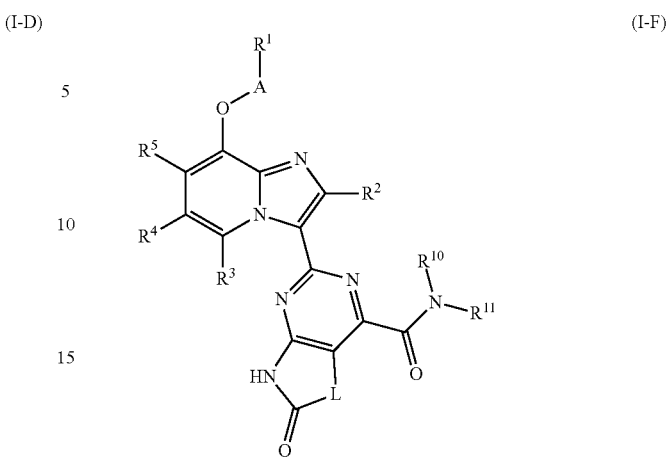

(I-F)

in which A, $R^1$, $R^2$, $R^3$, $R^4$, $R^5$, $R^{10}$, $R^{11}$ and L each have the meanings given above, and the resulting compounds of the formula (I) are optionally, optionally with the appropriate (i) solvents and/or (ii) acids or bases, converted into their solvates, salts and/or solvates of the salts.

The compounds of the formulae (I-A), (I-B), (I-C), (I-D), (I-E) and (I-F) form a subset of the compounds according to the invention of the formula (I).

The preparation processes described can be illustrated by way of example by the following synthesis schemes (Schemes 1 and 2):

Scheme 1:

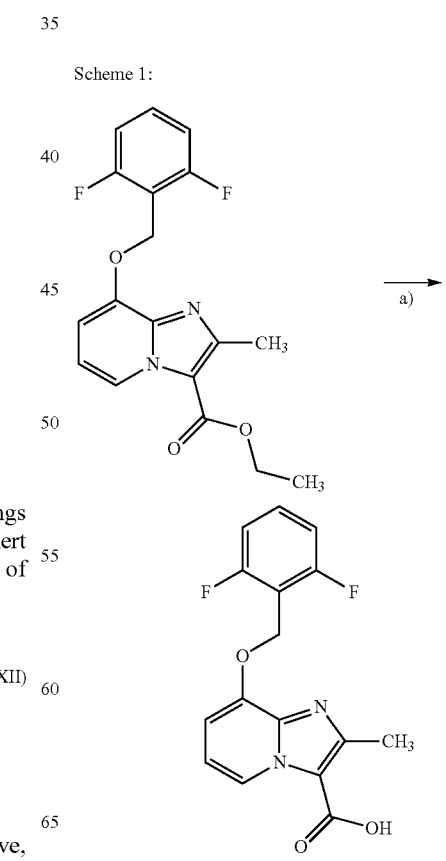

21
-continued
22
-continued
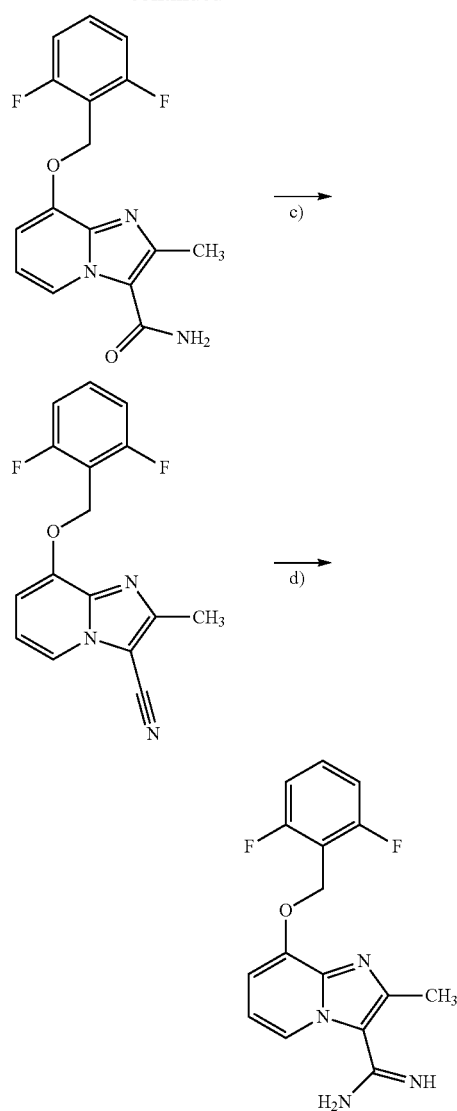
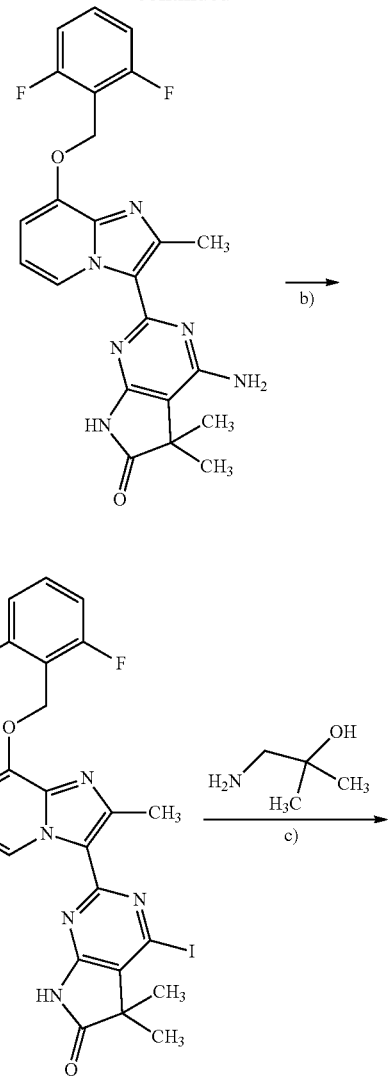
[a]: lithium hydroxide, THF/methanol/ H₂O, RT; b): EDCl, HOBT, NH₄Cl, N,N-diisopropylethylamine, CH₂Cl₂, RT; c): trifluoroacetic anhydride, pyridine, THF, RT; d): NH₄Cl, trimethylaluminum, toluene, reflux].
Scheme 2:
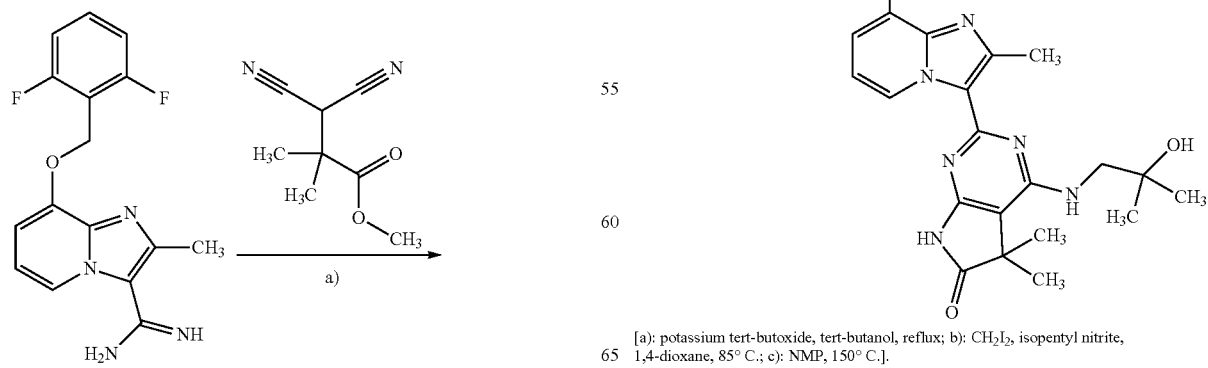
[a]: potassium tert-butoxide, tert-butanol, reflux; b): CH₂I₂, isopentyl nitrite, 1,4-dioxane, 85° C.; c): NMP, 150° C.].

Scheme 3:
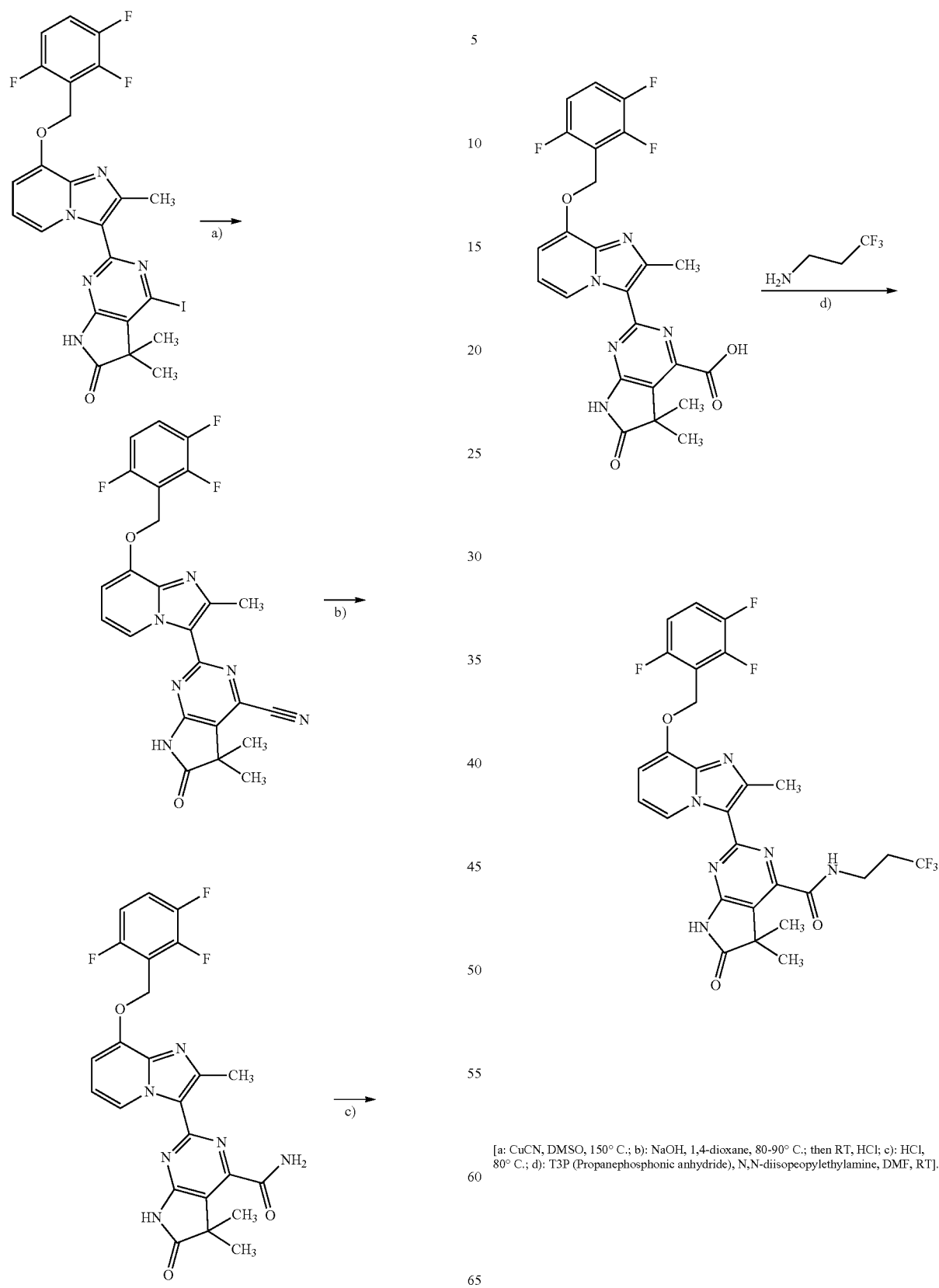
[a: CuCN, DMSO, 150° C.; b): NaOH, 1,4-dioxane, 80-90° C.; then RT, HCl; c): HCl, 80° C.; d): T3P (Propanephosphonic anhydride), N,N-diisopeopylethylamine, DMF, RT].

Scheme 4:
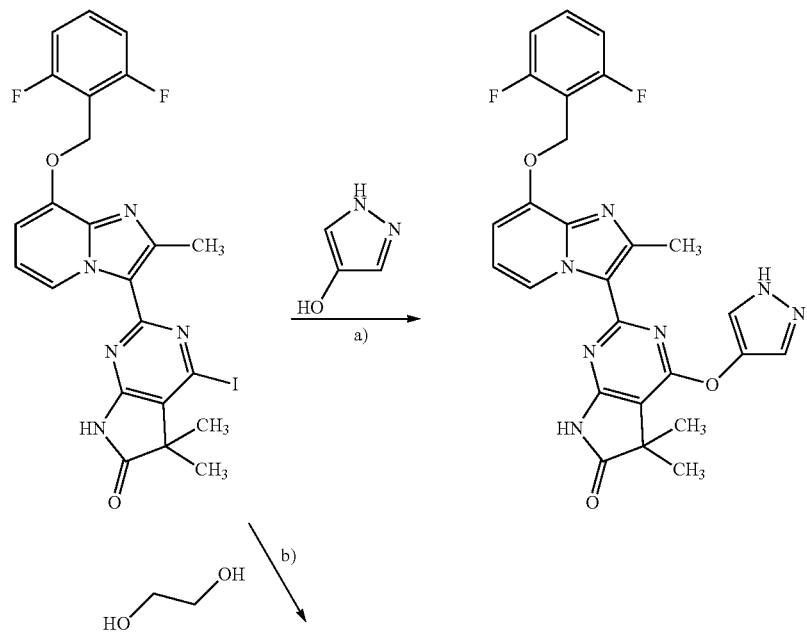
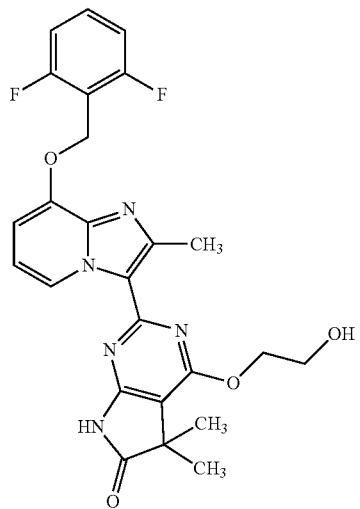
[a]: Cu₂O, Cs₂CO₃, 2-hydroxybenzaldehyde oxime, acetonitrile, 160° C.; microwave; b): CuI, 3,4,7,8-tetramethyl-1,10-phenanthroline, Cs₂CO₃, toluene, 140° C.].

Scheme 5:
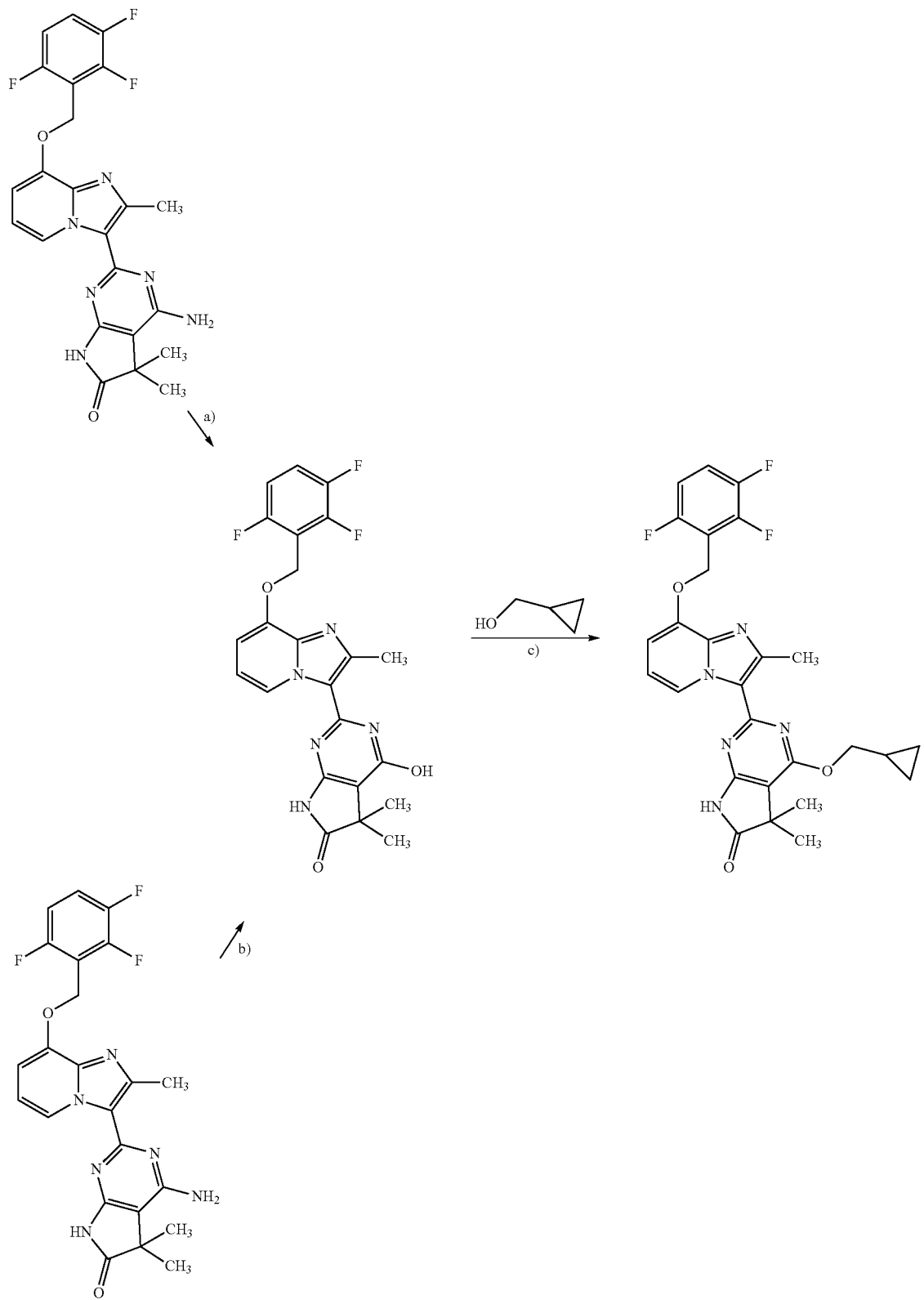
[a): sodium nitrate, TFA/water, 0° C.; b): CH₂I₂, isopentyl nitrite, 1,4-dioxane/water, 85° C.; c): PPh₃, DIAD (diisopropyl azodicarboxylate), THF, RT].

The preparation process for the triazine-substituted working examples can be illustrated in an exemplary manner by the synthesis scheme below (Scheme 3):

Scheme 6:

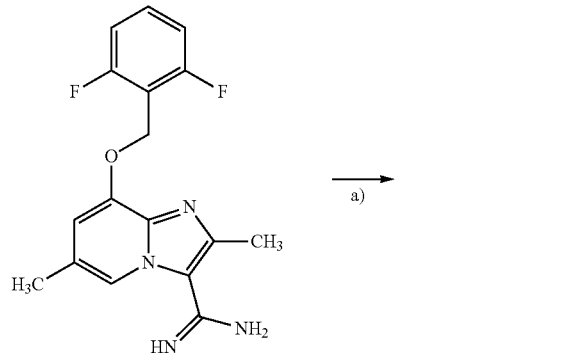

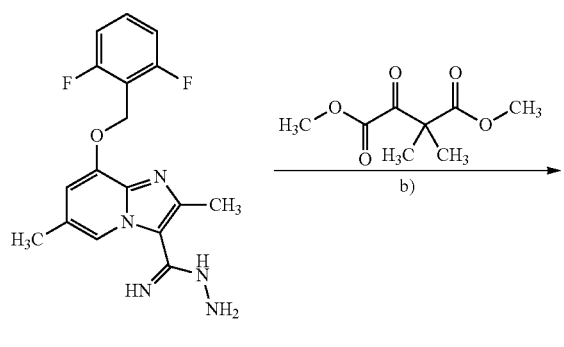

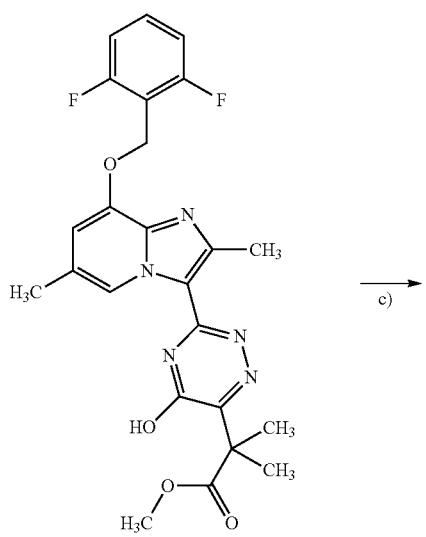

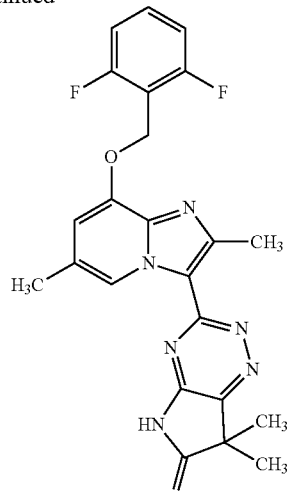

[a]: hydrazine hydrate, NEt₃, EtOH b): EtOH c): (i) POCl₃; (ii) conc. NH₃, acetonitrile].

The compounds of the formulae (VII), (X), (XI) and (XII) are commercially available, known from the literature or can be prepared in analogy to processes known from the literature.

Inert solvents for the process steps (III)→(IV) and (I-E)+(XII)→(I-F) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

Suitable condensing agents for the amide formation in process steps (III)→(IV) and (I-E)+(XII)→(I-F) are, for example, carbodiimides such as N,N'-diethyl-, N,N'-dipropyl-, N,N'-diisopropyl- and N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride (T3P), 1-chloro-N,N,2-trimethylprop-1-en-1-amine, diethyl cyanophosphonate, bis(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate or sodium bicarbonate or potassium bicarbonate, or organic bases such as trialkylamines, e.g. triethylamine, N-methylmorpholine, N-methylpiperidine or N,N-diisopropylethylamine. Preference is given to using TBTU in combination with N-methylmorpholine, HATU in combination with N,N-diisopropylethylamine or 1-chloro-N,N,2-trimethylprop-1-en-1-amine.

The condensations (III)→(IV) and (I-E)+(XII)→(I-F) are generally carried out within a temperature range from −20° C. to +100° C., preferably at 0° C. to +60° C. The conversion can be carried out under atmospheric, elevated or reduced pressure (for example from 0.5 to 5 bar). In general, the reactions are carried out at atmospheric pressure.

Alternatively, the carboxylic acid of the formula (III) or (I-E) can also first be converted to the corresponding carbonyl chloride and the latter can then be reacted directly or in a separate conversion with an amine of the formula (IV) to give the compounds of the invention. The formation of carbonyl chlorides from carboxylic acids is effected by the methods known to those skilled in the art, for example by treatment with thionyl chloride, sulphuryl chloride or oxalyl chloride, in the presence of a suitable base, for example in the presence of pyridine, and optionally with addition of dimethylformamide, optionally in a suitable inert solvent.

The hydrolysis of the ester group $T^1$ in the compounds of the formula (II) is effected by customary methods, by treating the esters in inert solvents with acids or bases, in which latter case the salts formed at first are converted to the free carboxylic acids by treating with acid. In the case of the tert-butyl esters, the ester hydrolysis is preferably effected with acids. In the case of the benzyl esters, the ester hydrolysis is preferably effected by hydrogenolysis with palladium on activated carbon or Raney nickel.

Suitable inert solvents for this reaction are water or the organic solvents customary for ester hydrolysis. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulphoxide. It is also possible to use mixtures of the solvents mentioned. In the case of a basic ester hydrolysis, preference is given to using mixtures of water with dioxane, tetrahydrofuran, methanol and/or ethanol.

Suitable bases for the ester hydrolysis are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates, such as sodium carbonate, potassium carbonate or calcium carbonate. Particular preference is given to sodium hydroxide or lithium hydroxide.

Suitable acids for the ester cleavage are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, optionally with addition of water. Preference is given to hydrogen chloride or trifluoroacetic acid in the case of the tert-butyl esters and to hydrochloric acid in the case of the methyl esters.

The ester hydrolysis is generally carried out within a temperature range from 0° C. to +100° C., preferably at +0° C. to +50° C.

These conversions can be performed at atmospheric, elevated or reduced pressure (for example from 0.5 to 5 bar). In general, the reactions are in each case carried out at atmospheric pressure.

Inert solvents for the process step (IV)→(V) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, ethyl acetate, acetonitrile, pyridine, dimethyl sulphoxide, N,N-dimethylformamide, N,N'-dimethylpropyleneurea (DMPU) or N-methylpyrrolidone (NMP). It is likewise possible to use mixtures of the solvents mentioned. Preference is given to tetrahydrofuran.

The reaction (IV)→(V) is generally carried out within a temperature range from +20° C. to +100° C., preferably within the range from +20° C. to +50° C., optionally in a microwave. The conversion can be carried out at atmospheric, elevated or reduced pressure (for example in the range from 0.5 to 5 bar). In general, the reaction is carried out at atmospheric pressure.

Inert solvents for the process step (V)→(VI) are hydrocarbons such as benzene, toluene, xylene, hexane, cyclohexane or mineral oil fractions, or other solvents such as acetonitrile, pyridine, dimethyl sulphoxide, N,N-dimethylformamide, N,N'-dimethylpropyleneurea (DMPU) or N-methylpyrrolidone (NMP). It is likewise possible to use mixtures of the solvents mentioned. Toluene is preferred.

The reaction (V)→(VI) is generally carried out within a temperature range from +20° C. to +150° C., preferably within the range from +80° C. to +130° C., optionally in a microwave. The conversion can be carried out at atmospheric, elevated or reduced pressure (for example in the range from 0.5 to 5 bar). In general, the reaction is carried out at atmospheric pressure.

Inert solvents for the process step (VI)+(VII)→(VIII) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile, sulpholane or else water. It is also possible to use mixtures of the solvents mentioned. Preference is given to tert-butanol.

Suitable bases for the process step (VI)+(VII)→(VIII) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to potassium tert-butoxide.

The reaction (VI)+(VII)→(VIII) is generally carried out within a temperature range of +20° C. to +150° C., preferably at +75° C. to +100° C., optionally in a microwave. The conversion can be carried out under atmospheric, elevated or reduced pressure (for example from 0.5 to 5 bar). In general, the reaction is carried out at atmospheric pressure.

Process step (VIII)→(IX) is carried out with or without solvent. Suitable solvents are all organic solvents which are inert under the reaction conditions. Preferred solvents are acetonitrile, 1,4-dioxane and dimethoxyethane.

The reaction (VIII)→(IX) is generally carried out within a temperature range from +20° C. to +100° C., preferably within the range from +50° C. to +100° C., optionally in a microwave. The conversion can be carried out at atmospheric, elevated or reduced pressure (for example in the range from 0.5 to 5 bar). In general, the reaction is carried out at atmospheric pressure.

Suitable halogen sources in the reaction (VIII)→(IX) are, for example, diiodomethane, a mixture of caesium iodide, iodine and copper(I) iodide, copper(II) bromide, copper(II) chloride or potassium iodide.

Inert solvents for the process steps (IX)+(X)→(I-A) and (IX)+(XI)→(I-B) and (IX)→(I-C) are, for example, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is also possible to use mixtures of the solvents mentioned. Preference is given to DMSO and NMP.

The reactions (IX)+(X)→(I-A) and (IX)+(XI)→(I-B) and (IX)→(I-C) are generally carried out within a temperature range from +20° C. to +180° C., preferably in the range from +120° C. to +180° C., optionally in a microwave. The conversion can be carried out at atmospheric, elevated or reduced pressure (for example in the range from 0.5 to 5 bar). In general, the reactions are carried out at atmospheric pressure.

The reaction (IX)+(XI)→(I-B) is carried out in the presence of a suitable copper catalyst such as, for example, copper(I) iodide, with addition of 3,4,7,8-tetramethyl-1,10-phenanthroline, and a suitable base such as, for example, alkaline earth metal carbonates such as lithium carbonate, sodium carbonate, potassium carbonate, calcium carbonate or caesium carbonate, preferably caesium carbonate.

Suitable bases for the process step (I-C)→(I-D) are sodium hydroxide/aqueous sodium hydroxide solution, potassium hydroxide, lithium hydroxide, barium hydroxide or mixtures thereof, if appropriate with addition of water. Preference is given to using aqueous sodium hydroxide solution.

Suitable solvents for the reaction (IC)→(I-D) are water, THF, 1,4-dioxane, DMF or DMSO. It is also possible to use mixtures of the solvents mentioned.

The conversion (I-C)→(I-D) is generally conducted within a temperature range of +20° C. to +100° C., preferably at 65° C. to +100° C. The conversion can be carried out under atmospheric, elevated or reduced pressure (for example from 0.5 to 5 bar). In general, the reaction is carried out at atmospheric pressure.

Suitable acids for the process step (I-D)→(I-E) are hydrogen chloride/hydrochloric acid, hydrogen bromide/hydrobromic acid, sulphuric acid, acetic acid or mixtures thereof, optionally with addition of water. Preference is given to using hydrochloric acid.

Suitable solvents for the reaction (I-D)→(I-E) are water, THF, 1,4-dioxane, DMF or DMSO. It is also possible to use mixtures of the solvents mentioned.

The conversion (I-D)→(I-E) is generally conducted within a temperature range of +20° C. to +100° C., preferably at 75° C. to +100° C. The conversion can be carried out under atmospheric, elevated or reduced pressure (for example from 0.5 to 5 bar). In general, the reaction is carried out at atmospheric pressure.

The compounds of the formula (II) are known from the literature or can be prepared by reacting a compound of the formula (XIII)

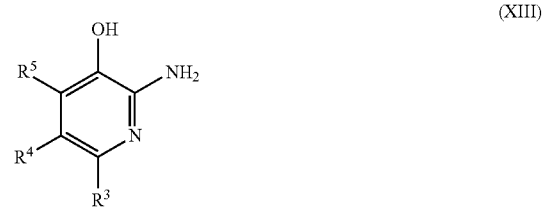

(XIII)

in which $R^3$, $R^4$ and $R^5$ have the meanings given above in an inert solvent in the presence of a suitable base with a compound of the formula (XIV)

(XIV)

in which $R^1$ has the meaning given above and $X^1$ represents chlorine, bromine, iodine, O-triflate or O-mesylate, to give a compound of the formula (XV)

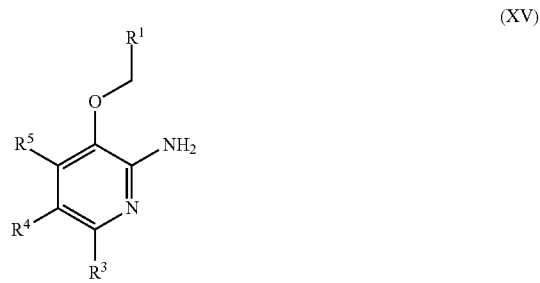

(XV)

in which $R^1$, $R^3$, $R^4$ and $R^5$ each have the meanings given above, and then reacting this in an inert solvent with a compound of the formula (XVI)

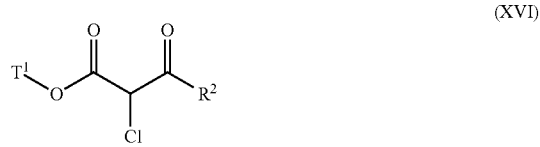

(XVI)

in which $R^2$ and $T^1$ each have the meanings given above.

The process described is illustrated in an exemplary manner by the scheme below (Scheme 3):

Scheme 3:

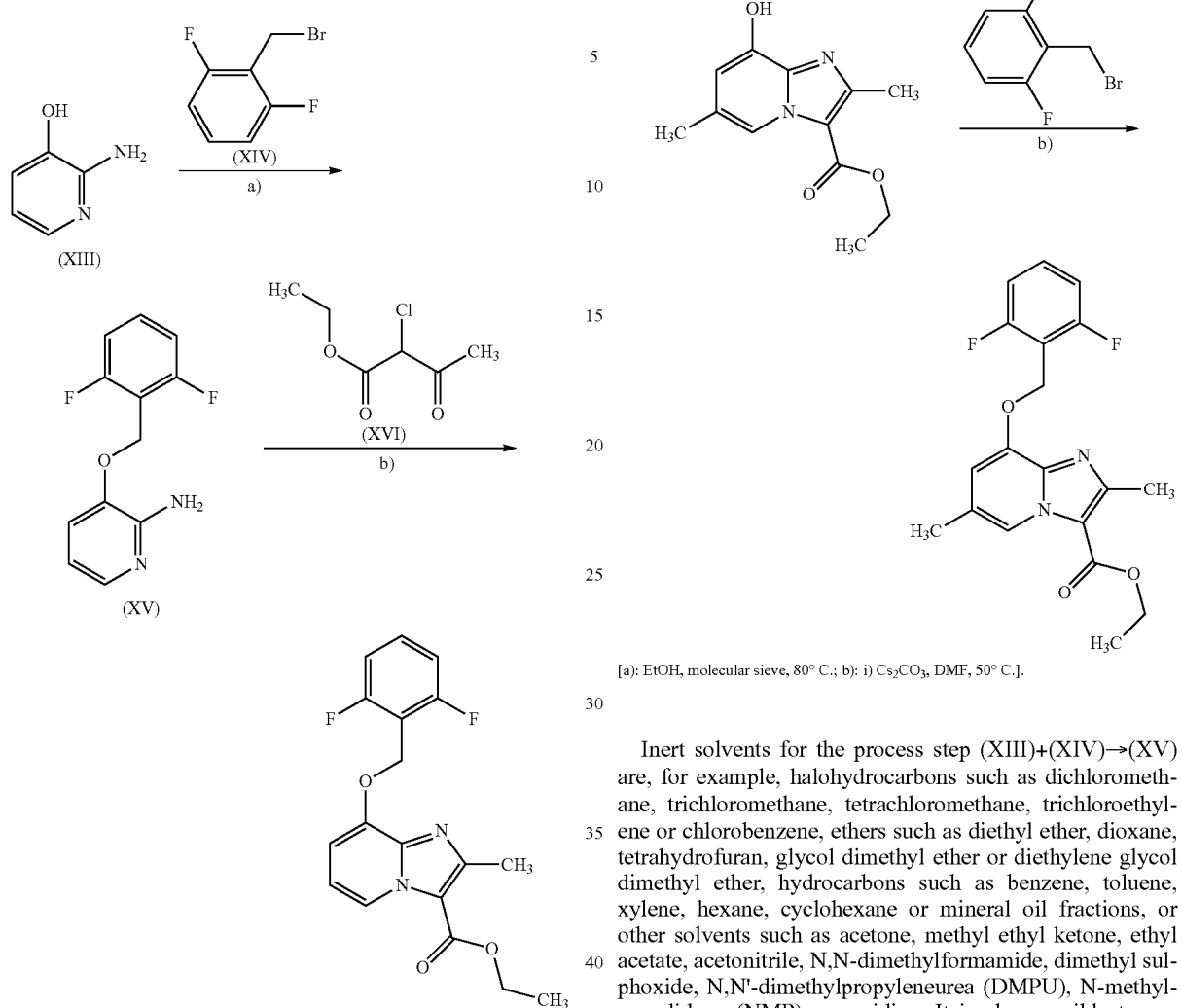

[a]: i) NaOMe, MeOH, RT; ii) DMSO, RT; b): EtOH, molecular sieve, 80° C.].

The synthesis sequence shown can be modified such that the respective reaction steps are carried out in a different order. An example of such a modified synthesis sequence is shown in Scheme 4.

Scheme 4:

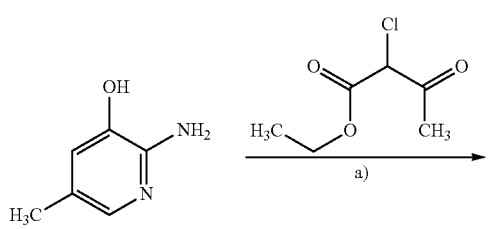

[a]: EtOH, molecular sieve, 80° C.; b): i) Cs₂CO₃, DMF, 50° C.].

Inert solvents for the process step (XIII)+(XIV)→(XV) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, dimethyl sulphoxide, N,N'-dimethylpropyleneurea (DMPU), N-methylpyrrolidone (NMP) or pyridine. It is also possible to use mixtures of the solvents mentioned. Preference is given to using dimethylformamide or dimethyl sulphoxide.

Suitable bases for the process step (XIII)+(XIV)→(XV) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, optionally with addition of an alkali metal iodide, for example sodium iodide or potassium iodide, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium carbonate, caesium carbonate or sodium methoxide.

The reaction is generally effected within a temperature range from 0° C. to +120° C., preferably at +20° C. to +80°

C., optionally in a microwave. The conversion can be carried out under atmospheric, elevated or reduced pressure (for example from 0.5 to 5 bar).

Inert solvents for the ring closure to give the imidazo[1,2-a]pyridine base skeleton (XV)+(XVI)→(II) are the customary organic solvents. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulphoxide. It is also possible to use mixtures of the solvents mentioned. Preference is given to using ethanol.

The ring closure is generally effected within a temperature range from +50° C. to +150° C., preferably at +50° C. to +100° C., optionally in a microwave.

The ring closure (XV)+(XVI)→(II) is optionally carried out in the presence of dehydrating reaction additives, for example in the presence of molecular sieve (pore size 4 Å). The reaction (XV)+(XVI)→(II) is carried out using an excess of the reagent of the formula (XVI), for example with 1 to 20 equivalents of the reagent (XVI), where the addition of this reagent can be carried out all at once or in several portions.

Further compounds of the invention can optionally also be prepared by conversions of functional groups of individual substituents, especially those listed for $R^6$, proceeding from the compounds of the formula (I) obtained by above processes. These conversions are performed by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester hydrolysis, etherification, ether hydrolysis, formation of carbonamides, and introduction and removal of temporary protective groups.

The compounds according to the invention act as potent stimulators of soluble guanylate cyclase and/or inhibitors of phosphodiesterase 5, have useful pharmacological properties and can be used for preventing and treating disorders in humans and animals. The compounds of the invention offer a further treatment alternative and thus enlarge the field of pharmacy.

The compounds of the invention bring about vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. In addition, the compounds of the invention enhance the action of substances which increase the cGMP level, for example EDRF (endothelium-derived relaxing factor), NO donors, protoporphyrin IX, arachidonic acid or phenylhydrazine derivatives.

The compounds of the invention are suitable for the treatment and/or prophylaxis of cardio- and cerebrovascular, pulmonary, thromboembolic and fibrotic disorders.

The compounds of the invention can therefore be used in medicaments for the treatment and/or prophylaxis of cardiovascular disorders, for example hypertension, resistant hypertension, acute and chronic heart failure, coronary heart disease, stable and unstable angina pectoris, peripheral and cardiac vascular disorders, arrhythmias, atrial and ventricular arrhythmias and impaired conduction, for example atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation, for example pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term "heart failure" encompasses both acute and chronic forms of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure, and acute phases of worsening of existing chronic heart failure (worsening heart failure).

In addition, the compounds of the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetelipoproteinaemia, sitosterolaemia, xanthomatosis, Tangier disease, adiposity, obesity and of combined hyperlipidaemias and metabolic syndrome.

The compounds of the invention can also be used for the treatment and/or prophylaxis of primary and secondary Raynaud's phenomenon, microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing. The inventive compounds are also suitable for the treatment of muscular dystrophy, such as Becker-Kiener muscular dystrophy (BMD) and Duchenne muscular dystrophy (DMD).

The compounds of the invention are furthermore suitable for treating urological disorders, for example benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI), for example mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds of the invention are also suitable for the treatment and/or prophylaxis of kidney disorders, in particular of acute and chronic renal insufficiency and acute and chronic renal failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also encompasses the use of the compounds of the invention for the treatment and/or prophylaxis of sequelae of renal insufficiency, for example pulmonary oedema, heart failure, uraemia, anaemia, electrolyte disorders (for example hyperkalaemia, hyponatraemia) and disorders in bone and carbohydrate metabolism.

In addition, the compounds of the invention are also suitable for the treatment and/or prophylaxis of asthmatic disorders, pulmonary arterial hypertension (PAH) and other forms of pulmonary hypertension (PH) including left-heart disease-, HIV-, sickle cell anaemia-, thromboembolism (CTEPH), sarcoidosis-, COPD- or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF). In addition, the compounds mentioned can be used as bronchodilators.

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeldt-Jakob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

In addition, the compounds of the invention are also suitable for controlling cerebral blood flow and are effective agents for controlling migraines. They are also suitable for the prophylaxis and control of sequelae of cerebral infarction (cerebral apoplexy) such as stroke, cerebral ischaemias and craniocerebral trauma. The compounds of the invention can likewise be used for controlling states of pain and tinnitus.

In addition, the compounds of the invention have anti-inflammatory action and can therefore be used as anti-inflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

Furthermore, the compounds of the invention can also be used for the treatment and/or prophylaxis of autoimmune diseases.

The compounds of the invention are also suitable for the treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, digital ulcerations, morphea, keloids, hypertrophic scarring (also following surgical procedures), naevi, diabetic retinopathy, proliferative vitroretinopathy and disorders of the connective tissue (for example sarcoidosis).

The compounds of the invention are also suitable for controlling postoperative scarring, for example as a result of glaucoma operations.

The compounds of the invention can also be used cosmetically for ageing and keratinized skin.

Moreover, the compounds of the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, especially the disorders mentioned above.

The present invention further provides for the use of the compounds according to the invention for producing a medicament for the treatment and/or prophylaxis of disorders, especially the disorders mentioned above.

The present invention further provides for the use of the compounds according to the invention for producing a medicament for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for the treatment and/or prophylaxis of disorders, in particular the disorders mentioned above, using an effective amount of at least one of the compounds of the invention.

The present invention further provides a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the compounds of the invention.

The compounds according to the invention can be used alone or, if required, in combination with other active compounds. The present invention further provides medicaments comprising at least one of the compounds of the invention and one or more further active compounds, especially for the treatment and/or prophylaxis of the aforementioned disorders. Preferred examples of active compounds suitable for combinations include:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances;

hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or active compounds which alter lipid metabolism, by way of example and with preference from the group of thyroid receptor agonists, cholesterol synthesis inhibitors, preferred examples being HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, dabigatran, melagatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1-receptor blocker, by way of example and with preference prazosin.

In a preferred embodiment of the invention, the compounds of the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan or embursatan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone or eplerenone.

In a preferred embodiment of the invention, the compounds of the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds of the invention are administered in combination with a CETP inhibitor, by way of example and with preference dalcetrapib, BAY 60-5521, anacetrapib or CETP vaccine (CETi-1).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds of the invention can be converted to the administration forms mentioned. This can be accomplished in a manner known per se by mixing with inert non-toxic pharmaceutically suitable auxiliaries. These auxiliaries include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary in some cases to deviate from the stated amounts, specifically as a function of body weight, route of administration, individual response to the active compound, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

A. EXAMPLES

Abbreviations and Acronyms
aq. aqueous solution
abs. absolute
calc. calculated
br. broad signal (NMR coupling pattern)
CAS No. Chemical Abstracts Service number
δ shift in the NMR spectrum (stated in ppm)
d doublet (NMR coupling pattern)
TLC thin-layer chromatography
DCI direct chemical ionization (in MS)
DMAP 4-N,N-dimethylaminopyridine
DMF dimethylformamide
DMSO dimethyl sulphoxide
EDCI N-[3-(dimethylamino)propyl]-N'-ethylcarbodiimide
eq. equivalent(s)
ESI electrospray ionization (in MS)
Et ethyl
h hour(s)
HATU N-[(dimethylamino)(3H-[1,2,3]triazolo[4,5-b]-pyridin-3-yloxy)methylene]-N-methylmethanaminium hexafluorophosphate
HOBT 1H-benzotriazol-1-ol
HPLC high-pressure, high-performance liquid chromatography
HRMS high-resolution mass spectrometry
conc. concentrated
LC-MS liquid chromatography-coupled mass spectrometry
LiHMDS lithium hexamethyldisilazide
m multiplet
Me methyl
min minute(s)
MS mass spectrometry
NMP 1-methyl-2-pyrrolidone
NMR nuclear magnetic resonance spectrometry
Pd$_2$dba$_3$ tris(dibenzylideneacetone)dipalladium
Ph phenyl
q quartet (NMR coupling pattern)
quint. quintet (NMR coupling pattern)
R$_F$ retention factor (in thin-layer chromatography)
RT room temperature
R$_t$ retention time (in HPLC)
s singlet (NMR coupling pattern)
SFC supercritical fluid chromatography
t triplet (NMR coupling pattern)
THF tetrahydrofuran
TBTU (benzotriazol-1-yloxy)bisdimethylaminomethylium fluoroborate
UV ultraviolet spectrometry
v/v volume to volume ratio (of a solution)
Xantphos 4,5-bis(diphenylphosphino)-9,9-dimethylxanthene
XPHOS dicyclohexyl(2',4',6'-triisopropylbiphenyl-2-yl)phosphine LC/MS and HPLC Methods:

Method 1 (LC-MS):

Instrument: Waters ACQUITY SQD UPLC system; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 2 (LC-MS):

Instrument: Micromass Quattro Premier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 3 (LC-MS):

MS instrument type: Waters Micromass Quattro Micro; HPLC instrument type: Agilent 1100 series; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 4 (LC-MS):

MS instrument: Waters SQD; HPLC instrument: Waters UPLC; column: Zorbax SB-Aq (Agilent), 50 mm×2.1 mm, 1.8 m; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 5 (LC-MS):

MS instrument: Waters ZQ 2000; HPLC instrument: Agilent 1100, 2-column system, autosampler: HTC PAL; column: YMC-ODS-AQ, 50 mm×4.6 mm, 3.0 m; mobile phase A: water+0.1% formic acid, mobile phase B: acetonitrile+0.1% formic acid; gradient: 0.0 min 100% A—0.2 min 95% A—1.8 min 25% A—1.9 min 10% A—2.0 min 5% A—3.2 min 5% A—3.21 min 100% A→3.35 min 100% A; oven: 40° C.; flow rate: 3.0 ml/min; UV detection: 210 nm.

Method 6 (Preparative HPLC):

Column: Macherey-Nagel VP 50/21 Nucleosil 100-5 C18 Nautilus. Flow rate: 25 ml/min. Gradient: A=acetonitrile, B=water+0.1% formic acid, 0 min 10% A; 2.00 min 10% A; 6.00 min 90% A; 7.00 min 90% A; 7.10 min 10% A; 8 min 10% A; UV detection: 220 nm Method 7 (Preparative HPLC):

Column: Phenomenex Gemini C18; 110 A, AXIA, 5 μm, 21.2×50 mm 5 micron; gradient: A=water+0.1% conc. ammonia, B=acetonitrile, 0 min=10% B, 2 min=10% B, 6 min=90% B, 7 min=90% B, 7.1 min=10% B, 8 min=10% B, flow rate 25 ml/min, UV detection 220 nm.

Method 8 (Preparative HPLC):

Column: Axia Gemini 5µ C18 110 A, 50×21.5 mm, P/NO: 00B-4435-PO-AX, S/NO: 35997-2, gradient: A=water+0.1% conc. aq. ammonia, B=acetonitrile, 0 min=30% B, 2 min=30% B, 6 min=100% B, 7 min=100% B, 7.1 min=30% B, 8 min=30% B, flow rate 25 ml/min, UV detection 220 nm.

Method 9 (Preparative HPLC):

Column: Macherey-Nagel VP 50/21 Nucleosil 100-5 C18 Nautilus. Flow rate: 25 ml/min. Gradient: A=water+0.1% formic acid, B=methanol, 0 min=30% B, 2 min=30% B, 6 min=100% B, 7 min=100% B, 7.1 min=30% B, 8 min=30% B, flow rate 25 ml/min, UV detection 220 nm.

Method 10 (Preparative HPLC):

Column: Macherey-Nagel VP 50/21 Nucleosil 100-5 C18 Nautilus. Flow rate: 25 ml/min. Gradient: A=water+0.1% conc. aq. ammonia, B=methanol, 0 min=30% B, 2 min=30% B, 6 min=100% B, 7 min=100% B, 7.1 min=30% B, 8 min=30% B, flow rate 25 ml/min, UV detection 220 nm.

Method 11 (Preparative HPLC):

MS instrument: Waters, HPLC instrument: Waters (column Waters X-Bridge C18, 18 mm×50 mm, 5 µm, mobile phase A: water+0.05% triethylamine, mobile phase B: acetonitrile (ULC)+0.05% triethylamine, gradient: 0.0 min 95% A—0.15 min 95% A—8.0 min 5% A—9.0 min 5% A; flow rate: 40 ml/min; UV detection: DAD; 210-400 nm).

or:

MS instrument: Waters, HPLC instrument: Waters (column Phenomenex Luna 5µ C18(2) 100 A, AXIA Tech. 50×21.2 mm, mobile phase A: water+0.05% formic acids, mobile phase B: acetonitrile (ULC)+0.05% formic acid, gradient: 0.0 min 95% A—0.15 min 95% A—8.0 min 5% A—9.0 min 5% A; flow rate: 40 ml/min; UV detection: DAD; 210-400 nm).

Method 12 (LC-MS):

MS instrument: Waters SQD; HPLC instrument: Waters UPLC; column: Zorbax SB-Aq (Agilent), 50 mm×2.1 mm, 1.8 µm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 13 (DCI-MS):

Instrument: DSQ II; Thermo Fisher-Scientific; DCI with NH$_3$, flow rate: 1.1 ml/min; source temperature: 200° C.; ionization energy 70 eV; heat DCI filament to 800° C.; mass range 80-900.

Method 14 (GC-MS):

Instrument: Micromass GCT, GC6890; column: Restek RTX-35, 15 m×200 m×0.33 m; constant helium flow rate: 0.88 ml/min; oven: 70° C.; inlet: 250° C.; gradient: 70° C., 30° C./min→310° C. (maintain for 3 min).

Method 15 (MS):

Instrument: Waters ZQ; ionization type: ESI (+); mobile phase: acetonitrile/water.

Method 16 (LCMS):

Instrument: Waters ACQUITY SQD UPLC system; column: Waters Acquity UPLC HSS T3 1.8µ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.60 ml/min; UV detection: 208-400 nm.

Method 17 (LC-MS):

Instrument: Micromass Quattro Premier with Waters UPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A oven: 50° C.; flow rate: 0.3 ml/min; UV detection: 210 nm.

Method 18 (Preparative HPLC):

Chromatorex C18 10µ 250×20 mm gradient: A=water+0.5% formic acid, B=acetonitrile, 0 min=5% B, 3 min=5% B pre-rinse without substance, then injection, 5 min=5% B, 25 min=30% B, 38 min=30% B, 38.1 min=95% B, 43 min=95% B, 43.01 min=5% B, 48.0 min=5% B flow rate 20 ml/min, wavelength 210 nm.

Method 19 (Preparative HPLC):

Chromatorex C18 10µ 250×20 mm gradient: A=water+0.5% formic acid, B=acetonitrile, 0 min=5% B, 3 min=5% B pre-rinse without substance, then injection, 5 min=5% B, 25 min=50% B, 38 min=50% B, 38.1 min=95% B, 43 min=95% B, 43.01 min=5% B, 48.0 min=5% B flow rate 20 ml/min, wavelength 210 nm.

Method 20 (Preparative HPLC):

XBridge Prep. C18 5µ 50×19 mm gradient: A=water+0.5% ammonium hydroxide, B=acetonitrile, 0 min=5% B, 3 min=5% B pre-rinse without substance, then injection, 5 min=5% B, 25 min=50% B, 38 min=50% B, 38.1 min=95% B, 43 min=95% B, 43.01 min=5% B, 48.0 min=5% B flow rate 15 ml/min, wavelength 210 nm.

Method 21 (Preparative HPLC)

Chromatorex 10µ 250×20 mm gradient: A=water, B=acetonitrile, 0 min=5% B, 3 min=5% B pre-rinse without substance, then injection, 5 min=5% B, 25 min=95% B, 38 min=95% B, 38.1 min=5% B, 40 min=5% B, flow rate 20 ml/min, wavelength 210 nm.

Method 22 (LC-MS):

MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 23 (LC-MS):

Instrument: Agilent MS Quad 6150; HPLC: Agilent 1290; column: Waters Acquity UPLC HSS T3 1.8 50×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A oven: 50° C.; flow rate: 1.20 ml/min; UV detection: 205-305 nm.

Method 24 (LC-MS):

MS instrument type: Waters Synapt G2S; UPLC instrument type: Waters Acquity I-CLASS; column: Waters, HSST3, 2.1×50 mm, C18 1.8 µm; mobile phase A: 1 l of water+0.01% formic acid; mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm.

Method 25 (FIA/MS, ES):

Instrument: Waters ZQ 2000; electrospray ionization; mobile phase A: 1 l of water+0.25 ml of 99% strength formic acid, mobile phase B: 1 l of acetonitrile+0.25 ml of 99% strength formic acid; 25% A, 75% B; flow rate: 0.25 ml/min Unless stated otherwise, the percentages in the tests and examples which follow are percentages by weight; parts are parts by weight. Solvent ratios, dilution ratios and concentration data for the liquid/liquid solutions are based in each case on volume.

The multiplicities of proton signals in $^1$H NMR spectra reported in the paragraphs which follow represent the signal form observed in each case and do not take account of any higher-order signal phenomena. In all $^1$H NMR spectra data, the chemical shifts δ are stated in ppm.

When compounds of the invention are purified by preparative HPLC by the above-described methods in which the eluents contain additives, for example trifluoroacetic acid, formic acid or ammonia, the compounds of the invention may be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

The imidazopyridines described below in synthesis intermediates and working examples of the invention may under acidic conditions always be present as salts, even in substoichiometric amounts, without this being apparent in the $^1$H NMR and without any particular specification and notification thereof in the respective IUPAC names and structural formulae.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na$^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Starting Compounds and Intermediates:

Example 1A

3-[(2,6-Difluorobenzyl)oxy]pyridine-2-amine

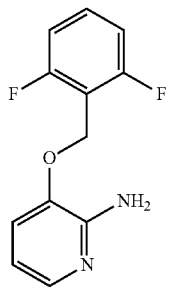

At RT, 51 g of sodium methoxide (953 mmol, 1.05 equivalents) were initially charged in 1000 ml of methanol, 100 g of 2-amino-3-hydroxypyridine (908 mmol, 1 equivalent) were added and the mixture was stirred at RT for another 15 min. The reaction mixture was concentrated under reduced pressure, the residue was taken up in 2500 ml of DMSO and 197 g of 2,6-difluorobenzyl bromide (953 mmol, 1.05 equivalents) were added. After 4 h at RT, the reaction mixture was poured onto 20 l of water, the mixture was stirred for a further 15 min and the solid was filtered off. The solid was washed with 1 l of water and 100 ml of isopropanol and 500 ml of petroleum ether and dried under high vacuum. This gave 171 g of the title compound (78% of theory).

$^1$H-NMR (400 MHz, DMSO-d$_6$): δ=5.10 (s, 2 H); 5.52 (br. s, 2 H), 6.52 (dd, 1 H); 7.16-7.21 (m, 3 H); 7.49-7.56 (m, 2 H).

Example 2A

Ethyl 8-[(2,6-difluorobenzyl)oxy]-2-methylimidazo[1,2-a]pyridine-3-carboxylate

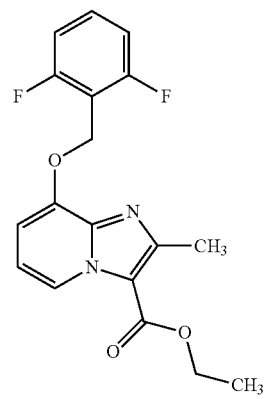 [SMILES: CCOC(=O)c1c(C)nc2c(OCc3c(F)cccc3F)cccn12]

170 g of 3-[(2,6-difluorobenzyl)oxy]pyridine-2-amine (Example 1A; 719 mmol, 1 equivalent) were initially charged in 3800 ml of ethanol, and 151 g of powdered molecular sieve 3 Å and 623 g of ethyl 2-chloroacetoacetate (3.6 mol, 5 equivalents) were added. The reaction mixture was heated at reflux for 24 h and then filtered off through silica gel and concentrated under reduced pressure. The mixture was kept at RT for 48 h and the solid formed was filtered off. The solid was then stirred three times with a little isopropanol and then filtered off, and washed with diethyl ether. This gave 60.8 g (23% of theory) of the title compound. The combined filtrates of the filtration steps were concentrated and the residue was chromatographed on silica gel using the mobile phase cyclohexane/diethyl ether. This gave a further 46.5 g (18% of theory; total yield: 41% of theory) of the title compound.

LC-MS (Method 1): R$_t$=1.01 min

MS (ESpos): m/z=347 (M+H)$^+$ $^1$H-NMR (400 MHz, DMSO-d$_6$): δ=1.36 (t, 3 H); 2.54 (s, 3 H; hidden by DMSO signal); 4.36 (q, 2 H); 5.33 (s, 2 H); 7.11 (t, 1 H); 7.18-7.27 (m, 3 H); 7.59 (quint, 1 H); 8.88 (d, 1 H).

Example 3A

8-[(2,6-Difluorobenzyl)oxy]-2-methylimidazo[1,2-a]pyridine-3-carboxylic acid

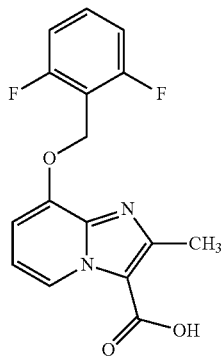 [SMILES: Cc1nc2c(OCc3c(F)cccc3F)cccn2c1C(=O)O]

107 g of ethyl 8-[(2,6-difluorobenzyl)oxy]-2-methylimidazo[1,2-a]pyridine-3-carboxylate (Example 2A; 300 mmol, 1 equivalent) were dissolved in 2.8 l of THF/methanol (1:1), 1.5 l of 1 N aqueous lithium hydroxide solution (1.5 mol, 5 equivalents) were added and the mixture was stirred at RT for 16 h. The organic solvents were removed under reduced pressure and the resulting aqueous solution was, in an ice bath, adjusted to pH 3-4 using 1 N aqueous hydrochloric acid. The resulting solid was filtered off, washed with water and isopropanol and dried under reduced pressure. This gave 92 g (95% of theory) of the title compound.

LC-MS (Method 1): $R_t$=0.62 min

MS (ESpos): m/z=319.1 (M+H)$^+$ $^1$H-NMR (400 MHz, DMSO-d$_6$): δ=2.55 (s, 3 H; superposed by DMSO signal); 5.32 (s, 2 H); 7.01 (t, 1 H); 7.09 (d, 1 H); 7.23 (t, 2 H); 7.59 (quint, 1 H); 9.01 (d, 1 H).

Example 4A

5-Chloro-2-nitropyridin-3-ol

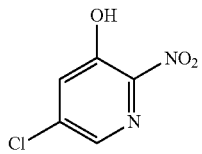 [SMILES: O=[N+]([O-])c1ncc(Cl)cc1O]

With ice cooling, 30 g of 5-chloropyridin-3-ol (232 mmol, 1 equivalent) were dissolved in 228 ml of concentrated sulphuric acid, and 24 ml of concentrated nitric acid were added slowly at 0° C. The reaction was warmed to RT, stirred overnight and then stirred into an ice/water mixture and stirred for another 30 min. The solid was filtered off, washed with cold water and air-dried. This gave 33 g (82% of theory) of the title compound which was used without further purification for the next reaction.

LC-MS (Method 1): $R_t$=0.60 min

MS (ESneg): m/z=172.9/174.9 (M−H)$^−$ $^1$H-NMR (400 MHz, DMSO-d$_6$): δ=7.71 (d, 1 H); 8.10 (d, 1 H); 12.14 (br. 1 H).

Example 5A

5-Chloro-3-[(2,6-difluorobenzyl)oxy]-2-nitropyridine

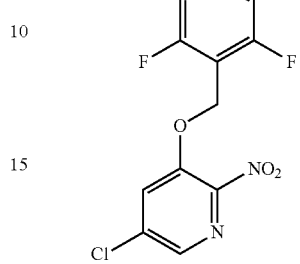

33 g of 5-chloro-2-nitropyridin-3-ol (Example 4A; 189 mmol, 1 equivalent) and 61.6 g of caesium carbonate (189 mmol, 1 equivalent) were initially charged in 528 ml of DMF, 40.4 g of 2,6-difluorobenzyl bromide (189 mmol, 1 equivalent) were added and the mixture was stirred at RT overnight. The reaction mixture was stirred into water/1N aqueous hydrochloric acid. The solid was filtered off, washed with water and air-dried. This gave 54.9 g (97% of theory) of the title compound.

$^1$H-NMR (400 MHz, DMSO-d$_6$): δ=5.46 (s, 2 H); 7.22 (t, 2 H); 7.58 (q, 1 H); 8.28 (d, 1 H); 8.47 (d, 1 H).

Example 6A

5-Chloro-3-[(2,6-difluorobenzyl)oxy]pyridine-2-amine

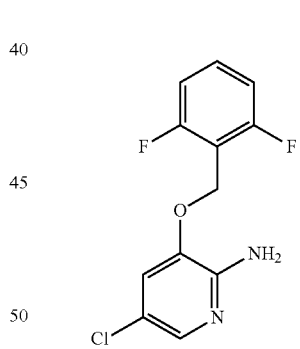

59.7 g of 5-chloro-3-[(2,6-difluorobenzyl)oxy]-2-nitropyridine (Example 5A; 199 mmol, 1 equivalent) were initially charged in 600 ml of ethanol, 34.4 g of iron powder (616 mmol, 3.1 equivalents) were added and the mixture was heated to reflux. 152 ml of concentrated hydrochloric acid were slowly added dropwise, and the mixture was boiled at reflux for a further 30 min. The reaction mixture was cooled and stirred into an ice/water mixture. The resulting mixture was adjusted to pH 5 using sodium acetate. The solid was filtered off, washed with water and air-dried and then dried under reduced pressure at 50° C. This gave 52.7 g (98% of theory) of the title compound.

LC-MS (Method 1): $R_t$=0.93 min

MS (ESpos): m/z=271.1/273.1 (M+H)$^+$

¹H-NMR (400 MHz, DMSO-d₆): δ=5.14 (s, 2 H); 5.82 (br. s, 2 H); 7.20 (t, 2 H); 7.35 (d, 1 H); 7.55 (q, 1 H); 7.56 (d, 1 H).

Example 7A

Ethyl 6-chloro-8-[(2,6-difluorobenzyl)oxy]-2-methylimidazo[1,2-a]pyridine-3-carboxylate

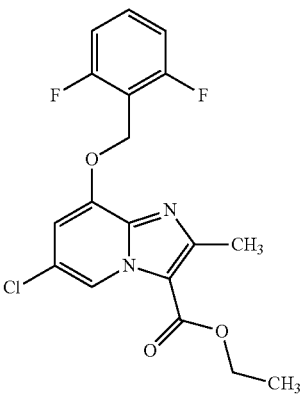 [SMILES: CCOC(=O)c1c(C)nc2c(OCc3c(F)cccc3F)cc(Cl)cn12]

40 g of 5-chloro-3-[(2,6-difluorobenzyl)oxy]pyridine-2-amine (Example 6A; 147.8 mmol, 1 equivalent) were initially charged in 800 ml of ethanol, 30 g of powdered molecular sieve 3 Å and 128 g of ethyl 2-chloroacetoacetate (739 mmol, 5 equivalents) were added and the mixture was heated at reflux overnight. The reaction mixture was concentrated, and the residue was taken up in ethyl acetate and filtered. The ethyl acetate phase was washed with water, dried, filtered and concentrated. This gave 44 g (78% of theory) of the title compound.

LC-MS (Method 1): R_t=1.27 min
MS (ESpos): m/z=381.2/383.2 (M+H)⁺
¹H-NMR (400 MHz, DMSO-d₆): δ=1.36 (t, 3 H); 2.54 (s, 3 H; hidden by DMSO signal); 4.37 (q, 2 H); 5.36 (s, 2 H); 7.26 (t, 2 H); 7.38 (d, 1 H); 7.62 (q, 1 H); 8.92 (d, 1 H).

Example 8A

6-Chloro-8-[(2,6-difluorobenzyl)oxy]-2-methylimidazo[1,2-a]pyridine-3-carboxylic acid

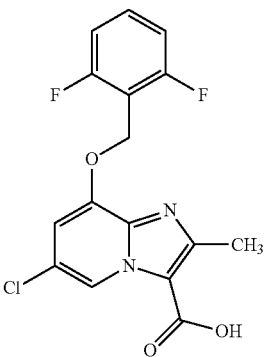 [SMILES: Cc1nc2c(OCc3c(F)cccc3F)cc(Cl)cn2c1C(=O)O]

44 g of ethyl 6-chloro-8-[(2,6-difluorobenzyl)oxy]-2-methylimidazo[1,2-a]pyridine-3-carboxylate (Example 7A; 115 mmol, 1 equivalent) were dissolved in 550 ml of THF and 700 ml of methanol, 13.8 g of lithium hydroxide (dissolved in 150 ml of water; 577 mmol, 5 equivalents) were added and the mixture was stirred at RT overnight. 1 N aqueous hydrochloric acid was added and the mixture was concentrated under reduced pressure. The solid obtained was filtered off and washed with water. This gave 34 g of the title compound (84% of theory).

LC-MS (Method 2): R_t=1.03 min
MS (ESpos): m/z=353.0/355.0 (M+H)⁺
¹H-NMR (400 MHz, DMSO-d₆): δ=2.54 (s, 3 H; superposed by DMSO signal); 5.36 (s, 2 H); 7.26 (t, 2 H); 7.34 (d, 1 H); 7.61 (q, 1 H); 8.99 (d, 1 H); 13.36 (br. s, 1 H).

Example 9A

6-Chloro-8-[(2,6-difluorobenzyl)oxy]-2-methylimidazo[1,2-a]pyridine-3-carboxamide

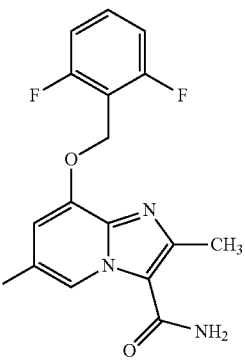

7.0 g (19.85 mmol) of 6-chloro-8-[(2,6-difluorobenzyl)oxy]-2-methylimidazo[1,2-a]pyridine-3-carboxylic acid from Example 8A were initially charged in 379 ml of dichloromethane, 5.71 g (29.77 mmol) of 1-(3-dimethylaminopropyl)-3-ethylcarbodiimide hydrochloride and 4.02 g (29.77 mmol) of 1-hydroxy-1H-benzotriazole hydrate were added and the mixture was stirred at room temperature for 10 min. Subsequently, 5.31 g (99.23 mmol) of ammonium chloride and 24.20 ml (138.9 mmol) of N,N-diisopropylethylamine were added and the mixture was stirred at room temperature overnight. Water was added to the reaction mixture, and the solid present was filtered off, then stirred with water at 50° C. for 30 min, filtered off again and washed with water. This gave 6.54 g (93% of theory) of the title compound.

LC-MS (Method 1): R_t=0.86 min
MS (ESpos): m/z=352 (M+H)⁺
¹H-NMR (400 MHz, DMSO-d₆): δ=2.53 (s, 3H), 5.34 (s, 2 H); 7.22 (d, 1 H); 7.25 (t, 2 H); 7.38 (br. s, 2 H), 7.55-7.66 (m, 1 H); 8.90 (d, 1 H).

Example 10A

6-Chloro-8-[(2,6-difluorobenzyl)oxy]-2-methylimidazo[1,2-a]pyridine-3-carbonitrile

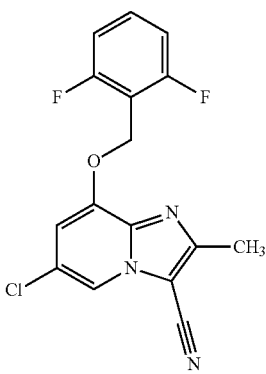 [SMILES: Cc1nc2c(OCc3c(F)cccc3F)cc(Cl)cn2c1C#N]

6.43 g (18.29 mmol) of 6-chloro-8-[(2,6-difluorobenzyl)oxy]-2-methylimidazo[1,2-a]pyridine-3-carboxamide from Example 9A were initially charged in 82 ml of THF, and 3.79 ml (46.82 mmol) of pyridine were added. At RT, 6.61 ml (46.82 mmol) of trifluoroacetic anhydride were then added dropwise, and the reaction mixture was stirred at RT for 1 h. Subsequently, the mixture was added to water and extracted three times with ethyl acetate. The combined organic phases were washed once with saturated aqueous sodium bicarbonate solution, once with 1 N aqueous hydrochloric acid and once with saturated aqueous sodium chloride solution, dried over sodium sulphate and concentrated on a rotary evaporator. The residue was dried under reduced pressure overnight. This gave 6.09 g (90% of theory; purity: 90%) of the title compound.

LC-MS (Method 1): $R_t$=1.11 min
MS (ESpos): m/z=334 (M+H)$^+$
$^1$H-NMR (400 MHz, DMSO-$d_6$): δ=2.43 (s, 3 H), 5.37 (s, 2 H), 7.25 (t, 2 H), 7.37-7.39 (m, 1 H), 7.56-7.66 (m, 1 H), 8.46-8.50 (m, 1 H).

Example 11A

6-Chloro-8-[(2,6-difluorobenzyl)oxy]-2-methylimidazo[1,2-a]pyridine-3-carboximidamide

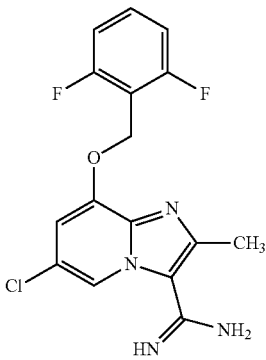 [SMILES: Cc1nc2c(OCc3c(F)cccc3F)cc(Cl)cn2c1C(=N)N]

1.70 g (4.59 mmol; purity 90%) of 6-chloro-8-[(2,6-difluorobenzyl)oxy]-2-methylimidazo[1,2-a]pyridine-3-carbonitrile from Example 10A were reacted analogously to the procedure of Example 22A. This gave 1.79 g (62% of theory; purity about 56%) of the title compound.

LC-MS (Method 1): $R_t$=0.60 min
MS (ESpos): m/z=351 (M+H)$^+$

Example 12A

5-Bromo-3-[(2,6-difluorobenzyl)oxy]pyridine-2-amine

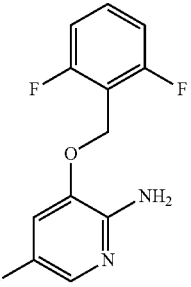

32.6 g of 3-[(2,6-difluorobenzyl)oxy]pyridine-2-amine (Example 1A; 138 mmol, 1 equivalent) were suspended in 552 ml of 10% strength aqueous sulphuric acid, and the mixture was cooled to 0° C. 8.5 ml of bromine (165 mmol, 1.2 equivalents) were dissolved in 85 ml of acetic acid and then, over 90 min, added dropwise to the reaction solution, cooled with ice. After the addition had ended, the mixture was stirred at 0° C. for a further 90 min and then diluted with 600 ml of ethyl acetate, and the aqueous phase was separated off. The aqueous phase was extracted with ethyl acetate. The organic phases were combined, washed with saturated aqueous sodium bicarbonate solution, dried and concentrated. The residue was dissolved in dichloromethane and chromatographed on silica gel (petroleum ether/ethyl acetate gradient as mobile phase). This gave 24 g (55% of theory) of the title compound.

LC-MS (Method 1): $R_t$=0.96 min
MS (ESpos): m/z=315.1/317.1 (M+H)$^+$
$^1$H-NMR (400 MHz, DMSO-$d_6$): δ=5.14 (s, 2 H); 5.83 (br. s, 2 H); 7.20 (t, 2 H); 7.42 (d, 1 H); 7.54 (q, 1 H); 7.62 (d, 1 H).

Example 13A

Ethyl 6-bromo-8-[(2,6-difluorobenzyl)oxy]-2-methylimidazo[1,2-a]pyridine-3-carboxylate

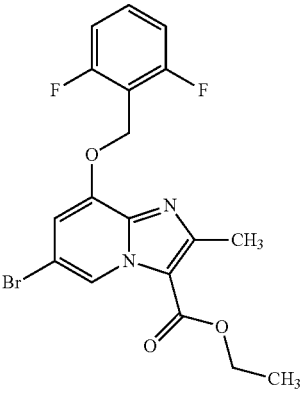

16 g of powdered molecular sieve 3 Å and 52.7 ml of ethyl 2-chloroacetoacetate (380.8 mmol, 5 equivalents) were added to 24 g of 5-bromo-3-[(2,6-difluorobenzyl)oxy]pyridine-2-amine (Example 12A; 76.2 mmol; 1 equivalent) in 400 ml of ethanol, and the mixture was heated at reflux overnight. A further 8 g of molecular sieve were added and the mixture was heated at reflux for a further 24 h. The reaction mixture was concentrated under reduced pressure, and the residue was taken up in dichloromethane and chromatographed on silica gel (mobile phase: dichloromethane/methanol 20:1). The product-containing fractions were concentrated and the residue was stirred with 100 ml of diethyl ether for 30 min. The solid was then filtered off, washed with a little diethyl ether and dried. This gave 15 g (45% of theory) of the title compound.

LC-MS (Method 2): $R_t$=1.43 min
MS (ESpos): m/z=414.9/416.8 (M+H)$^+$
$^1$H-NMR (400 MHz, DMSO-d$_6$): δ=1.36 (t, 3 H); 2.54 (s, 3 H; hidden by DMSO signal); 4.37 (q, 2 H); 5.36 (s, 2 H); 7.25 (t, 2 H); 7.42 (d, 1 H); 7.61 (q, 1 H); 9.00 (d, 1 H).

Example 14A

Ethyl 8-[(2,6-difluorobenzyl)oxy]-2,6-dimethylimidazo[1,2-a]pyridine-3-carboxylate

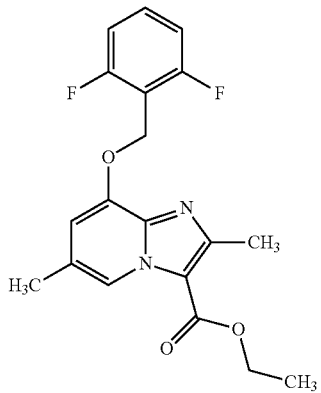 [SMILES: CCOC(=O)c1c(C)nc2c(OCc3c(F)cccc3F)cc(C)cn12]

Method 1:

600 mg of ethyl 6-bromo-8-[(2,6-difluorobenzyl)oxy]-2-methylimidazo[1,2-a]pyridine-3-carboxylate (Example 13A; 1.4 mmol, 1 equivalent) and 230 mg of 1,1'-bis(diphenylphosphino)ferrocenepalladium(II) dichloride/dichloromethane complex (0.282 mmol, 20 mol %) were dissolved in 25 ml of THF, and 0.88 ml (1.76 mmol, 1.2 equivalents) of a 2 M solution of methylzinc chloride in THF was added. The reaction mixture was heated in the microwave for 40 min at 100° C., then filtered through Celite and subsequently concentrated under reduced pressure. The residue was chromatographed (Biotage Isolera Four). This gave 225 mg (38% of theory) of the title compound.

Method 2:

20.00 g (85.38 mmol) of ethyl 8-hydroxy-2,6-dimethylimidazo[1,2-a]pyridine-3-carboxylate from Example 19A, 19.44 g (93.91 mmol) of 2,6-difluorobenzyl bromide and 61.20 g (187.83 mmol) of caesium carbonate in 1.18 l of DMF were stirred at 60° C. for 5 h. The reaction mixture was then poured into 6.4 l of 10% strength aqueous sodium chloride solution and then twice extracted with ethyl acetate. The combined organic phases were washed with 854 ml of a 10% strength aqueous sodium chloride solution, dried and concentrated, and the residue was dried at RT under high vacuum overnight. This gave 28.2 g (92% of theory; purity about 90%) of the title compound.

LC-MS (Method 1): $R_t$=1.05 min
MS (ESpos): m/z=361.1 (M+H)$^+$
$^1$H-NMR (400 MHz, DMSO-d$_6$): δ=1.38 (t, 3 H); 2.36 (s, 3 H); 2.52 (s, 3H hidden by DMSO signal); 4.35 (q, 2 H); 5.30 (s, 2 H); 7.10 (s, 1 H); 7.23 (t, 2 H); 7.59 (q, 1 H); 8.70 (s, 1 H).

Example 15A

8-[(2,6-Difluorobenzyl)oxy]-2,6-dimethylimidazo[1,2-a]pyridine-3-carboxylic acid

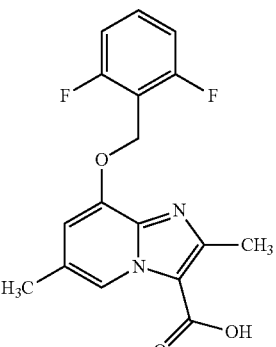

220 mg of ethyl 8-[(2,6-difluorobenzyl)oxy]-2,6-dimethylimidazo[1,2-a]pyridine-3-carboxylate (Example 14A; 0.524 mmol, 1 equivalent) were dissolved in 7 ml of THF/methanol (1:1), 2.6 ml of 1 N aqueous lithium hydroxide solution (2.6 mmol, 5 equivalents) were added and the mixture was stirred at RT for 16 h. The mixture was concentrated under reduced pressure and the residue was acidified with 1N aqueous hydrochloric acid and stirred for 15 min. The solid was filtered off, washed with water and dried under reduced pressure. This gave 120 mg of the title compound (60% of theory).

LC-MS (Method 1): $R_t$=0.68 min
MS (ESpos): m/z=333.1 (M+H)$^+$
$^1$H-NMR (400 MHz, DMSO-d$_6$): δ=2.34 (s, 3 H); 2.52 (s, 3H hidden by DMSO signal); 5.28 (s, 2 H); 7.09 (s, 1 H); 7.23 (t, 2 H); 7.58 (q, 1 H); 8.76 (s, 1 H); 13.1 (br. s, 1 H).

Example 16A 3-(Benzyloxy)-5-bromopyridine-2-amine

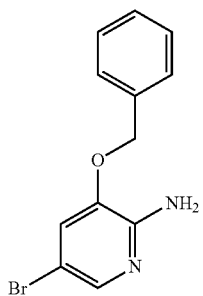 [SMILES: Nc1ncc(Br)cc1OCc1ccccc1]

The target compound is known from the literature and described:
1) Palmer, A. M. et al. J Med. Chem. 2007, 50, 6240-6264.
2) ALTANA WO2005/58325
3) ALTANA WO2005/90358
4) Cui, J. T. et al. J Med. Chem. 2011, 54, 6342-6363

Further Preparation Method:

200 g (1 mol) of 2-amino-3-benzyloxypyridine were initially charged in 4 l of dichloromethane, and at 0° C. a solution of 62 ml (1.2 mol) of bromine in 620 ml of dichloromethane was added over 30 min. After the addition had ended, the reaction solution was stirred at 0° C. for 60 min. About 4 l of saturated aqueous sodium bicarbonate solution were then added to the mixture. The organic phase was removed and concentrated. The residue was purified by silica gel column chromatography (petroleum ether/ethyl acetate 6:4) and the product fractions were concentrated. This gave 214 g (77% of theory) of the title compound.

LC-MS (Method 1): $R_t$=0.92 min

MS (ESpos): m/z=279 (M+H)$^+$ $^1$H-NMR (400 MHz, DMSO-d$_6$): δ=5.16 (s, 2H), 5.94-6.00 (m, 2H), 7.26-7.29 (m, 1H), 7.31-7.36 (m, 1H), 7.37-7.43 (m, 2H), 7.47-7.52 (m, 2H), 7.57-7.59 (m, 1H).

Example 17A

Ethyl 8-(benzyloxy)-6-bromo-2-methylimidazo[1,2-a]pyridine-3-carboxylate

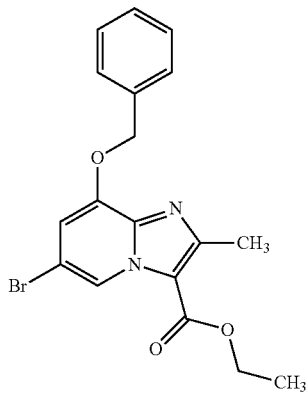

Under argon, 200 g (0.72 mol) of 3-(benzyloxy)-5-bromopyridine-2-amine from Example 16A, 590 g (3.58 mol) of ethyl 2-chloroacetoacetate and 436 g of 3 Å molecular sieve were suspended in 6 l of ethanol, and the suspension was stirred at reflux for 72 h. The reaction mixture was filtered off through silica gel and concentrated. The residue was purified by silica gel chromatography (petroleum ether: ethyl acetate=9:1, then 6:4) and the product fractions were concentrated. This gave 221 g (79% of theory) of the target compound.

LC-MS (Method 16): $R_t$=1.31 min

MS (ESpos): m/z=389 (M+H)$^+$ $^1$H-NMR (400 MHz, DMSO-d$_6$): δ=1.36 (t, 3 H), 2.58 (s, 3 H), 4.32-4.41 (m, 2 H), 5.33 (s, 2 H), 7.28-7.32 (m, 1 H), 7.36-7.47 (m, 3 H), 7.49-7.54 (m, 2 H), 8.98 (d, 1 H).

Example 18A

Ethyl 8-(benzyloxy)-2,6-dimethylimidazo[1,2-a]pyridine-3-carboxylate

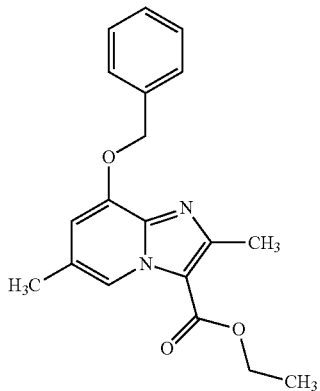 [SMILES: CCOC(=O)c1c(C)nc2c(OCc3ccccc3)cc(C)cn12]

Under argon, 105 g (270 mmol) of ethyl 8-(benzyloxy)-6-bromo-2-methylimidazo[1,2-a]pyridine-3-carboxylate from Example 17A were suspended in 4.2 l of 1,4-dioxane, and 135.4 g (539 mmol, purity 50%) of trimethylboroxine, 31.2 g (27 mmol) of tetrakis(triphenylphosphine)palladium(0) and 78.3 g (566 mmol) of potassium carbonate were added in succession and the mixture was stirred under reflux for 8 h. The precipitate of the reaction mixture, cooled to RT, was removed by filtration over silica gel, and the filtrate was concentrated. The residue was dissolved in dichloromethane and purified by silica gel chromatography (dichloromethane: ethyl acetate=9:1). This gave 74 g (84.6% of theory) of the target compound.

LC-MS (Method 16): $R_t$=1.06 min

MS (ESpos): m/z=325 (M+H)$^+$ $^1$H-NMR (400 MHz, DMSO-d$_6$): δ=1.35 (t, 3 H), 2.34 (br. s, 3 H), 2.56 (s, 3 H), 4.31-4.38 (m, 2 H), 5.28 (br. s, 2 H), 6.99-7.01 (m, 1 H), 7.35-7.47 (m, 3 H), 7.49-7.54 (m, 2 H), 8.68-8.70 (m, 1 H).

Example 19A

Ethyl 8-hydroxy-2,6-dimethylimidazo[1,2-a]pyridine-3-carboxylate

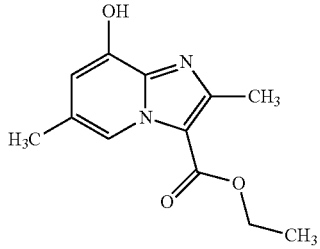 [SMILES: CCOC(=O)c1c(C)nc2c(O)cc(C)cn12]

74 g (228 mmol) of ethyl 8-(benzyloxy)-2,6-dimethylimidazo[1,2-a]pyridine-3-carboxylate from Example 18A were initially charged in 1254 ml of dichloromethane and 251 ml of ethanol, and 20.1 g of 10% palladium on activated carbon (moist with water, 50%) were added under argon. Overnight, the reaction mixture was hydrogenated at RT and under atmospheric pressure. The reaction mixture was filtered off through silica gel and concentrated. The crude product was purified by silica gel chromatography (dichloromethane:methanol=95:5). This gave 50.4 g (94% of theory) of the target compound.

DCI-MS: (Method 13) (ESpos): m/z=235.2 (M+H)$^+$ $^1$H-NMR (400 MHz, DMSO-d$_6$): δ=1.35 (t, 3 H), 2.27 (s, 3 H), 2.58 (s, 3 H), 4.30-4.38 (m, 2 H), 6.65 (d, 1 H), 8.59 (s, 1 H), 10.57 (br. s, 1H).

Example 20A

8-[(2,6-Difluorobenzyl)oxy]-2-methylimidazo[1,2-a]pyridine-3-carboxamide

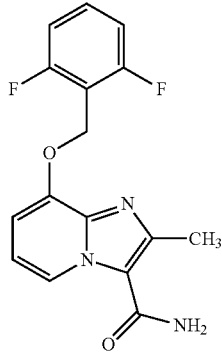

Under argon, 5.0 g of 8-[(2,6-difluorobenzyl)oxy]-2-methylimidazo[1,2-a]pyridine-3-carboxylic acid (Example 3A, 15.71 mmol, 1 equivalent) were initially charged in 300 ml of dichloromethane, 4.52 g of 1-(3-dimethylaminopropyl)-3-ethylcarbodiimide hydrochloride (23.56 mmol, 1.5 equivalents) and 3.61 g of 1-hydroxy-1H-benzotriazole hydrate (HOBT, 23.56 mmol, 1.5 equivalents) were added successively at RT and the mixture was stirred at RT for 10 min. 4.20 g of ammonium chloride (78.55 mmol, 5 equivalents) and 19.15 ml of N,N-diisopropylethylamine (109.96 mmol, 7 equivalents) were then added, and the mixture was stirred at RT overnight. The mixture was then concentrated under reduced pressure, dichloromethane was added to the residue, and the solid was filtered off, washed well with dichloromethane and dried under reduced pressure overnight. This gave 5.38 g (108% of theory) of the title compound which was reacted further without purification.

LC-MS (Method 1): R$_t$=0.65 min
MS (ESpos): m/z=318.2 (M+H)$^+$

Example 21A

8-[(2,6-Difluorobenzyl)oxy]-2-methylimidazo[1,2-a]pyridine-3-carbonitrile

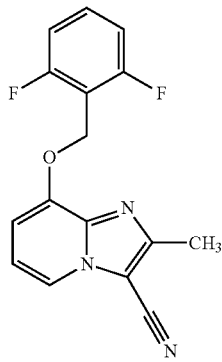 [SMILES: Cc1nc2c(OCc3c(F)cccc3F)cccn2c1C#N]

912 mg of 8-[(2,6-difluorobenzyl)oxy]-2-methylimidazo[1,2-a]pyridine-3-carboxamide (Example 20A, 2.87 mmol, 1 equivalent) were initially charged in 13 ml of THF, and 0.6 ml of pyridine (7.36 mmol, 2.56 equivalents) was added. Subsequently, at RT, 1.04 ml (7.36 mmol, 2.56 equivalents) of trifluoroacetic anhydride were added dropwise and the mixture was stirred at RT overnight. Subsequently, the reaction mixture was added to water and extracted three times with ethyl acetate. The combined organic phases were washed once with saturated aqueous sodium bicarbonate solution, once with 1 N aqueous hydrochloric acid and once with saturated aqueous sodium chloride solution, dried over sodium sulphate and concentrated on a rotary evaporator. The residue was dried under reduced pressure overnight. This gave 787 mg (91% of theory) of the title compound.

LC-MS (Method 1): R$_t$=0.97 min
MS (ESpos): m/z=300.1 (M+H)$^+$ $^1$H-NMR (400 MHz, DMSO-d$_6$): δ=2.44 (s, 3 H), 5.33 (s, 2 H), 7.10-7.16 (m, 1 H), 7.18-7.28 (m, 3 H), 7.54-7.64 (m, 1 H), 8.22 (d, 1 H).

Example 22A

8-[(2,6-Difluorobenzyl)oxy]-2-methylimidazo[1,2-a]pyridine-3-carboximidamide

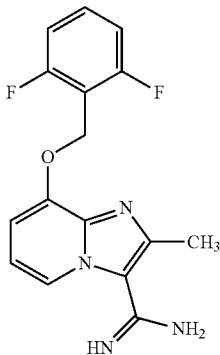 [SMILES: Cc1nc2c(OCc3c(F)cccc3F)cccn2c1C(=N)N]

Solution A:

Under argon, 135 mg (2.53 mmol, 2.52 equivalents) of ammonium chloride were initially charged in 3.9 ml of toluene, and the mixture was cooled to 0° C. At this temperature, 1.26 ml of 2 M trimethylaluminium in toluene (2.53 mmol, 2.52 equivalents) were added, and the solution was stirred at RT for 2 h.

In another flask, 300 mg of 8-[(2,6-difluorobenzyl)oxy]-2-methylimidazo[1,2-a]pyridine-3-carbonitrile (Example 21A, 1.0 mmol, 1 equivalent) were initially charged in 3.3 ml of toluene, 2 ml of the solution prepared beforehand were added at RT and the mixture was stirred at 110° C. for 1 h. Subsequently, two more times solution A was added to the reaction mixture, until all the starting material had been consumed. The mixture was then cooled, silica gel and a 1:1 mixture of dichloromethane/methanol were added at RT and the mixture was stirred at RT for 30 min. The silica gel was filtered off and washed with methanol, and the mother liquor was concentrated. The residue was purified on a silica gel column (mobile phase: pure dichloromethane; dichloromethane: methanol=10:2). This gave 138 mg (43% of theory) of the title compound.

LC-MS (Method 1): R$_t$=0.51 min
MS (ESpos): m/z=317.1 (M+H)$^+$

¹H-NMR (400 MHz, DMSO-d₆): δ=2.46 (s, 3 H), 5.32 (s, 2 H), 7.04 (t, 1 H), 7.14 (d, 1 H), 7.24 (t, 2 H), 7.53-7.66 (m, 1 H), 8.17 (d, 1 H), 9.31 (d, 3 H).

Example 23A

8-[(2,6-Difluorobenzyl)oxy]-N-hydroxy-2-methyl-imidazo[1,2-a]pyridine-3-carboximidamide

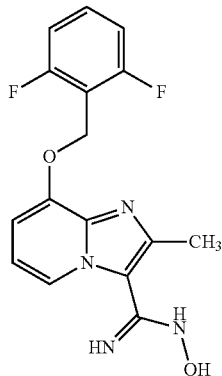 [SMILES: Cc1nc2c(OCc3c(F)cccc3F)cccn2c1C(=N)NO]

50.0 g (148.9 mmol) of 8-[(2,6-difluorobenzyl)oxy]-2-methylimidazo[1,2-a]pyridine-3-carbonitrile from Example 21A were suspended in ethanol (1.5 l), 51.75 g (744.6 mmol) of hydroxylamine hydrochloride and 103 ml (744.6 mmol) of triethylamine were added and the mixture was stirred at RT overnight. The mixture was then concentrated almost to dryness, water (2.0 l) and ethanol (100 ml) were added and the mixture was stirred for 1 h. A solid formed, which was filtered off and washed with water. This solid was dried under high vacuum overnight. This gave 38.5 g (68% of theory; purity 87%) of the title compound.

LC-MS (Method 1): R$_t$=0.56 min
MS (ESpos): m/z=333.2 (M+H)⁺

Example 24A

8-[(2,6-Difluorobenzyl)oxy]-2-methylimidazo[1,2-a]pyridine-3-carboximidamide acetate

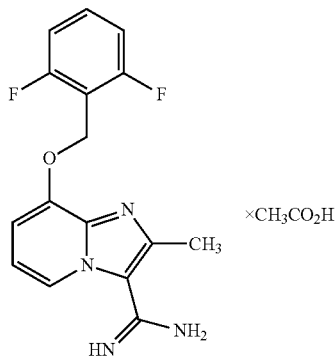 [SMILES: Cc1nc2c(OCc3c(F)cccc3F)cccn2c1C(=N)N]

37.5 g (98.4 mmol, purity 87%) of 8-[(2,6-difluorobenzyl)oxy]-N-hydroxy-2-methylimidazo[1,2-a]pyridine-3-carboximidamide from Example 23A were initially charged in acetic acid (1.0 l), and 11.14 ml (118.08 mmol) of acetic anhydride were added. 7.5 g of palladium/carbon (10%, moist) were added, and the mixture was hydrogenated at atmospheric pressure for 16 h. The mixture was then filtered through kieselguhr and washed with ethanol. After concentration, three times in each case 500 ml of toluene were added to the residue, and the mixture was concentrated to dryness. The residue was stirred with 200 ml of ethyl acetate and filtered, and the residue was then dried. This gave 22.0 g (59% of theory) of the title compound.

LC-MS (Method 1): R$_t$=0.51 min
MS (ESpos): m/z=317.2 (M−CH₃CO₂H+H)⁺
¹H-NMR (400 MHz, DMSO-d₆): δ=1.82 (s, 3H), 2.46 (s, 3 H), 5.31 (s, 2 H), 6.93 (t, 1 H), 7.01 (d, 1 H), 7.21-7.25 (m, 2 H), 7.55-7.63 (m, 1 H), 8.55 (br d, 1 H).

Example 25A

8-[(2,6-Difluorobenzyl)oxy]-2,6-dimethylimidazo[1,2-a]pyridine-3-carboxamide

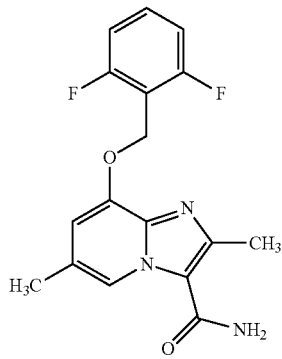

7.0 g (21.07 mmol) of 8-[(2,6-difluorobenzyl)oxy]-2,6-dimethylimidazo[1,2-a]pyridine-3-carboxylic acid from Example 15A were initially charged in 403 ml of dichloromethane, 6.06 g (31.60 mmol) of 1-(3-dimethylaminopropyl)-3-ethylcarbodiimide hydrochloride and 4.27 g (31.60 mmol) of 1-hydroxy-1H-benzotriazole hydrate were added and the mixture was stirred at room temperature for 10 min. Subsequently, 5.63 g (105.32 mmol) of ammonium chloride and 25.68 ml (147.5 mmol) of N,N-diisopropylethylamine were added and the mixture was stirred at room temperature overnight. Water was added to the reaction mixture, and the solid present was filtered off, then stirred with water at 50° C. for 30 min, filtered off again and washed with water. This gave 4.59 g (65% of theory) of the title compound. The combined filtrate fractions (dichloromethane/water) were separated into the phases. The dichloromethane phase was washed in each case once with saturated aqueous sodium bicarbonate solution and saturated aqueous sodium chloride solution. The organic phase was dried over sodium sulphate, filtered and concentrated. The residue was stirred with a little acetonitrile and filtered off. This gave another 1.29 g (17% of theory; purity: 93%) of the title compound.

LC-MS (Method 1): R$_t$=0.64 min
MS (ESpos): m/z=332 (M+H)⁺
¹H-NMR (400 MHz, DMSO-d₆): δ=2.31 (s, 3H), 2.50 (s, 3 H; hidden under the DMSO signal); 5.28 (s, 2 H); 6.92 (s, 1 H); 7.22 (t, 2 H); 7.35 (br. s, 2 H); 7.53-7.63 (m, 1 H); 8.62 (s, 1 H).

Example 26A

8-[(2,6-Difluorobenzyl)oxy]-2,6-dimethylimidazo[1,2-a]pyridine-3-carbonitrile

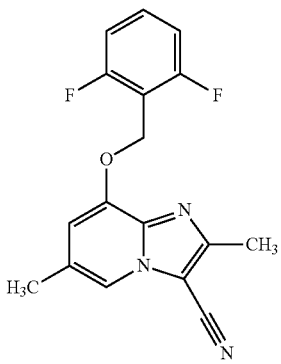

5.70 g (17.20 mmol) of 8-[(2,6-difluorobenzyl)oxy]-2,6-dimethylimidazo[1,2-a]pyridine-3-carboxamide Example 25A were initially charged in 77 ml of THF, and 3.56 ml (44.0 mmol) of pyridine were added. At RT, 6.22 ml (44.0 mmol) of trifluoroacetic anhydride were then added dropwise, and the reaction mixture was stirred at RT for 3 h. The mixture was then added to water and extracted three times with ethyl acetate. The combined organic phases were washed once with saturated aqueous sodium bicarbonate solution, once with 1 N aqueous hydrochloric acid and once with saturated aqueous sodium chloride solution, dried over sodium sulphate and concentrated. The residue was dried under reduced pressure overnight. This gave 5.47 g (99% of theory) of the title compound.

LC-MS (Method 1): $R_t$=1.12 min
MS (ESpos): m/z=314 (M+H)$^+$
$^1$H-NMR (400 MHz, DMSO-$d_6$): δ=2.37 (s, 3 H), 2.41 (s, 3 H), 5.31 (s, 2 H), 7.12 (s, 1 H), 7.23 (t, 2 H), 7.54-7.63 (m, 1 H), 8.09 (s, 1 H).

Example 27A

8-[(2,6-Difluorobenzyl)oxy]-2,6-dimethylimidazo[1,2-a]pyridine-3-carboximidamide

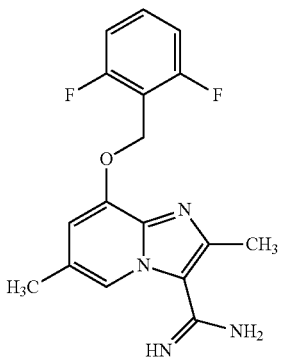

5.47 g (17.46 mmol; purity 98%) of 8-[(2,6-difluorobenzyl)oxy]-2,6-dimethylimidazo[1,2-a]pyridine-3-carbonitrile from Example 26A were reacted analogously to the procedure of Example 22A. This gave 1.28 g (22% of theory) of the title compound.

LC-MS (Method 1): $R_t$=0.60 min
MS (ESpos): m/z=331.3 (M+H)$^+$
$^1$H-NMR (400 MHz, DMSO-$d_6$): δ=2.35 (s, 3 H), 2.43 (s, 3 H), 5.31 (s, 2 H), 7.06 (s, 1 H), 7.24 (t, 2 H), 7.54-7.65 (m, 1 H), 8.02 (s, 1 H), 9.25 (br. s, 3 H).

Example 28A

Methyl 3,3-dicyano-2,2-dimethylpropanoate

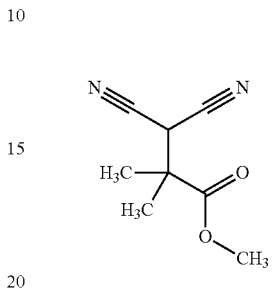

Under argon, 1.82 g of 60% sodium hydride (45.41 mmol, 1 equivalent) were initially charged in 91 ml of THF, and 3.0 g of malononitrile (45.41 mmol, 1 equivalent) were added slowly at RT. At RT, 5.9 ml of methyl alpha-bromoisobutyrate (45.41 mmol, 1 equivalent) were then added and the mixture was stirred further at RT overnight. Another 5.9 ml of methyl alpha-bromoisobutyrate (45.41 mmol, 1 equivalent) were added, and the mixture was stirred further at 50° C. overnight. The mixture was then cooled, saturated aqueous sodium bicarbonate solution was added and the mixture was extracted three times with ethyl acetate. The combined organic phases were washed once with saturated sodium chloride solution, dried over sodium sulphate and concentrated on a rotary evaporator. The residue was separated on a silica gel column (mobile phase: pure cyclohexane; cyclohexane/ethyl acetate=8:2). This gave 6.47 g (86% of theory) of the title compound.

$^1$H-NMR (400 MHz, CDCl$_3$): δ=1.53 (s, 6 H), 3.83 (s, 3 H), 4.14 (s, 1 H).

Example 29A rac-3-(3,4-Difluorophenyl)-3-(1,3-dioxo-1,3-dihydro-2H-isoindol-2-yl)propanoic acid

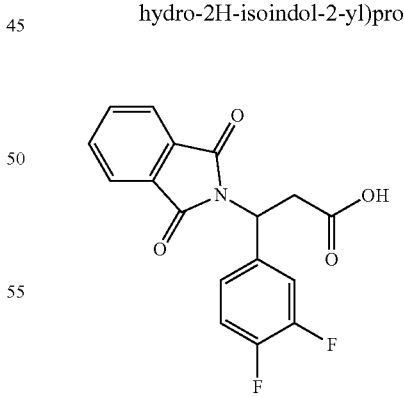

1. Step:
697 g of 3,4-difluorobenzaldehyde (4.76 mol, 1 equivalent) were stirred together with 495 g of malonic acid (4.76 mol, 1 equivalent) and 733 g of ammonium acetate (9.52 mol, 2 equivalents) in 2788 ml of ethanol at reflux under argon for 20 h. Then the mixture was cooled to RT and stirred at RT overnight. The solid formed was filtered off, washed with ethanol and diethyl ether and dried under reduced pressure. 590 g (62% of theory) of rac-3-amino-3-(3,4-difluorophenyl)propanoic acid were obtained.

rac-3-Amino-3-(3,4-difluorophenyl)propanoic acid

LC-MS (Method 1): $R_t$=0.27 min

MS (ESpos): m/z=202.0 (M+H)$^+$

2. Step:

0.20 g (0.99 mmol) of rac-3-amino-3-(3,4-difluorophenyl)propanoic acid and 0.15 g (0.99 mmol) of phthalic anhydride were dissolved in 0.8 ml of DMF and heated at reflux at 135° C. overnight. The reaction solution was added to about 9 ml of water. The resulting suspension was extracted twice with ethyl acetate. The combined organic phases were washed with water, dried over sodium sulphate, filtered and concentrated. The crude product was purified by preparative HPLC (RP18 column; mobile phase: acetonitrile/water gradient with addition of 0.1% TFA). This gave 0.2 g of the title compound (61% of theory).

LC-MS (Method 1): $R_t$=0.97 min

MS (ESpos): m/z=332 (M+H)$^+$ $^1$H-NMR (400 MHz, DMSO-$d_6$): δ=3.24-3.3.33 (m, 1H), 3.44-3.52 (m, 1H), 5.63-5.70 (m, 1H), 7.23-7.28 (m, 1H), 7.36-7.47 (m, 1H), 7.49-7.57 (m, 1H), 7.82-7.90 (m, 4H), 12.51 (br s, 1H).

Example 30A rac-tert-Butyl [2-(3,4-difluorophenyl)-2-(1,3-dioxo-1,3-dihydro-2H-isoindol-2-yl)ethyl]carbamate

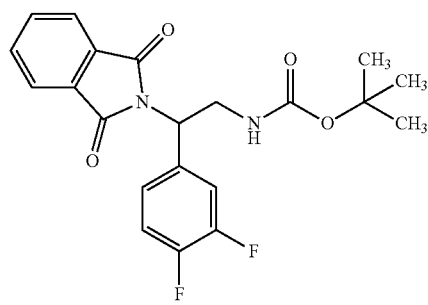 [SMILES: CC(C)(C)OC(=O)NCC(c1ccc(F)c(F)c1)N1C(=O)c2ccccc2C1=O]

Under argon, a solution of 5.0 g of rac-3-(3,4-difluorophenyl)-3-(1,3-dioxo-1,3-dihydro-2H-isoindol-2-yl)propanoic acid (Example 29A, 15.09 mmol) and 3.06 g of triethylamine (30.19 mmol) was initially charged in 65 ml of toluene, 4.36 g of diphenylphosphorus azidate (15.85 mmol) were added and the mixture was stirred at RT for 3.5 h. Subsequently, 65 ml of tert-butanol were added and the mixture was stirred under reflux overnight. After cooling, the reaction solution was concentrated and purified by flash chromatography (mobile phase: petroleum ether/ethyl acetate 2:1, isocratic). This gave 3.1 g of the title compound (45% of theory).

LC-MS (Method 1): $R_t$=1.19 min

MS (ESpos): m/z=403 (M+H)$^+$ $^1$H-NMR (400 MHz, DMSO-$d_6$): δ=1.26 (s, 9H), 3.73-3.90 (m, 2H), 5.32-5.39 (m, 1H), 7.20-7.27 (m, 2H), 7.36-7.46 (m, 1H), 7.48-7.56 (m, 1H), 7.81-7.91 (m, 4H).

Example 31A rac-tert-Butyl [2-amino-2-(3,4-difluorophenyl)ethyl]carbamate

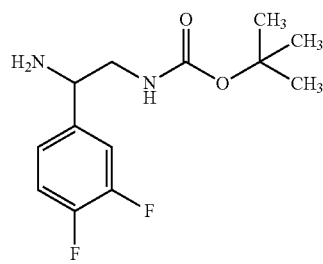 [SMILES: CC(C)(C)OC(=O)NCC(N)c1ccc(F)c(F)c1]

6.13 g of rac-tert-butyl [2-(3,4-difluorophenyl)-2-(1,3-dioxo-1,3-dihydro-2H-isoindol-2-yl)ethyl]carbamate (Example 30A, purity about 60%, about 9.14 mmol) were initially charged in 13.1 ml of 40% aqueous methylamine solution, and the mixture was stirred in a closed vessel at 60° C. overnight. The reaction mixture was concentrated and the residue was purified by silica gel chromatography (mobile phase: dichloromethane:methanol:diethylamine 30:1:0.1; 20:1:0.1). This gave 1.83 g of the title compound (74% of theory).

LC-MS (Method 2): $R_t$=0.65 min

MS (ESpos): m/z=273 (M+H)$^+$ $^1$H-NMR (400 MHz, DMSO-$d_6$): δ=1.33 (s, 9H), 1.96 (br s, 2H), 2.92-3.10 (m, 2H), 3.81-3.88 (m, 1H), 6.76-6.82 (m, 1H), 7.11-7.17 (m, 1H), 7.27-7.40 (m, 2H).

Example 32A ent-tert-Butyl [2-amino-2-(3,4-difluorophenyl)ethyl]carbamate (enantiomer A)

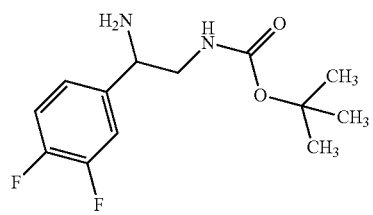 [SMILES: CC(C)(C)OC(=O)NCC(N)c1ccc(F)c(F)c1]

100 mg of rac-tert-butyl [2-amino-2-(3,4-difluorophenyl)ethyl]carbamate (Example 31A) were separated into the enantiomers on a chiral phase [column: Daicel Chiralpak AY-H, 5 μm, 250×20 mm, mobile phase: 80% isohexane, 20% ethanol+0.2% diethylamine, flow rate 15 ml/min; 30° C., detection: 220 nm].

Yield: 43 mg of enantiomer A (>99% ee)

$R_t$=4.58 min [Daicel Chiralpak AY-H, 5 μm, 250×4.6 mm; mobile phase: 80% isohexane, 20% ethanol+0.2% diethylamine; flow rate 1.0 ml/min; 30° C.; detection: 220 nm].

Example 33A ent-tert-Butyl
[2-amino-2-(3,4-difluorophenyl)ethyl]carbamate
(enantiomer B)

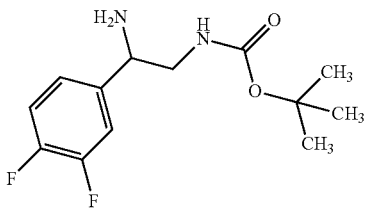 [SMILES: CC(C)(C)OC(=O)NCC(N)c1ccc(F)c(F)c1]

100 mg of rac-tert-butyl [2-amino-2-(3,4-difluorophenyl)ethyl]carbamate (Example 31A) were separated into the enantiomers on a chiral phase [column: Daicel Chiralpak AY-H, 5 μm, 250×20 mm, mobile phase: 80% isohexane, 20% ethanol+0.2% diethylamine, flow rate 15 ml/min; 30° C., detection: 220 nm].

Yield: 44 mg of enantiomer B (>99% ee)

$R_t$=5.61 min [Daicel Chiralpak AY-H, 5 μm, 250×4.6 mm; mobile phase: 80% isohexane, 20% ethanol+0.2% diethylamine; flow rate 1.0 ml/min; 30° C.; detection: 220 nm].

Example 34A ent-1-(3,4-Difluorophenyl)ethane-1,2-diamine
dihydrochloride (enantiomer A)

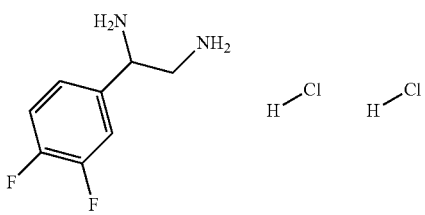 [SMILES: NCC(N)c1ccc(F)c(F)c1 ; Cl ; Cl]

528 mg (1.94 mmol) of ent-tert-butyl [2-amino-2-(3,4-difluorophenyl)ethyl]carbamate (enantiomer A) (Example 32A) were initially charged in 10 ml of diethyl ether, 9.7 ml of hydrochloric acid (2 N in diethyl ether) were added and the mixture was stirred at room temperature for 2 days. The reaction mixture was concentrated and dried under high vacuum. This gave 475 mg (99% of theory) of the title compound.

LC-MS (Method 1): $R_t$=0.17 min
MS (ESpos): m/z=173 (M−2HCl+H)$^+$

Example 35A

Methyl 3,3-dicyano-2-(trifluoromethyl)acrylate

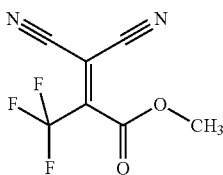

The synthesis of this compound is described in Journal of Fluorine Chemistry, 1991, vol. 51, #3 pp. 323-334.

Example 36A

Methyl 2-(dicyanomethyl)-3,3,3-trifluoro-2-methyl-propanoate (racemate)

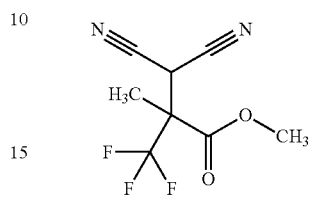

3.00 g (14.698 mmol) of methyl 3,3-dicyano-2-(trifluoromethyl)acrylate from Example 35A were dissolved in tetrahydrofuran (30 ml) and the solution was cooled to 0° C. 7.35 ml (22.047 mmol) of methylmagnesium chloride (3 M in THF) were then added dropwise such that the temperature did not exceed 5° C. After the addition had ended, the mixture was stirred for another 10 min. 1N aqueous hydrochloric acid was then added to the reaction, and the mixture was subsequently extracted with ethyl acetate. The phases were separated and the aqueous phase was extracted twice more with ethyl acetate. The combined organic phases were washed with saturated aqueous sodium chloride solution, dried over sodium sulphate, filtered and concentrated. The crude product was subsequently chromatographed on silica gel (mobile phase: cyclohexane, then cyclohexane:ethyl acetate 9:1 (v:v)). Concentration gave 3.24 g (63% of theory) of the title compound.

$^1$H-NMR (400 MHz, CDCl$_3$): δ=1.81 (s, 3H), 3.95 (s, 3H), 4.48 (s, 1H).

Example 37A tert-Butyl (1-{[(2-{8-[(2,6-difluorobenzyl)oxy]-2-methylimidazo[1,2-a]pyridin-3-yl}-5,5-dimethyl-6-oxo-6,7-dihydro-5H-pyrrolo[2,3-d]pyrimidin-4-yl)amino]methyl}cyclopropyl)carbamate

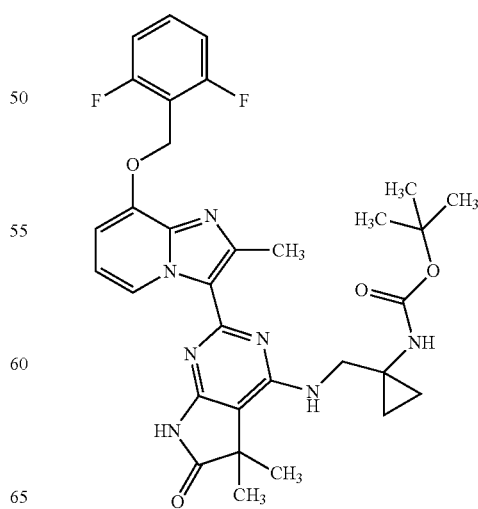

100 mg (171 µmol) of 4-chloro-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one from Example 4 were initially charged in 1.5 ml of NMP, 128 mg (685 mol) of tert-butyl [1-(aminomethyl)cyclopropyl]carbamate and 0.03 ml (171 µmol) of N,N-diisopropylethylamine were added and the mixture was stirred in the microwave at 150° C. for 5 h. Another 32 mg (171 µmol) of tert-butyl [1-(aminomethyl)cyclopropyl]carbamate were then added, and the mixture was stirred in the microwave at 150° C. for 2 h. The reaction solution was diluted with acetonitrile/water/TFA and purified by preparative HPLC (RP18 column, mobile phase: acetonitrile/water gradient with addition of 0.1% TFA). This gave 73 mg (59% of theory, purity 86%) of the title compound.

LC-MS (Method 1): $R_t$=1.01 min

MS (ESpos): m/z=620 (M+H)$^+$

Example 38A

Ethyl 8-(benzyloxy)-2-methylimidazo[1,2-a]pyridine-3-carboxylate

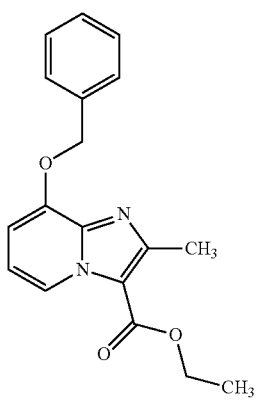 [SMILES: CCOC(=O)c1c(C)nc2c(OCc3ccccc3)cccn12]

25 g of 2-amino-3-benzyloxypyridine (124.8 mmol, 1 equivalent) were dissolved in 781 ml of ethanol, 102.7 g of ethyl 2-chloroacetoacetate (624.2 mmol, 5 equivalents) and 15 g of 4 Å molecular sieve were added and the mixture was heated at reflux (bath temperature 100° C.) for 2 d. Then, the mixture was concentrated and excess ethyl 2-chloroacetoacetate was distilled off on a rotary evaporator using dry ice cooling. The residue was purified by silica gel chromatography (mobile phase cyclohexane:ethyl acetate=9:1, 4:1). This gave 20.81 g of the title compound (54% of theory).

LC-MS (Method 2): $R_t$=1.12 min

MS (ESpos): m/z=311 (M+H)$^+$ $^1$H-NMR (400 MHz, DMSO-$d_6$): δ=1.35 (t, 3H), 2.59 (s, 3H), 4.34 (q, 2H), 5.32 (s, 2H), 7.01-7.09 (m, 2H), 7.33-7.48 (m, 3H), 7.52 (d, 2H), 8.81-8.86 (m, 1H).

Example 39A 8-(Benzyloxy)-2-methylimidazo[1,2-a]pyridine-3-carboxylic acid

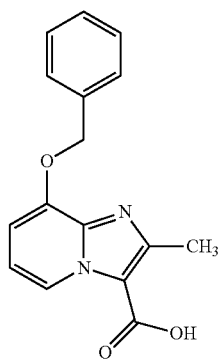 [SMILES: Cc1nc2c(OCc3ccccc3)cccn2c1C(=O)O]

253 ml of 2 N aqueous sodium hydroxide solution were added to a solution of 15.7 g of ethyl 8-(benzyloxy)-2-methylimidazo[1,2-a]pyridine-3-carboxylate (50.59 mmol) from Example 38A in 253 ml of 1,4-dioxane, and the mixture was stirred at RT for 14 h. 101 ml of 6 N aqueous hydrochloric acid were then added. The solid formed was filtered off, washed with water and methyl tert-butyl ether and then dried under reduced pressure at 40° C. overnight. This gave 15.49 g (108% of theory) of 8-(benzyloxy)-2-methylimidazo[1,2-a]pyridine-3-carboxylic acid.

LC-MS (Method 2): $R_t$=0.66 min

MS (ESpos): m/z=283.0 (M+H)$^+$ $^1$H-NMR (400 MHz, DMSO-$d_6$): δ=2.67 (s, 3H), 5.41 (s, 2H), 7.30 (m, 1H), 7.35-7.48 (m, 4H), 7.57 (d, 2H), 9.02 (d, 1H).

Example 40A 8-(Benzyloxy)-2-methylimidazo[1,2-a]pyridine-3-carboxamide

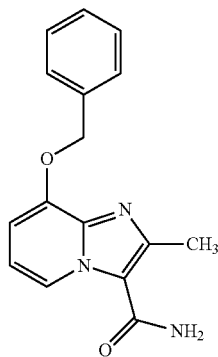 [SMILES: Cc1nc2c(OCc3ccccc3)cccn2c1C(N)=O]

Under argon, 52.5 g (16.22 mmol, purity 84%) of 8-(benzyloxy)-2-methylimidazo[1,2-a]pyridine-3-carboxylic acid (Example 39A) were initially charged in 2 l of dichloromethane, 44.92 g (234.3 mmol) of 1-(3-dimethylaminopropyl)-3-ethylcarbodiimide hydrochloride and 35.9 g (234.3 mmol) of 1-hydroxy-1H-benzotriazole hydrate were added successively at RT and the mixture was stirred at RT for 10 min.

Subsequently, 41.78 g (781.1 mmol) of ammonium chloride and 190.5 ml (1093.5 mmol) of N,N-diisopropylethylamine were added and the mixture was stirred further at RT for 3 d. 4.49 g (23.43 mmol) of 1-(3-dimethylaminopropyl)-3-ethylcarbodiimide hydrochloride, 3.59 g (23.43 mmol) of 1-hydroxy-1H-benzotriazole hydrate, 4.18 g (78.1 mmol) of ammonium chloride and 14.13 g (109.4 mmol) of N,N-diisopropylethylamine were added in each case and the mixture was once again stirred overnight at RT. After the reaction time had ended, 2 l of water were added to the mixture and the precipitate formed was filtered off. The solid was washed twice with in each case 500 ml of water and dichloromethane and dried. The organic phase was washed with water and concentrated. The residue was combined with the solid and stirred with tert-butyl methyl ether. The product was washed with tert-butyl methyl ether and dried under high vacuum. This gave 40.80 g (93% of theory) of the title compound.

LC-MS (Method 1): $R_t$=0.58 min

MS (ESpos): m/z=282 (M+H)$^+$ $^1$H NMR (400 MHz, DMSO-d$_6$) δ=2.56 (s, 3 H), 5.28 (s, 2 H), 6.90 (d, 2 H), 7.38 (d, 1 H), 7.43 (t, 2 H), 7.51 (d, 2 H), 8.75 (dd, 1 H).

Example 41A 8-(Benzyloxy)-2-methylimidazo[1,2-a]pyridine-3-carbonitrile

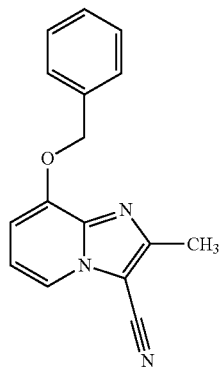 [SMILES: Cc1nc2c(OCc3ccccc3)cccn2c1C#N]

358 g (1.273 mol) of 8-(benzyloxy)-2-methylimidazo[1,2-a]pyridine-3-carboxamide (Example 40A) were initially charged in 5.65 l of THF, and 263.5 ml (3.258 mol) of pyridine were added. At RT, 460.1 ml (3.258 mmol) of trifluoroacetic anhydride were then added dropwise, and the reaction mixture was stirred at RT overnight. After the reaction time had ended, the mixture was added to 20 l of ethyl acetate and washed in each case once with 2.69 l of 1 N aqueous hydrochloric acid, 2.69 l of 10% strength aqueous sodium bicarbonate solution and 6.27 l of water. The insoluble solid was filtered off and dried.

This solid was dissolved in 22 l of ethyl acetate and washed again with 6 l of water. The organic phase was dried and concentrated. This gave 140 g (42% of theory) of the title compound.

The organic phase of the first phase separation was dried, concentrated and dried under high vacuum. The residue was dissolved in 33 l of ethyl acetate and stirred with 20 l of 10% strength aqueous sodium bicarbonate solution at RT for 7 h. The organic phase was removed, washed with 10% strength aqueous sodium chloride solution, dried and concentrated. The residue obtained was dried under high vacuum. This gave another 153 g (46% of theory) of the title compound.

MS (ESpos): m/z=264 (M+H)$^+$ $^1$H NMR (500 MHz, DMSO-d$_6$) δ=2.47 (s, 3 H), 5.32 (s, 2 H), 7.07-7.11 (m, 2 H), 7.35-7.49 (m, 1 H), 7.43 (t, 2 H), 7.51 (d, 2 H), 8.15-8.20 (m, 1 H).

Example 42A

8-Hydroxy-2-methylimidazo[1,2-a]pyridine-3-carbonitrile

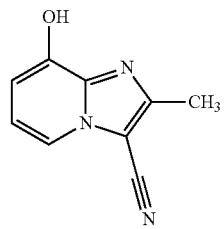

68 g (258 mmol) of 8-(benzyloxy)-2-methylimidazo[1,2-a]pyridine-3-carbonitrile (Example 41A) were initially charged in 1.7 l of dichloromethane and 425 ml of ethanol, and 28 g of 10% palladium on activated carbon (moist with water, 50%) were added under argon. The reaction mixture was hydrogenated at RT and under standard pressure for 8 h. Another 13.6 g of 10% palladium on activated carbon (moist with water 50%) were added, and the mixture was hydrogenated at RT for another 4 h. The product which precipitated during the reaction was re-dissolved in 20 l of dichloromethane/methanol (7/3) and the mixture was stirred at RT for 45 min. The reaction mixture was filtered off through kieselguhr and concentrated. The resulting crystals were suspended in tert-butyl methyl ester, filtered off with suction and dried under HV. This gave 38.5 g (86% of theory) of the title compound.

LC-MS (Method 1): $R_t$=0.54 min

MS (ESpos): m/z=174 (M+H)$^+$

Example 43A

2-Methyl-8-[(2,3,6-trifluorobenzyl)oxy]imidazo[1,2-a]pyridine-3-carbonitrile

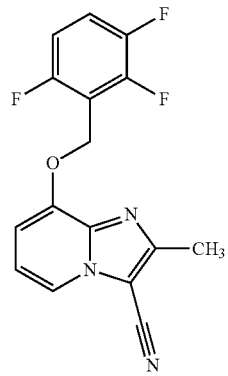 [SMILES: Cc1nc2c(OCc3c(F)ccc(F)c3F)cccn2c1C#N]

4.90 g (28.28 mmol) of 8-hydroxy-2-methylimidazo[1,2-a]pyridine-3-carbonitrile (Example 42A) and 20.27 g of caesium carbonate (62.22 mmol) were initially charged in 390 ml of DMF, 7 g (31.11 mmol) of 2-(bromomethyl)-1,3,4-trifluorobenzene were added and the mixture was stirred at 60° C. for 30 min. The reaction mixture was poured onto water and stirred at RT for 30 min. The precipitated solid was filtered off, washed with water and dried under high vacuum. This gave 8.8 g (98% of theory) of the title compound.

LC-MS (Method 1): $R_t$=1.01 min

MS (ESpos): m/z=318 (M+H)$^+$ $^1$H NMR (400 MHz, DMSO-d$_6$) δ=2.45 (s, 3 H), 5.38 (s, 2 H), 7.11-7.17 (m, 1 H), 7.21 (d, 1 H), 7.25-7.34 (m, 1 H), 7.62-7.73 (m, 1 H), 8.23 (d, 1 H).

Example 44A

N-Hydroxy-2-methyl-8-[(2,3,6-trifluorobenzyl)oxy]imidazo[1,2-a]pyridine-3-carboximidamide

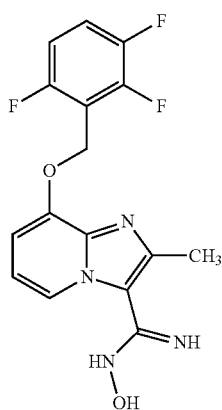 [SMILES: Cc1nc2c(OCc3c(F)ccc(F)c3F)cccn2c1C(=N)NO]

18.20 g (57.36 mmol) of 2-methyl-8-[(2,3,6-trifluorobenzyl)oxy]imidazo[1,2-a]pyridine-3-carbonitrile from Example 43A were suspended in 610 ml of ethanol, and 39.86 g (573.64 mmol) of hydroxylamine hydrochloride were then added. 79.96 ml (573.64 mmol) of triethylamine were added dropwise and the mixture was stirred at RT overnight. The mixture was then concentrated on a rotary evaporator at 40-45° C. to a third of its volume, water (250 ml) was added and the mixture was concentrated again to about 250 ml. 0.7 l of water was added. The solid obtained was filtered off and washed with water. The solid was, as a suspension in acetonitrile (50 ml), concentrated under reduced pressure and dried under high vacuum overnight. This gave 20.9 g (91% of theory, purity 87%) of the title compound.

LC-MS (Method 1): $R_t$=0.57 min

MS (ESpos): m/z=351 (M+H)$^+$ $^1$H NMR (400 MHz, DMSO-d$_6$) δ=2.40 (s, 3 H), 5.34 (s, 2 H), 5.90 (br. s, 2 H), 6.81-6.93 (m, 2 H), 7.24-7.33 (m, 1 H), 7.60-7.73 (m, 1 H), 8.33 (d, 1 H), 9.79 (s, 1 H).

Example 45A

2-Methyl-8-[(2,3,6-trifluorobenzyl)oxy]imidazo[1,2-a]pyridine-3-carboximidamide

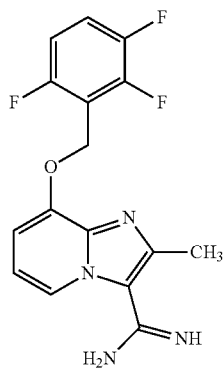

24.18 g (60.74 mmol) of N-hydroxy-2-methyl-8-[(2,3,6-trifluorobenzyl)oxy]imidazo[1,2-a]pyridine-3-carboximidamide from Example 44A were dissolved in 167 ml of acetic acid, 6.59 ml (69.85 mmol) of acetic anhydride were added and the mixture was stirred at RT for 15 min. 39.71 g (607.43 mmol) of zinc dust (<10 μm) were then added with vigorous stirring, and the mixture was stirred at RT for 30 min. The reaction mixture was diluted with 170 ml of water, resulting in heavy foaming. The solid was filtered off and washed twice with 50 ml of a water/acetic acid (1/1) mixture. With cooling, the filtrate was added dropwise to 733 ml of 33% strength aqueous ammonia solution and stirred at RT for 30 min. The solid formed was filtered off, washed with water and dried under high vacuum overnight. This gave 22.32 g (73% of theory, purity 66%) of the title compound. The filtrate was extracted three times with dichloromethane. The combined organic phases were washed with saturated aqueous sodium chloride solution, dried over sodium sulphate, filtered, concentrated on a rotary evaporator at 40-45° C. and dried under high vacuum overnight. This gave an additional 1.72 g (7% of theory; purity: 81%) of the title compound.

LC-MS (Method 1): $R_t$=0.50 min

MS (ESpos): m/z=335 (M+H)$^+$

Example 46A

8-[(2,6-Difluorobenzyl)oxy]-2-methylimidazo[1,2-a]pyridine-3-carboximidohydrazide

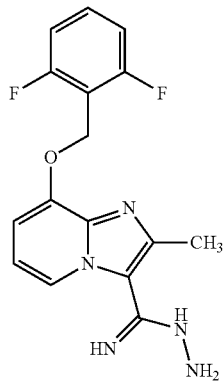 [SMILES: Cc1nc2c(OCc3c(F)cccc3F)cccn2c1C(=N)NN]

456 mg (1.44 mmol) of 8-[(2,6-difluorobenzyl)oxy]-2-methylimidazo[1,2-a]pyridine-3-carboximidamide from Example 22A were initially charged in 12 ml of ethanol, and 0.80 ml (5.77 mmol) of triethylamine and 0.088 ml (1.44 mmol) of hydrazine hydrate (80%) were added at 0° C. The mixture was stirred initially at 0° C. for 10 min and then overnight at RT. The reaction mixture was concentrated on a rotary evaporator at RT. The residue was dried under high vacuum. This gave 501 mg (105% of theory) of the title compound. The product was used for the next step without further purification.

LC-MS (Method 1): $R_f$=0.51 min

MS (EIpos): m/z=332 [M+H]$^+$

Example 47A

Methyl 2-(3-{8-[(2,6-difluorobenzyl)oxy]-2-methylimidazo[1,2-a]pyridin-3-yl}-5-hydroxy-1,2,4-triazin-6-yl)-2-methylpropanoate

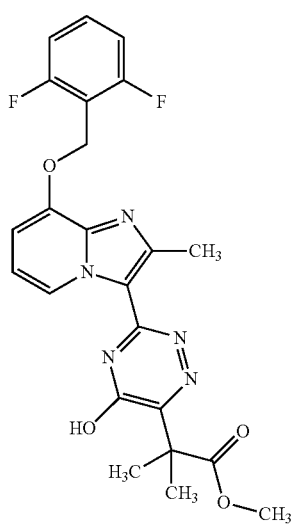 [SMILES: COC(=O)C(C)(C)c1nnc(-c2c(C)nc3c(OCc4c(F)cccc4F)cccn23)nc1O]

0.291 g (1.55 mmol) of dimethyl 2,2-dimethyl-3-oxobutanedioate (described in C. J. A. Daley et al. J. Am. Chem. Soc. 2002, 124(14), 3680-3691) was initially charged in 7 ml of ethanol and heated to reflux. A suspension of 0.341 g (1.03 mmol) of 8-[(2,6-difluorobenzyl)oxy]-2-methylimidazo[1,2-a]pyridine-3-carboximidohydrazide from Example 46A in 15 ml of ethanol was added dropwise thereto. The mixture was stirred under reflux overnight. After cooling, the mixture was concentrated and diethyl ether was added to the residue. The precipitate formed was filtered off, washed with diethyl ether and dried under high vacuum. This gave 0.407 g (45% of theory; purity about 54%) of the title compound (crude) which was used for the subsequent step without further purification.

LC-MS (Method 1): $R_f$=0.86 min

MS (EIpos): m/z=470 [M+H]$^+$

Example 48A

Methyl 2-(5-chloro-3-{8-[(2,6-difluorobenzyl)oxy]-2-methylimidazo[1,2-a]pyridin-3-yl}-1,2,4-triazin-6-yl)-2-methylpropanoate

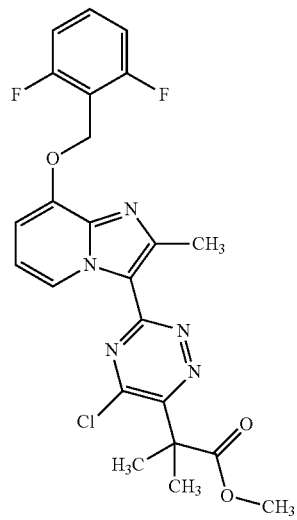 [SMILES: COC(=O)C(C)(C)c1nnc(-c2c(C)nc3c(OCc4c(F)cccc4F)cccn23)nc1Cl]

6.0 ml of phosphoryl chloride were added to 450 mg (0.52 mmol; purity about 54%) of methyl 2-(3-{8-[(2,6-difluorobenzyl)oxy]-2-methylimidazo[1,2-a]pyridin-3-yl}-5-hydroxy-1,2,4-triazin-6-yl)-2-methylpropanoate from Example 47A, and the mixture was stirred at RT overnight. The mixture was then stirred at 50° C. for 7 h. The reaction mixture was used without any further purification for the subsequent reaction.

LC-MS (Method 1): $R_f$=1.20 min

MS (EIpos): m/z=488 [M+H]$^+$.

Example 49A

8-[(2,6-Difluorobenzyl)oxy]-2,6-dimethylimidazo[1,2-a]pyridine-3-carboximidohydrazide

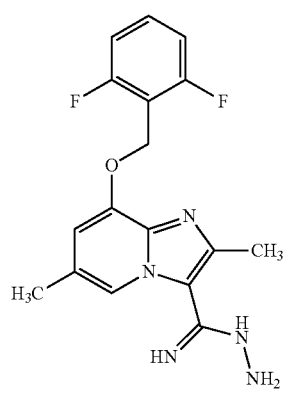

600 mg (1.82 mmol) of 8-[(2,6-difluorobenzyl)oxy]-2,6-dimethylimidazo[1,2-a]pyridine-3-carboximidamide from Example 27A were initially charged in 15 ml of ethanol, and 2.03 ml (14.53 mmol) of triethylamine and 0.22 ml (3.63 mmol) of hydrazine hydrate (80%) were added. The mixture was stirred at 50° C. overnight. The reaction mixture was concentrated on a rotary evaporator at RT. The residue was dried under high vacuum. This gave 581 mg (109% of theory) of the title compound. The product was used for the next step without further purification.

LC-MS (Method 1): $R_t$=0.55 min

MS (EIpos): m/z=346 [M+H]$^+$

Example 50A

Methyl 2-(3-{8-[(2,6-difluorobenzyl)oxy]-2,6-dimethylimidazo[1,2-a]pyridin-3-yl}-5-hydroxy-1,2,4-triazin-6-yl)-2-methylpropanoate

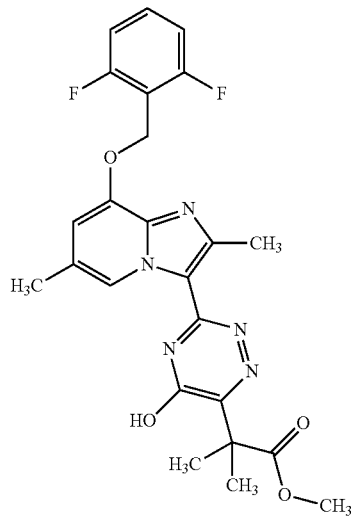

0.514 g (2.73 mmol) of dimethyl 2,2-dimethyl-3-oxobutanedioate (described in C. J. A. Daley et al. J. Am. Chem. Soc. 2002, 124(14), 3680-3691) was initially charged in 13 ml of ethanol and heated to reflux. A suspension of 0.629 g (1.82 mmol) of 8-[(2,6-difluorobenzyl)oxy]-2,6-dimethylimidazo[1,2-a]pyridine-3-carboximidohydrazide from Example 49A in 27 ml of ethanol was added dropwise thereto, and the mixture was stirred under reflux overnight. After cooling, the mixture was concentrated. Diethyl ether was added to the residue, and the precipitate formed was stirred at RT for 30 min, filtered off, washed with diethyl ether and dried under high vacuum. This gave 0.713 g (81% of theory) of the title compound which was used for the next step without further purification.

LC-MS (Method 1): $R_t$=0.89 min

MS (EIpos): m/z=484 [M+H]$^+$

Example 51A

Methyl 2-(5-chloro-3-{8-[(2,6-difluorobenzyl)oxy]-2,6-dimethylimidazo[1,2-a]pyridin-3-yl}-1,2,4-triazin-6-yl)-2-methylpropanoate

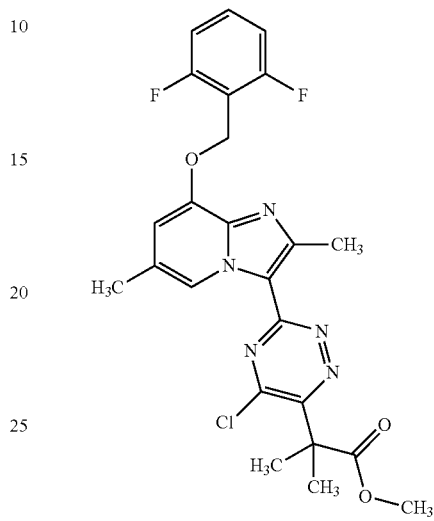

8.5 ml of phosphoryl chloride were added to 658 mg (1.36 mmol) of methyl 2-(3-{8-[(2,6-difluorobenzyl)oxy]-2,6-dimethylimidazo[1,2-a]pyridin-3-yl}-5-hydroxy-1,2,4-triazin-6-yl)-2-methylpropanoate from Example 50A, and the mixture was stirred at RT overnight. The reaction mixture was used without any further purification for the subsequent reaction.

LC-MS (Method 1): $R_t$=1.27 min

MS (EIpos): m/z=502 [M+H]$^+$.

Example 52A

2-Amino-3-fluoro-2-(fluoromethyl)propanonitrile

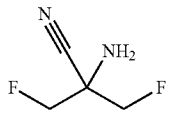

8.75 g (178.6 mmol) of sodium cyanide were initially charged in 132 ml of 2N ammonia solution in methanol. 15.0 g (159.5 mmol) of 1,3-difluoroacetone and 9.55 g (178.6 mmol) of ammonium chloride were added at RT. The suspension was stirred at an oil bath temperature of 70° C. for 2 h. 300 ml of diethyl ether were added to the cooled reaction mixture, the mixture was stirred for 10 min and the solid was filtered off. The filtrate was concentrated under reduced pressure (50° C., 70 mbar). This gave 19.2 g (100% of theory) of the target compound. The product was converted further without further purification.

GC-MS (Method 14): $R_t$=1.78 min

MS (ESpos): m/z=121 (M+H)$^+$

Example 53A

Benzyl (2-cyano-1,3-difluoropropan-2-yl)carbamate

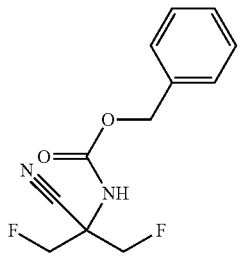 [SMILES: N#CC(CF)(CF)NC(=O)OCc1ccccc1]

5.0 g (41.6 mmol) of 2-amino-3-fluoro-2-(fluoromethyl)propanonitrile from Example 52A were initially charged in 14.5 ml (83.3 mmol) of N,N-diisopropylethylamine. 10.65 g (62.5 mmol) of benzyl chloroformate were slowly added dropwise at RT and the mixture was stirred at RT for three days. The reaction mixture was diluted with 25 ml of dichloromethane and, at 0° C., added dropwise to a solution of 12.9 g (124.9 mmol) of N-(2-aminoethyl)ethane-1,2-diamine in 225 ml of dichloromethane, and the mixture was stirred for 10 min. 200 ml of saturated ammonium chloride solution were then added dropwise at RT. The phases were separated and the aqueous phase was extracted three times with dichloromethane. The combined organic phases were concentrated. The crude product was subsequently chromatographed on silica gel (mobile phase: cyclohexane:ethyl acetate gradient). This gave 4.40 g (42% of theory) of the title compound.

GC-MS (Method 1): $R_t$=0.92 min
MS (ESpos): m/z=255 (M+H)$^+$

Example 54A

Benzyl tert-butyl-[3-fluoro-2-(fluoromethyl)propane-1,2-diyl]biscarbamate

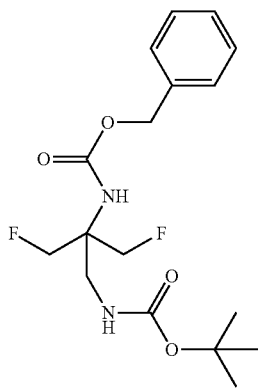 [SMILES: CC(C)(C)OC(=O)NCC(CF)(CF)NC(=O)OCc1ccccc1]

3.28 g (12.90 mmol) of benzyl (2-cyano-1,3-difluoropropan-2-yl)carbamate from Example 53A were initially charged in 52 ml of abs. ethanol at RT. 2.44 g (64.5 mmol) of sodium borohydride were added in portions at RT, and the mixture was stirred at RT for 2.5 h. A solution of 3.66 g (16.77 mmol) of di-tert-butyl dicarbonate in 37 ml of abs. ethanol was then slowly added dropwise at RT, and stirring was then continued for 30 min. A further 281 mg (1.29 mmol) of di-tert-butyl dicarbonate were added, and the mixture was stirred for 15 min. 100 ml of saturated ammonium chloride solution were added to the reaction mixture, and the mixture was adjusted to a pH of about 4 using about 45 ml of 1 N aqueous hydrochloric acid. The reaction mixture was freed from ethanol under reduced pressure, and water was then added. The solid formed was filtered off, washed with water and dried under high vacuum. This gave 3.37 g (73% of theory) of the title compound.

GC-MS (Method 1): $R_t$=1.07 min
MS (ESpos): m/z=359 (M+H)$^+$

Example 55A

Benzyl [1-amino-3-fluoro-2-(fluoromethyl)propan-2-yl]carbamate

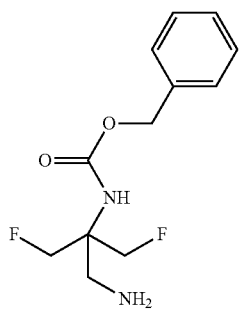 [SMILES: NCC(CF)(CF)NC(=O)OCc1ccccc1]

5 ml of dichloromethane and 2 ml of trifluoroacetic acid were added to 1.00 g (2.79 mmol) of benzyl tert-butyl-[3-fluoro-2-(fluoromethyl)propan-1,2-diyl]biscarbamate from Example 54A and the mixture was stirred at RT for 30 min. The reaction mixture was concentrated under reduced pressure. Saturated aqueous sodium bicarbonate solution (pH 8-9) was added to the residue and the mixture was extracted four times with dichloromethane. The combined organic phases were washed once with saturated sodium chloride solution, dried over sodium sulphate, concentrated at 25° C. and dried under high vacuum. This gave 745 mg of the title compound (103% of theory). The product was converted further without further purification.

GC-MS (Method 22): $R_t$=1.98 min
MS (ESpos): m/z=259 (M+H)$^+$

Example 56A

3-Fluoro-2-(fluoromethyl)propane-1,2-diamine

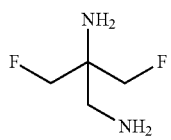

89 mg (0.344 mmol) of benzyl [1-amino-3-fluoro-2-(fluoromethyl)propan-2-yl]carbamate from Example 55A were initially charged in 0.38 ml of 1-methyl-2-pyrrolidone, and 22 mg of 10% palladium on activated carbon were added under argon. The reaction mixture was hydrogenated at RT and under standard pressure for 4 h. The reaction mixture was filtered through a PTFE syringe filter (0.45 µm) and the filter was then washed with 0.2 ml of 1-methyl-2-pyrrolidone. The combined solutions were used directly for the next reaction.

Example 57A rac-Benzyl 4-amino-3,3-difluoropyrrolidine-1-carboxylate (racemate)

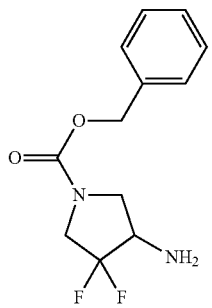 [SMILES: NC1CN(C(=O)OCc2ccccc2)CC1(F)F]

500 mg (1.77 mmol) of benzyl 4-azido-3,3-difluoropyrrolidine-1-carboxylate (WO 2011088045) were initially charged in 1.25 ml of THF and 0.25 ml of water. With ice bath cooling, 8.9 ml of trimethylphosphine (1 M solution in THF) were slowly added dropwise, and the mixture was stirred at RT for 15 min. Saturated aqueous sodium bicarbonate solution was added and the reaction mixture was freed from THF under reduced pressure and at 30° C. The residue was extracted three times with ethyl acetate. The combined organic phases were washed once with saturated sodium chloride solution, dried over sodium sulphate and concentrated. The residue was separated on a silica gel column (mobile phase: pure cyclohexane; cyclohexane/ethyl acetate gradient). This gave 372 mg (82% of theory) of the title compound.

LC-MS (Method 22): $R_t$=1.98 min
MS (ESpos): m/z=257 (M+H)$^+$

Example 58A rac-4,4-Difluoropyrrolidine-3-amine (racemate)

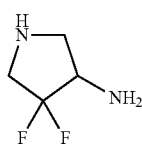

90 mg (0.35 mmol) of benzyl 4-amino-3,3-difluoropyrrolidine-1-carboxylate from Example 57A were initially charged in 0.39 ml of 1-methyl-2-pyrrolidone, and 22 mg of 10% palladium on activated carbon were added under argon. The reaction mixture was hydrogenated at RT and under standard pressure for 2 h. The reaction mixture was filtered through a PTFE syringe filter (0.45 µm) and the filter was then washed with 0.2 ml of 1-methyl-2-pyrrolidone. The combined solutions were used directly for the next reaction.

Example 59A

3-Azabicyclo[3.1.0]hexan-1-amine dihydrochloride

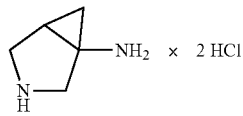

The synthesis to form the title compound is described in: M. Gensini et al., Eur. J. Org. Chem. 2002, 2499-2507.

Example 60A rac-2-{[1,1-Difluoropropan-2-ylidene]amino}-2-phenylethanol (racemate)

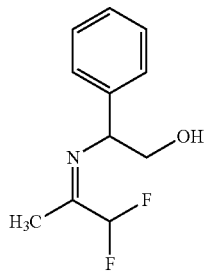

Under argon, 8.0 g (85.05 mmol) of 1,1-difluoroacetone were initially charged in 90.6 ml of dichloromethane, and 2 g of magnesium sulphate and 2 g of 4 Å molecular sieve (powder) were added. After addition of 12.02 g (87.60 mmol) of rac-2-amino-2-phenylethanol, the mixture was stirred under reflux overnight. The mixture was filtered off through Celite, washing with dichloromethane. The filtrate was concentrated and dried. Silica gel chromatography was carried out (mobile phase: cyclohexane/ethyl acetate gradient). This gave 9.6 g (53% of theory) of the target compound.

LC-MS (Method 22): $R_t$=2.20 min
MS (ESIpos): m/z=214 (M+H)$^+$.

Example 61A 3,3-Difluoro-2-[(2-hydroxy-1-phenylethyl)amino]-2-methylpropanenitrile (diastereomers)

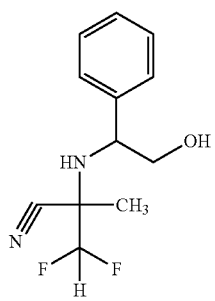 [SMILES: CC(C#N)(NC(CO)c1ccccc1)C(F)F]

Under argon, 9.6 g (45.02 mmol) of rac-2-{[1,1-difluoropropan-2-ylidene]amino}-2-phenylethanol from Example 60A were initially charged in 116 ml of ethanol, 14.01 ml (112.55 mmol) of trimethylsilyl cyanide were added and the mixture was stirred under reflux for 16 h. Another 10 ml (80.39 mmol) of trimethylsilyl cyanide were then added, and the mixture was stirred under reflux for a further 16 h. The reaction solution was cooled to RT and concentrated, and three times in each case 100 ml of toluene were added and the mixture was concentrated. Purification was carried out by preparative SFC [ethylpyridine-SFC, 5 μm, 125×30 mm; mobile phase: carbon dioxide/methanol gradient; flow rate: 100 ml/min; wavelength: 220 nm; temperature: 40° C.]. This gave 6.97 g (64% of theory) of the target compound.

LC-MS (Method 1): $R_t$=0.86 min and 0.90 min.
MS (ESIneg): m/z=241 (M+H)$^+$.

Example 62A

2-[(3-Amino-1,1-difluoro-2-methylpropan-2-yl)amino]-2-phenylethanol trifluoroacetate (diastereomers)

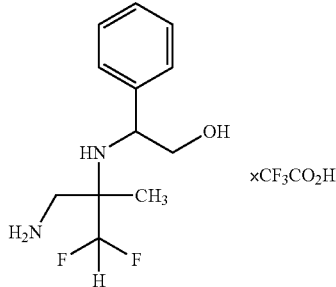 [SMILES: CC(CN)(NC(CO)c1ccccc1)C(F)F]

1.0 g (4.16 mmol) of 3,3-difluoro-2-[(2-hydroxy-1-phenylethyl)amino]-2-methylpropanonitrile (diastereomers) from Example 61A were initially charged in 100 ml of tert-butyl methyl ether, the mixture was cooled to 0° C., 197 mg (5.20 mmol) of lithium aluminium hydride were added and the mixture was stirred at RT for 16 h. Subsequently, the mixture was cooled to 0° C., and first 416 μl of water and then 416 μl of 2 N aqueous sodium hydroxide solution and 832 μl of water were added. The resulting mixture was filtered through Celite, washing with tert-butyl methyl ether and a little methanol. The filtrate was concentrated, acetonitrile/water/TFA were added to the residue and the product was purified by preparative HPLC (RP18 column, mobile phase: acetonitrile/water gradient with addition of 0.1% TFA). This gave 866 mg (58% of theory) of the target compounds.

LC-MS (Method 1): $R_t$=0.44 min and 0.46 min.
MS (ESIpos): m/z=245 (M−TFA+H)$^+$.

Example 63A rac-3,3-Difluoro-2-methylpropane-1,2-diamine (racemate)

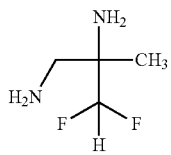

82 mg (0.336 mmol) of rac-2-[(3-amino-1,1-difluoro-2-methylpropan-2-yl)amino]-2-phenylethanol from Example 62A were washed with saturated aqueous sodium bicarbonate solution and extracted with methyl tert-butyl ether. The organic phases were combined, dried and concentrated. The free amine was then initially charged in 0.33 ml of 1-methyl-2-pyrrolidone, and 71 mg of 10% palladium on activated carbon were added under argon. The reaction mixture was hydrogenated at RT and under standard pressure over the weekend. The reaction mixture was filtered through a PTFE syringe filter (0.45 μm). The filter was washed with 0.2 ml of 1-methyl-2-pyrrolidone. The combined solutions were used directly for the next reaction.

Example 64A

2-Methyl-4-phenyl-2-(trifluoromethyl)-1,3-oxazolidine (diastereomers)

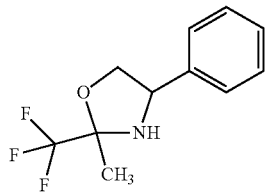 [SMILES: CC1(C(F)(F)F)NC(c2ccccc2)CO1]

45 g (328.0 mmol) of rac-2-amino-2-phenylethanol and 8.24 g (32.8 mmol) of pyridinium p-toluenesulphonate were added to 55.13 g (492.0 mmol) of 1,1,1-trifluoroacetone in toluene (1.35 l). The reaction mixture was heated under reflux on a water separator for 16 h. The mixture was cooled to 0° C., and the solid formed was filtered off and dried under high vacuum. This gave 68.6 g (77% of theory, purity 85%) of the target compound.

LC-MS (Method 1): $R_t$=0.99 min
MS (ESIpos): m/z=232 (M+H)$^+$.
$^1$H-NMR (400 MHz, DMSO-d$_6$): δ=1.54 (s, 3H), 3.56 (t, 1H), 3.81 (d, 1H), 4.28 (t, 1H), 4.35-4.43 (m, 1H), 7.29-7.47 (m, 5H).

Example 65A 3,3,3-Trifluoro-2-[(2-hydroxy-1-phenylethyl)amino]-2-methylpropanonitrile (diastereomers)

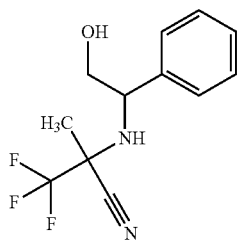 [SMILES: CC(C#N)(NC(CO)c1ccccc1)C(F)(F)F]

52.8 g (228.3 mmol) of 2-methyl-4-phenyl-2-(trifluoromethyl)-1,3-oxazolidine (diastereomers) from Example 64A were initially charged under argon in dichloromethane (2 l) and cooled to 0° C. 42.85 ml (342.5 mmol) of trimethylsilyl cyanide and 42.1 ml (342.5 mmol) of boron trifluoride-diethyl ether complex were added gradually and the mixture was stirred at RT for 16 h. Subsequently, the reaction solution was poured into 1.5 l of saturated sodium bicarbonate solution. 400 g of sodium bicarbonate were then added, and the solution was adjusted to pH 10 with conc. aqueous sodium hydroxide solution. The aqueous solution was extracted three times with 500 ml of dichloromethane, and the combined organic phases were dried over sodium sulphate, filtered off and concentrated. This gave 56.8 g (96% of theory, 2 diastereomers) of the target compound.

LC-MS (Method 1): $R_t$=0.89 min and 0.93 min.
MS (ESIneg): m/z=303 (M−H+HCOOH)⁻.

Example 66A

2-[(3-Amino-1,1,1-trifluoro-2-methylpropan-2-yl)amino]-2-phenylethanol (diastereomers)

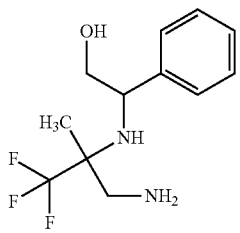 [SMILES: CC(CN)(NC(CO)c1ccccc1)C(F)(F)F]

31 g (120.0 mmol) of 3,3,3-trifluoro-2-[(2-hydroxy-1-phenylethyl)amino]-2-methylpropanonitrile from Example 65A were initially charged in tert-butyl methyl ether (3.1 l) and cooled to 0° C., 18.25 g (480.2 mmol) of lithium aluminium hydride were added and the reaction mixture was stirred at RT for 16 h. Subsequently, the mixture was cooled to 0° C., first quenched with 24 ml of water, then admixed with 24 ml of 15% aqueous potassium hydroxide solution and 48 ml of water. The resulting mixture was filtered through silica gel and washed with tert-butyl methyl ether. The organic phase was separated off, dried over sodium sulphate, filtered and concentrated. This gave 29.2 g (83% of theory, purity 89%) of the target compound.

LC-MS (Method 1): $R_t$=0.52 min
MS (ESIpos): m/z=263 (M+H)⁺.

Example 67A tert-Butyl {3,3,3-trifluoro-2-[(2-hydroxy-1-phenylethyl)amino]-2-methylpropyl}carbamate (diastereomers)

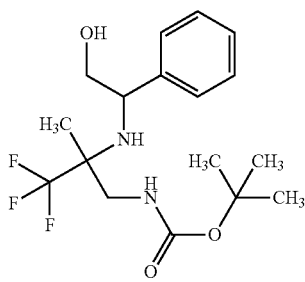 [SMILES: CC(C)(C)OC(=O)NCC(C)(NC(CO)c1ccccc1)C(F)(F)F]

29.1 ml (209.8 mmol) of triethylamine and 23.98 g (109.9 mmol) of di-tert-butyl dicarbonate (dissolved in 286 ml of THF) were added to 26.2 g (99.9 mmol) of 2-[(3-amino-1,1,1-trifluoro-2-methylpropan-2-yl)amino]-2-phenylethanol (diastereomers) from Example 66A in THF (500 ml). The reaction mixture was stirred at RT for 16 h. Subsequently, the reaction mixture was concentrated and taken up in 500 ml each of saturated aqueous sodium bicarbonate solution and ethyl acetate. The phases were separated and the organic phase was dried over sodium sulphate, filtered off and concentrated. This gave 39.80 g (110% of theory) of the target compound, which were used for the next step without further purification.

FIA-MS (Method 25, ESpos): m/z=363 (M+H)⁺

Example 68A rac-tert-Butyl (2-amino-3,3,3-trifluoro-2-methylpropyl)carbamate

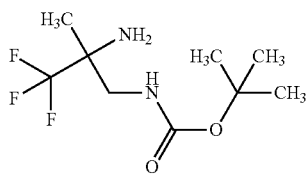 [SMILES: CC(C)(C)OC(=O)NCC(C)(N)C(F)(F)F]

39 g (107.6 mmol) of tert-butyl-{3,3,3-trifluoro-2-[(2-hydroxy-1-phenylethyl)amino]-2-methylpropyl}carbamate from Example 67A were initially charged under argon in ethanol (700 ml), and 5.44 g (53.8 mmol) of palladium(II) hydroxide (20% on activated carbon, water-moist, about 60%) were added. The reaction mixture was hydrogenated at standard pressure for 16 h. Then the reaction mixture was filtered through silica gel and concentrated. The residue was purified by silica gel chromatography (cyclohexane/ethyl acetate gradient: 9/1 to 6/4). This gave 15.8 g (61% of theory) of the target compound.

FIA-MS (Method 25, ESpos): m/z=243 (M+H)⁺
¹H-NMR (400 MHz, CDCl₃): δ=1.22 (s, 3H), 1.45 (s, 9H), 3.13-3.23 (m, 1H), 3.37-3.48 (m, 1H), 4.89 (br. s, 1H).

Example 69A rac-3,3,3-Trifluoro-2-methylpropane-1,2-diamine dihydrochloride

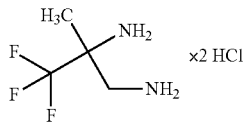

15 g (61.9 mmol) of rac-tert-butyl (2-amino-3,3,3-trifluoro-2-methylpropyl)carbamate from Example 68A in dioxane (188 ml) were admixed with 188 ml of 4 M hydrogen chloride in dioxane. The reaction mixture was stirred at RT for 16 h, then concentrated and stored under argon. This gave 14.4 g (108% of theory) of the target compound, which was not purified any further.

FIA-MS (Method 25, ESpos): m/z=143 (M−2HCl+H)⁺
¹H-NMR (400 MHz, D₂O): δ=1.40 (s, 3H), 3.21-3.31 (m, 2H).

WORKING EXAMPLES

Example 1

4-Amino-2-{8-[(2,6-difluorobenzyl)oxy]-2-methyl-imidazo[1,2-a]pyridin-3-yl}-5,5-dimethyl-5,7-dihydro-6H-pyrrolo[2,3-d]pyrimidin-6-one

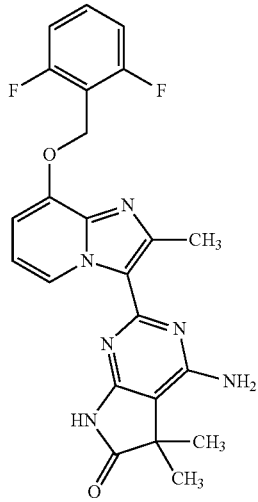 [SMILES: Cc1nc2c(OCc3c(F)cccc3F)cccn2c1-c1nc(N)c2c(n1)NC(=O)C2(C)C]

Under argon, 135 mg of 8-[(2,6-difluorobenzyl)oxy]-2-methylimidazo[1,2-a]pyridine-3-carboximidamide (Example 22A, 0.42 mmol, 1 equivalent) were initially charged in 8 ml of tert-butanol, 71.8 mg of potassium tert-butoxide (0.64 mmol, 1.5 equivalents) and 85 mg of methyl 3,3-dicyano-2,2-dimethylpropanoate (Example 28A, 0.51 mmol, 1.2 equivalents) in 2 ml of tert-butanol were added successively at RT and the mixture was heated at reflux overnight. The mixture was then cooled, water was added and the mixture was stirred at RT for 10 min. The solid formed was filtered off with suction, washed with water and dried under reduced pressure overnight. This gave 117.6 mg (61% of theory) of the title compound.

LC-MS (Method 1): $R_t$=0.73 min

MS (ESpos): m/z=451 (M+H)$^+$ $^1$H-NMR (400 MHz, DMSO-d$_6$): δ=1.35 (s, 6 H), 2.73 (s, 3 H), 5.31 (s, 2 H), 6.72 (br. s, 2 H), 6.92 (t, 1 H), 7.00 (d, 1 H), 7.24 (t, 2 H), 7.53-7.65 (m, 1 H), 9.67 (d, 1 H), 10.89 (s, 1 H).

Example 2

2-{8-[(2,6-Difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one

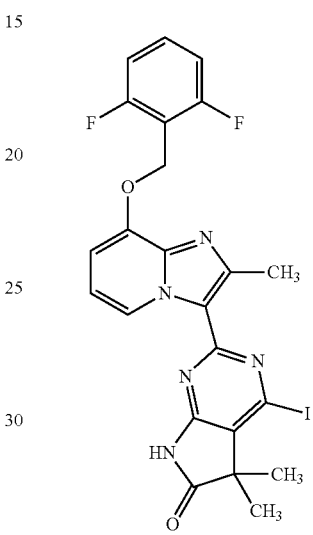

Under argon, 15.0 g (33.30 mmol) of 4-amino-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one from Example 1 were stirred together with 53.69 g (200.47 mmol) of diiodomethane and 23.48 g (200.47 mmol) of isopentyl nitrite in 268 ml of abs. 1,4-dioxane at 85° C. overnight. 15.34 g (57.28 mmol) of diiodomethane and 6.70 g (57.28 mmol) of isopentyl nitrite were added and the mixture was stirred at 85° C. overnight. Another 7.67 g (28.64 mmol) of diiodomethane and 3.35 g (28.64 mmol) of isopentyl nitrite were added and the mixture was stirred at 85° C. overnight. The reaction solution was concentrated and the residue was dissolved in dichloromethane and purified by silica gel chromatography (dichloromethane; dichloromethane/methanol=75:1 to 30:1). This gave 9.07 g (48% of theory) of the title compound.

LC-MS (Method 1): $R_t$=1.04 min

MS (ESpos): m/z=562 (M+H)$^+$ $^1$H NMR (400 MHz, DMSO-d$_6$) δ=1.41 (s, 6 H), 2.71 (s, 3 H), 5.34 (s, 2 H), 5.76 (s, 1 H), 7.06-7.14 (m, 2 H), 7.24 (t, 2 H), 7.56-7.65 (m, 1 H), 9.41 (d, 1 H), 11.68 (s, 1 H).

Example 3

2-{8-[(2,6-Difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one trifluoroacetate

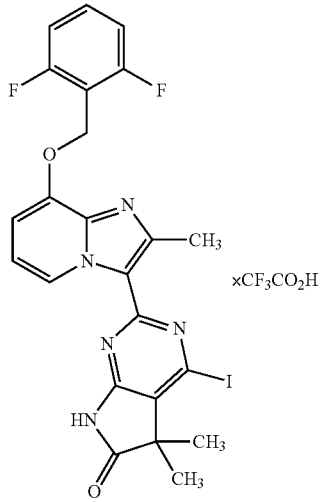 [SMILES: Cc1nc2c(OCc3c(F)cccc3F)cccn2c1-c1nc(I)c2c(n1)NC(=O)C2(C)C]

Under argon, 4.0 g (8.88 mmol) of 4-amino-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one from Example 1 were initially charged together with 11.13 g (41.56 mmol) of diiodomethane and 4.87 g (41.56 mmol) of isopentyl nitrite in 73 ml of abs. 1,4-dioxane, and the mixture was stirred at 85° C. overnight. The reaction solution was concentrated, dissolved in acetonitrile/water/TFA and purified by preparative HPLC (RP18 column, mobile phase: acetonitrile/water gradient with addition of 0.1% TFA). This gave 2.45 g (38% of theory; purity about 93%) of the title compound.

LC-MS (Method 1): $R_t$=1.05 min
MS (ESpos): m/z=562 (M−TFA+H)$^+$

Example 4

4-Chloro-2-{8-[(2,6-difluorobenzyl)oxy]-2-methyl-imidazo[1,2-a]pyridin-3-yl}-5,5-dimethyl-5,7-dihydro-6H-pyrrolo[2,3-d]pyrimidin-6-one

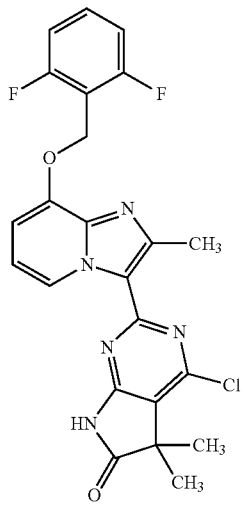 [SMILES: Cc1nc2c(OCc3c(F)cccc3F)cccn2c1-c1nc(Cl)c2c(n1)NC(=O)C2(C)C]

Under argon, 500 mg (1.11 mmol) of 4-amino-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one from Example 1 were initially charged together with 746 mg (5.55 mmol) of copper(II) chloride and 195 mg (1.67 mmol) of isopentyl nitrite in 20 ml of abs. acetonitrile, and the mixture was stirred at 85° C. for 5 h. 2.22 ml of 1 N aqueous hydrochloric acid were added and the mixture was then extracted three times with ethyl acetate. The phases were separated and the aqueous phase was extracted twice more with ethyl acetate. The combined organic phases were washed with saturated aqueous sodium chloride solution, dried over sodium sulphate, filtered and concentrated. The residue was dissolved in acetonitrile/water/TFA and purified by preparative HPLC (RP18 column, mobile phase: acetonitrile/water gradient with addition of 0.1% TFA). The product fractions were concentrated, dissolved in dichloromethane and a little methanol and washed twice with saturated aqueous sodium bicarbonate solution. The combined organic phases were reextracted twice with dichloromethane. The combined organic phases were dried over sodium sulphate, filtered and concentrated. This gave 158 mg (30% of theory) of the title compound.

LC-MS (Method 1): $R_t$=1.05 min
MS (ESpos): m/z=470 (M+H)$^+$
$^1$H NMR (400 MHz, DMSO-$d_6$) δ=1.45 (s, 6 H), 2.79 (s, 3 H), 5.43 (s, 2 H), 7.26 (t, 2 H), 7.34-7.43 (m, 1 H), 7.45-7.52 (m, 1 H), 7.56-7.68 (m, 1 H), 9.52 (d, 1 H), 11.96 (s, 1 H).

Example 5

2-{8-[(2,6-Difluorobenzyl)oxy]-2-methylimidazo[1,2-a]pyridin-3-yl}-4-hydroxy-5,5-dimethyl-5,7-dihydro-6H-pyrrolo[2,3-d]pyrimidin-6-one trifluoroacetate

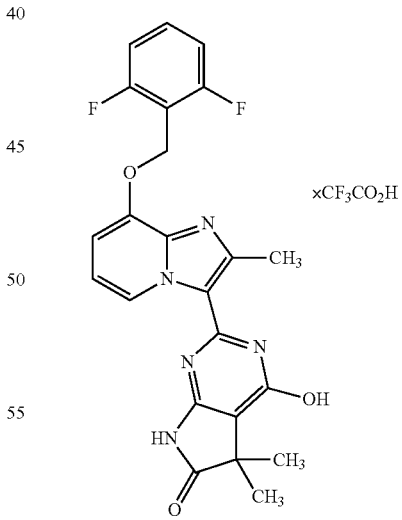

100 mg (0.21 mmol) of 4-amino-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one from Example 1 were dissolved in 0.84 ml of TFA. At 0° C., 0.09 ml (5.19 mmol) of water and 21.5 mg (0.31 mmol) of sodium nitrite were added and the solution was stirred at 0° C. for 5 min. The reaction mixture was added to 3.5 ml of water. The precipitate formed was filtered off, washed with water and dried under high vacuum. This gave 121 mg (99% of theory) of the title compound.

LC-MS (Method 1): $R_t$=0.75 min

MS (ESpos): m/z=452 (M−TFA+H)$^+$ $^1$H NMR (400 MHz, DMSO-$d_6$) δ=1.34 (s, 6 H), 5.43 (br. s, 2 H), 7.18-7.68 (m, 5 H), 9.82 (br. s, 1 H), 11.32 (br. s, 1 H), 12.18 (br. s, 1 H) [further signal under solvent peaks].

Example 6 rac-4-Amino-2-{8-[(2,6-difluorobenzyl)oxy]-2-methylimidazo[1,2-a]pyridin-3-yl}-5-methyl-5-(trifluoromethyl)-5,7-dihydro-6H-pyrrolo[2,3-d]pyrimidin-6-one (racemate)

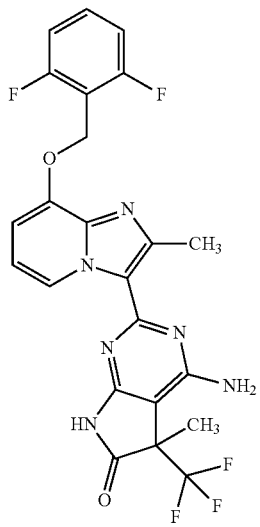 [SMILES: Cc1nc2c(OCc3c(F)cccc3F)cccn2c1-c1nc(N)c2c(n1)NC(=O)C2(C)C(F)(F)F]

Under argon, 1.39 g (3.69 mmol) of 8-[(2,6-difluorobenzyl)oxy]-2-methylimidazo[1,2-a]pyridine-3-carboximidamide acetate (Example 24A) were initially charged in 47.5 ml of tert-butanol, 621 mg (5.53 mmol) of potassium tert-butoxide and 974 mg (4.43 mmol) of methyl 2-(dicyanomethyl)-3,3,3-trifluoro-2-methylpropanoate (Example 36A; racemate) in 16 ml of tert-butanol were added successively at RT and the mixture was heated at reflux overnight. The mixture was then cooled and concentrated. Water was added to the residue and the mixture was stirred at RT for 10 min. The precipitate formed was filtered, washed with water and dried under reduced pressure overnight. This gave 1.6 g (77% of theory; purity: 90%) of the title compound.

LC-MS (Method 1): $R_t$=0.82 min

MS (ESpos): m/z=505 (M+H)$^+$ $^1$H NMR (500 MHz, DMSO-$d_6$) δ=1.11 (s, 1 H), 1.72 (s, 3 H), 2.74 (s, 3 H), 5.28-5.38 (m, 2 H), 6.82-6.99 (m, 3 H), 7.04 (d, 1 H), 7.19-7.29 (m, 3 H), 7.53-7.64 (m, 1 H), 9.71 (d, 1 H).

Example 7 rac-2-{8-[(2,6-Difluorobenzyl)oxy]-2-methylimidazo[1,2-a]pyridin-3-yl}-4-iodo-5-methyl-5-(trifluoromethyl)-5,7-dihydro-6H-pyrrolo[2,3-d]pyrimidin-6-one trifluoroacetate (racemate)

Under argon, 1.50 g (2.68 mmol; purity 90%) of rac-4-amino-2-{8-[(2,6-difluorobenzyl)oxy]-2-methylimidazo[1,2-a]pyridin-3-yl}-5-methyl-5-(trifluoromethyl)-5,7-dihydro-6H-pyrrolo[2,3-d]pyrimidin-6-one (racemate) from Example 6, 3.58 g (13.38 mmol) of diiodomethane and 1.57 g (13.38 mmol) of isopentyl nitrite were initially charged in 23.4 ml of abs. 1,4-dioxane, and the mixture was stirred at 85° C. overnight. The reaction solution was concentrated, the residue was dissolved in acetonitrile/water/TFA and purified by preparative HPLC (RP18 column, mobile phase: acetonitrile/water gradient with addition of 0.1% TFA). This gave 0.65 g (29% of theory; purity about 86%) of the title compound.

LC-MS (Method 1): $R_t$=1.17 min

MS (ESpos): m/z=616 (M−TFA+H)$^+$

Example 8 rac-2-{8-[(2,6-Difluorobenzyl)oxy]-2-methylimidazo[1,2-a]pyridin-3-yl}-4-hydroxy-5-methyl-5-(trifluoromethyl)-5,7-dihydro-6H-pyrrolo[2,3-d]pyrimidin-6-one trifluoroacetate

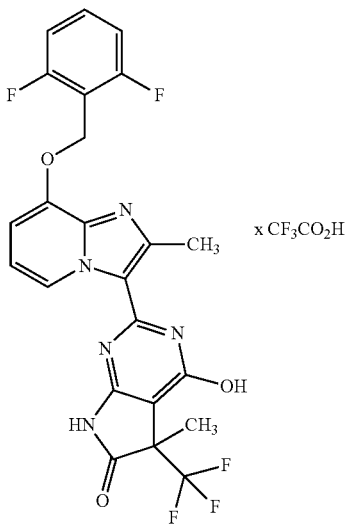 [SMILES: Cc1nc2c(OCc3c(F)cccc3F)cccn2c1-c1nc(O)c2c(n1)NC(=O)C2(C)C(F)(F)F]

The target compound was formed as a by-product in the preparation of Example 7. This gave 135 mg (8% of theory) of the title compound.

LC-MS (Method 1): $R_t$=0.88 min
MS (ESpos): m/z=506 (M−TFA+H)$^+$

Example 9

4-Amino-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one

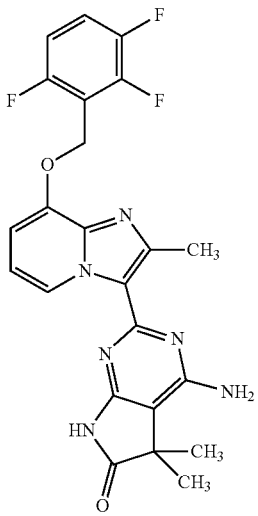 [SMILES: Cc1nc2c(OCc3c(F)ccc(F)c3F)cccn2c1-c1nc(N)c2c(n1)NC(=O)C2(C)C]

Under argon, 7.31 g (15.52 mmol, purity about 71%) of 2-methyl-8-[(2,3,6-trifluorobenzyl)oxy]imidazo[1,2-a]pyridine-3-carboximidamide (Example 45A) were initially charged in 300 ml of tert-butanol, 1.25 ml (21.86 mmol) of acetic acid, 3.68 g (32.79 mmol) of potassium tert-butoxide and 4.36 g (26.23 mmol) of methyl 3,3-dicyano-2,2-dimethylpropanoate (Example 28A) in 10 ml of tert-butanol were added successively at RT and the mixture was heated under reflux overnight. The mixture was then cooled, and 700 ml of water were added. The precipitate formed was filtered off, washed with water and dried under reduced pressure overnight. In order to remove the residual amount of water, the solid was suspended in acetonitrile using ultrasound for 1 h, concentrated on a rotary evaporator and dried under high vacuum overnight. This gave 6.20 g (79% of theory; purity: 92%) of the title compound.

LC-MS (Method 1): $R_t$=0.71 min
MS (ESpos): m/z=469 (M+H)$^+$
$^1$H NMR (400 MHz, DMSO-d$_6$) δ=1.35 (s, 6 H), 2.74 (s, 3 H), 5.37 (s, 2 H), 6.73 (s, 2 H), 6.91 (t, 1 H), 7.00 (d, 1 H), 7.24-7.35 (m, 1 H), 7.61-7.73 (m, 1 H), 9.69 (d, 1 H), 10.89 (s, 1 H).

Example 10

4-Iodo-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one

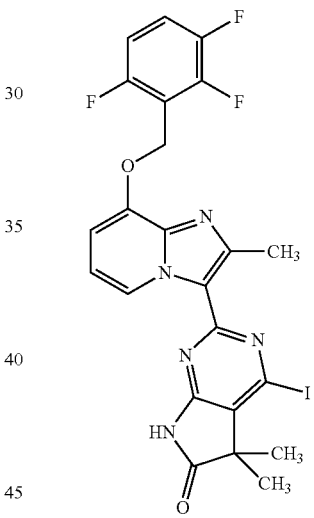

Under argon, 6.00 g (12.81 mmol) of 4-amino-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one from Example 9 were initially charged with 17.15 g (64.04 mmol) of diiodomethane, 7.50 g (64.04 mmol) of isopentyl nitrite and 10 g of activated 4 Å molecular sieve (powder<50 μm) in 120 ml of abs. 1,4-dioxane, and the mixture was stirred at 85° C. for 22 h. 6.86 g (25.62 mmol) of diiodomethane and 3.00 g (25.62 mmol) of isopentyl nitrite were then added and the mixture was stirred at 85° C. for 18 h. The mixture was cooled and the molecular sieve was filtered off. The filter residue was washed with dioxane. The combined filtrates were concentrated on a rotary evaporator and the crude product was purified by silica gel chromatography (dichloromethane; cyclohexane; cyclohexane/ethyl acetate gradient). This gave 4.51 g (56% of theory, purity 92%) of the title compound.

LC-MS (Method 1): $R_t$=1.06 min
MS (ESpos): m/z=580 (M+H)$^+$
$^1$H NMR (400 MHz, DMSO-d$_6$) δ=1.42 (s, 6 H), 2.72 (s, 3 H), 5.39 (s, 2 H), 7.05-7.15 (m, 2 H), 7.25-7.35 (m, 1 H), 7.62-7.74 (m, 1 H), 9.42 (d, 1 H), 11.68 (s, 1 H).

Example 11

4-Hydroxy-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one

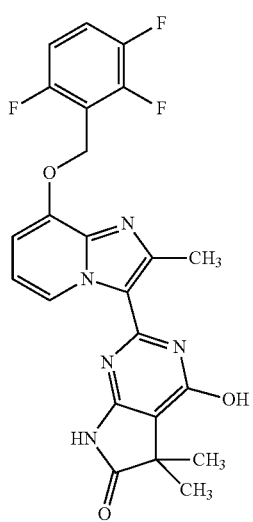 [SMILES: Cc1nc2c(OCc3c(F)ccc(F)c3F)cccn2c1-c1nc(O)c2c(n1)NC(=O)C2(C)C]

The target compound was formed as a by-product in the preparation of Example 10. This gave 693 mg (12% of theory, purity 94%) of the title compound.

LC-MS (Method 1): $R_t$=0.75 min
MS (ESpos): m/z=470 (M+H)$^+$

Example 12

4-[(2-Amino-2-methylpropyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one

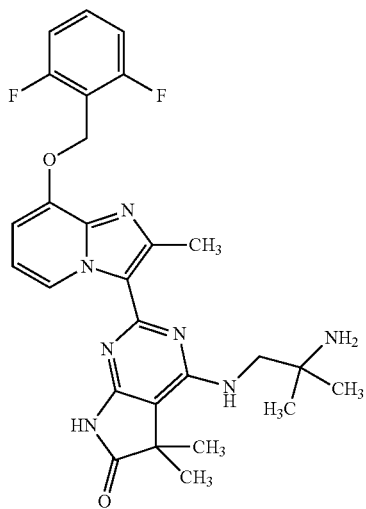 [SMILES: Cc1nc2c(OCc3c(F)cccc3F)cccn2c1-c1nc(NCC(C)(C)N)c2c(n1)NC(=O)C2(C)C]

70 mg (0.10 mmol) of 2-{8-[(2,6-difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one trifluoroacetate from Example 3 were initially charged in 1.1 ml of NMP, 46 mg (0.52 mmol) of 2-methylpropane-1,2-diamine were added and the mixture was stirred in the microwave at 150° C. for 2 h. Another 46 mg (0.52 mmol) of 2-methylpropane-1,2-diamine were then added, and the mixture was stirred in the microwave at 150° C. for 1 h. The reaction solution was dissolved with acetonitrile/water/formic acid and purified by preparative HPLC (RP18 column, mobile phase: acetonitrile/water gradient with addition of 0.1% formic acid). The product fractions were concentrated, dissolved in dichloromethane and a little methanol and washed twice with saturated aqueous sodium bicarbonate solution. The combined aqueous phases were reextracted twice with dichloromethane. The combined organic phases were dried over sodium sulphate, filtered and concentrated. This gave 38 mg (67% of theory) of the title compound.

LC-MS (Method 1): $R_t$=0.66 min
MS (ESpos): m/z=522 (M+H)$^+$
$^1$H NMR (400 MHz, DMSO-$d_6$) δ=1.04 (s, 6 H), 1.39 (s, 6 H), 2.73 (s, 3 H), 3.45 (d, 2 H), 5.31 (s, 2 H), 6.32 (t, 1 H), 6.96 (t, 1 H), 7.02 (d, 1 H), 7.23 (t, 2 H), 7.55-7.64 (m, 1 H), 9.62 (d, 1 H), 10.98 (br. s, 1 H).

Example 13 rac-4-[(2-Amino-2-methylpentyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one (racemate)

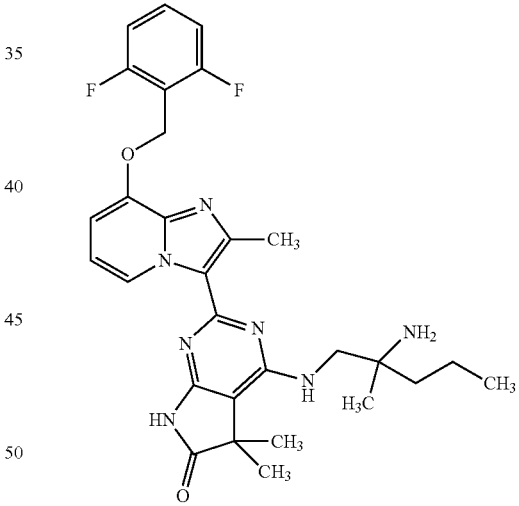

50 mg (0.07 mmol) of 2-{8-[(2,6-difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one trifluoroacetate from Example 3 were initially charged in 0.5 ml of NMP, 66 mg (0.35 mmol) of rac-2-methylpentane-1,2-diamine dihydrochloride (racemate) and 0.15 ml (0.83 mmol) of N,N-diisopropylethylamine were added and the mixture was stirred in the microwave at 150° C. for 6 h. Another 40 mg (0.21 mmol) of 2-methylpentane-1,2-diamine dihydrochloride and 0.08 ml (0.42 mmol) of N,N-diisopropylethylamine were then added, and the mixture was stirred in the microwave at 150° C. for 1.5 h. The reaction solution was diluted with acetonitrile/water/TFA and purified by preparative HPLC (RP18 column, mobile phase: acetonitrile/water gradient with addition of 0.1% TFA). The product fractions were concentrated, dissolved in dichloromethane and a little methanol and washed twice with saturated aqueous sodium bicarbonate solution. The combined aqueous phases were reextracted twice with dichloromethane. The combined organic phases were dried over sodium sulphate, filtered and concentrated. The crude product was purified again by thick-layer chromatography (mobile phase: dichloromethane:methanol=10:1). This gave 3 mg (7% of theory) of the title compound.

LC-MS (Method 1): $R_t$=0.73 min
MS (ESpos): m/z=550 (M+H)$^+$
$^1$H NMR (400 MHz, DMSO-d$_6$) δ=0.79-0.87 (m, 3 H), 1.03 (s, 3 H), 1.29-1.43 (m, 10 H), 2.73 (s, 3 H), 3.48-3.63 (m, 2 H), 5.31 (s, 2 H), 6.19-6.25 (m, 1 H), 6.95 (t, 1 H), 7.02 (d, 1 H), 7.23 (t, 2 H), 7.55-7.64 (m, 1 H), 9.58 (d, 1 H), 11.00 (br. s, 1 H).

Example 14 ent-4-{[2-Amino-2-(3,4-difluorophenyl)ethyl]amino}-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one

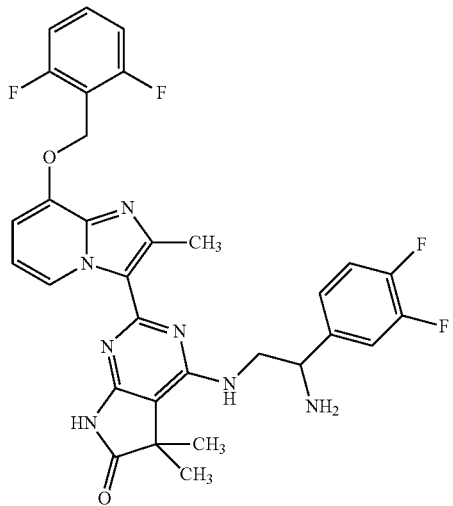 [SMILES: Cc1nc2c(OCc3c(F)cccc3F)cccn2c1-c1nc(NCC(N)c2ccc(F)c(F)c2)c2c(n1)NC(=O)C2(C)C]

120 mg (0.18 mmol) of 2-{8-[(2,6-difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one trifluoroacetate from Example 3 were initially charged in 1.8 ml of NMP, 174 mg (0.71 mmol) of ent-1-(3,4-difluorophenyl)ethane-1,2-diamine dihydrochloride (enantiomer A) from Example 34A and 0.27 ml (1.56 mmol) of N,N-diisopropylethylamine were added and the mixture was stirred in the microwave at 150° C. for 6 h. The reaction solution was diluted with acetonitrile/water/TFA and purified by preparative HPLC (RP18 column, mobile phase: acetonitrile/water gradient with addition of 0.1% TFA). The product fractions were concentrated, dissolved in dichloromethane and a little methanol and washed twice with saturated aqueous sodium bicarbonate solution. The combined aqueous phases were extracted twice with dichloromethane. The combined organic phases were dried over sodium sulphate, filtered and concentrated. The crude product was purified again by thick-layer chromatography (mobile phase: dichloromethane:methanol=20:1). This gave 19 mg (17% of theory) of the title compound.

LC-MS (Method 1): $R_t$=0.69 min
MS (ESpos): m/z=606 (M+H)$^+$
$^1$H NMR (400 MHz, DMSO-d$_6$) δ=1.27 (s, 3 H), 1.33 (s, 3 H), 2.73 (s, 3 H), 3.51-3.61 (m, 1 H), 3.63-3.72 (m, 1 H), 4.24 (t, 1 H), 5.34 (s, 2 H), 6.58 (d, 1 H), 6.94 (t, 1 H), 7.04 (d, 1 H), 7.09-7.16 (m, 1 H), 7.22-7.34 (m, 3 H), 7.37-7.44 (m, 1 H), 7.56-7.66 (m, 1 H), 9.57 (d, 1 H), 10.93 (s, 1 H).

Example 15

2-{8-[(2,6-Difluorobenzyl)oxy]-2-methylimidazo[1,2-a]pyridin-3-yl}-4-[(trans-4-hydroxycyclohexyl)amino]-5,5-dimethyl-5,7-dihydro-6H-pyrrolo[2,3-d]pyrimidin-6-one

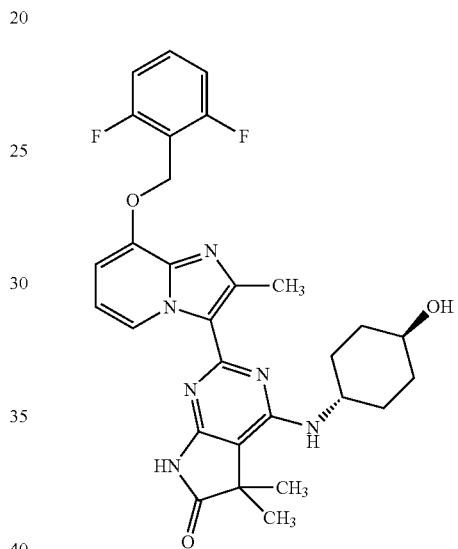

50 mg (0.07 mmol) of 2-{8-[(2,6-difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one trifluoroacetate from Example 3 were initially charged in 0.6 ml of NMP, 26 mg (0.22 mmol) of trans-4-aminocyclohexanol and 0.04 ml (0.22 mmol) of N,N-diisopropylethylamine were added and the mixture was stirred in the microwave at 150° C. for 3 h. The reaction solution was diluted with acetonitrile/water/formic acid and purified by preparative HPLC (RP18 column, mobile phase: acetonitrile/water gradient with addition of 0.1% formic acid). The product fractions were concentrated, dissolved in dichloromethane and a little methanol and washed twice with saturated aqueous sodium bicarbonate solution. The combined aqueous phases were extracted twice with dichloromethane. The combined organic phases were dried over sodium sulphate, filtered and concentrated. This gave 5 mg (12% of theory) of the title compound.

LC-MS (Method 1): $R_t$=0.82 min
MS (ESpos): m/z=549 (M+H)$^+$
$^1$H NMR (400 MHz, DMSO-d$_6$) δ=1.21-1.40 (m, 8 H), 1.43-1.59 (m, 2 H), 1.85-1.95 (m, 4 H), 2.73 (s, 3 H), 3.35-3.48 (m, 1 H), 4.05-4.15 (m, 1 H), 4.58 (d, 1 H), 5.32 (s, 2 H), 6.16 (d, 1 H), 6.95 (t, 1 H), 7.03 (d, 1 H), 7.25 (t, 2 H), 7.56-7.66 (m, 1 H), 9.58 (d, 1 H), 10.92 (s, 1 H).

Example 16

2-{8-[(2,6-Difluorobenzyl)oxy]-2-methylimidazo[1,2-a]pyridin-3-yl}-4-[(2-hydroxy-2-methylpropyl)amino]-5,5-dimethyl-5,7-dihydro-6H-pyrrolo[2,3-d]pyrimidin-6-one

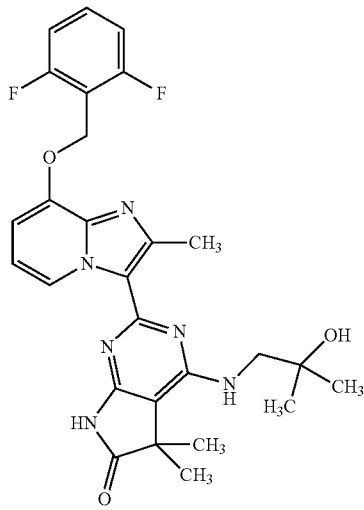 [SMILES: Cc1nc2c(OCc3c(F)cccc3F)cccn2c1-c1nc(NCC(C)(C)O)c2c(n1)NC(=O)C2(C)C]

200 mg (0.28 mmol) of 2-{8-[(2,6-difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one trifluoroacetate from Example 3 were initially charged in 2.8 ml of NMP, 123 mg (1.38 mmol) of 1-amino-2-methylpropan-2-ol were added and the mixture was stirred in the microwave at 150° C. for 6 h. The reaction solution was dissolved with acetonitrile/water/TFA and purified by preparative HPLC (RP18 column, mobile phase: acetonitrile/water gradient with addition of 0.1% TFA). The product fractions were concentrated, dissolved in dichloromethane and a little methanol and washed twice with saturated aqueous sodium bicarbonate solution. The combined aqueous phases were reextracted twice with dichloromethane. The combined organic phases were dried over sodium sulphate, filtered and concentrated. This gave 89 mg (60% of theory) of the title compound.

LC-MS (Method 1): $R_t$=0.81 min
MS (ESpos): m/z=523 (M+H)$^+$
$^1$H NMR (400 MHz, DMSO-d$_6$) δ=1.13 (s, 6 H), 1.39 (s, 6 H), 2.74 (s, 3 H), 3.56 (d, 2 H), 4.64 (s, 1 H), 5.31 (s, 2 H), 6.20 (t, 1 H), 6.94 (t, 1 H), 7.01 (d, 1 H), 7.23 (t, 2 H), 7.55-7.64 (m, 1 H), 9.60 (d, 1 H), 10.97 (s, 1 H).

The exemplary compounds shown in Table 1 were prepared analogously to Example 16 by reacting 2-{8-[(2,6-difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one from Example 2 or the corresponding trifluoroacetate salt from Example 3 with the appropriate commercially available or above-described amines (3-10 equivalents) under the reaction conditions described (reaction time: 1-9 h; temperature: 150° C.) in the microwave. If salts of the amines were used, N,N-diisopropylethylamine (3-10 equivalents) were added.

Illustrative Workup of the Reaction Mixture:

The reaction mixture was diluted with water/TFA and purified by preparative HPLC (RP18 column, mobile phase: acetonitrile/water gradient with addition of 0.1% TFA or 0.05% formic acid). Additionally or alternatively, the crude product was purified by thick-layer chromatography or silica gel chromatography (mobile phase: dichloromethane/methanol). The product-containing fractions were concentrated.

The residue was, if necessary, taken up in dichloromethane and washed with saturated aqueous sodium bicarbonate solution. The aqueous phase was extracted twice with dichloromethane, and the combined organic phases were dried over sodium sulphate, filtered, concentrated and lyophilized.

TABLE 1

| Example | IUPAC name/structure (Yield) | Analytical data |
| --- | --- | --- |
| 17 | 2-{8-[(2,6-difluorobenzyl)oxy]-2-methylimidazo[1,2-a]pyridin-3-yl}-4-{[(1-hydroxycyclopropyl)methyl]amino}-5,5-dimethyl-5,7-dihydro-6H-pyrrolo[2,3-d]pyrimidin-6-one<br />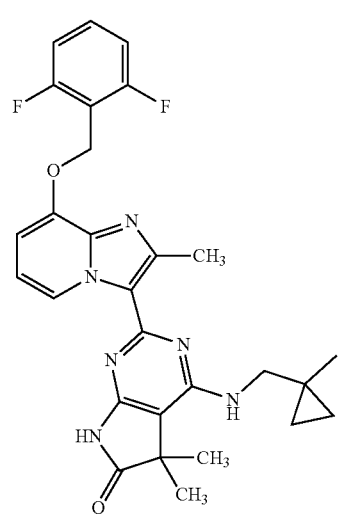 [SMILES: Cc1nc2c(OCc3c(F)cccc3F)cccn2c1-c1nc(NCC2(C)CC2)c2c(n1)NC(=O)C2(C)C]<br />(6% of theory) | LC-MS (Method 1): $R_t$ = 0.79 min<br />MS (ESpos): m/z = 521 (M + H)$^+$<br />$^1$H NMR (400 MHz, DMSO-d$_6$) = 0.50-0.59 (m, 4 H), 1.37 (s, 6 H), 2.72 (s, 3 H), 3.76 (d, 2 H), 5.32 (s, 2 H), 5.45 (s, 1 H), 6.44 (t, 1 H), 6.94 (t, 1 H), 7.01 (d, 1 H), 7.24 (t, 2 H), 7.55-7.64 (m, 1 H), 9.56 (d, 1 H), 10.95 (s, 1 H). |

| Example | IUPAC name/structure (Yield) | Analytical data |
|---|---|---|
| 18 | rac-2-{8-[(2,6-difluorobenzyl)oxy]-2-methylimidazo[1,2-a]pyridin-3-yl}-5,5-dimethyl-4-[(3,3,3-trifluoro-2-hydroxypropyl)amino]-5,7-dihydro-6H-pyrrolo[2,3-d]pyrimidin-6-one<br>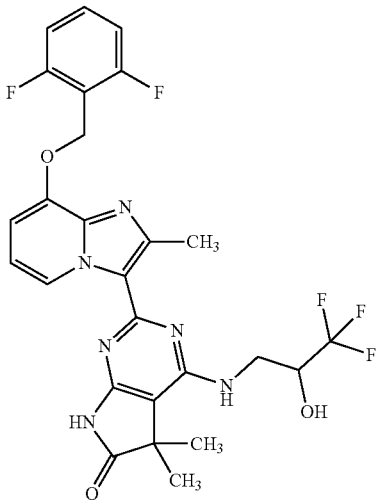 [SMILES: Cc1nc2c(OCc3c(F)cccc3F)cccn2c1-c1nc(NCC(O)C(F)(F)F)c2c(n1)NC(=O)C2(C)C]<br>(11% of theory) | LC-MS (Method 1): $R_t$ = 0.85 min<br>MS (ESpos): m/z = 563 (M + H)$^+$<br>$^1$H NMR (400 MHz, DMSO-$d_6$) δ = 1.36/1.37 (2 x s, 6 H), 2.71 (s, 3 H), 3.55-3.66 (m, 1 H), 3.80-3.91 (m, 1 H), 4.25-4.39 (m, 1 H), 5.32 (s, 2 H), 5.45 (s, 1 H), 6.49 (d, 1 H), 6.79 (t, 1 H), 6.92 (t, 1 H), 7.03 (d, 1 H), 7.24 (t, 2 H), 7.55-7.65 (m, 1 H), 9.53 (d, 1 H), 11.00 (s, 1 H). |
| 19 | 2-{8-[(2,6-difluorobenzyl)oxy]-2-methylimidazo[1,2-a]pyridin-3-yl}-5,5-dimethyl-4-[(3,3,3-trifluoropropyl)amino]-5,7-dihydro-6H-pyrrolo[2,3-d]pyrimidin-6-one<br>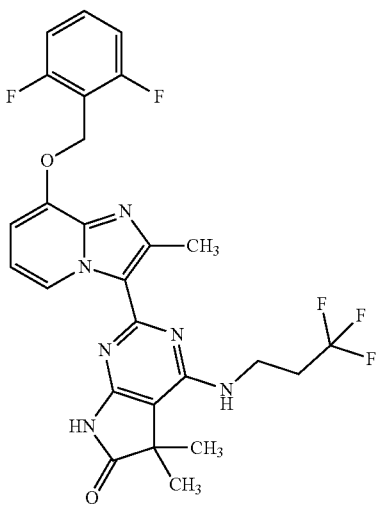 [SMILES: Cc1nc2c(OCc3c(F)cccc3F)cccn2c1-c1nc(NCCC(F)(F)F)c2c(n1)NC(=O)C2(C)C]<br>(33% of theory) | LC-MS (Method 1): $R_t$ = 0.94 min<br>MS (ESpos): m/z = 547 (M + H)$^+$<br>$^1$H NMR (400 MHz, DMSO-$d_6$) δ = 1.36 (s, 6 H), 2.57-2.69 (m 2 H), 2.72 (s, 3 H), 3.73-3.81 (m, 2 H), 5.33 (s, 2 H), 6.76 (t, 1 H), 6.93 (t, 1 H), 7.02 (d, 1 H), 7.23 (t, 2 H), 7.54-7.63 (m, 1 H), 9.54 (d, 1 H), 10.95 (s, 1 H). |

TABLE 1-continued

| Example | IUPAC name/structure (Yield) | Analytical data |
|---|---|---|
| 20 | rac-4-{[2-amino-3-(4-methoxyphenyl)-2-methylpropyl]amino}-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one<br>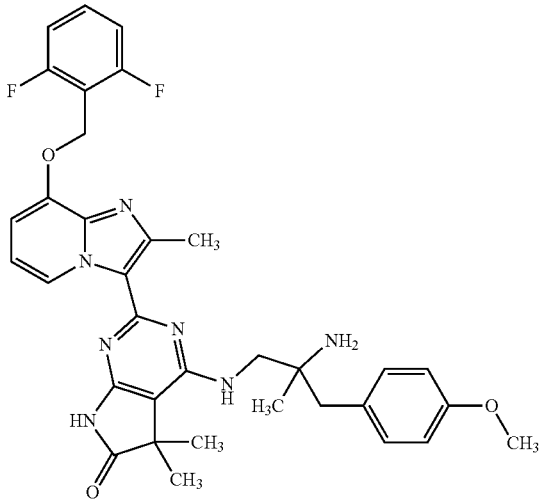 [SMILES: COc1ccc(CC(C)(N)CNc2nc(-c3c(C)nc4c(OCc5c(F)cccc5F)cccn34)nc3c2C(C)(C)C(=O)N3)cc1]<br>(40% of theory; purity 90%) | LC-MS (Method 1): $R_t$ = 0.76 min<br>MS (ESpos): m/z = 628 (M + H)$^+$<br>$^1$H NMR (400 MHz, DMSO-d$_6$) δ = 1.25 (s, 3 H), 1.39 (s, 6 H), 2.62 (s, 3 H), 2.68-2.79 (m, 2 H), 3.39-3.66 (m, 2H), 3.72 (s, 3 H), 5.31 (s, 2 H), 6.08-6.20 (m, 1 H), 6.83 (d, 2 H), 6.92 (t, 1 H), 7.02 (d, 1 H), 7.16 (d, 2 H), 7.23 (t, 2 H), 7.55-7.64 (m, 1 H), 9.51 (d, 1 H), 10.98 (br. s, 1 H). |
| 21 | rac-4-[(2-amino-3-methoxy-2-methylpropyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one<br>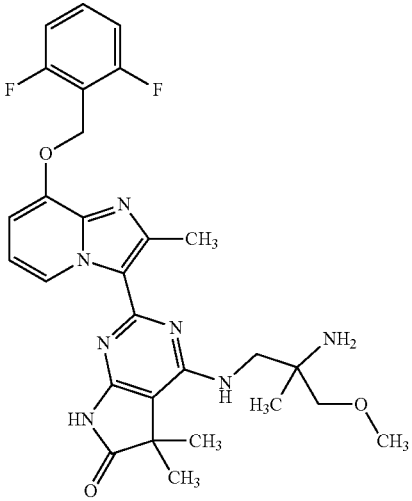 [SMILES: COCC(C)(N)CNc1nc(-c2c(C)nc3c(OCc4c(F)cccc4F)cccn23)nc2c1C(C)(C)C(=O)N2]<br>(77% of theory) | LC-MS (Method 1): $R_t$ = 0.67 min<br>MS (ESpos): m/z = 552 (M + H)$^+$<br>$^1$H NMR (400 MHz, DMSO-d$_6$) δ = 1.02 (s, 3 H), 1.39 (s, 6 H), 1.62 (br. s, 2 H), 2.73 (s, 3 H), 3.19 (s, 2 H), 3.26 (s, 3 H), 3.45-3.54 (m, 1 H), 3.56-3.63 (m, 1 H), 5.32 (s, 2 H), 6.17-6.23 (m, 1 H), 6.94 (t, 1 H), 7.02 (d, 1 H), 7.23 (t, 2 H), 7.56-7.65 (m, 1 H), 9.61 (d, 1 H), 10.97 (br. s, 1 H). |

TABLE 1-continued

| Example | IUPAC name/structure (Yield) | Analytical data |
|---|---|---|
| 22 | 2-{8-[(2,6-difluorobenzyl)oxy]-2-methylimidazo[1,2-a]pyridin-3-yl}-4-{[(2S)-2,3-dihydroxypropyl]amino}-5,5-dimethyl-5,7-dihydro-6H-pyrrolo[2,3-d]pyrimidin-6-one<br><br>(39% of theory, purity 93%) | LC-MS (Method 1): $R_t$ = 0.72 min<br>MS (ESpos): m/z = 525 (M + H)$^+$<br>$^1$H NMR (400 MHz DMSO-d$_6$) δ = 1.36 (s, 6 H), 2.73 (s, 3 H), 3.38-3.53 (m, 3 H), 3.57-3.69 (m, 1 H), 3.71-3.84 (m, 1 H), 4.56-4.72 (m, 1 H), 4.77-4.88 (m, 1 H), 5.32 (s, 2 H), 6.50 (t, 1 H), 6.93 (t, 1 H), 7.01 (d, 1 H), 7.19-7.30 (m, 2 H), 7.55-7.66 (m, 1 H), 9.58 (d, 1 H), 10.93 (br. s, 1H). |
| 23 | 2-{8-[(2,6-difluorobenzyl)oxy]-2-methylimidazo[1,2-a]pyridin-3-yl}-4-{[(2R)-2,3-dihydroxypropyl]amino}-5,5-dimethyl-5,7-dihydro-6H-pyrrolo[2,3-d]pyrimidin-6-one<br><br>(54% of theory) | LC-MS (Method 1): $R_t$ = 0.72 min<br>MS (ESpos): m/z = 525 (M + H)$^+$<br>$^1$H NMR (400 MHz, DMSO-d$_6$) δ = 1.36 (s, 6 H), 2.73 (s, 3 H), 3.38-3.53 (m, 3 H), 3.57-3.69 (m, 1 H), 3.71-3.84 (m, 1 H), 4.56-4.72 (m, 1 H), 4.77-4.88 (m, 1 H), 5.32 (s, 2 H), 6.48 (br. s, 1 H), 6.93 (t, 1 H), 7.01 (d, 1 H), 7.18-7.30 (m, 2 H), 7.55-7.66 (m, 1 H), 9.58 (d, 1 H), 10.93 (br. s, 1 H). |

TABLE 1-continued

| Example | IUPAC name/structure (Yield) | Analytical data |
|---|---|---|
| 24 | 2-{8-[(2,6-difluorobenzyl)oxy]-2-methylimidazo[1,2-a]pyridin-3-yl}-4-[(2-hydroxyethyl)amino]-5,5-dimethyl-5,7-dihydro-6H-pyrrolo[2,3-d]pyrimidin-6-one trifluoroacetate<br>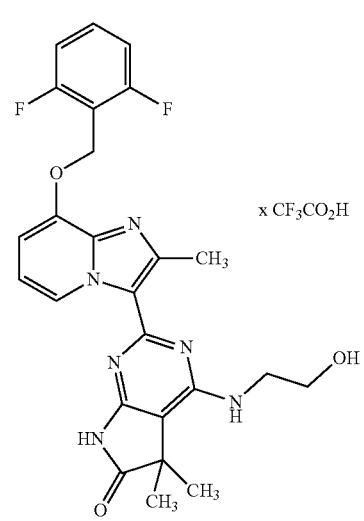 [SMILES: Cc1nc2c(OCc3c(F)cccc3F)cccn2c1-c1nc(NCCO)c2c(n1)NC(=O)C2(C)C]<br>(63% of theory) | LC-MS (Method 1): $R_t$ = 0.76 min<br>MS (ESpos): m/z = 495 (M − TFA + H)$^+$<br>$^1$H NMR (400 MHz, DMSO-d$_6$) δ = 1.37 (s, 6 H), 2.81 (s, 3 H), 3.53-3.63 (m, 5 H), 5.45 (s, 2 H), 6.77 (br. s, 1 H), 7.22-7.31 (m, 2 H), 7.39 (br. s, 1 H), 7.46-7.68 (m, 2 H), 9.73 (d, 1 H), 11.04 (s, 1 H). |
| 25 | rac-4-[(2-amino-3,3,3-trifluoropropyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one<br>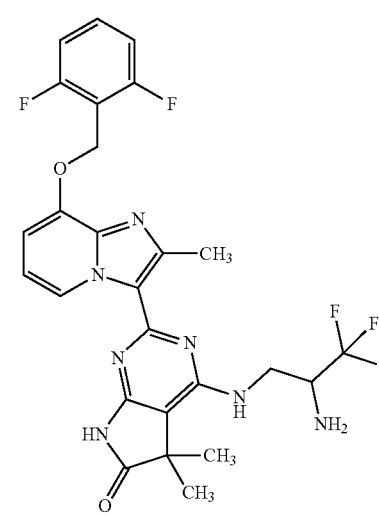<br>(14% of theory, purity 94%) | LC-MS (Method 1): $R_t$ = 0.81 min<br>MS (ESpos): m/z = 562 (M + H)$^+$<br>$^1$H NMR (500 MHz, DMSO-d$_6$) δ = 1.37/1.39 (2 x s, 6 H), 2.72 (s, 3 H), 3.39-3.49 (m, 1 H), 3.60-3.71 (m, 1 H), 3.88-3.98 (m, 1 H), 5.33 (s, 2 H), 6.68 t, 1 H), 6.93 (t, 1 H), 7.02 (d, 1 H), 7.18-7.30 (m, 2 H), 7.53-7.64 (m, 1 H), 9.54 (d, 1 H), 10.98 (s, 1 H). |

TABLE 1-continued

| Example | IUPAC name/structure (Yield) | Analytical data |
|---|---|---|
| 26 | 2-{8-[(2,6-difluorobenzyl)oxy]-2-methylimidazo[1,2-a]pyridin-3-yl}-4-{[2-(3,3-difluoropyrrolidin-1-yl)ethyl]amino}-5,5-dimethyl-5,7-dihydro-6H-pyrrolo[2,3-d]pyrimidin-6-one<br>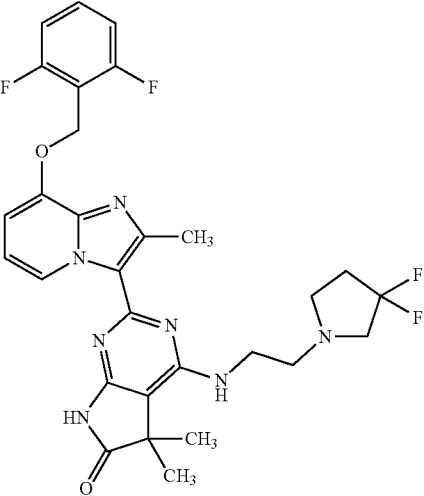 [SMILES: Cc1nc2c(OCc3c(F)cccc3F)cccn2c1-c1nc(NCCN2CCC(F)(F)C2)c2c(n1)NC(=O)C2(C)C]<br>(15% of theory) | LC-MS (Method 1): $R_t$ = 0.79 min<br>MS (ESpos): m/z = 584 (M + H)$^+$<br>$^1$H NMR (500 MHz, DMSO-d$_6$) δ = 1.35 (s, 6 H), 2.13-2.29 (m, 2 H), 2.67-2.81 (m, 7 H), 2.95 (t, 2 H), 3.62 (d, 2 H), 5.33 (s, 2 H), 6.59 (t, 1 H), 6.93 (t, 1 H), 7.01 (d, 1 H), 7.24 (t, 2 H), 7.53-7.63 (m, 1 H), 9.56 (d, 1 H), 10.91 (s, 1 H). |
| 27 | rac-4-[(2-amino-3,3,4,4-tetrafluorobutyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one<br>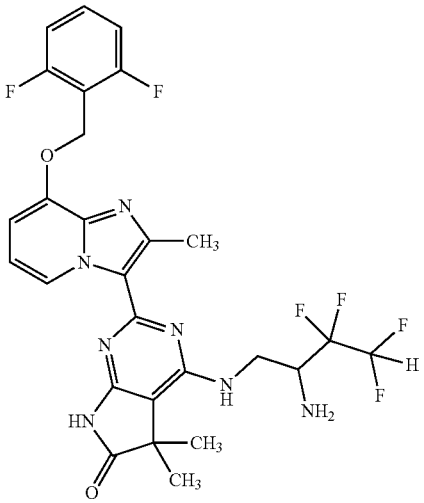 [SMILES: Cc1nc2c(OCc3c(F)cccc3F)cccn2c1-c1nc(NCC(N)C(F)(F)C(F)F)c2c(n1)NC(=O)C2(C)C]<br>(13% of theory) | LC-MS (Method 1): $R_t$ = 0.86 min<br>MS (ESpos): m/z = 594 (M + H)$^+$<br>$^1$H NMR (400 MHz, DMSO-d$_6$) δ = 1.37 and 1.39 (2 s, 6 H), 2.71 (s, 3 H), 3.39-3.49 (m, 1 H), 3.50-3.62 (m, 1 H), 3.94-4.04 (m, 1 H), 5.32 (s, 2 H), 6.60 (t, 1 H), 6.91 (t, 1 H), 7.04 (d, 1 H), 7.19-7.29 (m, 2 H), 7.55-7.65 (m, 1 H), 9.53 (d, 1 H), 10.97 (s, 1 H). |

| Example | IUPAC name/structure (Yield) | Analytical data |
| --- | --- | --- |
| 28 | 2-{8-[(2,6-difluorobenzyl)oxy]-2-methylimidazo[1,2-a]pyridin-3-yl}-4-[(4-hydroxy-4-methylcyclohexyl)amino]-5,5-dimethyl-5,7-dihydro-6H-pyrrolo[2,3-d]pyrimidin-6-one formate (Diastereomer 1)<br><br>(15% of theory) | LC-MS (Method 1): $R_t$ = 0.85 min<br>MS (ESpos): m/z = 563 (M − $HCO_2H$ + H)$^+$<br>$^1$H NMR (500 MHz, DMSO-$d_6$) δ = 1.20 (s, 3 H), 1.37 (s, 6 H), 1.45-1.65 (m, 6 H), 1.78-1.86 (m, 2 H), 2.73 (s, 3 H), 4.11-4.21 (m, 1 H), 4.34 (s, 1 H), 5.33 (s, 2 H), 6.08 (d, 1 H), 6.95 (t, 1 H), 7.02 (d, 1 H), 7.24 (t, 2 H), 7.53-7.63 (m, 1 H), 9.57 (d, 1 H), 10.89 (s, 1 H). |
| 29 | 2-{8-[(2,6-difluorobenzyl)oxy]-2-methylimidazo[1,2-a]pyridin-3-yl}-4-[(4-hydroxy-4-methylcyclohexyl)amino]-5,5-dimethyl-5,7-dihydro-6H-pyrrolo[2,3-d]pyrimidin-6-one formate (Diastereomer 2)<br><br>(19% of theory, purity 92%) | LC-MS (Method 1): $R_t$ = 0.88 min<br>MS (ESpos): m/z = 563 (M − $HCO_2H$ + H)$^+$<br>$^1$H NMR (500 MHz, DMSO-$d_6$) δ = 1.16 (s, 3 H), 1.32-1.45 (m, 8 H), 1.57-1.71 (m, 4 H), 1.80-1.93 (m, 2 H), 2.72 (s, 3 H), 3.99-4.11 (m, 1 H), 5.33 (s, 2 H), 6.19 (d, 1 H), 6.93 (t, 1 H), 7.00 (d, 1 H), 7.24 (t, 2 H), 7.59 (t, 1 H), 8.16 (s, 1 H), 9.57 (d, 1 H), 10.86 (s, 1 H). |

| Example | IUPAC name/structure (Yield) | Analytical data |
|---|---|---|
| 30 | 2-{8-[(2,6-difluorobenzyl)oxy]-2-methylimidazo[1,2-a]pyridin-3-yl}-4-[(3-hydroxycyclobutyl)amino]-5,5-dimethyl-5,7-dihydro-6H-pyrrolo[2,3-d]pyrimidin-6-one [cis/trans mixture]<br>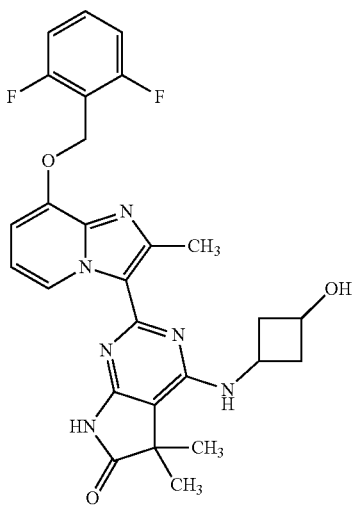 [SMILES: Cc1nc2c(OCc3c(F)cccc3F)cccn2c1-c1nc2c(c(NC3CC(O)C3)n1)C(C)(C)C(=O)N2]<br>(8% of theory) | LC-MS (Method 1): $R_t$ = 0.73 min<br>MS (ESpos): m/z = 521 (M + H)$^+$<br>$^1$H NMR (400 MHz, DMSO-d$_6$) δ = 1.38 (s, 6 H), 1.98-2.09 and 2.18-2.30 (m, 2 H), 2.37-2.47 and 2.58-2.69 (m, 2 H), 2.71-2.75 (m, 3 H), 3.87-3.96 and 4.27-4.38 (m, 1 H), 4.14-4.17 and 4.68-4.76 (m, 1 H), 5.02 and 5.09 (d, 1 H), 5.32 (s, 2 H), 6.48-6.58 (m, 1 H), 6.91-7.06 (m, 2 H), 7.19-7.28 (m, 2 H), 7.56-7.64 (m, 1 H), 9.53-9.60 (m, 1 H), 10.89 (s, 1 H). |

Example 31

4-[(2-Amino-2-methylpropyl)amino]-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one formate

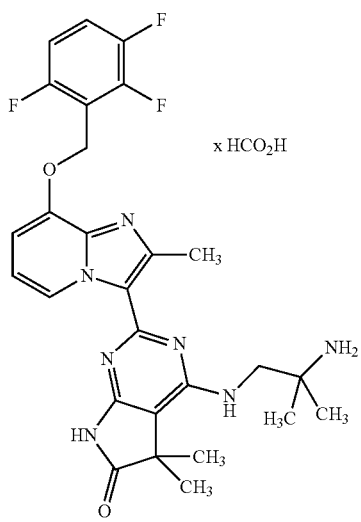 [SMILES: Cc1nc2c(OCc3c(F)ccc(F)c3F)cccn2c1-c1nc(NCC(C)(C)N)c2c(n1)NC(=O)C2(C)C]

73 mg (0.126 mmol) of 4-iodo-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one from Example 10 were initially charged in 0.47 ml of NMP, 56 mg (0.63 mmol) of 2-methylpropane-1,2-diamine were added and the mixture was stirred in a closed vessel at 130° C. for 4.5 h. The reaction mixture was purified by preparative HPLC (RP18 column, mobile phase: acetonitrile/water gradient with addition of 0.05% formic acid). This gave 37 mg (51% of theory) of the title compound.

LC-MS (Method 1): $R_t$=0.62 min

MS (ESpos): m/z=541 (M−HCO$_2$H+H)$^+$ $^1$H NMR (400 MHz, DMSO-d$_6$) δ=1.17 (s, 6 H), 1.41 (s, 6 H), 2.74 (s, 3 H), 3.61-3.69 (m, 2 H), 5.37 (s, 2 H), 6.64-6.74 (m, 1 H), 7.94-7.06 (m, 2 H), 7.26-7.35 (m, 1 H), 7.61-7.74 (m, 1 H), 8.32 (br. s, 2 H), 9.56 (d, 1 H), 11.00 (br. s, 1 H).

The exemplary compounds shown in Table 2 were prepared analogously to Example 31 by reacting the corresponding iodides from Example 10, Example 2 or Example 3 with the appropriate commercially available or above-described amines or diamines (4-6 equivalents; if appropriate as hydrochloride salts) and optionally with addition of 1,8-diazabicyclo[5.4.0]undec-7-ene (4-12 equivalents) under the reaction conditions described (reaction time: 1-5 h; temperature: 130° C.) in a closed vessel.

Illustrative Workup of the Reaction Mixture:

The reaction mixture was diluted and purified by preparative HPLC (RP18 column, mobile phase: acetonitrile/water gradient with addition of 0.1% TFA or 0.05% formic acid). Additionally or alternatively, the crude product was purified by silica gel chromatography (mobile phase: dichloromethane/methanol).

If appropriate, the product-containing fractions were concentrated, and the residue was taken up in dichloromethane and washed with saturated aqueous sodium bicarbonate solution. The aqueous phase was extracted twice with dichloromethane, and the combined organic phases were dried over sodium sulphate, filtered, concentrated and lyophilized.

TABLE 2

| Example | IUPAC name/structure (Yield) | Analytical data |
|---|---|---|
| 32 | rac-rel-4-[(1R,5S)-1-amino-3-azabicyclo[3.1.0]hex-3-yl]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one formate 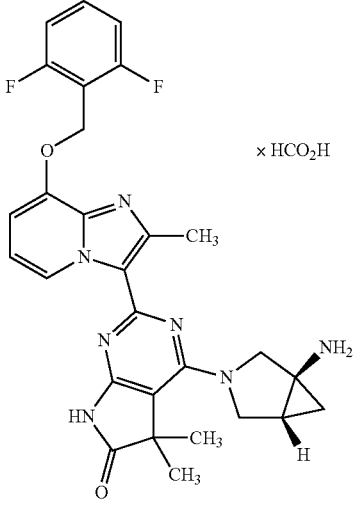 [SMILES: Cc1nc2c(OCc3c(F)cccc3F)cccn2c1-c1nc2c(c(N3C[C@H]4C[C@@]4(N)C3)n1)C(C)(C)C(=O)N2] (22% of theory) [1)] | LC-MS (Method 1): $R_t$ = 0.62 min<br>MS (ESpos): m/z = 532 (M – $HCO_2H$ + H)⁺<br>¹H NMR (500 MHz, DMSO-d₆) δ = 0.48-0.58 (m, 1 H), 0.88-0.98 (m, 1 H), 1.39 (s, 6 H), 1.47-1.59 (m, 1 H), 2.73 (s, 3 H), 3.55-3.65 (m, 1 H), 3.73-3.87 (m, 2 H), 4.04-4.10 (m, 1 H), 5.33 (s, 2 H), 6.97(t, 1 H), 7.03 (d, 1 H), 7.23 (t, 2 H), 7.55-7.65 (m, 1 H), 8.14 (s, 1 H), 9.53 (d, 1 H), 11.09 (br. s, 1 H). |
| 33 | 4-{[2-amino-3-fluoro-2-(fluoromethyl)propyl]amino}-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one 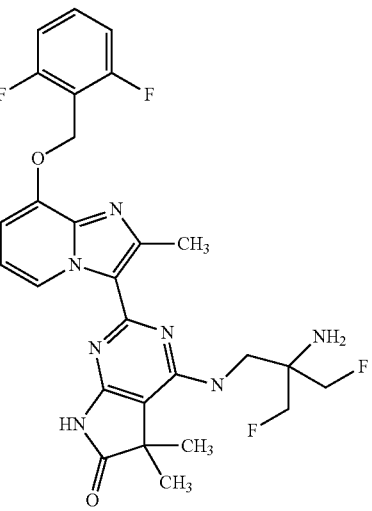 (10% of theory) | LC-MS (Method 1): $R_t$ = 0.61 min<br>MS (ESpos): m/z = 558 (M + H)⁺<br>¹H NMR (500 MHz, DMSO-d₆) δ = 1.40 (s, 6 H), 2.73 (s, 3 H), 3.72 (d, 2 H), 4.21 (d, 1 H), 4.28-4.34 (m, 2H), 4.42 (d, 1 H), 5.33 (s, 2 H), 6.38 (t, 1 H), 6.93 (t, 1 H), 7.03 (d, 1 H), 7.24 (t, 2 H), 7.56-7.65 (m, 1 H), 9.58 (d, 1 H), 10.98 (s, 1 H). |

TABLE 2-continued

| Example | IUPAC name/structure (Yield) | Analytical data |
|---|---|---|
| 34 | 4-[(2-hydroxy-2-methylpropyl)amino]-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one<br>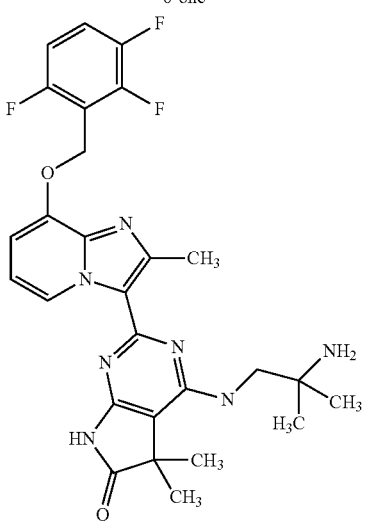<br>(20% of theory) | LC-MS (Method 1): $R_t$ = 0.81 min<br>MS (ESpos): m/z = 541 (M + H)$^+$<br>$^1$H NMR (500 MHz, DMSO-d$_6$) δ = 1.14 (s, 6 H), 1.40 (s, 6 H), 2.73 (s, 3 H), 3.57 (d, 2 H), 4.62 (s, 1 H), 5.38 (s, 2 H), 6.18 (t, 1 H), 6.94 (t, 1 H), 7.01 (d, 1 H), 7.25-7.33 (m, 1 H), 7.62-7.70 (m, 1 H), 9.60 (d, 1 H), 10.94 (s, 1 H). |
| 35 | rac-4-[(2-amino-3-methoxy-2-methylpropyl)amino]-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one formate<br>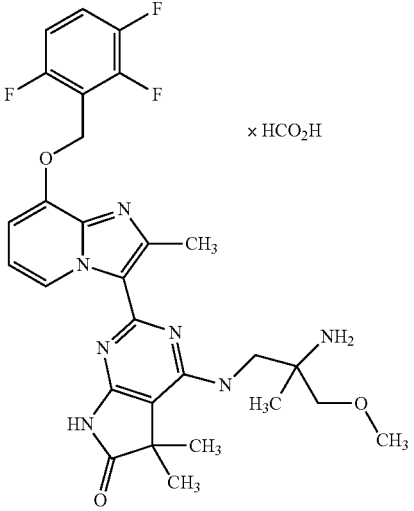 [SMILES: COCC(C)(N)CNc1nc(-c2c(C)nc3c(OCc4c(F)ccc(F)c4F)cccn23)nc2c1C(C)(C)C(=O)N2]<br>(43% of theory) | LC-MS (Method 1): $R_t$ = 0.62 min<br>MS (ESpos): m/z = 570 (M − HCO$_2$H + H)$^+$<br>$^1$H NMR (500 MHz, DMSO-d$_6$) δ = 1.08 (s, 3 H), 1.39 (s, 6 H), 2.74 (s, 3 H), 3.20-3.26 (m, 5 H), 3.53-3.58 (m, 1 H), 3.65-3.70 (m, 1 H), 5.38 (s, 2 H), 6.33 (t, 1 H), 6.94 (t, 1 H), 7.02 (d, 1 H), 7.26-7.33 (m, 1 H), 7.62-7.70 (m, 1 H), 8.25 (s, 1 H), 9.59 (d, 1 H), 10.98 (br. s, 1 H). |

TABLE 2-continued

| Example | IUPAC name/structure (Yield) | Analytical data |
|---|---|---|
| 36 | 2-{8-[(2,6-difluorobenzyl)oxy]-2-methylimidazo[1,2-a]pyridin-3-yl}-4-[(2S)-2-(hydroxymethyl)pyrrolidin-1-yl]-5,5-dimethyl-5,7-dihydro-6H-pyrrolo[2,3-d]pyrimidin-6-one<br><br>(64% of theory) [2)] | LC-MS (Method 1): $R_t$ = 0.81 min<br>MS (ESpos): m/z = 535 (M + H)$^+$<br>$^1$H NMR (500 MHz, DMSO-d$_6$) δ = 1.34 (s, 3 H), 1.48 (s, 3 H), 1.87-2.14 (m, 5 H), 2.73 (s, 3 H), 3.37-3.43 (m, 1 H), 3.57-3.64 (m, 2 H), 3.72-3.78 (m, 1 H), 4.57-4.62 (m, 1 H), 4.78 (t, 1 H), 5.33 (s, 2 H), 6.93 (t, 1 H), 7.02 (d, 1 H), 7.23 (t, 2 H), 7.57-7.65 (m, 1 H), 9.57 (d, 1 H), 11.08 (br. s, 1 H). |
| 37 | 2-{8-[(2,6-difluorobenzyl)oxy]-2-methylimidazo[1,2-a]pyridin-3-yl}-4-[(2R)-2-(hydroxymethyl)pyrrolidin-1-yl]-5,5-dimethyl-5,7-dihydro-6H-pyrrolo[2,3-d]pyrimidin-6-one<br><br>(48% of theory) [2)] | LC-MS (Method 1): $R_t$ = 0.82 min<br>MS (ESpos): m/z = 535 (M + H)$^+$<br>$^1$H NMR (500 MHz, DMSO-d$_6$) δ = 1.34 (s, 3 H), 1.48 (s, 3 H), 1.86-2.14 (m, 5 H), 2.73 (s, 3 H), 3.37-3.43 (m, 1 H), 3.57-3.64 (m, 2 H), 3.72-3.78 (m, 1 H), 4.57-4.62 (m, 1 H), 4.78 (t, 1 H), 5.33 (s, 2 H), 6.93 (t, 1 H), 7.03 (d, 1 H), 7.23 (t, 2 H), 7.57-7.65 (m, 1 H), 9.57 (d, 1 H), 11.08 (br. s, 1 H). |

TABLE 2-continued

| Example | IUPAC name/structure (Yield) | Analytical data |
|---|---|---|
| 38 | [1-(5,5-dimethyl-2-{2-methyl-8-[(2,3,6-trifluorobenzyl)oxy]imidazo[1,2-a]pyridin-3-yl}-6-oxo-6,7-dihydro-5H-pyrrolo[2,3-d]pyrimidin-4-yl)piperidin-4-yl]acetic acid<br>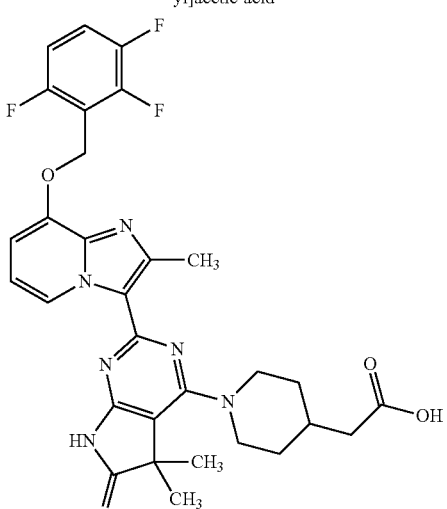<br>(28% of theory) | LC-MS (Method 1): $R_t$ = 0.85 min<br>MS (ESpos): m/z = 595 (M + H)$^+$<br>$^1$H NMR (400 MHz, DMSO-d$_6$) δ = 1.23-1.38 (m, 1 H), 1.40 (s, 6 H), 1.51-1.63 (m, 1 H), 1.75-1.93 (m, 2H), 1.94-2.08 (m, 1 H), 2.19-2.27 (m, 2 H), 2.73 (s, 3 H), 2.80 (t, 1 H), 3.04 (t, 1 H), 4.15-4.23 (m, 1 H), 4.27-4.35 (m, 1 H), 5.39 (s, 2 H), 6.97 (t, 1 H), 7.02 (d, 1 H), 7.27-7.34 (m, 1 H), 7.62-7.71 (m, 1 H), 9.52 (d, 1 H), 11.18 (s, 1 H), 12.24 (br. s, 1 H). |
| 39 | rac-4-[(2-amino-3,3-difluoro-2-methylpropyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one<br>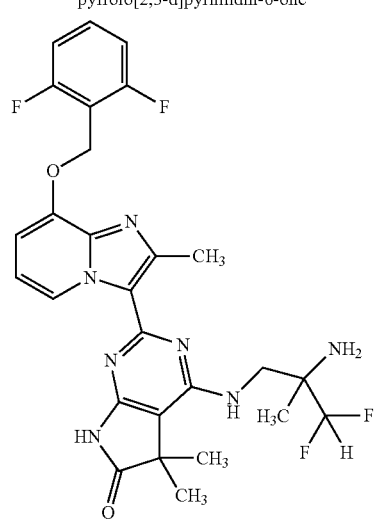<br>(14% of theory) | LC-MS (Method 1): $R_t$ = 0.64 min<br>MS (ESpos): m/z = 558 (M + H)$^+$<br>$^1$H NMR (400 MHz, DMSO-d$_6$) δ = 1.30 (s, 3 H), 1.41 (s, 6 H), 2.73 (s, 3 H), 3.77-3.87 (m, 1 H), 3.99-4.09 (m, 1 H), 5.38 (s, 2 H), 6.24 (t, 1 H), 6.54-6.63 (m, 1 H), 7.02-7.14 (m, 1 H), 7.24 (t, 2 H), 7.56-7.66 (m, 1 H), 8.48 (br. s, 2 H), 9.48 (d, 1 H), 11.16 (s, 1 H). |

[1] rac-rel-(1R,5S)-3-Azabicyclo[3.1.0]hexane-1-amine dihydrochloride (4 equivalents) and 1,8-diazabicyclo[5.4.0]undec-7-ene (8 equivalents) were employed in the reaction.

[2] An alternative workup was used: Acetonitrile and water were added to the reaction mixture. The precipitate formed was filtered off, washed with a little acetonitrile and water and dried under high vacuum.

Example 40 rac-4-[(2-Amino-3,3,3-trifluoro-2-methylpropyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one

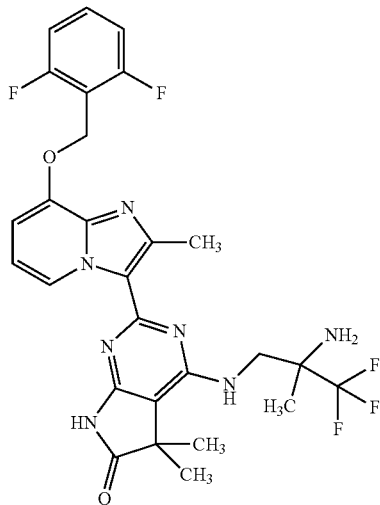 [SMILES: Cc1nc2c(OCc3c(F)cccc3F)cccn2c1-c1nc(NCC(C)(N)C(F)(F)F)c2c(n1)NC(=O)C2(C)C]

Preparation of the free amine: 160 mg (0.90 mmol) of rac-3,3,3-trifluoro-2-methylpropane-1,2-diamine dihydrochloride from Example 69A were dissolved in dichloromethane/methanol and passed over an ion exchange column (StratoSpheres™ PL-HCO3 MP) which had been flushed with 1 ml of dichloromethane. The column was rinsed with 2 ml of dichloromethane and the solution (contains the free amine) was concentrated.

70 mg (0.15 mmol) of 4-chloro-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one from Example 4 were initially charged in 1.3 ml of NMP, rac-3,3,3-trifluoro-2-methylpropane-1,2-diamine (about 115 mg; 0.82 mmol; dissolved in 0.3 ml of NMP) and 0.15 ml (0.88 mmol) of N,N-diisopropylethylamine were added and the mixture was stirred in the microwave at 150° C. for 3 h. Another 81 mg (0.57 mmol) of rac-3,3,3-trifluoro-2-methylpropane-1,2-diamine (preparation as described above) were then added, and the mixture was stirred in the microwave at 150° C. for 2 h. The reaction solution was diluted with acetonitrile/water/TFA and purified by preparative HPLC (RP18 column, mobile phase: acetonitrile/water gradient with addition of 0.1% TFA). The product fractions were concentrated, dissolved in dichloromethane and a little methanol and washed twice with saturated aqueous sodium bicarbonate solution. The combined aqueous phases were extracted twice with dichloromethane. The combined organic phases were dried over sodium sulphate, filtered and concentrated. This gave 31 mg (36% of theory) of the title compound.

LC-MS (Method 1): $R_t$=0.86 min
MS (ESpos): m/z=576 (M+H)$^+$
$^1$H NMR (400 MHz, DMSO-$d_6$) δ=1.15 (s, 3 H), 1.40 (s, 6 H), 2.06-2.16 (br. s, 2 H), 2.73 (s, 3H), 3.66 (dd, 1 H), 3.93 (dd, 1 H), 5.33 (s, 2 H), 6.36 (t, 1 H), 6.94 (t, 1 H), 7.02 (d, 1 H), 7.20-7.28 (m, 2 H), 7.54-7.64 (m, 1 H), 9.58 (d, 1 H), 11.00 (s, 1 H).

Example 41 rac-4-[(2-Amino-2-methylpropyl)amino]-2-{8-[(2,6-difluorobenzyl)oxy]-2-methylimidazo[1,2-a]pyridin-3-yl}-5-methyl-5-(trifluoromethyl)-5,7-dihydro-6H-pyrrolo[2,3-d]pyrimidin-6-one

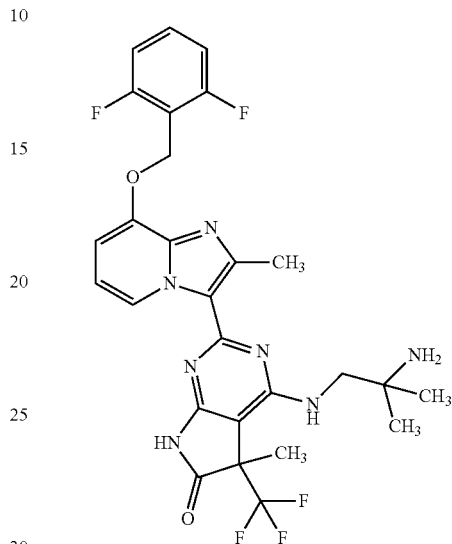

80 mg (0.09 mmol) (purity 86%) of rac-2-{8-[(2,6-difluorobenzyl)oxy]-2-methylimidazo[1,2-a]pyridin-3-yl}-4-iodo-5-methyl-5-(trifluoromethyl)-5,7-dihydro-6H-pyrrolo[2,3-d]pyrimidin-6-one trifluoroacetate from Example 7 were initially charged in 1 ml of NMP, 49 µl (0.47 mmol) of 1,2-diamino-2-methylpropane were added and the mixture was stirred in the microwave at 150° C. for 3 h. The reaction solution was dissolved with acetonitrile/water/TFA and purified by preparative HPLC (RP18 column, mobile phase: acetonitrile/water gradient with addition of 0.1% TFA). The product fractions were concentrated, dissolved in dichloromethane and a little methanol and washed twice with saturated aqueous sodium bicarbonate solution. The combined aqueous phases were extracted twice with dichloromethane. The combined organic phases were dried over sodium sulphate, filtered and concentrated. This gave 33 mg (60% of theory) of the title compound.

LC-MS (Method 1): $R_t$=0.71 min
MS (ESpos): m/z=576 (M+H)$^+$
$^1$H NMR (400 MHz, DMSO-$d_6$) δ=1.11 (d, 6 H), 1.75 (s, 3 H), 2.75 (s, 3 H), 3.43-3.43 (m, 1 H), 3.57-67 (m, 1 H), 5.33 (s, 2 H), 6.36 (br. s, 1 H), 7.02 (t, 1 H), 7.06 (d, 1 H), 7.20-7.29 (m, 2 H), 7.55-7.65 (m, 1 H), 9.55 (d, 1 H).

Example 42

4-{[(1-Aminocyclopropyl)methyl]amino}-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one

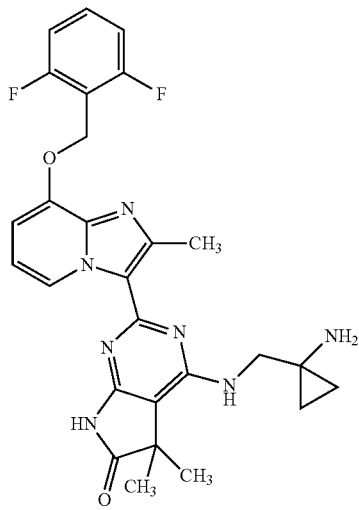 [SMILES: Cc1nc2c(OCc3c(F)cccc3F)cccn2c1-c1nc(NCC2(N)CC2)c2c(n1)NC(=O)C2(C)C]

2 ml of 2 M aqueous hydrochloric acid in diethyl ether were added to a solution of 73 mg (0.1 mmol) (purity 86%) of tert-butyl (1-{[(2-{8-[(2,6-difluorobenzyl)oxy]-2-methylimidazo[1,2-a]pyridin-3-yl}-5,5-dimethyl-6-oxo-6,7-dihydro-5H-pyrrolo[2,3-d]pyrimidin-4-yl)amino]methyl}cyclopropyl)carbamate from Example 37A in 1 ml of diethyl ether. The mixture was stirred at RT for a further 16 h. The mixture was subsequently concentrated and dried under high vacuum, and the residue was dissolved in acetonitrile/water and purified by preparative HPLC (RP18 column, mobile phase: acetonitrile/water gradient with addition of 0.1% TFA). The product fractions were concentrated, dissolved in dichloromethane and a little methanol and washed twice with saturated aqueous sodium bicarbonate solution. The combined aqueous phases were extracted twice with dichloromethane. The combined organic phases were dried over sodium sulphate, filtered and concentrated. This gave 17 mg (31% of theory) of the title compound.

LC-MS (Method 1): $R_t$=0.64 min

MS (ESpos): m/z=520 (M+H)$^+$ $^1$H NMR (400 MHz, DMSO-d$_6$) δ=0.37-0.43 (m, 2 H), 0.49-0.55 (m, 2 H), 1.38 (s, 6 H), 1.91 (br. s, 2 H), 2.72 (s, 3 H), 3.62 (d, 2 H), 5.32 (s, 2 H), 6.48-6.56 (m, 1 H), 6.91-7.05 (m, 2 H), 7.19-7.29 (m, 2 H), 7.55-7.64 (m, 1 H), 9.55 (d, 1 H), 10.93 (br. s, 1 H).

Example 43

2-{8-[(2,6-Difluorobenzyl)oxy]-2-methylimidazo[1,2-a]pyridin-3-yl}-4-(4-hydroxy-1H-pyrazol-1-yl)-5,5-dimethyl-5,7-dihydro-6H-pyrrolo[2,3-d]pyrimidin-6-one

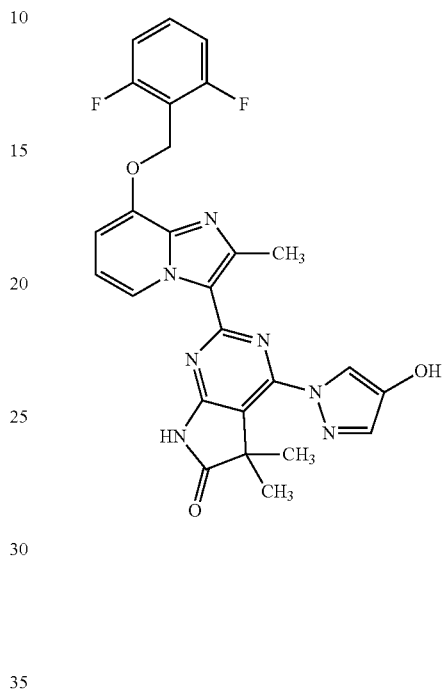

Under argon, 176 mg (2.10 mmol) of 1H-pyrazol-4-ol, 114 mg (0.35 mmol) of caesium carbonate, 5 mg (0.04 mmol) of copper(I) oxide and 19 mg (0.14 mmol) of 2-hydroxybenzaldehyde oxime were added in succession to a solution of 100 mg (0.18 mmol) (purity 86%) of 2-{8-[(2,6-difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one from Example 2 in 2 ml of acetonitrile. The reaction mixture was irradiated in the microwave at 160° C. for 2 h. The mixture was taken up in TFA/water, filtered through a Millipore filter and purified by preparative HPLC (RP18 column, mobile phase: acetonitrile/water gradient with addition of 0.1% TFA). The product-containing fractions were concentrated, dissolved in dichloromethane and a little 2 M ammonia in methanol and re-purified by thick-layer chromatography (mobile phase: dichloromethane/methanol=10:1). This gave 5 mg (5% of theory; purity about 95%) of the title compound.

LC-MS (Method 1): $R_t$=0.89 min

MS (ESpos): m/z=518 (M+H)$^+$ $^1$H NMR (500 MHz, DMSO-d$_6$) δ=1.56 (s, 6 H), 2.81 (s, 3 H), 5.36 (s, 2 H), 7.05 (t, 1 H), 7.11 (d, 1 H), 7.20-7.30 (m, 2 H), 7.54-7.64 (m, 1 H), 7.70 (s, 1 H), 8.15 (s, 1 H), 9.38 (br. s, 1 H), 9.48 (d, 1 H), 11.53-11.81 (m, 1 H).

Example 44

2-{8-[(2,6-Difluorobenzyl)oxy]-2-methylimidazo[1,2-a]pyridin-3-yl}-5,5-dimethyl-4-(1H-pyrazol-4-yloxy)-5,7-dihydro-6H-pyrrolo[2,3-d]pyrimidin-6-one

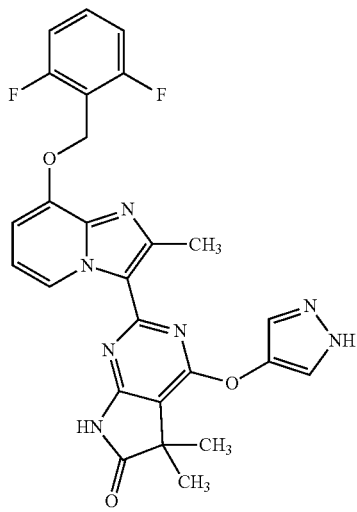 [SMILES: Cc1nc2c(OCc3c(F)cccc3F)cccn2c1-c1nc2c(c(Oc3cn[nH]c3)n1)C(C)(C)C(=O)N2]

The target compound was formed during the synthesis of the target compound of Example 43:

Under argon, 176 mg (2.10 mmol) of 1H-pyrazol-4-ol, 114 mg (0.35 mmol) of caesium carbonate, 5 mg (0.04 mmol) of copper(I) oxide and 19 mg (0.14 mmol) of 2-hydroxybenzaldehyde oxime were added in succession to a solution of 100 mg (0.18 mmol) (purity 86%) of 2-{8-[(2,6-difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one from Example 2 in 2 ml of acetonitrile. The reaction mixture was irradiated in the microwave at 160° C. for 2 h. The mixture was taken up in TFA/water, filtered through a Millipore filter and purified by preparative HPLC (RP18 column, mobile phase: acetonitrile/water gradient with addition of 0.1% TFA). The product-containing fractions were concentrated, dissolved in dichloromethane and a little 2 M ammonia in methanol and re-purified by thick-layer chromatography (mobile phase: dichloromethane/methanol=10/1). This gave 15 mg (16% of theory) of the title compound.

LC-MS (Method 1): $R_t$=0.83 min

MS (ESpos): m/z=518 (M+H)$^+$ $^1$H NMR (500 MHz, DMSO-d$_6$) δ=1.45 (s, 6 H), 5.31 (s, 2 H), 6.81 (t, 1 H), 7.05 (d, 1 H), 7.23 (t, 2 H), 7.56-7.61 (m, 2 H), 7.93 (br. s, 1 H), 9.17 (d, 1 H), 11.48 (s, 1 H), 12.89 (br. s, 1 H).

Example 45 ent-4-[(2-Amino-3-methoxy-2-methylpropyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one
(Enantiomer A)

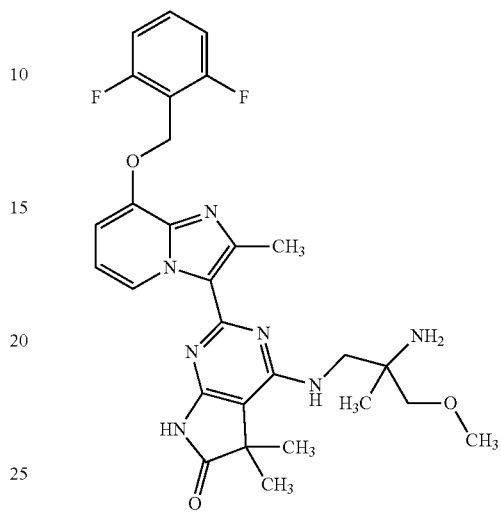

531 mg of rac-4-[(2-amino-3-methoxy-2-methylpropyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one (Example 21) were separated on a chiral phase into the enantiomers [column: Daicel Chiralpak OD-H, 5 μm, 250×20 mm, mobile phase: 50% isohexane, 50% ethanol+0.2% diethylamine, flow rate 15 ml/min; 40° C., detection: 220 nm].

Yield: 283 mg of enantiomer A (99% purity, >99% ee)

$R_t$=4.18 min [Daicel Chiralpak OD-H, 5 μm, 250×4.6 mm; mobile phase: 50% isohexane, 50% ethanol+0.2% diethylamine; flow rate 1.0 ml/min; 40° C.; detection: 235 nm].

Example 46 ent-4-[(2-Amino-3-methoxy-2-methylpropyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one (Enantiomer B)

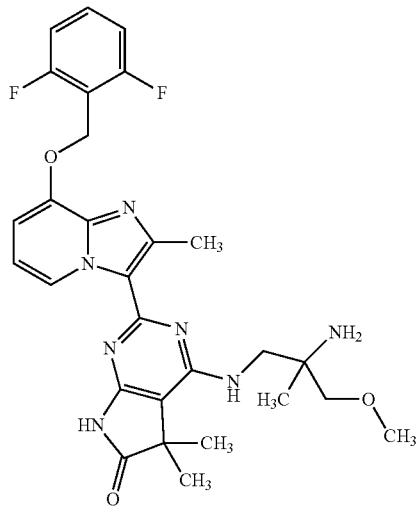 [SMILES: COCC(C)(N)CNc1nc(-c2c(C)nc3c(OCc4c(F)cccc4F)cccn23)nc2c1C(C)(C)C(=O)N2]

531 mg of rac-4-[(2-amino-3-methoxy-2-methylpropyl)amino]-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one (Example 21) were separated on a chiral phase into the enantiomers [column: Daicel Chiralpak OD-H, 5 µm, 250×20 mm, mobile phase: 50% isohexane, 50% ethanol+0.2% diethylamine, flow rate 15 ml/min; 40° C., detection: 220 nm].

Yield: 126 mg of enantiomer B (99% pure, >99% ee)

$R_t$=7.15 min [Daicel Chiralpak OD-H, 5 µm, 250×4.6 mm; mobile phase: 50% isohexane, 50% ethanol+0.2% diethylamine; flow rate 1.0 ml/min; 40° C.; detection: 235 nm].

Example 47

2-{8-[(2,6-Difluorobenzyl)oxy]-2-methylimidazo[1,2-a]pyridin-3-yl}-4-(2-hydroxyethoxy)-5,5-dimethyl-5,7-dihydro-6H-pyrrolo[2,3-d]pyrimidin-6-one

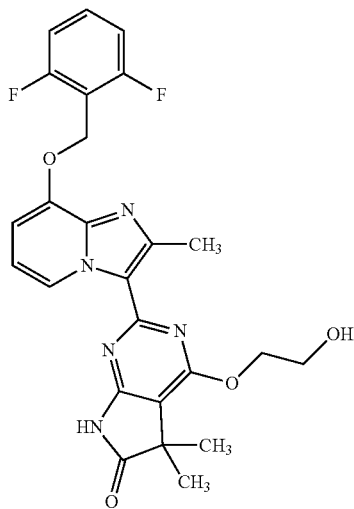 [SMILES: Cc1nc2c(OCc3c(F)cccc3F)cccn2c1-c1nc2c(c(OCCO)n1)C(C)(C)C(=O)N2]

100 mg (0.178 mmol) of 2-{8-[(2,6-difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one from Example 2 and 221 mg (3.56 mmol) of ethylene glycol were initially charged, and 8.4 mg (0.036 mmol) of 3,4,7,8-tetramethyl-1,10-phenanthroline, 3.4 mg (0.018 mmol) of copper(I) iodide and 116 mg (0.356 mmol) of caesium carbonate were added. The reaction mixture was then suspended in 3 ml of toluene. This suspension was stirred in the microwave at 140° C. for 6 h. The suspension was taken up in dichloromethane/water and extracted by shaking. The organic phase was concentrated. The residue was taken up in dichloromethane/a little methanol and purified by thick-layer chromatography (mobile phase: dichloromethane/methanol=30/1). This gave 3.4 mg (4% of theory, purity 81%) of the target compound.

LC-MS (Method 1): $R_t$=0.78 min

MS (ESpos): m/z=496 (M+H)$^+$

Example 48

2-{8-[(2,6-Difluorobenzyl)oxy]-2-methylimidazo[1,2-a]pyridin-3-yl}-5,5-dimethyl-6-oxo-6,7-dihydro-5H-pyrrolo[2,3-d]pyrimidine-4-carbonitrile

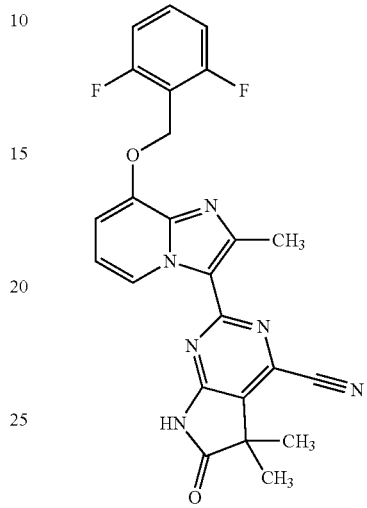

200 mg (0.36 mmol) of 2-{8-[(2,6-difluorobenzyl)oxy]-2-methylimidazo[1,2-a]pyridin-3-yl}-4-iodo-5,5-dimethyl-5,7-dihydro-6H-pyrrolo[2,3-d]pyrimidin-6-one from Example 2 and 35 mg (0.39 mmol) of copper(I) cyanide were dissolved in 3.8 ml of DMSO, and the mixture was stirred under argon at 150° C. for 2 h. The reaction mixture was cooled, saturated aqueous ammonium chloride solution/33% strength aqueous ammonia solution (3/1) and ethyl acetate were added carefully and the mixture was stirred at room temperature for 30 min. The mixture was filtered off with suction through Celite, washed with ethyl acetate, and the two phases of the filtrate were separated. The organic phase was washed three times with saturated aqueous ammonium chloride solution/33% strength aqueous ammonia solution (3/1) and once with saturated aqueous sodium chloride solution. The organic phase was then dried over sodium sulphate, concentrated and dried under high vacuum. The crude product was purified by preparative HPLC (RP18 column, mobile phase: methanol/water gradient with addition of 0.1% TFA). The product fractions were dissolved in dichloromethane and washed twice with saturated aqueous sodium bicarbonate solution. The combined aqueous phases were extracted once with dichloromethane. The combined organic phases were dried over sodium sulphate, filtered and concentrated by rotary evaporation. This gave 100 mg (60% of theory; purity about 95%) of the title compound.

LC-MS (Method 1): $R_t$=0.99 min

MS (ESpos): m/z=461 (M+H)$^+$ $^1$H NMR (400 MHz, DMSO-d$_6$) δ=1.48 (s, 6 H), 2.73 (s, 3 H), 5.35 (s, 2 H), 7.08-7.18 (m, 2 H), 7.19-7.28 (m, 2 H), 7.58-7.64 (m, 1 H), 9.42 (d, 1 H), 12.08 (br. s, 1 H).

Example 49

4-(Aminomethyl)-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one

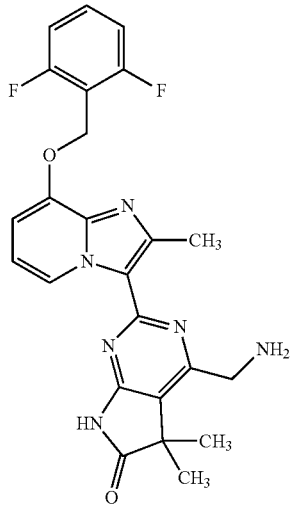 [SMILES: Cc1nc2c(OCc3c(F)cccc3F)cccn2c1-c1nc(CN)c2c(n1)NC(=O)C2(C)C]

138 mg (0.28 mmol; purity about 95%) of 2-{8-[(2,6-difluorobenzyl)oxy]-2-methylimidazo[1,2-a]pyridin-3-yl}-5,5-dimethyl-6-oxo-6,7-dihydro-5H-pyrrolo[2,3-d]pyrimidine-4-carbonitrile from Example 48 were dissolved in 26 ml of acetic acid, 15 mg of palladium/carbon (10%) were added and the mixture was hydrogenated at standard pressure for 3.5 h. After addition of a further 15 mg of palladium/carbon (10%), the mixture was hydrogenated at standard pressure for another 45 min. The reaction mixture was filtered through a Millipore filter, the filtrate was concentrated and the residue was purified by preparative HPLC (RP18 column, mobile phase: acetonitrile/water gradient with addition of 0.1% TFA). The product fractions were taken up in dichloromethane and washed twice with saturated aqueous sodium bicarbonate solution. The combined aqueous phases were extracted twice with dichloromethane. The combined organic phases were dried over sodium sulphate, filtered and concentrated. This gave 98 mg (74% of theory) of the target compound.

LC-MS (Method 1): $R_t$=0.53 min
MS (ESpos): m/z=465 (M+H)$^+$
$^1$H NMR (500 MHz, DMSO-$d_6$) δ=1.40 (s, 6 H), 2.76 (s, 3 H), 3.85 (s, 2 H), 5.33 (s, 2 H), 7.00 (t, 1 H), 7.06 (d, 1 H), 7.19-7.28 (m, 2 H), 7.57-7.64 (m, 1 H), 9.61 (d, 1 H).

Example 50

2-{8-[(2,6-Difluorobenzyl)oxy]-2-methylimidazo[1,2-a]pyridin-3-yl}-5,5-dimethyl-6-oxo-6,7-dihydro-5H-pyrrolo[2,3-d]pyrimidine-4-carboxamide hydrochloride

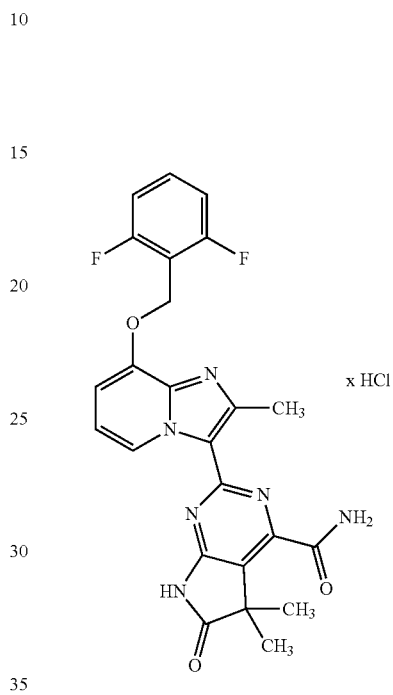

1.50 g (2.9 mmol; purity about 90%) of 2-{8-[(2,6-difluorobenzyl)oxy]-2-methylimidazo[1,2-a]pyridin-3-yl}-5,5-dimethyl-6-oxo-6,7-dihydro-5H-pyrrolo[2,3-d]pyrimidine-4-carbonitrile from Example 48 were initially charged in 13.9 ml of 1,4-dioxane, 3.62 ml (7.24 mmol) of 2 N aqueous sodium hydroxide solution were added and the mixture was stirred at 90° C. for 20 h. 17.4 ml of 1 N aqueous hydrochloric acid were added and the reaction mixture was concentrated. The residue was stirred with water, filtered off and washed with water. The solid that had been filtered off was dried under high vacuum. This gave 1.02 g (74% of theory) of the target compound. The product was converted further without further purification.

LC-MS (Method 17): $R_t$=1.74 min
MS (ESpos): m/z=479 (M+H)$^+$
$^1$H NMR (500 MHz, DMSO-$d_6$) δ=1.49 (s, 6 H), 2.80 (s, 3 H), 5.43 (s, 2 H), 7.19-7.32 (m, 3 H), 7.39 (br. s, 1 H), 7.57-7.64 (m, 1 H), 8.04 (d, 2 H), 9.51 (d, 1 H), 11.84 (s, 1 H).

Example 51

2-{8-[(2,6-Difluorobenzyl)oxy]-2-methylimidazo[1,2-a]pyridin-3-yl}-5,5-dimethyl-6-oxo-6,7-dihydro-5H-pyrrolo[2,3-d]pyrimidine-4-carboxylic acid

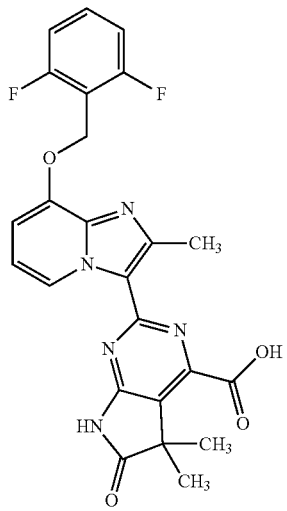 [SMILES: Cc1nc2c(OCc3c(F)cccc3F)cccn2c1-c1nc2c(c(C(=O)O)n1)C(C)(C)C(=O)N2]

17.3 ml of semi-concentrated hydrochloric acid, 7.6 ml of DMSO and 7.64 ml of 1,4-dioxane were added to 955 mg (1.85 mmol) of 2-{8-[(2,6-difluorobenzyl)oxy]-2-methyl-imidazo[1,2-a]pyridin-3-yl}-5,5-dimethyl-6-oxo-6,7-dihydro-5H-pyrrolo[2,3-d]pyrimidine-4-carboxamide hydrochloride from Example 50, and the mixture was stirred at 85° C. for 11 h. The reaction solution was concentrated on a rotary evaporator. Then the mixture was diluted with water and stirred at room temperature for 30 min. The solid present was filtered off and dried. This gave 256 mg (26% of theory; purity about 89%) of the target compound. The filtrate was extracted three times with ethyl acetate. The aqueous phase was concentrated to half its original volume. This resulted in the precipitation of a solid. This precipitate was filtered off and dried. This gave 323 mg (33% of theory; purity about 91%) of the target compound. The filtrate was extracted five times with dichloromethane. The combined organic phases were concentrated. The residue (DMSO-containing solution) was diluted with acetonitrile/water and, in portions, purified by preparative HPLC (RP18 column, mobile phase: acetonitrile/water gradient with addition of 0.1% TFA). This gave 105 mg (11% of theory; purity about 90%) of the target compound. In total, 684 mg (69% of theory; purity about 90%) of the target compound were obtained.

LC-MS (Method 1): $R_t$=0.68 min

MS (ESpos): m/z=480 (M+H)$^+$ $^1$H NMR (500 MHz, DMSO-d$_6$) δ=1.49 (s, 6 H), 2.84 (s, 3 H), 5.43 (s, 2 H), 7.20-7.29 (m, 2 H), 7.30-7.52 (m, 2 H), 7.56-7.64 (m, 1 H), 9.81 (d, 1 H), 11.91 (s, 1 H), 14.09 (br. s, 1 H).

Example 52

5,5-Dimethyl-2-{2-methyl-8-[(2,3,6-trifluorobenzyl)oxy]imidazo[1,2-a]pyridin-3-yl}-6-oxo-6,7-dihydro-5H-pyrrolo[2,3-d]pyrimidine-4-carbonitrile

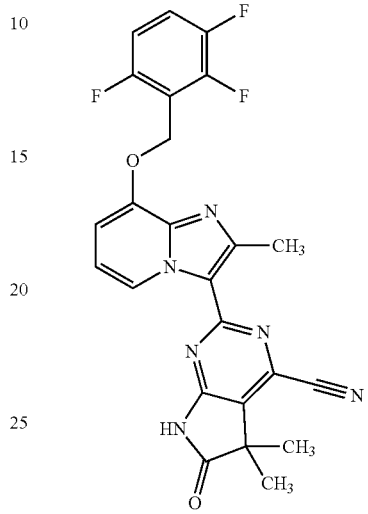

1.0 g (1.73 mmol) of 4-iodo-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one from Example 10 and 170 mg (1.90 mmol) of copper(I) cyanide were dissolved in 19 ml of DMSO, and the mixture was stirred under argon at 150° C. for 3 h. The reaction mixture was cooled, saturated aqueous ammonium chloride solution/33% strength aqueous ammonia solution (3/1) and ethyl acetate were added carefully and the mixture was stirred at room temperature for 30 min. The mixture was stirred over Celite, washed with ethyl acetate, and the two phases of the filtrate were separated. The organic phase was washed three times with saturated aqueous ammonium chloride solution/33% strength aqueous ammonia solution (3/1). The organic phase was then dried over sodium sulphate, concentrated on a rotary evaporator and dried under high vacuum. The Celite filter cake and the sodium sulphate residues were stirred with methanol/dichloromethane (1/1), filtered off and concentrated by rotary evaporation. The residue was washed with water and dried under high vacuum. All fractions of the title compound were combined (689 mg; 95% of theory) and reacted further without further purification.

LC-MS (Method 1): $R_t$=0.98 min

MS (ESpos): m/z=479 (M+H)$^+$ $^1$H NMR (400 MHz, DMSO-d$_6$) δ=12.08 (br. s, 1 H), 9.42 (d, 1 H), 7.62-7.74 (m, 1 H), 7.25-7.37 (m, 1 H), 7.08-7.21 (m, 2 H), 5.40 (s, 2 H), 2.74 (s, 3 H), 1.48 (s, 6 H).

Example 53

5,5-Dimethyl-2-{2-methyl-8-[(2,3,6-trifluorobenzyl)oxy]imidazo[1,2-a]pyridin-3-yl}-6-oxo-6,7-dihydro-5H-pyrrolo[2,3-d]pyrimidine-4-carboxamide

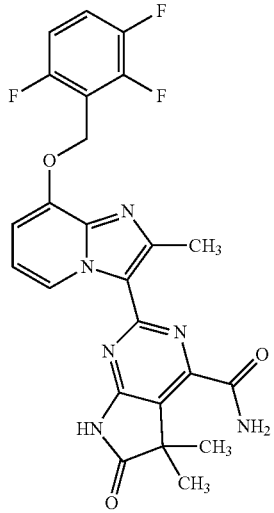

689 mg (1.44 mmol) of 5,5-dimethyl-2-{2-methyl-8-[(2,3,6-trifluorobenzyl)oxy]imidazo[1,2-a]pyridin-3-yl}-6-oxo-6,7-dihydro-5H-pyrrolo[2,3-d]pyrimidine-4-carbonitrile from Example 52 were initially charged in 7 ml of 1,4-dioxane, 1.8 ml (3.58 mmol) of 2 N aqueous sodium hydroxide solution were added and the mixture was stirred at 80° C. overnight. 3.6 ml of 1 N aqueous hydrochloric acid were added and the reaction mixture was concentrated. The residue was stirred with water, filtered off and washed with water. The solid that had been filtered off was dried under high vacuum. This gave 680 mg (95% of theory) of the target compound. The product was converted further without further purification.

LC-MS (Method 1): $R_t$=0.78 min

MS (ESpos): m/z=497 (M+H)$^+$ $^1$H NMR (400 MHz, DMSO-d$_6$) δ=1.49 (s, 6 H), 2.77 (s, 3 H), 5.41 (s, 2 H), 7.02-7.22 (m, 2 H), 7.24-7.35 (m, 1 H), 7.61-7.72 (m, 1 H), 8.00 (d, 2 H), 9.44 (d, 1 H), 11.77 (s, 1 H).

Example 54

5,5-Dimethyl-2-{2-methyl-8-[(2,3,6-trifluorobenzyl)oxy]imidazo[1,2-a]pyridin-3-yl}-6-oxo-6,7-dihydro-5H-pyrrolo[2,3-d]pyrimidine-4-carboxylic acid

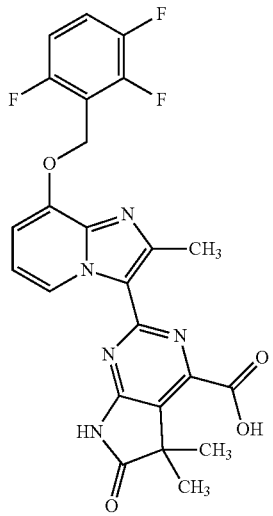 [SMILES: Cc1nc2c(OCc3c(F)ccc(F)c3F)cccn2c1-c1nc2c(c(C(N)=O)n1)C(C)(C)C(=O)N2]

11.9 ml of concentrated hydrochloric acid were added to 680 mg (1.37 mmol) of 5,5-dimethyl-2-{2-methyl-8-[(2,3,6-trifluorobenzyl)oxy]imidazo[1,2-a]pyridin-3-yl}-6-oxo-6,7-dihydro-5H-pyrrolo[2,3-d]pyrimidine-4-carboxamide from Example 53, and the mixture was stirred at 80° C. for 14 h. The reaction mixture was diluted with water. The precipitated solid was filtered off, washed with water and dried under high vacuum. This gave 426 mg (54% of theory, purity about 87%) of the target compound. The product was converted further without further purification.

LC-MS (Method 23): $R_t$=0.90 min

MS (ESpos): m/z=498 (M+H)$^+$ $^1$H NMR (400 MHz, DMSO-d$_6$) δ=1.47 (s, 6 H), 2.79 (s, 3 H), 5.40 (s, 2 H), 7.03-7.21 (m, 2 H), 7.26-7.36 (m, 1 H), 7.61-7.71 (m, 1 H), 9.74 (d, 1 H), 11.83 (s, 1 H), 13.99 (br. s, 1 H).

Example 55

N-Cyclopropyl-2-{8-[(2,6-difluorobenzyl)oxy]-2-methylimidazo[1,2-a]pyridin-3-yl}-5,5-dimethyl-6-oxo-6,7-dihydro-5H-pyrrolo[2,3-d]pyrimidine-4-carboxamide

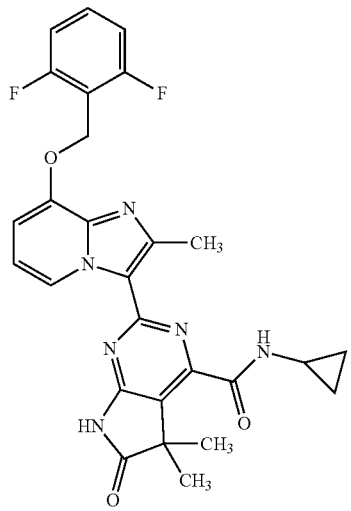 [SMILES: Cc1nc2c(OCc3c(F)cccc3F)cccn2c1-c1nc2c(c(C(=O)NC3CC3)n1)C(C)(C)C(=O)N2]

40 mg (0.076 mmol; purity about 90%) of 2-{8-[(2,6-difluorobenzyl)oxy]-2-methylimidazo[1,2-a]pyridin-3-yl}-5,5-dimethyl-6-oxo-6,7-dihydro-5H-pyrrolo[2,3-d]pyrimidine-4-carboxylic acid from Example 51, 8.7 mg (0.152 mmol) of cyclopropylamine and 40 µl (0.228 mmol) of N,N-diisopropylethylamine were dissolved in 1 ml of DMF at RT, and 68 µl (0.114 mmol; 50% in ethyl acetate) of 2,4,6-tripropyl-1,3,5,2,4,6-trioxatriphosphinane 2,4,6-trioxide (propanephosphonic anhydride=T3P) were then added. The mixture was stirred at RT for 2 h. The reaction solution was concentrated, TFA/water/acetonitrile were added and the mixture was purified by preparative HPLC (RP18 column, mobile phase: acetonitrile/water gradient with addition of 0.1% TFA).

The product fractions were concentrated, then taken up in dichloromethane and washed twice with saturated aqueous sodium bicarbonate solution. The combined aqueous phases were reextracted twice with dichloromethane. The combined organic phases were dried over sodium sulphate, filtered, concentrated and lyophilized. This gave 30 mg (75% of theory) of the target compound.

LC-MS (Method 1): $R_t$=0.88 min

MS (ESpos): m/z=519 (M+H)$^+$ $^1$H NMR (500 MHz, DMSO-d$_6$) δ=0.60-0.66 (m, 2 H), 0.76-0.82 (m, 2 H), 1.49 (s, 6 H), 2.73 (s, 3 H), 2.89-2.97 (m, 1 H), 5.34 (s, 2 H), 7.04 (t, 1 H), 7.09 (d, 1 H), 7.20-7.27 (m, 2 H), 7.57-7.64 (m, 1 H), 8.55 (d, 1 H), 9.40 (d, 1 H), 11.75 (s, 1 H).

The exemplary compounds shown in Table 3 were prepared analogously to Example 55 by reacting the carboxylic acids from Example 51 or Example 54 with the appropriate commercially available or above-described amines (2-10 equivalents), propanephosphonic anhydride (1.5-4.5 equivalents) and N,N-diisopropylethylamine (3-5 equivalents) under the reaction conditions described (reaction time: 1-48 h; temperature: RT).

Illustrative Workup of the Reaction Mixture:

The reaction mixture was diluted with water, TFA or formic acid and purified by preparative HPLC (RP18 column, mobile phase: acetonitrile/water gradient with addition of 0.1% TFA or 0.05% formic acid). Additionally or alternatively, the crude product was purified by thick-layer chromatography or silica gel chromatography (mobile phase: dichloromethane/methanol). The product-containing fractions were concentrated.

The residue was, if necessary, taken up in dichloromethane and washed with saturated aqueous sodium bicarbonate solution. The aqueous phase was extracted twice with dichloromethane, and the combined organic phases were dried over sodium sulphate, filtered, concentrated and lyophilized.

TABLE 3

| Example | IUPAC name/structure (Yield) | Analytical data |
|---|---|---|
| 56 | 2-{8-[(2,6-difluorobenzyl)oxy]-2-methylimidazo[1,2-a]pyridin-3-yl}-N-(2-hydroxy-2-methylpropyl)-5,5-dimethyl-6-oxo-6,7-dihydro-5H-pyrrolo[2,3-d]pyrimidine-4-carboxamide<br />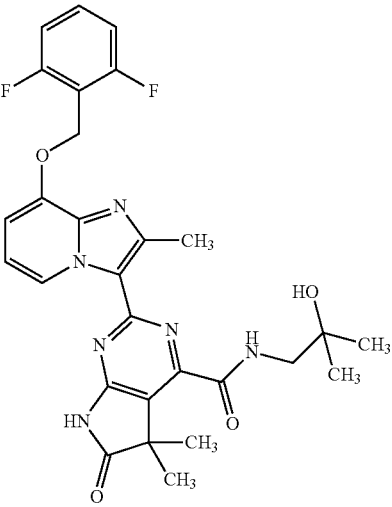 [SMILES: Cc1nc2c(OCc3c(F)cccc3F)cccn2c1-c1nc2c(c(C(=O)NCC(C)(C)O)n1)C(C)(C)C(=O)N2]<br />(64% of theory) | LC-MS (Method 1): $R_t$ = 0.83 min<br />MS (ESpos): m/z = 551 (M + H)$^+$<br />$^1$H NMR (400 MHz, DMSO-d$_6$) δ = 1.18 (s, 6 H), 1.51 (s, 6 H), 2.77 (s, 3 H), 4.77 (s, 1 H), 5.34 (s, 2 H), 7.02 (t, 1 H), 7.11 (d, 1 H), 7.20-7.29 (m, 2 H), 7.55-7.64 (m, 1 H), 8.51 (t, 1 H), 9.45 (d, 1 H), 11.78 (s, 1 H). [further signal hidden under solvent peak]. |

TABLE 3-continued

| Example | IUPAC name/structure (Yield) | Analytical data |
|---|---|---|
| 57 | rac-N-(2-amino-3,3,3-trifluoro-2-methylpropyl)-5,5-dimethyl-2-{2-methyl-8-[(2,3,6-trifluorobenzyl)oxy]imidazo[1,2-a]pyridin-3-yl}-6-oxo-6,7-dihydro-5H-pyrrolo[2,3-d]pyrimidine-4-carboxamide<br>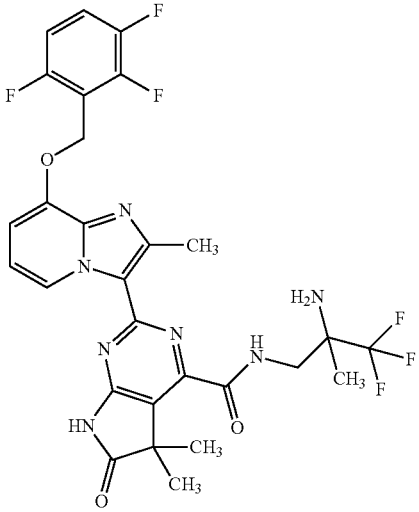 [SMILES: Cc1nc2c(OCc3c(F)ccc(F)c3F)cccn2c1-c1nc2c(c(C(=O)NCC(C)(N)C(F)(F)F)n1)C(C)(C)C(=O)N2]<br>(29% of theory) | LC-MS (Method 1): $R_t$ = 0.90 min<br>MS (ESpos): m/z = 622 (M + H)$^+$<br>$^1$H NMR (400 MHz, DMSO-d$_6$) δ = 1.19 (s, 3 H), 1.50 (s, 3 H), 1.51 (s, 3 H), 2.78 (s, 3 H), 3.37-3.42 (m, 1 H), 3.63-3.70 (m, 1 H), 5.40 (s, 2 H), 7.05 (t, 1 H), 7.11 (d, 1 H), 7.26-7.33 (m, 1 H), 7.63-7.71 (m, 1 H), 8.61-8.69(m, 1 H), 9.45 (d, 1 H), 11.80 (s, 1 H). |
| 58 | N-(2-amino-2-methylpropyl)-5,5-dimethyl-2-{2-methyl-8-[(2,3,6-trifluorobenzyl)oxy]imidazo[1,2-a]pyridin-3-yl}-6-oxo-6,7-dihydro-5H-pyrrolo[2,3-d]pyrimidin-4-carboxamide trifluoroacetate<br>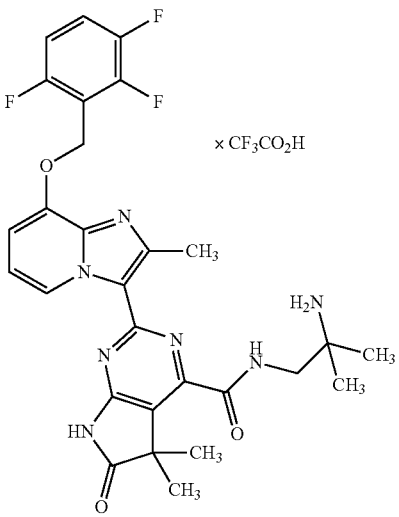 [SMILES: Cc1nc2c(OCc3c(F)ccc(F)c3F)cccn2c1-c1nc2c(c(C(=O)NCC(C)(C)N)n1)C(C)(C)C(=O)N2]<br>(27% of theory) $^{1)}$ | LC-MS (Method 1): $R_t$ = 0.67 min<br>MS (ESpos): m/z = 568 (M − TFA + H)$^+$<br>$^1$H NMR (400 MHz, DMSO-d$_6$) δ = 1.31 (s, 6 H), 1.52 (s, 6 H), 2.81 (s, 3 H), 5.44 (s, 2 H), 7.09 (t, 1 H), 7.23 (d, 1 H), 7.63-7.73 (m, 1 H), 7.86 (br. s, 3 H), 8.87-8.93 (m, 1 H), 9.50 (d, 1 H), 11.88 (s, 1 H) [further signal hidden under solvent peak (3.25-3.75 ppm)]. |

| Ex-ample | IUPAC name/structure (Yield) | Analytical data |
|---|---|---|
| 59 | 5,5-dimethyl-2-{2-methyl-8-[(2,3,6-trifluorobenzyl)oxy]imidazo[1,2-a]pyridin-3-yl}-6-oxo-N-(3,3,3-trifluoropropyl)-6,7-dihydro-5H-pyrrolo[2,3-d]pyrimidine-4-carboxamide<br><br>(47% of theory) | LC-MS (Method 1): $R_t$ = 0.97 min<br>MS (ESpos): m/z = 593 (M + H)$^+$<br>$^1$H NMR (400 MHz, DMSO-d$_6$) δ = 1.49 (s, 6 H), 2.55-2.69 (m, 2 H), 2.76 (s, 3 H), 3.58-3.65 (m, 2 H), 5.40 (s, 2 H), 7.01 (t, 1 H), 7.10 (d, 1 H), 7.25-7.35 (m, 1 H), 7.61-7.72 (m, 1 H), 8.74-8.82 (m, 1 H), 9.40 (d, 1 H), 11.78 (s, 1H), |
| 60 | 5,5-dimethyl-4-[(4-methylpiperazin-1-yl)carbonyl]-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one trifluoroacetate<br><br>(62% of theory) $^{1)}$ | LC-MS (Method 1): $R_t$ = 0.64 min<br>MS (ESpos): m/z = 580 (M − TFA + H)$^+$ |

TABLE 3-continued

| Example | IUPAC name/structure (Yield) | Analytical data |
|---|---|---|
| 61 | rac-4-[(4-amino-3,3-difluoropyrrolidin-1-yl)carbonyl]-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one trifluoroacetate 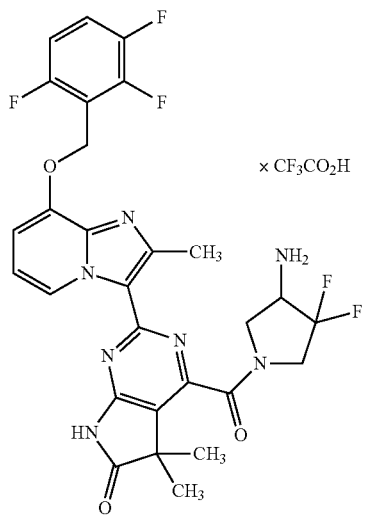 [SMILES: Cc1nc2c(OCc3c(F)ccc(F)c3F)cccn2c1-c1nc2c(c(C(=O)N3CC(N)C(F)(F)C3)n1)C(C)(C)C(=O)N2] (22% of theory) | LC-MS (Method 1): $R_t$ = 0.71 min MS (ESpos): m/z = 602 (M − TFA + H)$^+$ |
| 62 | rac-4-[(3-hydroxypyrrolidin-1-yl)carbonyl]-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one 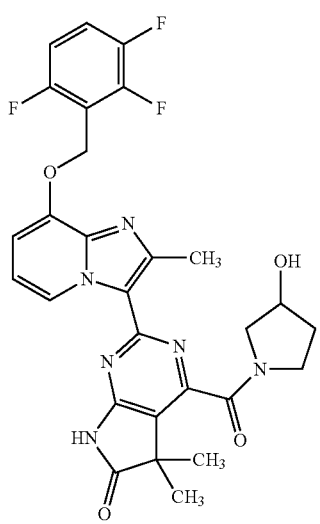 [SMILES: Cc1nc2c(OCc3c(F)ccc(F)c3F)cccn2c1-c1nc2c(c(C(=O)N3CCC(O)C3)n1)C(C)(C)C(=O)N2] (23% of theory) [1) | LC-MS (Method 1): $R_t$ = 0.71 min MS (ESpos): m/z = 567 (M+H)$^+$ |

TABLE 3-continued

| Example | IUPAC name/structure (Yield) | Analytical data |
|---|---|---|
| 63 | rac-4-{[3-(hydroxymethyl)pyrrolidin-1-yl]carbonyl}-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one<br />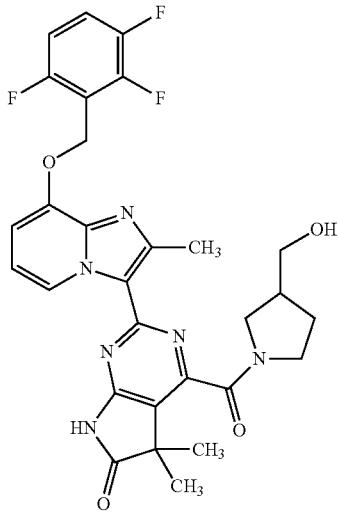 [SMILES: Cc1nc2c(OCc3c(F)ccc(F)c3F)cccn2c1-c1nc2c(c(C(=O)N3CCC(CO)C3)n1)C(C)(C)C(=O)N2]<br />(7% of theory) [1) | LC-MS (Method 1): $R_t$ = 0.73 min<br />MS (ESpos): m/z = 581 (M + H)+ |
| 64 | 5,5-dimethyl-2-{2-methyl-8-[(2,3,6-trifluorobenzyl)oxy]imidazo[1,2-a]pyridin-3-yl}-4-(piperazin-1-ylcarbonyl)-5,7-dihydro-6H-pyrrolo[2,3-d]pyrimidin-6-one trifluoroacetate<br />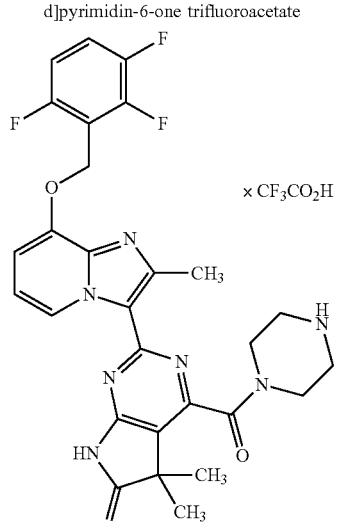<br />(11% of theory) [1) | LC-MS (Method 1): $R_t$ = 0.62 min<br />MS (ESpos): m/z = 566 (M − TFA + H)+ |

[1) The product was subsequently purified once more by preparative HPLC (RP18 column, mobile phase: acetonitrile/water gradient with addition of 1% TFA).

Example 65

N-[(2-{8-[(2,6-Difluorobenzyl)oxy]-2-methylimidazo[1,2-a]pyridin-3-yl}-5,5-dimethyl-6-oxo-6,7-dihydro-5H-pyrrolo[2,3-d]pyrimidin-4-yl)methyl]methanesulphonamide

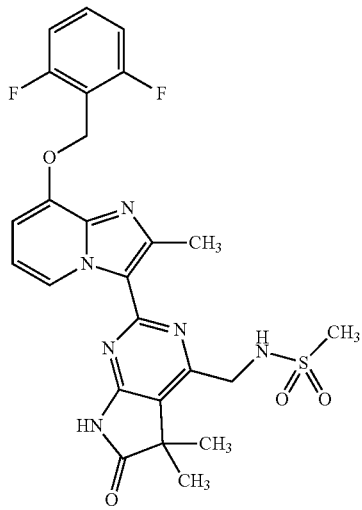 [SMILES: Cc1nc2c(OCc3c(F)cccc3F)cccn2c1-c1nc(CNS(C)(=O)=O)c2c(n1)NC(=O)C2(C)C]

Under argon, 30 mg (0.06 mmol) of 4-(aminomethyl)-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one from Example 49 were initially charged in 0.67 ml of dichloromethane/DMF (1/1). 18 mg (0.14 mmol) of N,N-diisopropylethylamine were added at RT and the mixture was stirred for 15 min. Subsequently, 8 mg (0.07 mmol) of methanesulphonyl chloride were added at RT and the mixture was stirred at room temperature for 1 h. Another 2.3 mg (0.02 mmol) of methanesulphonyl chloride were added and the mixture was stirred at RT for 1 h. The reaction solution was concentrated and the residue was taken up in dichloromethane and purified by thick-layer chromatography (mobile phase: dichloromethane/methanol=10/1). This gave 26 mg of the target compound (72% of theory).

LC-MS (Method 1): $R_t$=0.95 min

MS (ESpos): m/z=543 (M+H)$^+$ $^1$H NMR (500 MHz, DMSO-$d_6$) δ=1.43 (s, 6 H), 2.77 (s, 3 H), 2.98 (s, 3 H), 4.34 (d, 2 H), 5.34 (s, 2 H), 6.97 (t, 1 H), 7.07 (d, 1 H), 7.20-7.28 (m, 2 H), 7.56-7.64 (m, 1 H), 7.70-7.75 (m, 1 H), 9.71 (d, 1 H), 11.56 (s, 1 H).

Example 66

N-[(2-{8-[(2,6-Difluorobenzyl)oxy]-2-methylimidazo[1,2-a]pyridin-3-yl}-5,5-dimethyl-6-oxo-6,7-dihydro-5H-pyrrolo[2,3-d]pyrimidin-4-yl)methyl]cyclopropanecarboxamide

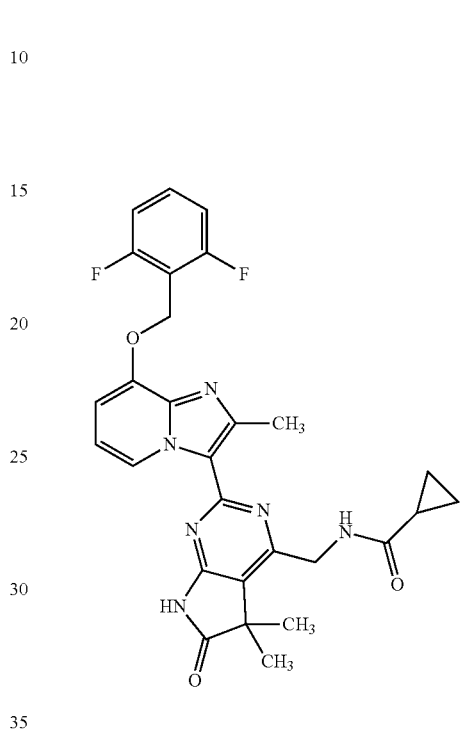

40 mg (0.08 mmol) of 4-(aminomethyl)-2-{8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one from Example 49 were initially charged. At 0° C. and under argon, 38 mg (0.30 mmol) of N,N-diisopropylethylamine and a solution of 10 mg (0.09 mmol) of cyclopropanecarbonyl chloride in 3 ml of tetrahydrofuran were added. The solution was stirred at RT for 1 h. The reaction solution was concentrated and the residue was taken up in dichloromethane/methanol and purified by thick-layer chromatography (mobile phase: dichloromethane/methanol=30/1). This gave 34 mg of the target compound (70% of theory, purity 92%).

LC-MS (Method 1): $R_t$=0.74 min

MS (ESpos): m/z=533 (M+H)$^+$ $^1$H NMR (500 MHz, DMSO-$d_6$) δ=0.68-0.73 (m, 4 H), 1.42 (s, 6 H), 1.70-1.78 (m, 1 H), 2.77 (s, 3 H), 4.47 (d, 2 H), 5.34 (s, 2 H), 6.98 (br. s, 1 H), 7.10 (br. s, 1 H), 7.20-7.28 (m, 2 H), 7.56-7.64 (m, 1 H), 8.73 (t, 1 H), 9.66 (d, 1 H), 11.53 (s, 1 H).

Example 67

4-Amino-2-{6-chloro-8-[(2,6-difluorobenzyl)oxy]-2-methylimidazo[1,2-a]pyridin-3-yl}-5,5-dimethyl-5,7-dihydro-6H-pyrrolo[2,3-d]pyrimidin-6-one

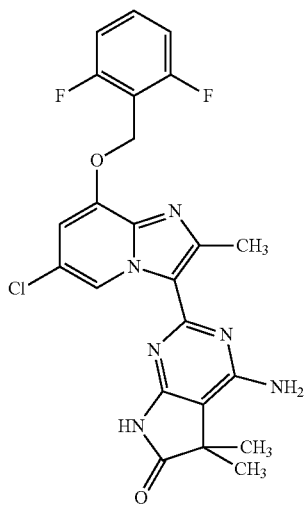 [SMILES: Cc1nc2c(OCc3c(F)cccc3F)cc(Cl)cn2c1-c1nc(N)c2c(n1)NC(=O)C2(C)C]

Under argon, 50 mg (0.08 mmol; purity about 56%) of 6-chloro-8-[(2,6-difluorobenzyl)oxy]-2-methylimidazo[1,2-a]pyridine-3-carboximidamide from Example 11A were initially charged in 0.9 ml of tert-butanol, 13.5 mg (0.12 mmol) of potassium tert-butoxide and 16 mg (0.10 mmol) of methyl 3,3-dicyano-2,2-dimethylpropanoate from Example 28A were added in succession at RT and the mixture was heated at reflux for 3 h. The reaction mixture was concentrated, water was added to the residue and the mixture was stirred at room temperature for 20 min. The solid was filtered off, washed thoroughly with water and dried. The crude product was dissolved in dichloromethane/methanol and purified by thick-layer chromatography (mobile phase: dichloromethane/2M ammonia in methanol 10/1). This gave 9 mg (23% of theory) of the title compound.

LC-MS (Method 1): $R_t$=0.90 min

MS (ESpos): m/z=485 (M+H)$^+$ $^1$H-NMR (500 MHz, DMSO-$d_6$): δ=1.35 (s, 6 H), 2.73 (s, 3 H), 5.35 (s, 2 H), 6.78 (br. s, 2 H), 7.18 (d, 1 H), 7.22-7.29 (m, 2 H), 7.58-7.66 (m, 1 H), 9.73 (d, 1 H), 10.95 (s, 1 H).

Example 68

3-{8-[(2,6-Difluorobenzyl)oxy]-2-methylimidazo[1,2-a]pyridin-3-yl}-7,7-dimethyl-5,7-dihydro-6H-pyrrolo[2,3-e][1,2,4]triazin-6-one

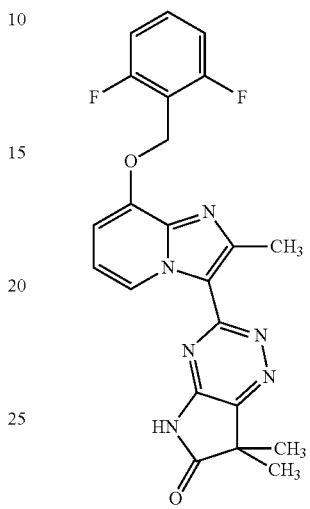

The reaction solution of methyl 2-(5-chloro-3-{8-[(2,6-difluorobenzyl)oxy]-2-methylimidazo[1,2-a]pyridin-3-yl}-1,2,4-triazin-6-yl)-2-methylpropanoate from Example 48A was diluted with 60 ml of dry acetonitrile and then slowly added dropwise at 0° C. to 60 ml of a 33% strength aqueous ammonia solution. The reaction mixture was stirred at room temperature overnight and then concentrated on a rotary evaporator. Water and ethyl acetate were added to the residue and the two phases were separated. The aqueous phase was extracted twice with ethyl acetate. The combined organic phases were dried over sodium sulphate, filtered and concentrated. The crude product was purified by preparative HPLC (RP18 column, mobile phase: acetonitrile/water gradient with addition of 0.05% formic acid). This gave 77 mg (34% of theory over 2 steps) of the target compound.

LC-MS (Method 1): $R_t$=0.79 min

MS (ESpos): m/z=437 (M+H)$^+$ $^1$H NMR (400 MHz, DMSO-$d_6$) δ=1.45 (s, 6 H), 2.73 (s, 3 H), 5.34 (s, 2 H), 7.08 (t, 1 H), 7.13 (d, 1 H), 7.20-7.30 (m, 2 H), 7.55-7.65 (m, 1 H), 9.45 (d, 1 H), 12.12 (s, 1 H).

Example 69

3-{8-[(2,6-Difluorobenzyl)oxy]-2,6-dimethylimidazo[1,2-a]pyridin-3-yl}-7,7-dimethyl-5,7-dihydro-6H-pyrrolo[2,3-e][1,2,4]triazin-6-one

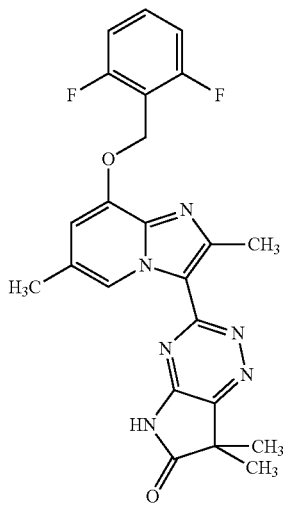

The reaction solution of methyl 2-(5-chloro-3-{8-[(2,6-difluorobenzyl)oxy]-2,6-dimethylimidazo[1,2-a]pyridin-3-yl}-1,2,4-triazin-6-yl)-2-methylpropanoate from Example 51A was diluted with 85 ml of dry acetonitrile and then slowly added dropwise at 0° C. to 85 ml of a 33% strength aqueous ammonia solution. The reaction mixture was stirred at room temperature overnight and then concentrated on a rotary evaporator. Water and ethyl acetate were added to the residue and the two phases were separated. The aqueous phase was extracted twice with ethyl acetate. The combined organic phases were dried over sodium sulphate, filtered and concentrated. Acetonitrile was added to the crude product. The precipitate formed was filtered off, washed with a little acetonitrile and dried under high vacuum. This gave 218 mg (35% of theory over 2 steps) of the target compound.

LC-MS (Method 1): $R_t$=0.88 min

MS (ESpos): m/z=451 (M+H)$^+$ $^1$H NMR (400 MHz, DMSO-d$_6$) δ=1.45 (s, 6 H), 2.39 (s, 3 H), 2.70 (s, 3 H), 5.33 (s, 2 H), 7.04 (s, 1 H), 7.20-7.39 (m, 2 H), 7.55-7.65 (m, 1 H), 9.30 (s, 1 H), 12.08 (s, 1 H).

Example 70

4-(Cyclopropylethynyl)-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one

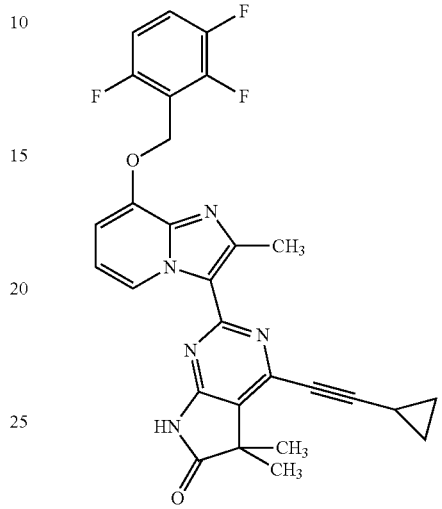

Under an atmosphere of argon, 200 mg (0.345 mmol) of 4-iodo-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one (Example 10) and 68 mg (1.036 mmol) of ethynylcyclopropane were initially charged in 5.6 ml of abs. THF. 105 mg (1.036 mmol) of diisopropylamine, 20 mg (0.104 mmol) of copper(I) iodide and 49 mg (0.070 mmol) of dichlorobis(triphenylphosphine)palladium(II) were added, and the mixture was heated at reflux for 48 h. The reaction mixture was cooled, filtered through Celite, washed with THF and concentrated, and the residue was purified by preparative HPLC (RP-C18, mobile phase: acetonitrile/water gradient with addition of 0.05% formic acid). This gave 83 mg of the target compound (44% of theory).

LC-MS (Method 1) $R_t$=0.98 min

MS (ESIpos): m/z=518 (M+H)$^+$ $^1$H-NMR (400 MHz, DMSO-d$_6$): δ [ppm]=0.86-0.92 (m, 2 H), 1.03-1.09 (m, 2 H), 1.40 (s, 6H), 1.72-1.80 (m, 1 H), 2.73 (s, 3 H), 5.38 (s, 2 H), 7.03-7.11 (m, 3 H), 7.26-7.34 (m, 1 H), 7.62-7.73 (m, 1 H), 9.47 (dd, 1 H), 11.58 (s, 1 H).

Example 71

4-(2-Cyclopropylethyl)-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one

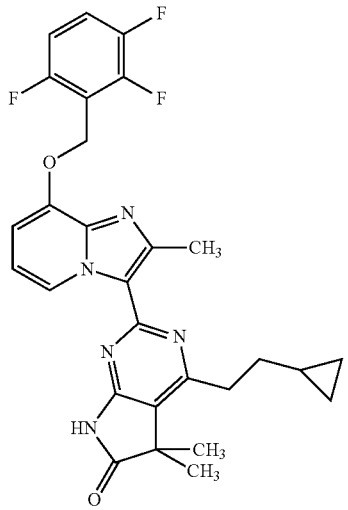 [SMILES: Cc1nc2c(OCc3c(F)ccc(F)c3F)cccn2c1-c1nc(CCC2CC2)c2c(n1)NC(=O)C2(C)C]

72 mg (0.14 mmol) of 4-(cyclopropylethynyl)-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one (Example 70) were dissolved in 14 ml of abs. methanol. The solution was hydrogenated in a flow hydrogenation reactor (H-Cube from Thales Nano, Budapest, model HC-2-SS) fitted with a 10% palladium/carbon cartridge at a hydrogen pressure of 10 bar. The reaction mixture was concentrated and the residue was purified by preparative HPLC (RP-C18, mobile phase: acetonitrile/water gradient with addition of 0.05% formic acid). This gave 15 mg of the target compound (20% of theory).

LC-MS (Method 1) $R_t$=1.03 min
MS (ESIpos): m/z=522 (M+H)$^+$
$^1$H-NMR (400 MHz, DMSO-d$_6$): δ [ppm]=0.05-0.12 (m, 2 H), 0.38-0.45 (m, 2 H), 0.76-0.86 (m, 1 H), 1.42 (s, 6 H), 1.70-1.78 (m, 2 H), 2.75 (s, 3 H), 2.82-2.89 (m, 2 H), 5.39 (s, 2 H), 6.99-7.08 (m, 2 H), 7.25-7.33 (m, 1 H), 7.62-7.72 (m, 1 H), 9.57 (dd, 1 H), 11.46 (s, 1 H).

Example 72

5,5-Dimethyl-2-{2-methyl-8-[(2,3,6-trifluorobenzyl)oxy]imidazo[1,2-a]pyridin-3-yl}-4-propyl-5,7-dihydro-6H-pyrrolo[2,3-d]pyrimidin-6-one

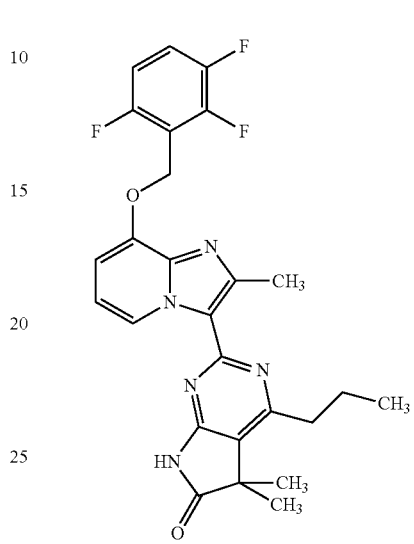

Under argon, 100 mg (0.173 mmol) of 4-iodo-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one (Example 10) were initially charged in 2.2 ml of dioxane. 3.7 mg (0.004 mmol) of PdCl$_2$(dppf) CH$_2$Cl$_2$ were then added, and 1.38 ml (0.69 mmol) of a 0.5 M solution of n-propylzinc bromide in tetrahydrofuran were added dropwise. The mixture was then heated in the microwave at 120° C. for 7 h. The reaction mixture was cooled, filtered off, washed with dioxane and concentrated, and the residue was purified by preparative HPLC (RP-C18, mobile phase: acetonitrile/water gradient with addition of 0.05% formic acid). The product fractions were purified once more by preparative thick-layer chromatography (mobile phase: dichloromethane/methanol=10/1). This gave 5.3 mg of the target compound (5% of theory; purity 74%).

LC-MS (Method 1) $R_t$=0.97 min
MS (ESIpos): m/z=496 (M+H)$^+$
$^1$H-NMR (400 MHz, DMSO-d$_6$): δ [ppm]=1.02 (t, 3 H), 1.42 (s, 6 H), 1.80-1.93 (m, 2 H), 2.73-2.81 (m, 2 H), 5.38 (s, 2 H), 6.97-7.08 (m, 2 H), 7.24-7.34 (m, 1 H), 7.60-7.72 (m, 1 H), 9.58 (d, 1 H), 11.46 (s, 1 H).

Example 73

5,5-Dimethyl-4-(2-methyl-1,3-thiazol-5-yl)-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one

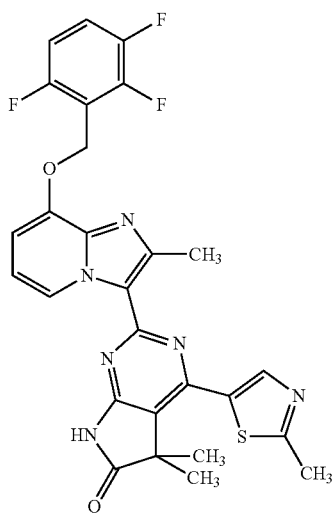 [SMILES: Cc1ncc(-c2nc(-c3c(C)nc4c(OCc5c(F)ccc(F)c5F)cccn34)nc3c2C(C)(C)C(=O)N3)s1]

Under an atmosphere of argon, 100 mg (0.173 mmol) of 4-iodo-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one (Example 10) were suspended in 3.8 ml of dioxane, and 117 mg (0.518 mmol) of 2-methyl-5-(4,4,5,5-tetramethyl-1,3,2-dioxaborolan-2-yl)-1,3-thiazole and 1.38 ml (0.69 mmol) of 0.5 M aqueous potassium carbonate solution were added. After 10 min, 44 mg (0.038 mmol) of tetrakis(triphenylphosphine)palladium(0) were added and the mixture was stirred at 140° C. in the microwave for 1 h. The reaction mixture was cooled, filtered through Celite, washed with dioxane and concentrated, and the residue was purified by preparative HPLC (RP-C18, mobile phase: acetonitrile/water gradient with addition of 0.05% formic acid). This gave 7 mg (7% of theory) of the target compound.

LC-MS (Method 1) $R_t$=0.91 min
MS (ESIpos): m/z=551 (M+H)$^+$
$^1$H-NMR (400 MHz, DMSO-d$_6$): δ [ppm]=1.51 (s, 6 H), 2.76 (s, 3 H), 2.79 (s, 3 H), 5.41 (s, 2 H), 7.04-7.14 (m, 2 H), 7.26-7.33 (m, 1 H), 7.61-7.73 (m, 1 H), 8.30 (s, 1 H), 9.51 (dd, 1 H), 11.77 (s, 1 H).

Example 74

5,5-Dimethyl-2-{2-methyl-8-[(2,3,6-trifluorobenzyl)oxy]imidazo[1,2-a]pyridin-3-yl}-4-(1H-pyrazol-5-yl)-5,7-dihydro-6H-pyrrolo[2,3-d]pyrimidin-6-one

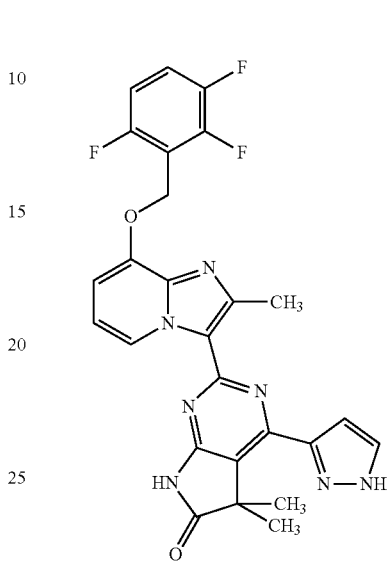

Under an atmosphere of argon, 100 mg (0.173 mmol) of 4-iodo-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one (Example 10) were suspended in 3.8 ml of dioxane, and 100 mg (0.518 mmol) of 5-(4,4,5,5-tetramethyl-1,3,2-dioxaborolan-2-yl)-1H-pyrazole and 1.38 ml (0.69 mmol) of 0.5 M aqueous potassium carbonate solution were added. After 10 min, 44 mg (0.038 mmol) of tetrakis(triphenylphosphine)palladium(0) were added and the mixture was stirred at 140° C. in the microwave for 30 min. The reaction mixture was cooled, filtered through Celite, washed with dioxane and concentrated, and the residue was purified by preparative HPLC (RP-C18, mobile phase: acetonitrile/water gradient with addition of 0.05% formic acid). This gave 41 mg (46% of theory) of the target compound.

LC-MS (Method 1) $R_t$=0.87 min
MS (ESIpos): m/z=520 (M+H)$^+$
$^1$H-NMR (400 MHz, DMSO-d$_6$): δ [ppm]=1.60 (s, 6 H), 2.82 (s, 3 H), 5.41 (s, 2 H), 7.05-7.09 (m, 3 H), 7.33-7.27 (m, 1 H), 7.63-7.71 (m, 1 H), 7.95-7.97 (m, 1 H), 9.61 (dd, 1 H), 11.55 (s, 1H), 13.48 (s, 1 H).

Example 75

5,5-Dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one formate

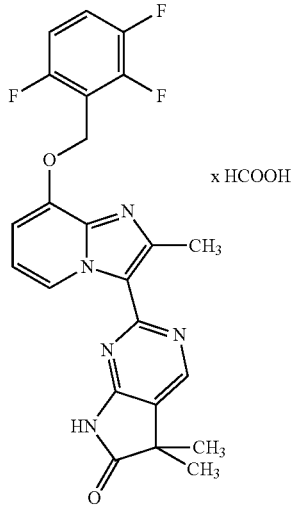 [SMILES: Cc1nc2c(OCc3c(F)ccc(F)c3F)cccn2c1-c1ncc2c(n1)NC(=O)C2(C)C]

x HCOOH

At standard pressure and RT, 100 mg (0.173 mmol) of 4-iodo-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one (Example 10) in DMF (4 ml) were hydrogenated with 19.6 mg of 10% strength palladium on carbon for 2 days. The mixture was filtered through Celite, washed with DMF and concentrated, and the residue was purified by preparative HPLC (RP-C18, mobile phase: acetonitrile/water gradient with addition of 0.05% formic acid). This gave 19 mg (22% of theory) of the target compound.

LC-MS (Method 1): $R_t$=0.83 min

MS (ESIpos): m/z=454 [M+—HCOOH+H]$^+$ $^1$H-NMR (400 MHz, DMSO-d$_6$): δ [ppm]=1.38 (s, 6 H), 2.74 (s, 3 H), 5.39 (s, 2 H), 6.97-7.04 (m, 1 H), 7.04-7.10 (m, 1 H), 7.25-7.33 (m, 1 H), 8.19 (s, 1 H), 8.60 (s, 1 H), 9.53 (d, 1 H), 11.48 (s, 1 H).

Example 76

4-(Cyclopropylmethoxy)-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one

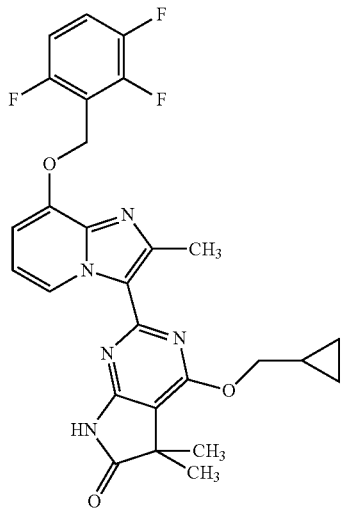 [SMILES: Cc1nc2c(OCc3c(F)ccc(F)c3F)cccn2c1-c1nc2c(c(OCC3CC3)n1)C(C)(C)C(=O)N2]

Under argon, 100 mg (0.213 mmol) of 4-hydroxy-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one (Example 11), 17 mg (0.23 mmol) of cyclopropylmethanol and 60 mg (0.23 mmol) of triphenylphosphine were suspended in 0.84 ml of THF, the mixture was left in an ultrasonic bath for 10 min, 49 mg (0.230 mmol) of diisopropyl azodicarboxylate (DIAD) were then added and the mixture was stirred at RT overnight. A further 6 mg (0.08 mmol) of cyclopropylmethanol, 20 mg (0.08 mmol) of triphenylphosphine and 14 mg (0.07 mmol) of diisopropyl azodicarboxylate were added, and the mixture was stirred at RT overnight. The reaction mixture was purified by preparative HPLC (RP-C18, mobile phase: acetonitrile/water gradient with addition of 0.05% formic acid). This gave 19 mg (17% of theory) of the target compound.

LC-MS (Method 1) $R_t$=1.06 min

MS (ESIpos): m/z=524 (M+H)$^+$ $^1$H-NMR (400 MHz, DMSO-d$_6$): δ [ppm]=0.37-0.42 (m, 2 H), 0.56-0.62 (m, 2 H), 1.27-1.39 (m, 1 H), 1.37 (s, 6 H), 2.76 (s, 3 H), 4.36 (d, 2 H), 5.39 (s, 2 H), 6.99-7.11 (m, 2 H), 7.26-7.34 (m, 1 H), 7.63-7.71 (m, 1 H), 9.52 (d, 1 H), 11.29 (s, 1 H).

Example 77

5,5-Dimethyl-2-{2-methyl-8-[(2,3,6-trifluorobenzyl)oxy]imidazo[1,2-a]pyridin-3-yl}-4-(3,3,3-trifluoropropoxy)-5,7-dihydro-6H-pyrrolo[2,3-d]pyrimidin-6-one

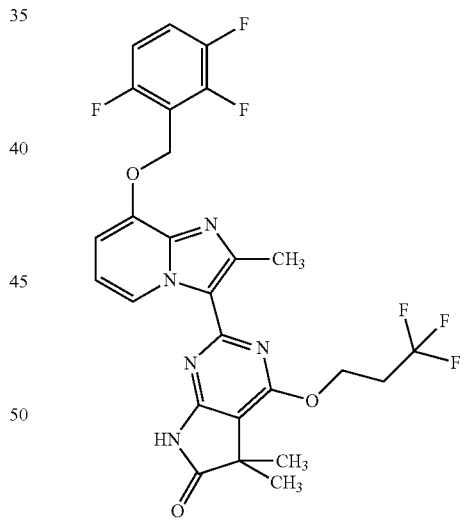

Under argon, 100 mg (0.213 mmol) of 4-hydroxy-5,5-dimethyl-2-{2-methyl-8-[(2,3,6-trifluorobenzyl)oxy]imidazo[1,2-a]pyridin-3-yl}-5,7-dihydro-6H-pyrrolo[2,3-d]pyrimidin-6-one (Example 11), 26 mg (0.23 mmol) of 3,3,3-trifluoropropan-1-ol and 60 mg (0.23 mmol) of triphenylphosphine were suspended in 0.84 ml of THF, the mixture was mixed in an ultrasonic bath for 10 min, 49 mg (0.230 mmol) of diisopropyl azodicarboxylate (DIAD) were then added and the mixture was stirred at RT overnight. A further 9 mg (0.08 mmol) of 3,3,3-trifluoropropan-1-ol, 20 mg (0.08 mmol) of triphenylphosphine and 15 mg (0.07 mmol) of diisopropyl azodicarboxylate were added, and the mixture was stirred at RT overnight. The reaction mixture was purified by preparative HPLC (RP-C18, mobile phase: acetonitrile/water gradient with addition of 0.05% formic acid). This gave 48 mg (40% of theory) of the target compound.

LC-MS (Method 1): $R_t$=1.04 min

MS (ESIpos): m/z=566 [M+H]$^+$ $^1$H-NMR (400 MHz, DMSO-d$_6$): δ [ppm]=1.34 (s, 6 H), 2.76 (s, 3 H), 2.83-2.95 (m, 2 H), 4.69-4.75 (m, 2 H), 5.39 (s, 2 H), 7.00-7.05 (m, 1 H), 7.07-7.11 (m, 1 H), 7.25-7.34 (m, 1 H), 7.62-7.72 (m, 1 H), 9.52 (dd, 1 H), 11.36 (s, 1 H).

B. Assessment of Pharmacological Efficacy

The following abbreviations are used:
ATP adenosine triphosphate
Brij35 polyoxyethylene(23) lauryl ether
BSA bovine serum albumin
DTT dithiothreitol
TEA triethanolamine The pharmacological action of the compounds of the invention can be demonstrated in the following assays:

B-1. Vasorelaxant Effect In Vitro

The determination of the relaxant activity of the compounds according to the invention on isolated vessels was carried out as described in JP Stasch et al., Br J Pharmacol. 2002; 135, 333-343. Rabbits are stunned by a blow to the neck and exsanguinated. The aorta is removed, freed from adhering tissue and divided into rings of width 1.5 mm, which are placed individually under prestress into 5 ml organ baths with carbogen-sparged Krebs-Henseleit solution at 37° C. having the following composition (each mM): sodium chloride: 119; potassium chloride: 4.8; calcium chloride dihydrate: 1; magnesium sulphate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders.

To obtain a contraction, phenylephrine is added to the bath cumulatively in increasing concentration. After several control cycles, the substance to be studied is added in increasing dosage each time in every further run, and the magnitude of the contraction is compared with the magnitude of the contraction attained in the last preceding run. This is used to calculate the concentration needed to reduce the magnitude of the control value by 50% (IC$_{50}$ value). The standard administration volume is 5 µl; the DMSO content in the bath solution corresponds to 0.1%.

B-2. Effect on a Recombinant Guanylate Cyclase Reporter Cell Line

The cellular activity of the compounds according to the invention is determined using a recombinant guanylate cyclase reporter cell line, as described in F. Wunder et al., Anal. Biochem. 339, 104-112 (2005).

Representative MEC values (MEC=minimum effective concentration) for the compounds of the invention are shown in Table 1 below (in some cases as mean values for individual determinations):

TABLE 1

| Example | MEC [µM] |
|---|---|
| 1 | 0.3 |
| 2 | 5.3 |
| 4 | 3 |
| 5 | 3 |
| 7 | 2 |
| 8 | 1 |
| 9 | 1 |
| 11 | 3 |
| 12 | 0.2 |
| 13 | 1 |
| 14 | 3 |
| 15 | 3 |
| 16 | 0.65 |
| 17 | 0.3 |
| 18 | 1 |
| 19 | 1 |
| 20 | 3 |
| 21 | 0.3 |
| 22 | 3 |
| 23 | 3 |
| 24 | 0.3 |
| 25 | 3 |
| 26 | 3 |
| 27 | 3 |
| 28 | 0.3 |
| 29 | 0.3 |
| 30 | 1 |
| 31 | 0.3 |
| 32 | 1 |
| 33 | 1 |
| 34 | 1 |
| 35 | 1 |
| 36 | 0.3 |
| 37 | 1 |
| 38 | 3 |
| 39 | 0.3 |
| 40 | 3 |
| 41 | 0.1 |
| 42 | 0.1 |
| 43 | 3 |
| 44 | 1 |
| 45 | 1 |
| 46 | 1 |
| 47 | 0.3 |
| 48 | 1 |
| 49 | 1 |
| 50 | 0.3 |
| 51 | 10 |
| 53 | 0.3 |
| 54 | 10 |
| 55 | 0.3 |
| 56 | 0.3 |
| 58 | 3 |
| 59 | 0.3 |
| 60 | 3 |
| 61 | 3 |
| 62 | 3 |
| 63 | 3 |
| 64 | 10 |
| 65 | 3 |
| 66 | 3 |
| 67 | 0.03 |
| 68 | 1 |
| 69 | 1 |
| 72 | 3 |
| 74 | 1 |
| 75 | 10 |

B-3. Inhibition of Human Phosphodiesterase 5 (PDE 5)

PDE 5 preparations are obtained from human platelets by disruption (Microfluidizer®, 800 bar, 3 passes), followed by centrifugation (75 000 g, 60 min, 4° C.) and ion exchange chromatography of the supernatant on a Mono Q 10/10 column (linear sodium chloride gradient, elution with a 0.2-0.3M solution of sodium chloride in buffer (20 mM Hepes pH 7.2, 2 mM magnesium chloride). Fractions having PDE 5 activity are combined (PDE 5 preparation) and stored at −80° C.

To determine their in vitro action on human PDE 5, the test substances are dissolved in 100% DMSO and serially diluted. Typically, dilution series (1:3) from 200 µM to 0.091 µM are prepared (resulting final concentrations in the test: 4 µM to 0.0018 µM). In each case 2 µl of the diluted substance solutions are placed into the wells of microtitre plates (Isoplate-96/200 W; Perkin Elmer). Subsequently, 50 µl of a dilution of the above-described PDE 5 preparation are added. The dilution of the PDE 5 preparation is chosen such that during the later incubation less than 70% of the substrate are converted (typical dilution: 1:100; dilution buffer: 50 mM tris/hydrochloric acid pH 7.5, 8.3 mM magnesium chloride, 1.7 mM EDTA, 0.2% BSA). The substrate, [8-$^3$H] cyclic guanosine-3',5'-monophosphate (1 µCi/µl; Perkin Elmer), is diluted 1:2000 with assay buffer (50 mM tris/hydrochloric acid pH 7.5, 8.3 mM magnesium chloride, 1.7 mM EDTA) to a concentration of 0.0005 µCi/µl. By addition of 50 µl (0.025 µCi) of the diluted substrate, the enzyme reaction is finally started. The test mixtures are incubated at room temperature for 60 min and the reaction is stopped by adding 25 µl of a suspension of 18 mg/ml yttrium scintillation proximity beads in water (phosphodiesterase beads for SPA assays, RPNQ 0150, Perkin Elmer). The microtitre plates are sealed with a film and left to stand at room temperature for 60 min. Subsequently, the plates are analysed for 30 s per well in a Microbeta scintillation counter (Perkin Elmer). $IC_{50}$ values are determined using the graphic plot of the substance concentration against percentage PDE 5 inhibition.

Representative $IC_{50}$ values for the compounds according to the invention are shown in the table below (Table 2; in some cases as means of individual determinations):

TABLE 2

| Example | $IC_{50}$ [nM] |
| --- | --- |
| 1 | 34 |
| 2 | 300 |
| 4 | 110 |
| 5 | 690 |
| 7 | 590 |
| 8 | 120 |
| 9 | 17 |
| 11 | 260 |
| 12 | 3.6 |
| 13 | 12 |
| 14 | 91 |
| 15 | 2.5 |
| 16 | 4.8 |
| 17 | 4.6 |
| 18 | 19 |
| 19 | 7.1 |
| 20 | 110 |
| 21 | 22 |
| 22 | 3.9 |
| 23 | 8.0 |
| 24 | 1.3 |
| 25 | 15 |
| 26 | 26 |
| 27 | 23 |
| 28 | 0.3 |
| 29 | 0.9 |
| 30 | 3.6 |
| 31 | 1.2 |
| 32 | 11 |
| 33 | 9.7 |
| 34 | 5.3 |
| 35 | 35 |
| 36 | 20 |
| 37 | 21 |
| 38 | 36 |
| 39 | 9.6 |
| 40 | 14 |
| 41 | 1.7 |
| 42 | 6.0 |
| 43 | 5.5 |
| 44 | 1.5 |
| 45 | 9.8 |
| 46 | 120 |
| 48 | 190 |
| 49 | 48 |
| 50 | 29 |
| 51 | 430 |
| 53 | 4.3 |
| 54 | 420 |
| 55 | 4.0 |
| 56 | 1.3 |
| 57 | 3.0 |
| 58 | 5.2 |
| 59 | 1.7 |
| 60 | 420 |
| 61 | 730 |
| 62 | 400 |
| 63 | 220 |
| 64 | 28 |
| 65 | 68 |
| 66 | 48 |
| 67 | 47 |
| 68 | 260 |
| 69 | 790 |
| 70 | 430 |
| 71 | 200 |
| 73 | 22 |
| 74 | 30 |
| 75 | 370 |
| 76 | 46 |
| 77 | 140 |

B-4. Blood Pressure Measurement on Anaesthetized Rats

Male Wistar rats having a body weight of 300-350 g are anaesthetized with thiopental (100 mg/kg i.p.). After tracheotomy, a catheter is introduced into the femoral artery to measure the blood pressure. The substances to be tested are administered as solutions, either orally by means of a gavage or intravenously via the femoral vein (Stasch et al. Br. J. Pharmacol. 2002; 135: 344-355).

B-5. Radiotelemetry Measurement of Blood Pressure in Conscious, Spontaneously Hypertensive Rats A commercially available telemetry system from DATA SCIENCES INTERNATIONAL DSI, USA, is employed for the blood pressure measurement on conscious rats described below.

The system consists of 3 main components:

implantable transmitters (Physiotel® telemetry transmitter)

receivers (Physiotel® receiver) which are linked via a multiplexer (DSI Data Exchange Matrix) to a data acquisition computer.

The telemetry system makes it possible to continuously record blood pressure, heart rate and body motion of conscious animals in their usual habitat.

Animal Material

The studies are conducted on adult female spontaneously hypertensive rats (SHR Okamoto) with a body weight of >200 g. SHR/NCrl from the Okamoto Kyoto School of Medicine, 1963, were a cross of male Wistar Kyoto rats having greatly elevated blood pressure and female rats having slightly elevated blood pressure, and were handed over at F13 to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The TA11 PA-C40 telemetry transmitters used are surgically implanted under aseptic conditions in the experimental animals at least 14 days before the first experimental use. The animals instrumented in this way can be used repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is used as control.

Experimental Outline

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute values are corrected in the diagram with the currently measured barometric pressure (Ambient Pressure Reference Monitor; APR-1) and stored as individual data. Further technical details are given in the extensive documentation from the manufacturer company (DSI).

Unless indicated otherwise, the test substances are administered at 9:00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed here to be the time 2 hours before administration, and so the selected data set encompasses the period from 7:00 am on the day of the experiment to 9:00 am on the following day.

The data are smoothed over a predefinable period by determination of the average (15-minute average) and transferred as a text file to a storage medium. The measured values presorted and compressed in this way are transferred to Excel templates and tabulated. For each day of the experiment, the data obtained are stored in a dedicated file bearing the number of the experiment. Results and test protocols are stored in files in paper form sorted by numbers.

Literature:

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994.

B-6. Determination of Organ-Protective Effects in a Long-Term Experiment on Rats The organ-protective effects of the compounds according to the invention are shown in a therapeutically relevant "low nitric oxide (NO)/high renin" hypertension model in rats. The study was carried out analogously to the recently published article (Sharkovska Y, et al. J Hypertension 2010; 28: 1666-1675). This involves treating renin-transgenic rats (TGR(mRen2)27) to which the NO synthase inhibitor L-NAME had been administered via drinking water simultaneously with the compound according to the invention or vehicle over several weeks. Haemodynamic and renal parameters are determined during the treatment period. At the end of the long-term study, organ protection (kidney, lung, heart, aorta) is shown by histopathological studies, biomarkers, expression analyses and cardiovascular plasma parameters.

B-7. Measurements of the Pulmonary Artery Pressure (PAP) in Conscious Dogs Under Hypoxia Conditions A telemetry system from DATA SCIENCES INTERNATIONAL DSI, USA, for example, is employed for the blood pressure measurement on conscious dogs described below. The system consists of implantable pressure transmitters, receiver and a data acquisition computer. The telemetry system makes it possible to continuously monitor blood pressures and heart rate of conscious animals. The telemetry transmitters used are surgically implanted under aseptic conditions in the experimental animals before the first experimental use. The animals instrumented in this way can be used repeatedly after the wound has healed and the implant has settled. The tests are carried out using adult male beagles. Technical details can be found in the documentation from the manufacturing company (DSI).

Substances and Solutions

The substances to be tested are each administered to a group of dogs (n=3-6), orally via a gelatine capsule or intravenously in suitable solvent mixtures. A vehicle-treated group of animals is employed as control.

Experimental Outline

For the measurements under hypoxia conditions, the animals are transferred to a chamber with a hypoxic atmosphere (oxygen content about 10%). This is established using commercially available hypoxia generators (from Hoehenbalance, Cologne, Germany). In a standard experiment, for example, one hour and five hours after substance administration the dogs are transferred to the hypoxia chamber for 30 min. About 10 min before and after entering the hypoxia chamber, as well as during the stay in the hypoxia chamber, pressures and heart rate are measured by telemetry.

Evaluation

In healthy dogs, under hypoxia there is a rapid increase in PAP. By substance administration, this increase can be reduced. To quantify the PAP increase and the differences in heart rate and systemic blood pressure, the data before and during the hypoxia period, smoothed by determination of means, are compared. The courses of the measured parameters are presented graphically using the Prism software (GraphPad, USA).

B-8. Determination of Pharmacokinetic Parameters Following Intravenous and Oral Administration The pharmacokinetic parameters of the compounds according to the invention are determined in male CD-1 mice, male Wistar rats and female beagles. Intravenous administration in the case of mice and rats is effected by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right Vena jugularis externa prior to substance administration. The operation is effected at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it can be stored at −20° C. until further processing.

An internal standard (which may also be a chemically unrelated substance) is added to the samples of the compounds of the invention, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by LC-MS/MS using C18 reversed-phase columns and variable eluent mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half-life), F (bioavailability), MRT (mean residence time) and CL (clearance), by means of a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $C_{blood}/C_{plasma}$ value.

B-9. Metabolic Study

To determine the metabolic profile of the compounds of the invention, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds of the invention were incubated with a concentration of about 0.1-10 µM. To this end, stock solutions of the compounds of the invention having a concentration of 0.01-1 mM in acetonitrile were prepared, and then pipetted with a 1:100 dilution into the incubation mixture. Liver microsomes and recombinant enzymes were incubated at 37° C. in 50 mM potassium phosphate buffer pH 7.4 with and without NADPH-generating system consisting of 1 mM $NADP^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%) and the protein was centrifuged off at about 15 000×g. The samples thus stopped were either analysed directly or stored at −20° C. until analysis.

The analysis is carried out by high-performance liquid chromatography with ultraviolet and mass spectrometry detection (HPLC-UV-MS/MS). To this end, the supernatants of the incubation samples are chromatographed with suitable C18 reversed-phase columns and variable eluent mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic reduction of the compound of the invention in the incubation mixtures.

B-10. Caco-2 Permeability Test

The permeability of a test substance was determined with the aid of the Caco-2 cell line, an established in vitro model for permeability prediction at the gastrointestinal barrier (Artursson, P. and Karlsson, J. (1991). Correlation between oral drug absorption in humans and apparent drug permeability coefficients in human intestinal epithelial (Caco-2) cells. Biochem. Biophys. 175 (3), 880-885). The Caco-2 cells (ACC No. 169, DSMZ, Deutsche Sammlung von Mikroorganismen und Zellkulturen, Braunschweig, Germany) were sown in 24-well plates having an insert and cultivated for 14 to 16 days. For the permeability studies, the test substance was dissolved in DMSO and diluted to the final test concentration with transport buffer (Hanks Buffered Salt Solution, Gibco/Invitrogen, with 19.9 mM glucose and 9.8 mM HEPES). In order to determine the apical to basolateral permeability ($P_{app}$A-B) of the test substance, the solution comprising the test substance was applied to the apical side of the Caco-2 cell monolayer, and transport buffer to the basolateral side. In order to determine the basolateral to apical permeability ($P_{app}$B-A) of the test substance, the solution comprising the test substance was applied to the basolateral side of the Caco-2 cell monolayer, and transport buffer to the apical side. At the start of the experiment, samples were taken from the respective donor compartment in order to ensure the mass balance. After an incubation time of two hours at 37° C., samples were taken from the two compartments. The samples were analysed by means of LC-MS/MS and the apparent permeability coefficients ($P_{app}$) were calculated. For each cell monolayer, the permeability of Lucifer Yellow was determined to ensure cell layer integrity. In each test run, the permeability of atenolol (marker for low permeability) and sulfasalazine (marker for active excretion) was also determined as quality control.

B-11. hERG Potassium Current Assay

The hERG (human ether-a-go-go related gene) potassium current makes a significant contribution to the repolarization of the human cardiac action potential (Scheel et al., 2011). Inhibition of this current by pharmaceuticals can in rare cases cause potentially lethal cardiac arrhythmia, and is therefore studied at an early stage during drug development.

The functional hERG assay used here is based on a recombinant HEK293 cell line which stably expresses the KCNH2(HERG) gene (Zhou et al., 1998). These cells are studied by means of the "whole-cell voltage-clamp" technique (Hamill et al., 1981) in an automated system (Patchliner™; Nanion, Munich, Germany), which controls the membrane voltage and measures the hERG potassium current at room temperature. The PatchControlHT™ software (Nanion) controls the Patchliner system, data capture and data analysis. The voltage is controlled by 2 EPC-10 quadro amplifiers controlled by the PatchMasterPro™ software (both: HEKA Elektronik, Lambrecht, Germany). NPC-16 chips with moderate resistance (~2 MΩ; Nanion) serve as the planar substrate for the voltage clamp experiments.

NPC-16 chips are filled with intra- and extracellular solution (cf. Himmel, 2007) and with cell suspension. After forming a gigaohm seal and establishing whole-cell mode (including several automated quality control steps), the cell membrane is clamped at the −80 mV holding potential. The subsequent voltage clamp protocol changes the command voltage to +20 mV (for 1000 ms), −120 mV (for 500 ms), and back to the −80 mV holding potential; this is repeated every 12 s. After an initial stabilization phase (about 5-6 minutes), test substance solution is introduced by pipette in rising concentrations (e.g. 0.1, 1, and 10 µmol/l) (exposure about 5-6 minutes per concentration), followed by several washing steps.

The amplitude of the inward "tail" current which is generated by a change in potential from +20 mV to −120 mV serves to quantify the hERG potassium current, and is described as a function of time (IgorPro™ Software). The current amplitude at the end of various time intervals (for example stabilization phase before test substance, first/second/third concentration of test substance) serves to establish a concentration/effect curve, from which the half-maximum inhibiting concentration $IC_{50}$ of the test substance is calculated.

Hamill O P, Marty A, Neher E, Sakmann B, Sigworth F J. Improved patch-clamp techniques for high-resolution current recording from cells and cell-free membrane patches. Pfluegers Arch 1981; 391:85-100.

Himmel H M. Suitability of commonly used excipients for electrophysiological in-vitro safety pharmacology assessment of effects on hERG potassium current and on rabbit Purkinje fiber action potential. J Pharmacol Toxicol Methods 2007; 56:145-158.

Scheel O, Himmel H, Rascher-Eggstein G, Knott T. Introduction of a modular automated voltage-clamp platform and its correlation with manual human ether-a-go-go related gene voltage-clamp data. Assay Drug Dev Technol 2011; 9:600-607.

Zhou Z F, Gong Q, Ye B, Fan Z, Makielski J C, Robertson G A, January C T. Properties of hERG channels stably expressed in HEK293 cells studied at physiological temperature. Biophys J 1998; 74:230-241.

C. Working Examples For Pharmaceutical Compositions

The compounds of the invention can be converted to pharmaceutical formulations as follows:

Tablet:
Composition:
100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.
Production:
The mixture of compound of the invention, lactose and starch is granulated with a 5% solution (w/w) of the PVP in water. The granules are dried and then mixed with the magnesium stearate for 5 minutes. This mixture is compressed using a conventional tabletting press (see above for format of the tablet). The guide value used for the pressing is a pressing force of 15 kN.

Suspension for Oral Administration:
Composition:
1000 mg of the compound of the invention, 1000 mg of ethanol (96%), 400 mg of Rhodigel® (xanthan gum from FMC, Pennsylvania, USA) and 99 g of water. 10 ml of oral suspension correspond to a single dose of 100 mg of the compound of the invention.
Production:
The Rhodigel is suspended in ethanol; the compound of the invention is added to the suspension. The water is added while stirring. The mixture is stirred for about 6 h until swelling of the Rhodigel is complete.

Solution for Oral Administration:
Composition:
500 mg of the compound of the invention, 2.5 g of polysorbate and 97 g of polyethylene glycol 400. 20 g of oral solution correspond to a single dose of 100 mg of the compound of the invention.
Production:
The compound of the invention is suspended in the mixture of polyethylene glycol and polysorbate with stirring. The stirring operation is continued until dissolution of the compound of the invention is complete.

i.v. Solution:
The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:
1. A compound of the formula (I)

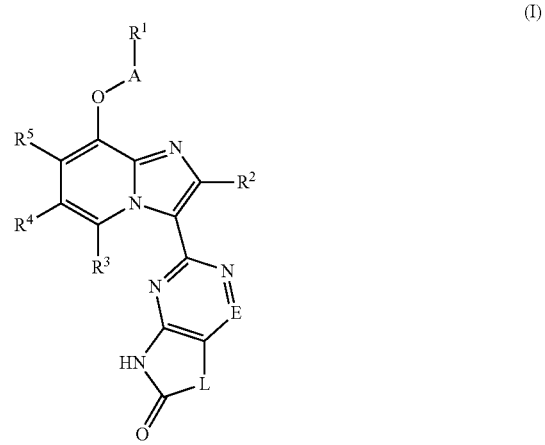

in which
A represents $CH_2$, $CD_2$ or $CH(CH_3)$,
$R^1$ represents $(C_4-C_6)$-alkyl, $(C_3-C_7)$-cycloalkyl or phenyl, where $(C_4$-$C_6)$-alkyl may be substituted by 1 or 2 substituents independently of one another selected from the group consisting of fluorine and trifluoromethyl, where $(C_3$-$C_7)$-cycloalkyl may be substituted by 1 to 4 substituents independently of one another selected from the group consisting of fluorine, trifluoromethyl and $(C_1$-$C_4)$-alkyl, and where phenyl may be substituted by 1 to 4 substituents independently of one another selected from the group consisting of halogen, cyano, monofluoromethyl, difluoromethyl, trifluoromethyl, $(C_1$-$C_4)$-alkyl, $(C_3$-$C_6)$-cycloalkyl, $(C_1$-$C_4)$-alkoxy, difluoromethoxy and trifluoromethoxy, $R^2$ represents hydrogen, $(C_1$-$C_4)$-alkyl, $(C_1$-$C_4)$-alkoxy-$(C_1$-$C_4)$-alkyl, cyclopropyl, monofluoromethyl, difluoromethyl or trifluoromethyl, $R^3$ represents hydrogen, $R^4$ represents hydrogen, halogen, cyano, monofluoromethyl, difluoromethyl, trifluoromethyl, $(C_1$-$C_4)$-alkyl, ethynyl, $(C_3$-$C_7)$-cycloalkyl or $(C_1$-$C_4)$-alkoxy, $R^5$ represents hydrogen, E represents nitrogen or $CR^6$,
where
$R^6$ represents hydrogen, deuterium, halogen, cyano, difluoromethyl, trifluoromethyl, $(C_1$-$C_6)$-alkyl, $(C_2$-$C_6)$-alkynyl, cyclopropyl, cyclobutyl, hydroxy, —$OR^7$, —$NR^8R^9$, hydroxycarbonyl, $(C_1$-$C_4)$-alkoxycarbonyl, —C(=O)—$NR^{10}R^{11}$,5- or 6-membered heteroaryl,
in which $(C_1$-$C_6)$-alkyl may be substituted by 1 to 3 substituents independently of one another selected from the group consisting of fluorine, difluoromethyl, trifluoromethyl, $(C_1$-$C_4)$-alkoxy, hydroxy, amino, —N(C=O)$R^{12}$, $(C_1$-$C_4)$-alkylsulphonylamino, $(C_3$-$C_6)$-cycloalkylsulphonylamino, cyclopropyl and cyclobutyl,
in which $R^{12}$ represents $(C_3$-$C_7)$-cycloalkyl or $(C_1$-$C_4)$-alkyl,
in which $(C_1$-$C_4)$-alkyl may be substituted by trifluoromethyl or difluoromethyl,
in which $(C_2$-$C_6)$-alkynyl may be substituted by 1 or 2 substituents independently of one another selected from the group consisting of difluoromethyl, trifluoromethyl, hydroxy, amino, cyclopropyl and cyclobutyl, in which 5- or 6-membered heteroaryl may be substituted by 1 to 3 substituents independently of one another selected from the group consisting of fluorine, chlorine, $(C_1$-$C_4)$-alkyl, hydroxy, amino and cyclopropyl,
in which $R^7$ represents $(C_1$-$C_6)$-alkyl or 5-membered heteroaryl,
in which $(C_1$-$C_6)$-alkyl may be substituted by trifluoromethyl, $(C_1$-$C_4)$-alkoxy, hydroxy, cyclopropyl or cyclobutyl,
in which $R^8$ represents hydrogen, $(C_1$-$C_6)$-alkyl or $(C_3$-$C_7)$-cycloalkyl,
in which $(C_3$-$C_7)$-cycloalkyl may be substituted by 1 to 3 substituents independently of one another selected from the group consisting of $(C_1$-$C_4)$-alkyl, hydroxy, amino, fluorine, trifluoromethyl and difluoromethyl,
and
in which $(C_1$-$C_6)$-alkyl may be substituted by 1 to 4 substituents independently of one another selected from the group consisting of fluorine, $(C_1$-$C_4)$-alkyl, $(C_3$-$C_7)$-cycloalkyl, $(C_1$-$C_4)$-alkoxy, hydroxy, amino, trifluoromethyl, difluoromethyl, monofluoromethyl, 5- to 7-membered azaheterocyclyl and phenyl,
in which phenyl may be substituted by 1 to 3 substituents independently of one another selected from the group consisting of halogen, cyano, $(C_1$-$C_4)$-alkyl and $(C_1$-$C_4)$-alkoxy,
in which 5- to 7-membered azaheterocyclyl may be substituted by 1 to 4 fluorine substituents,
and
in which $(C_3$-$C_7)$-cycloalkyl may be substituted by 1 to 3 substituents independently of one another selected from the group consisting of halogen, $(C_1$-$C_4)$-alkyl and hydroxy,
in which $R^9$ represents hydrogen or $(C_1$-$C_6)$-alkyl,
or
$R^8$ and $R^9$ together with the nitrogen atom to which they are attached form a 3- to 8-membered heterocycle,
in which the 3- to 8-membered heterocycle may be substituted by 1 or 2 substituents independently of one another selected from the group consisting of fluorine, $(C_1$-$C_4)$-alkyl, hydroxycarbonyl, $(C_1$-$C_4)$-alkoxycarbonyl, hydroxy and amino,
in which $(C_1$-$C_4)$-alkyl may be substituted by hydroxycarbonyl, $(C_1$-$C_4)$-alkoxycarbonyl, hydroxy or amino,
in which $R^{10}$ represents hydrogen, $(C_1$-$C_6)$-alkyl or $(C_3$-$C_7)$-cycloalkyl,
in which $(C_3$-$C_7)$-cycloalkyl may be substituted by 1 to 3 substituents independently of one another selected from the group consisting of $(C_1$-$C_6)$-alkyl, hydroxy, trifluoromethyl and difluoromethyl,
and
in which $(C_1$-$C_6)$-alkyl may be substituted by 1 to 4 substituents independently of one another selected from the group consisting of fluorine, $(C_3$-$C_7)$-cycloalkyl, $(C_1$-$C_4)$-alkoxy, hydroxy, amino, trifluoromethyl and difluoromethyl,
in which $R^{11}$ represents hydrogen or $(C_1$-$C_4)$-alkyl,
or
$R^{10}$ and $R^{11}$ together with the nitrogen atom to which they are attached form a 3- to 7-membered heterocycle,
in which the 3- to 7-membered heterocycle may be substituted by 1 to 3 substituents independently of one another selected from the group consisting of fluorine, $(C_1$-$C_4)$-alkyl, hydroxy and amino,
in which $(C_1$-$C_4)$-alkyl may be substituted by hydroxy, L represents a $\#^1$—$CR^{13A}R^{13B}$—$(CR^{14A}R^{14B})_m$–$\#^2$ group,
where
$\#^1$ represents the point of attachment to the carbonyl group,
$\#^2$ represents the point of attachment to the pyrimidine or triazine ring,
m represents a number 0, 1 or 2,
$R^{13A}$ represents hydrogen, trifluoromethyl or $(C_1$-$C_4)$-alkyl,
$R^{13B}$ represents hydrogen, difluoromethyl, trifluoromethyl, $(C_1$-$C_4)$-alkyl or $(C_3$-$C_7)$-cycloalkyl,
in which $(C_1$-$C_6)$-alkyl may be substituted by 1 to 3 substituents independently of one another selected from the group consisting of fluorine, cyano, trifluoromethyl, $(C_3-C_7)$-cycloalkyl, difluoromethoxy and trifluoromethoxy,
or
$R^{13A}$ and $R^{13B}$ together with the carbon atom to which they are attached form a 3- to 6-membered carbocycle,
$R^{14A}$ represents hydrogen, fluorine, $(C_1-C_4)$-alkyl or hydroxy,
$R^{14B}$ represents hydrogen, fluorine, $(C_1-C_4)$-alkyl or trifluoromethyl,
and the N-oxides, salts, solvates, salts of the N-oxides and solvates of the N-oxides and salts thereof.

2. The compound of claim 1 in which
A represents $CH_2$,
$R^1$ represents phenyl,
  where phenyl may be substituted by 1 to 4 substituents independently of one another selected from the group consisting of fluorine, chlorine, cyano and methyl,
$R^2$ represents hydrogen, methyl, ethyl or cyclopropyl,
$R^3$ represents hydrogen,
$R^4$ represents hydrogen, fluorine, chlorine, methyl or ethyl,
$R^5$ represents hydrogen,
E represents nitrogen or $CR^6$,
  where
  $R^6$ represents hydrogen, chlorine, iodine, cyano, $(C_1-C_6)$-alkyl, $(C_2-C_6)$-alkynyl, cyclopropyl, hydroxy, $-OR^7$, $-NR^8R^9$, hydroxycarbonyl, $(C_1-C_4)$-alkoxycarbonyl, $-C(=O)-NR^{10}R^{11}$ or 5-membered heteroaryl,
    in which $(C_1-C_6)$-alkyl may be substituted by 1 to 3 substituents independently of one another selected from the group consisting of fluorine, difluoromethyl, trifluoromethyl, methoxy, ethoxy, hydroxy, amino, $-N(C=O)R^{12}$, methylsulphonylamino, cyclopropyl and cyclobutyl,
      in which $R^{12}$ represents cyclopropyl, cyclobutyl, methyl or ethyl,
    in which $(C_2-C_6)$-alkynyl may be substituted by cyclopropyl or cyclobutyl,
    in which 5-membered heteroaryl may be substituted by chlorine, methyl, ethyl or hydroxy,
    in which $R^7$ represents $(C_1-C_4)$-alkyl or pyrazolyl,
      in which $(C_1-C_4)$-alkyl may be substituted by trifluoromethyl, methoxy, hydroxy or cyclopropyl,
    in which $R^8$ represents hydrogen, $(C_1-C_4)$-alkyl or $(C_3-C_6)$-cycloalkyl,
      in which $(C_3-C_6)$-cycloalkyl may be substituted by 1 to 4 substituents independently of one another selected from the group consisting of methyl, ethyl and hydroxy,
      and
      in which $(C_1-C_4)$-alkyl may be substituted by 1 to 4 substituents independently of one another selected from the group consisting of fluorine, $(C_1-C_4)$-alkyl, $(C_3-C_5)$-cycloalkyl, pyrrolidinyl, piperidinyl, methoxy, ethoxy, hydroxy, amino, trifluoromethyl, difluoromethyl, monofluoromethyl and phenyl,
        in which phenyl may be substituted by 1 to 3 substituents independently of one another selected from the group consisting of fluorine, chlorine, cyano and methoxy,
        in which pyrrolidinyl and piperidinyl may be disubstituted by fluorine,
        and
        in which $(C_3-C_7)$-cycloalkyl may be substituted by hydroxy,
    in which $R^9$ represents hydrogen or methyl,
    or
    $R^8$ and $R^9$ together with the nitrogen atom to which they are attached form a 4- to 7-membered heterocycle,
      in which the 4- to 7-membered heterocycle may be substituted by 1 or 2 substituents independently of one another selected from the group consisting of $(C_1-C_4)$-alkyl, hydroxycarbonyl, hydroxy and amino,
        in which $(C_1-C_4)$-alkyl may be substituted by hydroxycarbonyl, hydroxy or amino,
    in which $R^{10}$ represents hydrogen, $(C_1-C_4)$-alkyl or $(C_3-C_6)$-cycloalkyl,
      in which $(C_3-C_6)$-cycloalkyl may be substituted by 1 to 3 substituents independently of one another selected from the group consisting of methyl, ethyl and hydroxy,
      and
      in which $(C_1-C_4)$-alkyl may be substituted by 1 or 2 substituents independently of one another selected from the group consisting of fluorine, hydroxy, amino, trifluoromethyl and difluoromethyl,
    in which $R^{11}$ represents hydrogen or methyl,
    or
    $R^{10}$ and $R^{11}$ together with the nitrogen atom to which they are attached form a 4- to 6-membered heterocycle,
      in which the 4- to 6-membered heterocycle may be substituted by 1 to 3 substituents independently of one another selected from the group consisting of fluorine, methyl, ethyl, hydroxy and amino,
        in which methyl and ethyl may be substituted by hydroxy,
L represents a $\#^1-CR^{13A}R^{13B}-(CR^{14A}R^{14B})_m-\#^2$ group,
  where
  $\#^1$ represents the point of attachment to the carbonyl group,
  $\#^2$ represents the point of attachment to the pyrimidine or triazine ring,
  m represents a number 0,
  $R^{13A}$ represents hydrogen or methyl,
  $R^{13B}$ represents hydrogen, difluoromethyl, trifluoromethyl or methyl,
  or
  $R^{13A}$ and $R^{13B}$ together with the carbon atom to which they are attached form a cyclopropyl ring,
and the N-oxides, salts, solvates, salts of the N-oxides and solvates of the N-oxides and salts thereof.

3. The compound of claim 1 in which
A represents $CH_2$,
$R^1$ represents a phenyl group of the formula

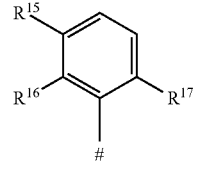

where
# represents the point of attachment to A,
and
$R^{15}$ represents hydrogen or fluorine,
$R^{16}$ and $R^{17}$ represent fluorine,
$R^2$ represents methyl,
$R^3$ represents hydrogen,
$R^4$ represents hydrogen, chlorine or methyl,
$R^5$ represents hydrogen,
E represents nitrogen or $CR^6$,
where
$R^6$ represents hydrogen, chlorine, ethynyl, hydroxy, —$OR^7$, —$NR^8R^9$, —C(=O)—$NR^{10}R^{11}$,1 H-pyrazol-1-yl or 1,3-thiazol-5-yl,
in which ethynyl is substituted by cyclopropyl,
in which 1H-pyrazol-1-yl and 1,3-thiazol-5-yl may be substituted by methyl, ethyl or hydroxy,
in which $R^7$ represents methyl, ethyl or 1H-pyrazol-4-yl,
in which methyl may be substituted by cyclopropyl,
in which ethyl may be substituted by trifluoromethyl, methoxy or hydroxy,
in which $R^8$ represents hydrogen, ethyl, propyl or ($C_4$-$C_6$)-cycloalkyl, in which ($C_4$-$C_6$)-cycloalkyl may be substituted by 1 or 2 methyl or hydroxy substituents,
and
in which ethyl and propyl may be substituted by 1 to 3 substituents independently of one another selected from the group consisting of fluorine, methyl, ethyl, propyl, cyclopropyl, methoxy, hydroxy, amino, trifluoromethyl, difluoromethyl, monofluoromethyl and phenyl,
in which phenyl may be substituted by 1 or 2 substituents independently of one another selected from the group consisting of fluorine, chlorine and methoxy,
and
in which ($C_4$-$C_7$)-cycloalkyl may be substituted by hydroxy,
in which $R^9$ represents hydrogen,
or
$R^8$ and $R^9$ together with the nitrogen atom to which they are attached form a piperidinyl, pyrrolidinyl or 3-azabicyclo[3.1.0]hex-3-yl ring,
in which the piperidinyl and pyrrolidinyl ring may be substituted by methyl,
in which methyl may be substituted by hydroxycarbonyl or hydroxy,
and
in which the 3-azabicyclo[3.1.0]hex-3-yl ring may be substituted by amino,
in which $R^{10}$ represents hydrogen, methyl, ethyl, n-propyl or cyclopropyl,
in which methyl, ethyl and n-propyl may be substituted by 1 or 2 substituents independently of one another selected from the group consisting of fluorine, amino and trifluoromethyl,
in which $R^{11}$ represents hydrogen,
or
$R^{10}$ and $R^{11}$ together with the nitrogen atom to which they are attached form a pyrrolidinyl, piperidinyl or piperazinyl ring,
in which the pyrrolidinyl ring may be substituted by 1 to 3 substituents independently of one another selected from the group consisting of fluorine, methyl, hydroxy and amino,
in which methyl may be substituted by hydroxy,
in which the piperazinyl ring may be substituted at the nitrogen atom by methyl, L represents a $\#^1$—$CR^{13A}R^{13B}$—$\#^2$ group,
where
$\#^1$ represents the point of attachment to the carbonyl group,
$\#^2$ represents the point of attachment to the pyrimidine or triazine ring,
$R^{13A}$ represents methyl,
$R^{13B}$ represents trifluoromethyl or methyl,
and the N-oxides, salts, solvates, salts of the N-oxides and solvates of the N-oxides and salts thereof.

4. A process for the compound of claim 1, comprising reacting a compound of the formula (II)

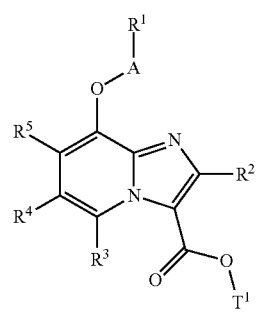

(II)

in which A, $R^1$, $R^2$, $R^3$, $R^4$ and $R^5$ each have the meanings given in claim 1 and
$T^1$ represents ($C_1$-$C_4$)-alkyl or benzyl,
in an inert solvent in the presence of a suitable base or acid to give a carboxylic acid of the formula (III)

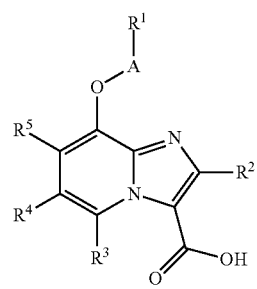

(III)

in which A, $R^1$, $R^2$, $R^3$, $R^4$ and $R^5$ each have the meanings given in claim 1, converting the carboxylic acid of formula (III) in an inert solvent under amide coupling conditions with an ammonium salt into a compound of the formula (IV)

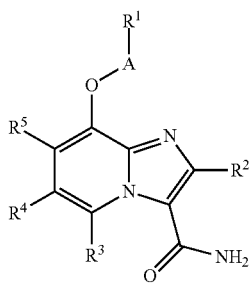

(IV)

in which A, R¹, R², R³, R⁴ and R⁵ each have the meanings given in claim 1, and reacting the compound of the formula (IV) in an inert solvent with trifluoroacetic anhydride to give a compound of the formula (V)

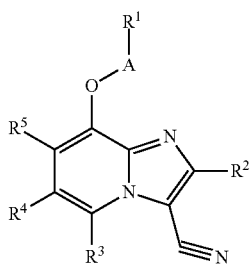

(V)

in which A, R¹, R², R³, R⁴ and R⁵ each have the meanings given in claim 1, converting the compound of the formula (V) in the presence of an alkylaluminum reagent in an inert solvent into an amidine of the formula (VI)

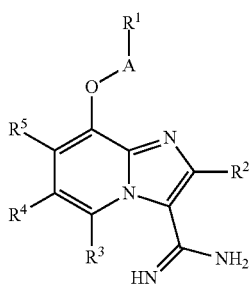

(VI)

in which A, R¹, R², R³, R⁴ and R⁵ each have the meanings given in claim 1,
  or
converting the compound of the formula (V) in a suitable solvent in the presence of a suitable base with hydroxylamine hydrochloride initially into a compound of the formula (VIa)

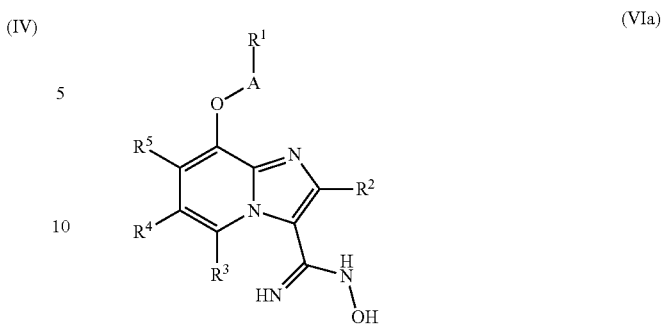

(VIa)

in which A, R¹, R², R³, R⁴ and R⁵ each have the meanings given in claim 1, and converting the compound of the formula (VIa) by hydrogenolysis in the presence of a palladium catalyst in an inert solvent into an amidine of the formula (VI), reacting the amidine of the formula (VI) in an inert solvent in the presence of a suitable base with a compound of the formula (VII)

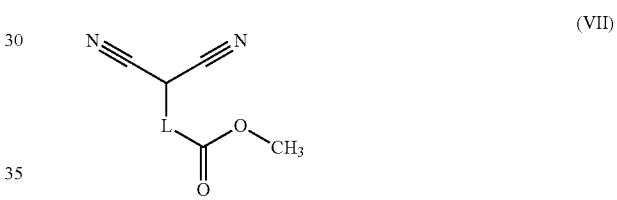

(VII)

to give a compound of the formula (VIII)

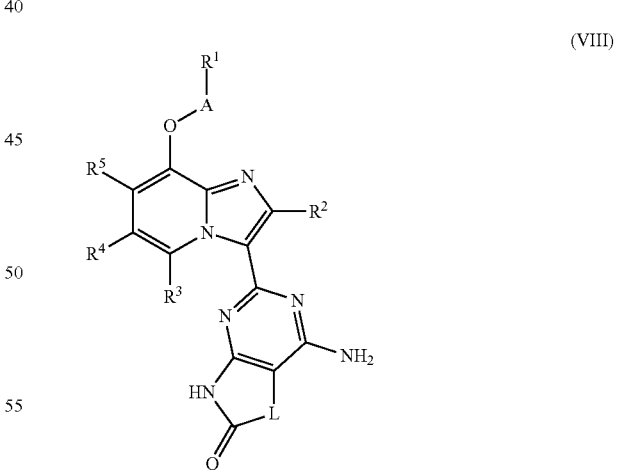

(VIII)

in which A, R¹, R², R³, R⁴, R⁵ and L each have the meanings given in claim 1, converting the compound of the formula (VIII) in an inert solvent with isopentyl nitrite and a halogen equivalent into a compound of the formula (IX)

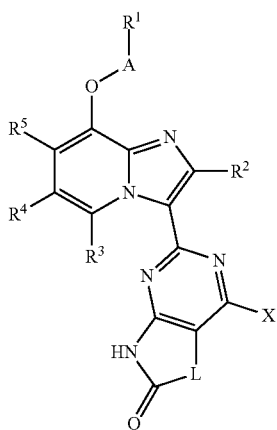

in which A, R$^1$, R$^2$, R$^3$, R$^4$, R$^5$ and L each have the meanings given in claim 1 and X represents chlorine, bromine or iodine, and

[A] reacting the compound of the formula (IX) in an inert solvent, optionally in the presence of a suitable base, with a compound of the formula (X)

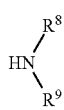

in which R$^8$ and R$^9$ have the meanings given in claim 1, to give a compound of the formula (I-A)

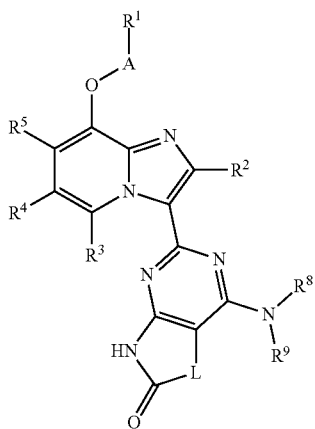

in which A, R$^1$, R$^2$, R$^3$, R$^4$, R$^5$, R$^8$, R$^9$ and L each have the meanings given in claim 1 or

[B] reacting the iodide of the formula (IX) in an inert solvent, optionally in the presence of a suitable base and copper(I) iodide, with a compound of the formula (XI)

HO—R$^7$ (XI)

in which R$^7$ has the meaning given in claim 1 to give a compound of the formula (I-B)

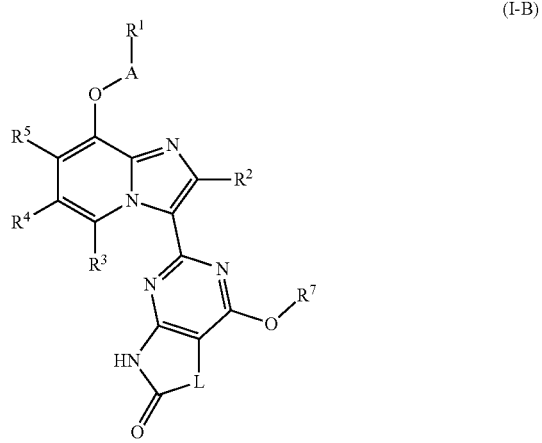

in which A, R$^1$, R$^2$, R$^3$, R$^4$, R$^5$, R$^7$ and L each have the meanings given in claim 1 or

[C] reacting the iodide of the formula (IX) in an inert solvent, optionally in the presence of a suitable base, with copper(I) cyanide to give a compound of the formula (I-C)

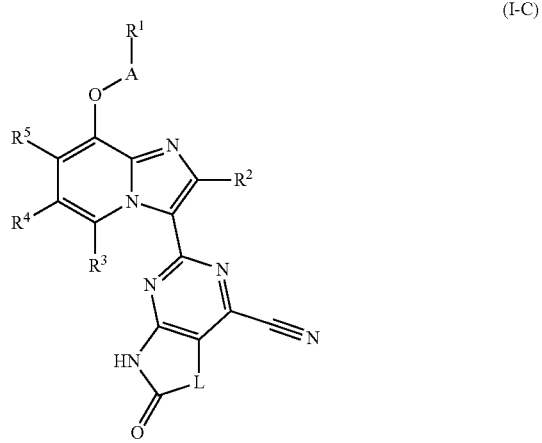

in which A, R$^1$, R$^2$, R$^3$, R$^4$, R$^5$ and L each have the meanings given in claim 1, and converting the compound of the formula (I-C) in an inert solvent with a suitable aqueous base into a compound of the formula (I-D)

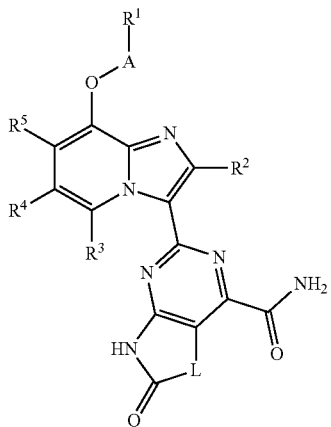

(I-D)

in which A, $R^1$, $R^2$, $R^3$, $R^4$, $R^5$ and L each have the meanings given in claim 1, and converting the compound of the formula (I-D) in an inert solvent with a suitable aqueous acid into an acid of the formula (I-E)

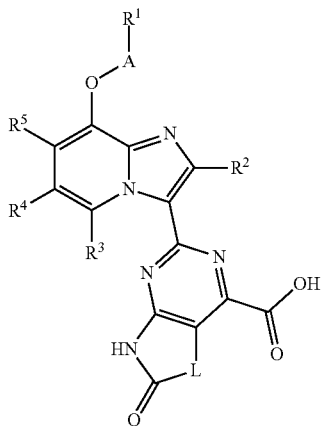

(I-E)

in which A, $R^1$, $R^2$, $R^3$, $R^4$, $R^5$ and L each have the meanings given in claim 1, and converting the compound of the formula (I-E) in an inert solvent under amide coupling conditions with an amine of formula (XII)

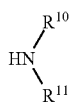

(XII)

in which $R^{10}$ and $R^{11}$ each have the meanings given in claim 1, into a compound of the formula (I-F)

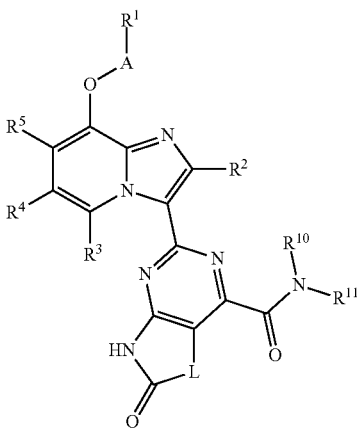

(I-F)

in which A, $R^1$, $R^2$, $R^3$, $R^4$, $R^5$, $R^{10}$, $R^{11}$ and L each have the meanings given in claim 1, and optionally converting the resulting compounds of the formula (I) optionally with the appropriate (i) solvents and/or (ii) acids or bases, into their solvates, salts and/or solvates of the salts.

5. A pharmaceutical composition comprising the compound of claim 1 in combination with an inert, non-toxic, pharmaceutically suitable auxiliary.

6. A pharmaceutical composition comprising the compound of claim 1 in combination with a further active compound selected from the group consisting of organic nitrates, NO donors, cGMP-PDE inhibitors, antithrombotic agents, hypotensive agents and lipid metabolism modifiers.

7. A method for the treatment of heart failure, angina pectoris, hypertension, pulmonary hypertension, ischaemias, vascular disorders, renal insufficiency, thromboembolic disorders, fibrotic disorders, arteriosclerosis, dementia disorders and erectile dysfunction comprising administering a therapeutically effective amount of the pharmaceutical composition of claim 5 to a patient in need thereof.

8. A method for the treatment of heart failure, angina pectoris, hypertension, pulmonary hypertension, ischaemias, vascular disorders, renal insufficiency, thromboembolic disorders, arteriosclerosis, dementia disorders and erectile dysfunction in humans and animals comprising administering a therapeutically effective amount of at least one compound of claim 1.

9. The process of claim 4, wherein the compound of the formula (VIa) is converted by hydrogenolysis in the presence of a palladium catalyst that is palladium on activated carbon in an inert solvent into an amidine of the formula (VI).

10. The process of claim 4, wherein the compound of the formula (VIa) is converted by hydrogenolysis in the presence of a palladium catalyst in an inert solvent that is ethanol or ethyl acetate into an amidine of the formula (VI).

11. The process of claim 9, wherein the compound of the formula (VIa) is converted by hydrogenolysis in the presence of a palladium catalyst in an inert solvent that is ethanol or ethyl acetate into an amidine of the formula (VI).

* * * * *